US012616712B2

(12) United States Patent
Verma

(10) Patent No.: US 12,616,712 B2
(45) Date of Patent: May 5, 2026

(54) STING AGONIST COMPRISING EXOSOMES FOR TREATING NEUROIMMUNOLOGICAL DISORDERS

(71) Applicant: LONZA SALES AG, Basel (CH)

(72) Inventor: Ajay Verma, Cambridge, MA (US)

(73) Assignee: LONZA SALES AG, Basel (CH)

( * ) Notice: Subject to any disclaimer, the term of this patent is extended or adjusted under 35 U.S.C. 154(b) by 948 days.

(21) Appl. No.: 17/754,177

(22) PCT Filed: Sep. 24, 2020

(86) PCT No.: PCT/US2020/052584
§ 371 (c)(1),
(2) Date: Jan. 13, 2023

(87) PCT Pub. No.: WO2021/062058
PCT Pub. Date: Apr. 1, 2021

(65) Prior Publication Data

US 2023/0241089 A1 Aug. 3, 2023

Related U.S. Application Data

(60) Provisional application No. 62/704,986, filed on Jun. 5, 2020, provisional application No. 62/989,528, filed on Mar. 13, 2020, provisional application No. 62/906,002, filed on Sep. 25, 2019.

(51) Int. Cl.

| | |
|---|---|
| *A61K 31/7084* | (2006.01) |
| *A61K 9/127* | (2006.01) |
| *A61K 38/20* | (2006.01) |
| *A61K 47/64* | (2017.01) |
| *A61P 25/00* | (2006.01) |
| *A61P 35/00* | (2006.01) |

(52) U.S. Cl.
CPC .......... *A61K 31/7084* (2013.01); *A61K 9/127* (2013.01); *A61K 38/208* (2013.01); *A61K 47/6425* (2017.08); *A61P 25/00* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 6,268,490 B1 | 7/2001 | Imanishi et al. | |
| 7,335,765 B2 | 2/2008 | Masakatsu et al. | |
| 8,821,943 B2 | 9/2014 | Kompella et al. | |
| 9,056,892 B2 | 6/2015 | Sun et al. | |
| 9,757,470 B2 | 9/2017 | Narasimhaswamy et al. | |
| 10,195,290 B1 | 2/2019 | Dooley et al. | |
| 2012/0322851 A1 | 12/2012 | Hardee et al. | |
| 2017/0348416 A1 | 12/2017 | Häsler et al. | |
| 2018/0193270 A1* | 7/2018 | Bolen | A61K 47/554 |
| 2019/0202936 A1 | 7/2019 | Dennis et al. | |
| 2019/0300513 A1* | 10/2019 | Altman | C07D 333/56 |
| 2020/0254028 A1* | 8/2020 | Goodman | A61K 39/02 |

FOREIGN PATENT DOCUMENTS

| | | |
|---|---|---|
| WO | 1998039352 A1 | 9/1998 |
| WO | 1999014226 A2 | 3/1999 |
| WO | 2000047599 A1 | 8/2000 |
| WO | 2000066604 A2 | 1/2001 |
| WO | 2001023613 A1 | 4/2001 |
| WO | 2004046160 A2 | 6/2004 |
| WO | 2007090071 A2 | 8/2007 |
| WO | 2007134181 A2 | 11/2007 |
| WO | 2007146511 A2 | 12/2007 |
| WO | 2008150729 A2 | 12/2008 |
| WO | 2008154401 A2 | 12/2008 |
| WO | 2009006478 A2 | 1/2009 |
| WO | 2009067647 A1 | 5/2009 |
| WO | 2010036698 A1 | 4/2010 |
| WO | 2010077578 A1 | 7/2010 |
| WO | 2011017521 A2 | 2/2011 |
| WO | 2011156202 A1 | 12/2011 |
| WO | 2013036868 A1 | 3/2013 |
| WO | 2013154798 A1 | 10/2013 |
| WO | 2013185052 A1 | 12/2013 |
| WO | 2014179335 A1 | 11/2014 |
| WO | 2014179760 A1 | 11/2014 |
| WO | 2014189805 A1 | 11/2014 |
| WO | 2014189806 A1 | 11/2014 |
| WO | 2015017652 A1 | 2/2015 |
| WO | 2015077354 A1 | 5/2015 |
| WO | 2015185565 A1 | 12/2015 |
| WO | 2016096577 A1 | 6/2016 |

(Continued)

OTHER PUBLICATIONS

Aguila, B. et al., "The IG superfamily protein PTGFRN coordinates survival signaling in glioblastoma multiforme", Cancer Letters, 462:33-42 (2019).
Bergstrom, D.E., "Unnatural Nucleosides With Unusual Base Pairing Properties," Current Protocols in Nucleic Acid Chemistry 37(1):1.4.1-1.4.32 (2009).
Besse, B. et al., "Dendritic cell-derived exosomes as maintenance immunotherapy after first line chemotherapy in NSCLC", Oncoimmunology 5(4):e107108 (2016).
"Codiak Biosciences, Inc., form S-1", (Apr. 2019), pp. 1-254.
Deleavey, G.F. and Damha, M.J., "Designing Chemically Modified Oligonucleotides for Targeted Gene Silencing," Chemistry & Biology 19(8):937-954 (2012).
"Development of the engExTM Platform for Engineered Exosomes and Therapeutic Potential of Codiak's exoSTING Highlighted at the 2019 American Association for Cancer Research Annual Meeting" BusinessWire, Apr. 1, 2019, accessed at URL:[https://www.businesswire.com/news/home/20190401005089/en/].

(Continued)

*Primary Examiner* — Celeste A Roney
(74) *Attorney, Agent, or Firm* — MEDLER FERRO WOODHOUSE & MILLS PLLC

(57) ABSTRACT

Provided herein are compositions comprising EV, e.g., exosome, which comprises STING agonists and methods of using such compositions for the treatment of neuroimmunological disorders. Methods of producing the compositions (e.g., EVs comprising a STING agonist) described herein are also provided.

22 Claims, 12 Drawing Sheets

Specification includes a Sequence Listing.

(56) References Cited

FOREIGN PATENT DOCUMENTS

| | | | | |
|---|---|---|---|---|
| WO | 2016120305 A1 | | 8/2016 | |
| WO | 2016096174 A1 | | 9/2016 | |
| WO | 2016145102 A1 | | 9/2016 | |
| WO | 2017027645 A1 | | 2/2017 | |
| WO | WO-2017027646 A1 | * | 2/2017 | ............ C07H 21/04 |
| WO | 2017075477 A1 | | 5/2017 | |
| WO | 2017175147 A1 | | 10/2017 | |
| WO | 2017175156 A1 | | 10/2017 | |
| WO | 2018100558 A1 | | 6/2018 | |
| WO | 2019099942 A1 | | 5/2019 | |
| WO | 2019183578 A1 | | 9/2019 | |
| WO | 2020101740 A1 | | 5/2020 | |
| WO | 2020191361 A2 | | 9/2020 | |

OTHER PUBLICATIONS

Dobeli, H. et al., "Role of the carboxy-terminal sequence on the biological activity of human immune interferon (IFN-y)", Journal of Biotechnology 7(3):199-216 (1988).

Dooley, K., et al., "Abstract 2150: engEx: A novel exosome engineering platform enabling targeted transfer of pharmacological molecules", Cancer Research, 79(13 Supplement): Abstract 2150 (2019).

Ernfors, P., et al., "Developmental and Regional Expression of Beta-nerve Growth Factor Receptor mRNA in the Chick and Rat," Neuron 1(10):983-996, Cell Press, United States (Dec. 1988).

Freier, S.M. and Altmann, K.H., "The Ups and Downs of Nucleic Acid Duplex Stability: Structure-stability Studies on Chemically-modified DNA: RNA Duplexes," Nucleic Acids Research 25(22):4429-4443 (1997).

Gayle, R.B. et al., "Identification of regions in interleukin-I alpha important for activity", Journal of Biological Chemistry 268(29):22105-22111 (1993).

GenBank, "*Homo sapiens* chromosome 1, GRCh38.p14 Primary Assembly," Accession No. NC_000001.11, accessed at URL:[https://www.ncbi.nlm.nih.gov/nuccore/NC_000001.11?report=graph#], 1 page.

GenBank, "*Homo sapiens* chromosome 12, GRCh38.p14 Primary Assembly," Accession No. NC_000012.12, accessed at URL:[https://www.ncbi.nlm.nih.gov/nuccore/NC_000012.12], 3 pages.

GenBank, "*Homo sapiens* chromosome 20, GRCh38.p14 Primary Assembly", Accession No. NC_000020.11, accessed at URL:[https://www.ncbi.nlm.nih.gov/nuccore/NC_000020.11/], 2 pages.

GenBank, "*Homo sapiens* transferrin (TF), transcript variant 1, mRNA," Accession No. NM_001063, accessed at URL:[https://www.ncbi.nlm.nih.gov/nuccore/NM_001063.4/], 10 pages.

GenBank, "*Homo sapiens* signal transducer and activator of transcription 6 (STAT6), transcript variant 1, mRNA", Accession No. NM_001178078.1, accessed at URL:[https://www.ncbi.nlm.nih.gov/nuccore/NM_001178078.1/], 6 pages.

GenBank, "*Homo sapiens* CCAAT enhancer binding protein beta (CEBPB), transcript variant 1, mRNA", Accession No. NM_001285878.1, accessed at URL:[https://www.ncbi.nlm.nih.gov/nuccore/NM_001285878.1/], 4 pages.

GenBank, "Mus musculus melanotransferrin (Meltf), mRNA," Accession No. NM_013900, accessed at URL:[https://www.ncbi.nlm.nih.gov/nuccore/NM_013900.2/], 6 pages.

GenBank, "*Homo sapiens* lactotransferrin (LTF), transcript variant 1, mRNA," Accession No. NM_002343, accessed at URL:[https://www.ncbi.nlm.nih.gov/nuccore/NM_002343.6/], 7 pages.

GenBank, "*Homo sapiens* transferrin (TF), mRNA," Accession No. XM_002793, accessed at URL:https://www.ncbi.nlm.nih.gov/nuccore/XM_002793.7?report=genbank], 2 pages.

GenBank, "*Homo sapiens* transferrin (TF), mRNA," Accession No. XM_039847, accessed at URL:[https://www.ncbi.nlm.nih.gov/nuccore/XM_039847.1?report=genbank], 2 pages.

Hirao, I., et al., "Natural Versus Artificial Creation of Base Pairs in DNA: Origin of Nucleobases From the Perspectives of Unnatural Base Pair Studies," Accounts of Chemical Research 45(12):2055-2065 (2012).

Ibáñez, C.F., et al., "Chimeric Molecules With Multiple Neurotrophic Activities Reveal Structural Elements Determining the Specificities of NGF and BDNF," The EMBO Journal 10(8):2105-2110, Wiley Blackwell, United Kingdom (Aug. 1991).

Jafari, B. et al., "Peptide-mediated drug delivery across the blood-brain barrier for targeting brain tumors", Expert Opinion on Drug Delivery 16(6):583-605 (2019).

Jang, S.C. et al., "Abstract 944: exoSTING: An engineered exosome therapeutic that selectively delivers STING agonist to the tumor resident antigen-presenting cells resulting in improved tumor antigenspecific adaptive immune response", Cancer Research 79(13 Supplement): Abstract 944 (2019).

Kamerkar, S. et al., "Genetic reprogramming of TAMS by engineered exosomes results in potent single agent anti-tumor activity", 80(60 Supplement): Abstract 5696 (2020).

Kramer, K. et al., "Monoclonal Antibody to Human Trk-A: Diagnostic and Therapeutic Potential in Neuroblastoma", European Journal of Cancer 33(12):2090-2091 (1997).

Leibrock, J., et al., "Molecular Cloning and Expression of Brain-derived Neurotrophic Factor," Nature 341(6238):149-152 (1989).

Lesauteur, L. et al. "Small Peptide Mimics of Nerve Growth Factor Bind TrkA Receptors and Affect Biological Responses", The Journal of Biological Chemistry 270(12):6564-6569 (1995).

Longo, F.M. et al., "Synthetic NGF Peptide Derivatives Prevent Neuronal Death Via a p75 Receptor-Dependent Mechanism", Journal of Neuroscience Research 48:1-17 (1997).

Mei, B. et al., "Rational design of a fully active, long-acting PEGylated factor VIII for hemophilia A treatment", Blood 116(2):270-279 (2010).

Mitsuoka, Y., et al., "A Bridged Nucleic Acid, 2',4'-BNA COC: Synthesis of Fully Modified Oligonucleotides Bearing Thymine, 5-Methylcytosine, Adenine and Guanine 2',4'-BNA COC Monomers and RNA-Selective Nucleic-Acid Recognition," Nucleic Acids Research 37(4):1225-1238 (2009).

Morita, K., et al., "2'-O,4'-C-Ethylene-Bridged Nucleic Acids (ENA): Highly Nuclease-Resistant and Thermodynamically Stable Oligonucleotides for Antisense Drug," Bioorganic and Medicinal Chemistry Letters 12(1):73-76 (2002).

Oh, T. et al., "Immunocompetent murine models for the study of glioblastoma immunotherapy", Journal of Translational Medicine 29(12):107 (2014).

Ohkuri, T. et al., "STING contributes to anti-glioma immunity via triggering type-I IFN signals in the tumor microenvironment", Cancer Immunology Research 2(12):1199-1208 (2014).

Ohkuri, T. et al., "Protective role of STING against gliomagenesis: Rational use of STING agonist in anti-glioma immunotherapy", Oncoimmunology 4(4):e999523 (2015).

Oller-Salvia, B. et al., "Blood-brain barrier shuttle peptides: an emerging paradigm for brain delivery", Chemical Society Reviews 45(7):4690-4707 (2016).

Papapetrou, E.P. et al., "Genetic Modification of Hematopoietic Stem Cells With Nonviral Systems: Past Progress and Future Prospects", Gene Therapy 12(Supplement 1):S118-S130 (2005).

Rodriguez, P.L. et al., "Minimal "Self" peptides that inhibit phagocytic clearance and enhance delivery of nanoparticles", Science 339(6122):971-975 (2013).

Ron, D. et al., "Expression of biologically active recombinant keratinocyte growth factor. Structure/function analysis of amino-terminal tnmcation mutants", Journal of Biological Chemistry 268(4):2984-2988 (1993).

Sellers, D.L., et al., "Targeted Axonal Import (TAxI) Peptide Delivers Functional Proteins Into Spinal Cord Motor Neurons After Peripheral Administration," Proceedings of the National Academy of Sciences of the United States of America 113(9):2514-2519, (2016).

Seth, P.P., et al., "Synthesis and Biophysical Evaluation of 2',4'-constrained 2'O-methoxyethyl and 2',4'-constrained 2'O-ethyl Nucleic Acid Analogues," Journal of Organic Chemistry 75(5):1569-1581 (2010).

Spengler, J., et al., "Abbreviated nomenclature for cyclic and branched homo- and hetero-detic peptides," Peptide Research 65(6):550-555 (2005).

(56) References Cited

OTHER PUBLICATIONS

Ubah, O.C., et al., "Next-generation Flexible Formats of VNAR Domains Expand the Drug Platform's Utility and Developability," Biochemical Society Transactions 46(6):1559-1565 (2018).
Uhlmann, E., "Recent Advances in the Medicinal Chemistry of Antisense Oligonucleotides," Current Opinion in Drug Discovery and Development 3(2):203-213 (2000).
UniProtKB, "CEBPB_HUMAN," Accession No. P17676, accessed at URL:[https://www.uniprot.org/uniprotkb/P17676/entry], 16 pages.
UniProtKB, "TFR1_HUMAN," Accession No. P20786, accessed at URL:[https://www.uniprot.org/uniprotkb/P02786/entry], 11 pages.
UniProtKb, "STAT6_HUMAN," Accession No. P42226, accessed at URL:[https://www.uniprot.org/uniprotkb/P42226/entry], 13 pages.
Verma, A., et al., "Intrathecal 99mTc-DTPA imaging of molecular passage from lumbar cerebrospinal fluid to brain and periphery in humans," Alzheimer's & Dementia 12(1):e12030 (2020).
"33rd Annual Meeting & Pre-Conference Programs of the Society for Immunotherapy of Cancer (SITC 2018)" Journal for ImmunoTherapy of Cancer 6(Supplement 1):115, pp. 1-192 (2018).

* cited by examiner

DAPI

CD206
M2 macrophage

LYVE1
Lymphatics

Protein X
Exosome

Exosome
CD206

Exosome
LYVE1

IFN-β In Situ Hyb (ISH)

FIG. 2B FIG. 2C

Coronal and Sagittal meninges ROI

Image analysis

Temporal response

Day 15 Enrollment MRI

Day 57 MRI

STING AGONIST COMPRISING EXOSOMES FOR TREATING NEUROIMMUNOLOGICAL DISORDERS

CROSS-REFERENCE TO RELATED APPLICATIONS

This application claims priority benefit of U.S. Provisional Application Nos. 62/906,002, filed Sep. 25, 2019; 62/989,528 filed Mar. 13, 2020; and 62/704,986 filed Jun. 5, 2020, each of which is herein incorporated by reference in its entirety.

REFERENCE TO SEQUENCE LISTING SUBMITTED ELECTRONICALLY VIA EFS-WEB

This application includes an electronically submitted sequence listing in .txt format. The .txt file contains a sequence listing entitled "0132-0276US1_ST25.txt" created on Mar. 9, 2026 and is 223,413 bytes in size. The sequence listing contained in this .txt file is part of the specification and is hereby incorporated by reference herein in its entirety.

BACKGROUND OF THE DISCLOSURE

Neuroimmunological disorders are some of the most devastating and difficult to treat. Examples of such diseases include gliomas, peripheral tumors that have metastasized to the brain or meninges (neoplastic meningitis), and chronic infectious meningitis. Gliomas are the most common type of tumors to affect the central nervous system. Ostrom, Q. T., et al., *Neuro Oncol* 16(7): 896-913 (2014). Gliomas comprise about 30 percent of all brain tumors and central nervous system tumors, and 80 percent of all malignant brain tumors. Gliomas typically begin in the glial cells that surround and support neurons in the brain, including astrocytes, oligodendrocytes, and ependymal cells. Hanif, F., et al., *Asian Pac J Cancer Prev* 18(1): 3-9 (2017). Of the gliomas, glioblastoma (also known as glioblastoma multiforme (GBM)) is the most common and the most aggressive.

Despite the aggressive standard of care currently used (e.g., surgery, radiation therapy, chemotherapy, and electric field therapy), there remains a need for more effective and comprehensive treatment options for neuroimmunological disorders, e.g., gliomas, e.g., glioblastoma multiforme (GBM). GBM is rarely curable. For instance, the current survival rate for GBM is 14-15 months after diagnosis with less than 3-5% of people surviving longer than five years. Without treatment, most patients succumb to the disease within just a few months. Omuro, A., et al., *JAMA* 310: 1842-1850 (2013). Prognosis generally worsens with age.

Extracellular vesicles (EVs) (e.g., exosomes) are important mediators of intercellular communication. They are also important biomarkers in the diagnosis and prognosis of many diseases, such as cancer. As drug delivery vehicles, EVs (e.g., exosomes) offer many advantages over traditional drug delivery methods (e.g., peptide immunization, DNA vaccines) as a new treatment modality in many therapeutic areas. However, despite its advantages, EVs (e.g., exosomes) have had limited clinical efficacy. For example, dendritic-cell derived exosomes (DEX) were investigated in a Phase II clinical trial as maintenance immunotherapy after first line chemotherapy in patients with inoperable non-small cell lung cancer (NSCLC). However, the trial was terminated because the primary endpoint (at least 50% of patients with progression-free survival (PFS) at 4 months after chemotherapy cessation) was not reached. Besse, B., et al., *Oncoimmunology* 5(4):e1071008 (2015).

Accordingly, new and more effective engineered EVs (e.g., exosomes) are required, particularly those that can be used to better treat neuroimmunological disorders, such as gliomas, peripheral tumors that have metastasized to the brain or meninges (neoplastic meningitis), and chronic infectious meningitis.

SUMMARY OF THE DISCLOSURE

Provided herein is a method of treating a neuroimmunological disorder in a subject in need thereof comprising administering to the subject a composition comprising an extracellular vesicle and a stimulator of interferon genes protein (STING) agonist ("exoSTING"). In some aspects, the composition is administered intrathecally or intratumorally.

In some aspects, the neuroimmunological disorder is a brain tumor. In some aspects, the brain tumor is a glioma. In some aspects, the glioma is a low grade glioma or a high grade glioma. In certain aspects, the glioma is oligodendroglioma, anaplastic astrocytomas, glioblastoma multiforme, diffuse intrinsic pontine glioma, IDH1 and IDH2-mutated glioma, or any combination thereof. In further aspects, the glioma is glioblastoma multiforme.

In some aspects, the neuroimmunological disorder is a neoplastic meningitis.

In some aspects, the neuroimmunological disorder is chronic infectious meningitis.

In some aspects, the extracellular vesicle is an exosome, a nanovesicle, an apoptotic body, a microvesicle, a lysosome, an endosome, a liposome, a lipid nanoparticle, a micelle, a multilamellar structure, a revesiculated vesicle, an extruded cell, or any combination thereof. In certain aspects, the extracellular vesicle is an exosome.

In some aspects, the STING agonist is associated with the extracellular vesicle. In certain aspects, the STING agonist is encapsulated within the extracellular vesicle. In further aspects, the STING agonist is linked to a lipid bilayer of the extracellular vesicle, optionally by a linker.

In some aspects, the extracellular vesicle overexpresses a PTGFRN protein. In certain aspects, the STING agonist is linked to the PTGFRN protein, optionally by a linker. In some aspects, the extracellular vesicle is produced by a cell that overexpresses a PTGFRN protein.

In some aspects, the extracellular vesicle further comprises a protein that binds to or enzymatically reacts with the STING agonist. In some aspects, the extracellular vesicle further comprises a ligand, a cytokine, or an antibody. In certain aspects, the ligand comprises CD40L, OX40L, and/or CD27L. In some aspects, the cytokine comprises IL-7, IL-12, and/or IL-15. In certain aspects, the antibody comprises an antagonistic antibody and/or an agonistic antibody.

In some aspects, the STING agonist is a cyclic dinucleotide. In other aspects, the STING agonist is a non-cyclic dinucleotide. In some aspects, the STING agonist comprises a lipid-binding tag. In certain aspects, the STING agonist is physically and/or chemically modified. In further aspects, the modified STING agonist has a polarity and/or a charge different from the corresponding unmodified STING agonist. In some aspects, the concentration of the STING agonist associated with the extracellular vesicle is about 0.01 μM to 100 μM. In certain aspects, the concentration of the STING agonist associated with the extracellular vesicle is about 0.01 μM to 0.1 μM, 0.1 μM to 1 μM, 1 μM to 10 μM, 10 μM to 50 μM, or 50 μM to 100 μM. In some aspects, the concentration of the STING agonist associated with the extracellular vesicle is about 1 μM to 10 μM.

In some aspects, the STING agonist is in the lumen of the extracellular vesicle and is not linked to a scaffold moiety.

In some aspects, the composition further comprises a pharmaceutically acceptable carrier.

In some aspects, administering a composition disclosed herein induces or modulates the immune response and/or the inflammatory response in the subject.

In some aspects, a method of treating a glioma disclosed herein further comprises administering an additional therapeutic agent. In certain aspects, the additional therapeutic agent is an immunomodulating agent. In some aspects, the additional therapeutic agent comprises an IL-12 moiety. In certain aspects, the IL-12 moiety is an IL-12 protein, a nucleic acid encoding the IL-12 protein, or any combination thereof. In some aspects, the IL-12 moiety is associated with a second extracellular vesicle.

In some aspects, the additional therapeutic agent is an antibody or antigen-binding fragment thereof. In certain aspects, the antibody or antigen-binding fragment thereof is an inhibitor of CTLA-4, PD-1, PD-L1, PD-L2, TIM-3, or LAG3.

In some aspects, administering a composition disclosed herein prevents metastasis of the glioma in the subject.

Also disclosed herein is a kit comprising a composition which comprises an extracellular vesicle and a STING agonist and instructions for use according to any of the methods disclosed herein.

In some aspects, the extracellular vesicle further comprises one or more antisense oligonucleotide (ASO).

In some aspects, the ASO comprises a nucleotide sequence that is complimentary to two or more contiguous nucleotides of an RNA transcript encoding a transcription factor.

In some aspects, the ASO comprises a nucleotide sequence that is complimentary to two or more contiguous nucleotides of an RNA transcript encoding STAT6.

In some aspects, the ASO comprises a nucleotide sequence that is complimentary to two or more contiguous nucleotides of an RNA transcript encoding CEBP/f.

BRIEF DESCRIPTION OF THE DRAWINGS

In FIG. 1A, exosome uptake within the meningeal lymphatics is shown using both PET scan and autoradiogram (top image). The bottom image in FIG. 1A provides an illustration of the meningeal lymphatics. FIGS. 1B-1G provide an immunofluorescence analysis showing the uptake of exosomes by the M2 macrophages (CD206+) and the lymphatic endothelial cells (LYVE1+). The top row (from left to right) shows immunofluorescence staining for DAPI alone (FIG. 1B), M2 macrophages (CD206+) alone (FIG. 1C), and lymphatic endothelial cells (LYVE1+) alone (FIG. 1D). The bottom row shows the following: (i) immunofluorescence staining for the exosomes based on Protein X expression (FIG. 1E), (ii) an overlay of the M2 macrophage (based on CD206 expression) with exosomes (based on Protein X expression) (FIG. 1F), and (iii) an overlay of the lymphatic endothelial cells (based on LYVE1 expression) with the exosomes (based on Protein X expression) (FIG. 1G). Exemplary overlap of exosome staining with M2 macrophage or lymphatic endothelial cell staining are indicated by an arrow in FIGS. 1F and 1G.

FIGS. 2A-2C are images of in situ hybridization showing IFN-β expression in meningeal macrophages.

FIG. 5A shows constructs comprising the extracellular domain of wild-type CD47 (with a C15S substitution) fused to either a flag-tagged (1083 and 1084) or non-flag-tagged (1085 and 1086) full length Scaffold X (1083 and 1086) or a truncated Scaffold X (1084 and 1085). FIG. 5B shows constructs comprising the extracellular domain of Velcro-CD47 fused to either a flag-tagged (1087 and 1088) or non-flag-tagged (1089 and 1090) full length Scaffold X (1087 and 1090) or a truncated Scaffold X (1088 and 1089). FIG. 5C shows constructs wherein the first transmembrane domain of wild-type CD47 (with a C15S substitution; 1127 and 1128) or Velcro-CD47 (1129 and 1130) is replaced with a fragment of Scaffold X, comprising the transmembrane domain and the first extracellular motif of Scaffold X. FIG. 5D shows various constructs comprising a minimal "self" peptide (GNYTCEVTELTREGETIIELK; SEQ ID NO: 400) fused to either a flag-tagged (1158 and 1159) or non-flag-tagged (1160 and 1161) full length Scaffold X (1158 and 1161) or a truncated Scaffold X (1159 and 1160).

FIG. 7A shows a survival curve for mice treated with one of the following: (i) ExoSTING, (ii) exosome comprising Scaffold X alone (i.e., no STING agonist) "PrX", (iii) Phosphate buffered saline (PBS), (iv) an anti-PD-L-1 mAb, and (v) Temozolamide. FIG. 7B shows MRI scans of the brain of an ExoSTING treated animal at day 15 and day 57 post tumor induction.

DETAILED DESCRIPTION OF THE DISCLOSURE

Figure 1A:
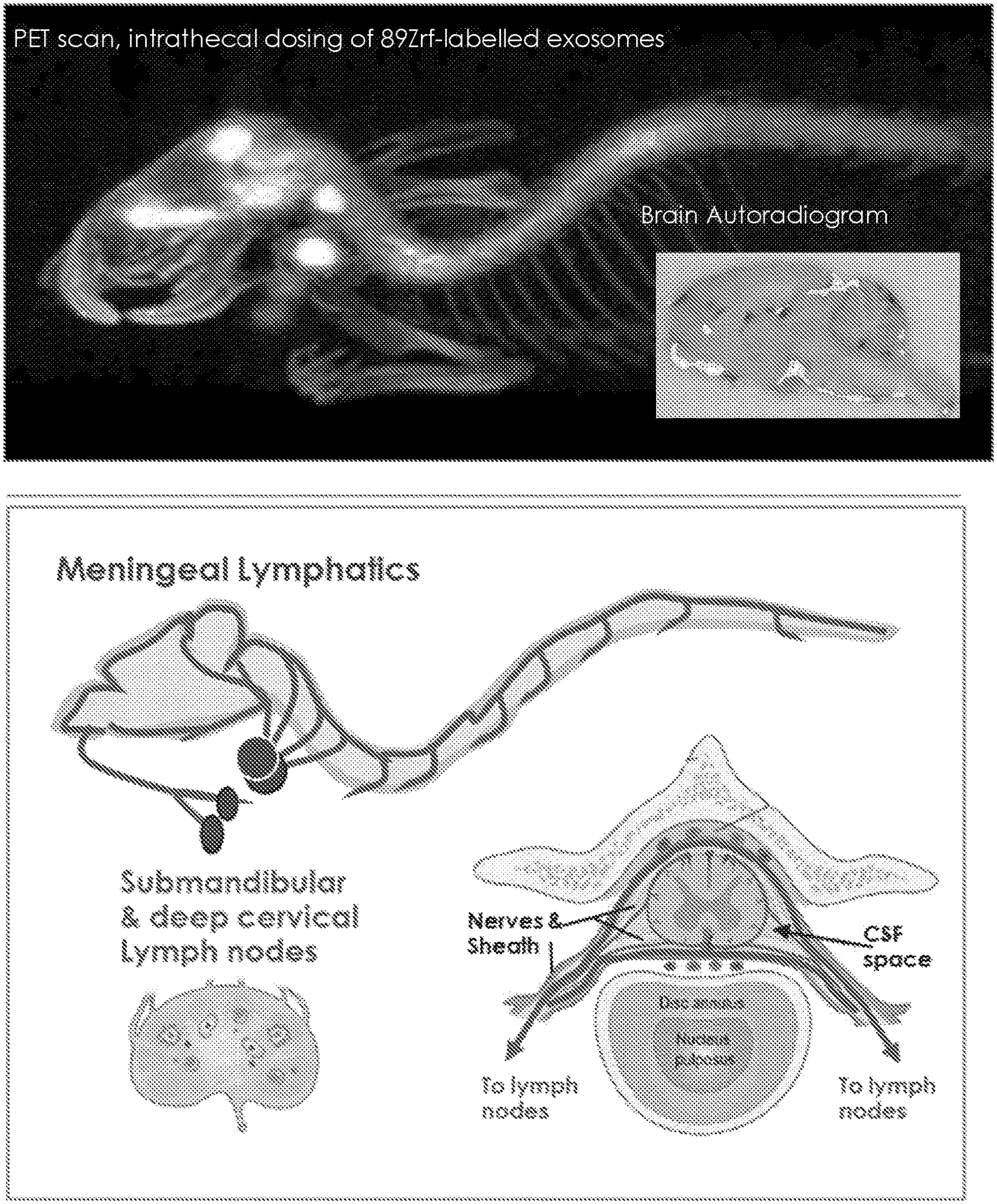
FIGS. 1A-1G show exosome uptake after intrathecal administration in an animal model.
Figure 1B:
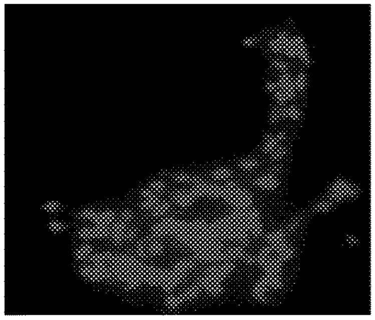
Figure 1C:
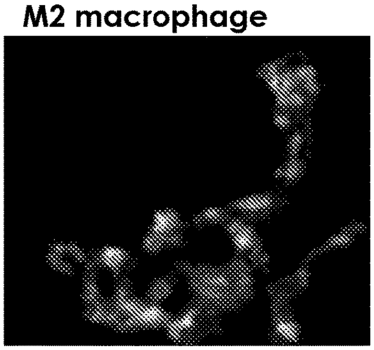
Figure 1D:
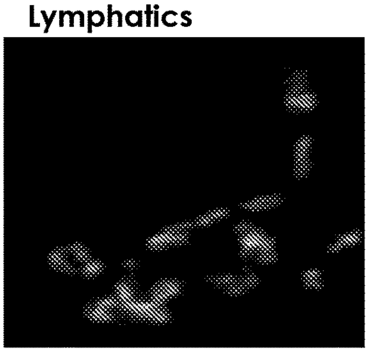
Figure 1E:
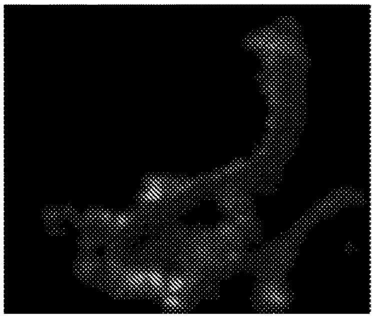
Figure 1F:
Figure 1G:
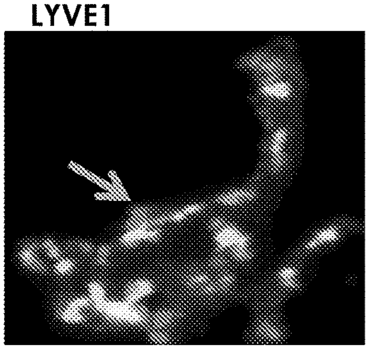
Figure 2A:
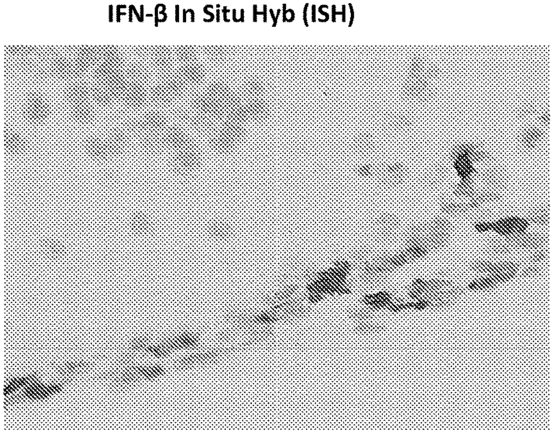
Figure 2A:
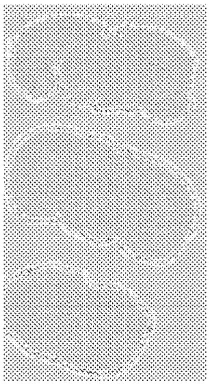
Figure 2A:
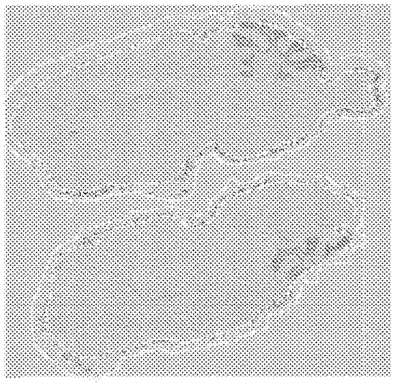
Figure 2D:
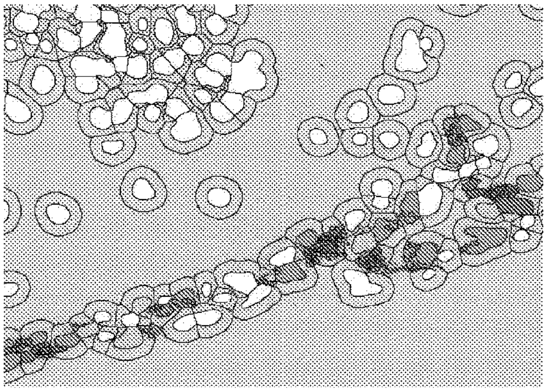
FIG. 2D is an image analysis of FIG. 2A, showing the outline of cells.
Figure 2E:
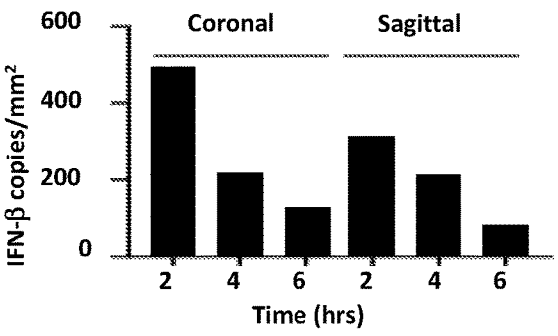
FIG. 2E is a graphical representation of IFN-β copies per $mm^2$ in coronal and sagittal cross sections of meninges following over time administration of an exosome comprising a STING agonist.

Before the present invention is described in greater detail, it is to be understood that this invention is not limited to particular aspects described, as such can, of course, vary. It is also to be understood that the terminology used herein is for the purpose of describing particular aspects only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible.

I. Definitions

It is noted that, as used herein and in the appended claims, the singular forms "a," "an," and "the" include plural referents unless the context clearly dictates otherwise. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values which are about the same quantity or amount as the recited value are also within the scope of the disclosure. Where a combination is disclosed, each subcombination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term "about" or "approximately" is used herein to mean approximately roughly, around, or in the region of. When the term "about" is used in conjunction with a numerical range, it modifies that range by extending the boundaries above and below the numerical values set forth. The term used herein means within 5% of the referenced amount, e.g., about 50% is understood to encompass a range of values from 47.5% to 52.5%.

As used herein, the term "extracellular vesicle" or "EV" refers to a cell-derived vesicle comprising a membrane that encloses an internal space. Extracellular vesicles comprise all membrane-bound vesicles (e.g., exosomes, nanovesicles) that have a smaller diameter than the cell from which they are derived. Generally extracellular vesicles range in diameter from 20 nm to 1000 nm, and can comprise various macromolecular payload either within the internal space (i.e., lumen), displayed on the external surface of the extracellular vesicle, and/or spanning the membrane. Said payload can comprise nucleic acids, proteins, carbohydrates, lipids, small molecules, and/or combinations thereof. In some aspects, an extracellular vesicle comprises a scaffold moiety. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, prokaryotic or eukaryotic cells, and/or cultured cells. In some aspects, extracellular vesicles are produced by cells that express one or more transgene products.

As used herein the term "exosome" refers to a cell-derived small (between 20-300 nm in diameter, more preferably 40-200 nm in diameter) vesicle comprising a membrane that encloses an internal space (i.e., lumen), and which is generated from said cell by direct plasma membrane budding or by fusion of the late endosome with the plasma membrane. The exosome is a species of extracellular vesicle. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. In some aspects, an exosome comprises a scaffold moiety. The exosome can be derived from a producer cell, and isolated from the producer cell based on its size, density, biochemical parameters, or a combination thereof. In some aspects, the exosomes of the present disclosure are produced by cells that express one or more transgene products.

As used herein, the term "nanovesicle" refers to a cell-derived small (between 20-250 nm in diameter, more preferably 30-150 nm in diameter) vesicle comprising a membrane that encloses an internal space, and which is generated from said cell by direct or indirect manipulation such that said nanovesicle would not be produced by said producer cell without said manipulation. Appropriate manipulations of said producer cell include but are not limited to serial extrusion, treatment with alkaline solutions, sonication, or combinations thereof. The production of nanovesicles may, in some instances, result in the destruction of said producer cell. Preferably, populations of nanovesicles are substantially free of vesicles that are derived from producer cells by way of direct budding from the plasma membrane or fusion of the late endosome with the plasma membrane. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. In some aspects, a nanovesicle comprises a scaffold moiety. The nanovesicle, once it is derived from a producer cell according to said manipulation, may be isolated from the producer cell based on its size, density, biochemical parameters, or a combination thereof.

As used herein, the term "surface-engineered exosome" (e.g., Scaffold X-engineered exosome) refers to an exosome with the membrane and/or the surface of the exosome modified in its composition so that the surface of the engineered exosome is different from that of the exosome prior to the modification or that of a naturally occurring exosome. The engineering can be on the surface of the exosome and/or in the membrane of the exosome, so that the surface of the exosome is changed. For example, the membrane is modified in its composition of a protein, a lipid, a small molecule, a carbohydrate, etc., so that the surface of the exosome is modified. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. In some aspects, a surface-engineered exosome comprises an exogenous protein (i.e., a protein that the exosome does not naturally express) or a fragment or variant thereof that can be exposed to the surface of the exosome, or can be an anchoring point (attachment) for a moiety exposed on the surface of the exosome. In other aspects, a surface-engineered exosome comprises a higher expression (e.g., higher number) of a natural exosome protein (e.g., Scaffold X) or a fragment or variant thereof that can be exposed to the surface of the exosome, or can be an anchoring point (attachment) for a moiety exposed on the surface of the exosome.

As used herein the term "lumen-engineered exosome" (e.g., Scaffold Y-engineered exosome) refers to an exosome with the membrane and/or the lumen of the exosome modified in its composition, so that the lumen of the engineered exosome is different from that of the exosome prior to the modification or that of a naturally occurring exosome. The engineering can be directly in the lumen and/or in the membrane of the exosome, so that the lumen of the exosome is changed. For example, the membrane is modified in its composition of a protein, a lipid, a small molecule, a carbohydrate, etc., so that the lumen of the exosome is modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some aspects, a lumen-engineered exosome comprises an exogenous protein (i.e., a protein that the exosome does not naturally express) or a fragment or variant thereof that can be exposed in the lumen of the exosome, or can be an anchoring point (attachment) for a moiety exposed on the inner layer of the exosome. In other aspects, a lumen-engineered exosome comprises a higher expression of a natural exosome protein (e.g., Scaffold X or Scaffold Y) or a fragment or variant thereof that can be exposed to the lumen of the exosome or can be an anchoring point (attachment) for a moiety exposed in the lumen of the exosome.

The term "modified," when used in the context of exosomes described herein, refers to an alteration or engineering of an EV, such that the modified EV is different from a naturally-occurring EV. In some aspects, a modified EV described herein comprises a membrane that differs in composition of a protein, a lipid, a small molecular, a carbohydrate, etc. compared to the membrane of a naturally-occurring EV (e.g., membrane comprises higher density or number of natural EV proteins and/or membrane comprises proteins that are not naturally found in EVs. In certain aspects, such modifications to the membrane changes the exterior surface of the EV. In certain aspects, such modifications to the membrane changes the lumen of the EV. An example of a modified EV (e.g., exosome) disclosed herein is an exoSTING.

As used herein, the term "exoSTING" refers to an EV (e.g., exosome) that has been modified to overexpress Scaffold X and loaded with a STING agonist. Examples of Scaffold X and STING agonists that can be used are provided elsewhere in the present disclosure.

As used herein, the term "scaffold moiety" refers to a molecule that can be used to anchor STING agonists disclosed herein or any other compound of interest (e.g., payload) to the EV either on the luminal surface or on the exterior surface of the EV. In certain aspects, a scaffold moiety comprises a synthetic molecule. In some aspects, a scaffold moiety comprises a non-polypeptide moiety. In other aspects, a scaffold moiety comprises a lipid, carbohydrate, or protein that naturally exists in the EV. In some aspects, a scaffold moiety comprises a lipid, carbohydrate, or protein that does not naturally exist in the exosome. In certain aspects, a scaffold moiety is Scaffold X. In some aspects, a scaffold moiety is Scaffold Y. In further aspects, a scaffold moiety comprises both Scaffold X and Scaffold Y. In some aspects, a scaffold moiety comprises Lamp-1, Lamp-2, CD13, CD86, Flotillin, Syntaxin-3, CD2, CD36, CD40, CD40L, CD41a, CD44, CD45, ICAM-1, Integrin alpha4, LiCAM, LFA-1, Mac-1 alpha and beta, Vti-1A and B, CD3 epsilon and zeta, CD9, CD18, CD37, CD53, CD63, CD81, CD82, CXCR4, FcR, GluR2/3, HLA-DM (MHC II), immunoglobulins, MHC-I or MHC-II components, TCR beta, tetraspanins, or combinations thereof.

As used herein, the term "Scaffold X" (also referred to herein as "Protein X") refers to exosome proteins that have recently been identified on the surface of exosomes. See, e.g., U.S. Pat. No. 10,195,290, which is incorporated herein by reference in its entirety. Non-limiting examples of Scaffold X proteins include: prostaglandin F2 receptor negative regulator ("the PTGFRN protein"); basigin ("the BSG protein"); immunoglobulin superfamily member 2 ("the IGSF2 protein"); immunoglobulin superfamily member 3 ("the IGSF3 protein"); immunoglobulin superfamily member 8 ("the IGSF8 protein"); integrin beta-1 ("the ITGB1 protein); integrin alpha-4 ("the ITGA4 protein"); 4F2 cell-surface antigen heavy chain ("the SLC3A2 protein"); and a class of ATP transporter proteins ("the ATP1A1 protein," "the ATP1A2 protein," "the ATP1A3 protein," "the ATP1A4 protein," "the ATP1B3 protein," "the ATP2B1 protein," "the ATP2B2 protein," "the ATP2B3 protein," "the ATP2B protein"). In some aspects, a Scaffold X protein can be a whole protein or a fragment thereof (e.g., functional fragment, e.g., the smallest fragment that is capable of anchoring another moiety on the exterior surface or on the luminal surface of the EV, e.g., exosome,). In some aspects, a Scaffold X can anchor a moiety (e.g., STING agonist) to the external surface or the luminal surface of the EVs, e.g., exosomes.

As used herein, the term "Scaffold Y" (also referred to herein as "Protein Y") refers to exosome proteins that were newly identified within the luminal surface of exosomes. See, e.g., International Appl. No. PCT/US2018/061679 (now published as WO/2019/099942) and WO/2020/101740), each of which is incorporated herein by reference in its entirety. Non-limiting examples of Scaffold Y proteins include: myristoylated alanine rich Protein Kinase C substrate ("the MARCKS protein"); myristoylated alanine rich Protein Kinase C substrate like 1 ("the MARCKSL1 protein"); and brain acid soluble protein 1 ("the BASP1 protein"). In some aspects, a Scaffold Y protein can be a whole protein or a fragment thereof (e.g., functional fragment, e.g., the smallest fragment that is capable of anchoring a moiety on the luminal surface of the EVs, e.g., exosomes,). In some aspects, a Scaffold Y can anchor a moiety (e.g., STING agonist) to the lumen of the EVs, e.g., exosomes.

As used herein, the term "fragment" of a protein (e.g., therapeutic protein, Scaffold X, or Scaffold Y) refers to an amino acid sequence of a protein that is shorter than the naturally-occurring sequence, N- and/or C-terminally deleted or any part of the protein deleted in comparison to the naturally occurring protein. As used herein, the term "functional fragment" refers to a protein fragment that retains protein function. Accordingly, in some aspects, a functional fragment of a Scaffold X protein retains the ability to anchor a moiety on the luminal surface and/or on the exterior surface of the EV. Similarly, in certain aspects, a functional fragment of a Scaffold Y protein retains the ability to anchor a moiety on the luminal surface of the EV. Whether a fragment is a functional fragment can be assessed by any art known methods to determine the protein content of EVs including Western Blots, FACS analysis and fusions of the fragments with autofluorescent proteins like, e.g., GFP. In certain aspects, a functional fragment of a Scaffold X protein retains at least about 50%, at least about 60%, at least about 70%, at least about 80%, at least about 90% or at least about 100% of the ability, e.g., an ability to anchor a moiety, of the naturally occurring Scaffold X protein. In some aspects, a functional fragment of a Scaffold Y protein retains at least about 50%, at least about 60%, at least about 70%, at least about 80%, at least about 90% or at least about 100% of the ability, e.g., an ability to anchor another molecule, of the naturally occurring Scaffold Y protein.

As used herein, the term "variant" of a molecule (e.g., functional molecule, antigen, Scaffold X and/or Scaffold Y) refers to a molecule that shares certain structural and functional identities with another molecule upon comparison by a method known in the art. For example, a variant of a protein can include a substitution, insertion, deletion, frameshift or rearrangement in another protein.

In some aspects, a variant of a Scaffold X comprises a variant having at least about 70% identity to the full-length, mature PTGFRN, BSG, IGSF2, IGSF3, IGSF8, ITGB1, ITGA4, SLC3A2, or ATP transporter proteins or a fragment (e.g., functional fragment) of the PTGFRN, BSG, IGSF2, IGSF3, IGSF8, ITGB1, ITGA4, SLC3A2, or ATP transporter proteins. In some aspects, variants or variants of fragments of PTGFRN share at least about 70%, at least about 80%, at least about 85%, at least about 90%, at least about 95%, at least about 96%, at least about 97%, at least about 98%, or at least about 99% sequence identity with PTGFRN according to SEQ ID NO: 1 or with a functional fragment thereof. In some aspects, the Scaffold X includes one or more mutations, e.g., conservative amino acid substitutions.

In some aspects, a variant of a Scaffold Y comprises a variant having at least 70% identity to MARCKS, MARCKSL1, BASP1 or a fragment of MARCKS, MARCKSL1, or BASP1. In some aspects variants or variants of fragments of BASP1 share at least about 70%, at least about 80%, at least about 85%, at least about 90%, at least about 95%, at least about 96%, at least about 97%, at least about 98%, or at least about 99% sequence identity with BASP1 according to SEQ ID NO: 49 or with a functional fragment thereof. In some aspects, the variant or variant of a fragment of Scaffold Y protein retains the ability to be specifically targeted to the lumen of EVs. In some aspects, the Scaffold Y includes one or more mutations, e.g., conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). B12seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity may be curated either automatically or manually.

As used herein, the terms "homologous" and "homology" are interchangeable with the terms "identity" and "identical."

The polynucleotide variants can contain alterations in the coding regions, non-coding regions, or both. In one aspect, the polynucleotide variants contain alterations which produce silent substitutions, additions, or deletions, but do not alter the properties or activities of the encoded polypeptide. In another aspect, nucleotide variants are produced by silent substitutions due to the degeneracy of the genetic code. In other aspects, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (J. Biol. Chem 268:22105-22111 (1993), incorporated herein by reference in its entirety) conducted extensive mutational analysis of human cytokine IL-la. They used random mutagenesis to generate over 3,500 individual IL-la mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some aspects, Scaffold X and/or Scaffold Y is modified at any convenient location.

As used herein the term "producer cell" refers to a cell used for generating an EV. A producer cell can be a cell cultured in vitro, or a cell in vivo. A producer cell includes, but not limited to, a cell known to be effective in generating EVs, e.g., exosomes, e.g., HEK293 cells, Chinese hamster ovary (CHO) cells, mesenchymal stem cells (MSCs), BJ human foreskin fibroblast cells, s9f cells, fHDF fibroblast cells, AGE.HN® neuronal precursor cells, CAP® amniocyte cells, adipose mesenchymal stem cells, and RPTEC/TERT1 cells. In certain aspects, a producer cell is an antigen-presenting cell. In some aspects, the producer cell is a bacterial cell. In some aspects, a producer cell is a dendritic cell, a B cell, a mast cell, a macrophage, a neutrophil, a Kupffer-Browicz cell, or a cell derived from any of these cells, or any combination thereof. In some aspects, the producer cell is not a bacterial cell. In other aspects, the producer cell is not an antigen-presenting cell.

As used herein the term "associated with" refers to encapsulation of a first moiety, e.g., a STING agonist, into a second moiety, e.g., extracellular vesicle, or to a covalent or non-covalent bond formed between a first moiety and a second moiety, e.g., a STING agonist and an extracellular vesicle, respectively, e.g., a scaffold moiety expressed in or on the extracellular vesicle and a STING agonist, e.g., Scaffold X (e.g., a PTGFRN protein), respectively, on the luminal surface of or on the external surface of the extracellular vesicle. In one aspect, the term "associated with" means a covalent, non-peptide bond or a non-covalent bond. For example, the amino acid cysteine comprises a thiol group that can form a disulfide bond or bridge with a thiol group on a second cysteine residue. Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity. In other aspects, the term "associated with" means that a state of encapsulation by a first moiety, e.g., extracellular vesicle of a second moiety, e.g., a STING agonist. In the encapsulation state, the first moiety and the second moiety can be linked to each other. In other aspects, the encapsulation means that the first moiety and the second moiety are not physically and/or chemically linked to each other.

As used herein the term "linked to" or "conjugated to" are used interchangeably and refer to a covalent or non-covalent bond formed between a first moiety and a second moiety, e.g., a STING agonist and an extracellular vesicle, respectively, e.g., a scaffold moiety expressed in or on the extracellular vesicle and a STING agonist, e.g., Scaffold X (e.g., a PTGFRN protein), respectively, on the luminal surface of or on the external surface of the extracellular vesicle.

The term "encapsulated", or grammatically different forms of the term (e.g., encapsulation, or encapsulating), refers to a status or process of having a first moiety (e.g., STING agonist) inside a second moiety (e.g., an EV, e.g., exosome) without chemically or physically linking the two moieties. In some aspects, the term "encapsulated" can be used interchangeably with "in the lumen of". Non-limiting examples of encapsulating a first moiety (e.g., STING agonist) into a second moiety (e.g., EVs, e.g., exosomes) are disclosed elsewhere herein.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some aspects, isolating or purifying as used herein is the process of removing, partially removing (e.g., a fraction) of the EVs from a sample containing producer cells. In some aspects, an isolated EV composition has no detectable undesired activity or, alternatively, the level or amount of the undesired activity is at or below an acceptable level or amount. In other aspects, an isolated EV composition has an amount and/or concentration of desired EVs at or above an acceptable amount and/or concentration. In other aspects, the isolated EV composition is enriched as compared to the starting material (e.g., producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some aspects, isolated EV preparations are substantially free of residual biological products. In some aspects, the isolated EV preparations are 100% free, 99% free, 98% free, 97% free, 96% free, 95% free, 94% free, 93% free, 92% free, 91% free, or 90% free of any contaminating biological matter. Residual biological products can include abiotic materials (including chemicals) or unwanted nucleic acids, proteins, lipids, or metabolites. Substantially free of residual biological products can also mean that the EV composition contains no detectable producer cells and that only EVs are detectable.

As used herein, the term "agonist" refers to a molecule that binds to a receptor and activates the receptor to produce a biological response. Receptors can be activated by either an endogenous or an exogenous agonist. Non-limiting examples of endogenous agonist include hormones, neurotransmitters, and cyclic dinucleotides. Non-limiting examples of exogenous agonist include drugs, small molecules, and cyclic dinucleotides. The agonist can be a full, partial, or inverse agonist.

As used herein, the term "antagonist" refers to a molecule that blocks or dampens an agonist mediated response rather than provoking a biological response itself upon bind to a receptor. Many antagonists achieve their potency by competing with endogenous ligands or substrates at structurally defined binding sites on the receptors. Non-limiting examples of antagonists include alpha blockers, betablocker, and calcium channel blockers. The antagonist can be a competitive, non-competitive, or uncompetitive antagonist.

The term “free STING agonist” as used herein means a STING agonist not associated with an extracellular vesicle, but otherwise identical to the STING agonist associated with the extracellular vesicle. Especially when compared to an extracellular vesicle associated with a STING agonist, the free STING agonist is the same STING agonist associated with the extracellular vesicle. In some aspects, when a free STING agonist is compared to an extracellular vesicle comprising the STING agonist in its efficacy, toxicity, and/or any other characteristics, the amount of the free STING agonist compared to the STING agonist associated with the extracellular vesicle is the same as the amount of the STING agonist associated with the EV.

As used herein, the term “ligand” refers to a molecule that binds to a receptor and modulates the receptor to produce a biological response. Modulation can be activation, deactivation, blocking, or damping of the biological response mediated by the receptor. Receptors can be modulated by either an endogenous or an exogenous ligand. Non-limiting examples of endogenous ligands include antibodies and peptides. Non-limiting examples of exogenous agonist include drugs, small molecules, and cyclic dinucleotides. The ligand can be a full, partial, or inverse ligand.

As used herein, the term “antibody” encompasses an immunoglobulin whether natural or partly or wholly synthetically produced, and fragments thereof. The term also covers any protein having a binding domain that is homologous to an immunoglobulin binding domain. “Antibody” further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, $(scFv)_2$, Fab, Fab', and $F(ab')_2$, $F(ab1)_2$, Fv, dAb, and Fd fragments, diabodies, and antibody-related polypeptides. Antibody includes bispecific antibodies and multispecific antibodies so long as they exhibit the desired biological activity or function.

As used herein the term “therapeutically effective amount” is the amount of reagent or pharmaceutical compound that is sufficient to a produce a desired therapeutic effect, pharmacologic and/or physiologic effect on a subject in need thereof. A therapeutically effective amount can be a “prophylactically effective amount” as prophylaxis can be considered therapy.

As used herein, the term “pharmaceutical composition” refers to one or more of the compounds described herein, such as, e.g., an EV mixed or intermingled with, or suspended in one or more other chemical components, such as pharmaceutically-acceptable carriers and excipients. One purpose of a pharmaceutical composition is to facilitate administration of preparations of EVs to a subject. The term “excipient” or “carrier” refers to an inert substance added to a pharmaceutical composition to further facilitate administration of a compound. The term “pharmaceutically-acceptable carrier” or “pharmaceutically-acceptable excipient” and grammatical variations thereof, encompasses any of the agents approved by a regulatory agency of the US Federal government or listed in the US Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term “payload” refers to a therapeutic agent that acts on a target (e.g., a target cell) that is contacted with the EV. Payloads that can be introduced into an EV and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, and siRNA), amino acids (e.g., amino acids comprising a detectable moiety or a toxin or that disrupt translation), polypeptides (e.g., enzymes), lipids, carbohydrates, and small molecules (e.g., small molecule drugs and toxins). In some aspects, a payload comprises an exogenous biologically active molecule (e.g., those disclosed herein).

As used herein, the term “biologically active molecule” refers to an agent that has activity in a biological system (e.g., a cell or a human subject), including, but not limited to a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof can be natural, synthetic or humanized, a peptide hormone, a receptor, a signaling molecule or other protein; a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g., a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which can be modified or unmodified; an amino acid or analogue thereof, which can be modified or unmodified; a non-peptide (e.g., steroid) hormone; a proteoglycan; a lipid; or a carbohydrate. In some aspects, antisense oligonucleotides include a phosphorodiamidate Morpholino oligomer (PMO) or a peptide-conjugated phosphorodiamidate morpholino oligomer (PPMO). In certain aspects, a biologically active molecule comprises a therapeutic molecule (e.g., an antigen, e.g., a glioma antigen). In some aspects, a biologically active molecule comprises a targeting moiety (e.g., an antibody or an antigen-binding fragment thereof), an adjuvant, an immune modulator, or any combination thereof. In some aspects, the biologically active molecule comprises a macromolecule (e.g., a protein, an antibody, an enzyme, a peptide, DNA, RNA, or any combination thereof). In some aspects, the biologically active molecule comprises a small molecule (e.g., an antisense oligomer (ASO), an siRNA, STING, a pharmaceutical drug, or any combination thereof). In some aspects, the biologically active molecules are exogenous to the exosome, i.e., not naturally found in the exosome.

As used herein, the term “therapeutic molecule” refers to any molecule that can treat and/or prevent a disease or disorder (e.g., neuroimmunological disorder, e.g., brain tumor, e.g., glioma) in a subject (e.g., human subject).

The terms “administration,” “administering” and variants thereof refer to introducing a composition, such as an EV, or agent into a subject and includes concurrent and sequential introduction of a composition or agent. The introduction of a composition or agent into a subject is by any suitable route, including intratumorally, orally, pulmonarily, intranasally, parenterally (intravenously, intra-arterially, intramuscularly, intraperitoneally, or subcutaneously), rectally, intralymphatically, intrathecally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

The term "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also include prophylaxis or prevention of a disease or condition or its symptoms thereof. In one aspect, the term "treating" or "treatment" means inducing an immune response in a subject against an antigen.

The term "prevent" or "preventing," as used herein, refers to decreasing or reducing the occurrence or severity of a particular outcome. In some aspects, preventing an outcome is achieved through prophylactic treatment.

As used herein, the term "modulate," "modulating", "modify," and/or "modulator" generally refers to the ability to alter, by increase or decrease, e.g., directly or indirectly promoting/stimulating/up-regulating or interfering with/inhibiting/down-regulating a specific concentration, level, expression, function or behavior, such as, e.g., to act as an antagonist or agonist. In some instances a modulator can increase and/or decrease a certain concentration, level, activity or function relative to a control, or relative to the average level of activity that would generally be expected or relative to a control level of activity.

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like).

The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some aspects, the subject is a mammal, and in other aspects the subject is a human.

As used herein, the term "substantially free" means that the sample comprising EVs comprise less than 10% of macromolecules by mass/volume (m/v) percentage concentration. Some fractions may contain less than 0.001%, less than 0.01%, less than 0.05%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, or less than 10% (m/v) of macromolecules.

As used herein, the term "macromolecule" means nucleic acids, exogenous proteins, lipids, carbohydrates, metabolites, or a combination thereof.

As used herein, the term "insubstantial," "reduced," or "negligible" refers to the presence, level, or amount of an inflammation response in a subject after administration of the sample comprising EVs encapsulating a STING agonist relative to the baseline inflammation response in the subject or compared to the subject inflammation response to the administration of a free STING agonist. For example, a negligible or insubstantial presence, level or amount of systemic inflammation may be less than 0.001%, less than 0.01%, less than 0.1%, less than 0.2%, less than 0.3%, less than 0.4%, less than 0.5%, less than 0.6%, less than 0.7%, less than 0.8%, less than 0.9%, less than 1%, less than 2%, less than 3%, less than 4%, less than 5%, less than 6%, less than 7%, less than 8%, less than 9%, less than 10%, less than 12%, less than 15%, less than 17%, less than 20%, or less than 25% of systemic inflammation as relative to the baseline inflammation in the subject or compared to the subject immune response to the administration of a free STING agonist. A level or amount of a systemic inflammation may be less than 0.1-fold, less than 0.5-fold, less than 0.5-fold, less than 1-fold, less than 1.5-fold, less than 2-fold relative to the baseline or compared to the inflammation response to the administration of a free STING agonist.

The term "antisense oligonucleotide" (ASO) refers to an oligomer or polymer of nucleosides, such as naturally-occurring nucleosides or modified forms thereof, that are covalently linked to each other through internucleotide linkages. The ASO useful for the disclosure includes at least one non-naturally occurring nucleoside. An ASO is at least partially complementary to a target nucleic acid, such that the ASO hybridizes to the target nucleic acid sequence.

The term "nucleic acids" or "nucleotides" is intended to encompass plural nucleic acids. In some aspects, the term "nucleic acids" or "nucleotides" refers to a target sequence, e.g., pre-mRNAs, mRNAs, or DNAs in vivo or in vitro. When the term refers to the nucleic acids or nucleotides in a target sequence, the nucleic acids or nucleotides can be naturally occurring sequences within a cell. In other aspects, "nucleic acids" or "nucleotides" refer to a sequence in the ASOs of the disclosure. When the term refers to a sequence in the ASOs, the nucleic acids or nucleotides can be non-naturally occurring, i.e., chemically synthesized, enzymatically produced, recombinantly produced, or any combination thereof. In some aspects, the nucleic acids or nucleotides in the ASOs are produced synthetically or recombinantly, but are not a naturally occurring sequence or a fragment thereof In some aspects, the nucleic acids or nucleotides in the ASOs are not naturally occurring because they contain at least one nucleoside analog that is not naturally occurring in nature.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogs" herein. Herein, a single nucleotide can be referred to as a monomer or unit. In certain aspects, the term "nucleotide analogs" refers to nucleotides having modified sugar moieties. Non-limiting examples of the nucleotides having modified sugar moieties (e.g., LNA) are disclosed elsewhere herein. In other aspects, the term "nucleotide analogs" refers to nucleotides having modified nucleobase moieties. The nucleotides having modified nucleobase moieties include, but are not limited to, 5-methyl-cytosine, isocytosine, pseudoisocytosine, 5-bromouracil, 5-propynyluracil, 6-aminopurine, 2-aminopurine, inosine, diaminopurine, and 2-chloro-6-aminopurine. In some aspects, the terms "nucleotide", "unit" and "monomer" are used interchangeably. It will be recognized that when referring to a sequence of nucleotides or monomers, what is referred to is the sequence of bases, such as A, T, G, C or U, and analogs thereof.

The term "nucleoside" as used herein is used to refer to a glycoside comprising a sugar moiety and a base moiety, and can therefore be used when referring to the nucleotide units, which are covalently linked by the internucleotide linkages between the nucleotides of the ASO. In the field of biotechnology, the term "nucleotide" is often used to refer to a nucleic acid monomer or unit. In the context of an ASO, the term "nucleotide" can refer to the base alone, i.e., a nucleobase sequence comprising cytosine (DNA and RNA), guanine (DNA and RNA), adenine (DNA and RNA), thymine (DNA) and uracil (RNA), in which the presence of the sugar backbone and internucleotide linkages are implicit. Likewise, particularly in the case of oligonucleotides where one or more of the internucleotide linkage groups are modified, the term "nucleotide" can refer to a "nucleoside." For example the term "nucleotide" can be used, even when specifying the presence or nature of the linkages between the nucleosides.

The term "nucleotide length" as used herein means the total number of the nucleotides (monomers) in a given sequence. The term "nucleotide length" is therefore used herein interchangeably with "nucleotide number."

As one of ordinary skill in the art would recognize, the 5' terminal nucleotide of an oligonucleotide does not comprise a 5' internucleotide linkage group, although it can comprise a 5' terminal group.

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates. In some aspects, the asymmetric center can be an asymmetric carbon atom. The term "asymmetric carbon atom" means a carbon atom with four different substituents. According to the Cahn-Ingold-Prelog Convention an asymmetric carbon atom can be of the "R" or "S" configuration.

As used herein, the term "bicyclic sugar" refers to a modified sugar moiety comprising a 4 to 7 membered ring comprising a bridge connecting two atoms of the 4 to 7 membered ring to form a second ring, resulting in a bicyclic structure. In some aspects, the bridge connects the C2' and C4' of the ribose sugar ring of a nucleoside (i.e., 2'-4' bridge), as observed in LNA nucleosides.

As used herein, a "coding region" or "coding sequence" is a portion of polynucleotide which consists of codons translatable into amino acids. Although a "stop codon" (TAG, TGA, or TAA) is typically not translated into an amino acid, it can be considered to be part of a coding region, but any flanking sequences, for example promoters, ribosome binding sites, transcriptional terminators, introns, untranslated regions ("UTRs"), and the like, are not part of a coding region. The boundaries of a coding region are typically determined by a start codon at the 5' terminus, encoding the amino terminus of the resultant polypeptide, and a translation stop codon at the 3' terminus, encoding the carboxyl terminus of the resulting polypeptide.

The term "non-coding region" as used herein means a nucleotide sequence that is not a coding region. Examples of non-coding regions include, but are not limited to, promoters, ribosome binding sites, transcriptional terminators, introns, untranslated regions ("UTRs"), non-coding exons and the like. Some of the exons can be wholly or part of the 5' untranslated region (5' UTR) or the 3' untranslated region (3' UTR) of each transcript. The untranslated regions are important for efficient translation of the transcript and for controlling the rate of translation and half-life of the transcript.

The term "region" when used in the context of a nucleotide sequence refers to a section of that sequence. For example, the phrase "region within a nucleotide sequence" or "region within the complement of a nucleotide sequence" refers to a sequence shorter than the nucleotide sequence, but longer than at least 10 nucleotides located within the particular nucleotide sequence or the complement of the nucleotides sequence, respectively. The term "sub-sequence" or "subsequence" can also refer to a region of a nucleotide sequence.

The term "downstream," when referring to a nucleotide sequence, means that a nucleic acid or a nucleotide sequence is located 3' to a reference nucleotide sequence. In certain aspects, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence.

As used herein, the term "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites, UTRs, and stem-loop structures. If a coding region is intended for expression in a eukaryotic cell, a polyadenylation signal and transcription termination sequence will usually be located 3' to the coding sequence.

The term "transcript" as used herein can refer to a primary transcript that is synthesized by transcription of DNA and becomes a messenger RNA (mRNA) after processing, i.e., a precursor messenger RNA (pre-mRNA), and the processed mRNA itself. The term "transcript" can be interchangeably used with "pre-mRNA" and "mRNA." After DNA strands are transcribed to primary transcripts, the newly synthesized primary transcripts are modified in several ways to be converted to their mature, functional forms to produce different proteins and RNAs, such as mRNA, tRNA, rRNA, lncRNA, miRNA and others. Thus, the term "transcript" can include exons, introns, 5' UTRs, and 3' UTRs.

The term "expression" as used herein refers to a process by which a polynucleotide produces a gene product, for example, a RNA or a polypeptide. It includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

In determining the degree of "complementarity" between the ASOs of the disclosure (or regions thereof) and the target region of the nucleic acid which encodes the target gene, e.g., mammalian STAT6 or CEBP/b (e.g., the STAT6 gene or the CEBP/b gene), such as those disclosed herein, the degree of "complementarity" (also, "homology" or "identity") is expressed as the percentage identity (or percentage homology) between the sequence of the ASO (or region thereof) and the sequence of the target region (or the reverse complement of the target region) that best aligns therewith. The percentage is calculated by counting the number of aligned bases that are identical between the two sequences, dividing by the total number of contiguous monomers in the ASO, and multiplying by 100. In such a comparison, if gaps exist, it is preferable that such gaps are merely mismatches rather than areas where the number of monomers within the gap differs between the ASO of the disclosure and the target region.

The term "complement" as used herein indicates a sequence that is complementary to a reference sequence. It is well known that complementarity is the base principle of DNA replication and transcription as it is a property shared between two DNA or RNA sequences, such that when they are aligned antiparallel to each other, the nucleotide bases at each position in the sequences will be complementary, much like looking in the mirror and seeing the reverse of things. Therefore, for example, the complement of a sequence of 5'" ATGC"3' can be written as 3'"TACG"5' or 5'" GCAT"3'. The terms "reverse complement", "reverse complementary", and "reverse complementarity" as used herein are interchangeable with the terms "complement", "complementary", and "complementarity." In some aspects, the term "complementary" refers to 100% match or complementarity (i.e., fully complementary) to a contiguous nucleic acid sequence within a target transcript, e.g., the STAT6 transcript or the CEBP/b transcript. In some aspects, the term "complementary" refers to at least about 80%, at least about 85%, at least about 90%, at least about 91%, at least about 92%, at least about 93%, at least about 94%, at least about 95%, at least about 96%, at least about 97%, at least about 98%, or at least about 99% match or complementarity to a contiguous nucleic acid sequence within a target transcript, e.g., a STAT6 transcript or a CEBP/b transcript.

The terms "corresponding to" and "corresponds to," when referencing two separate nucleic acid or nucleotide sequences can be used to clarify regions of the sequences that correspond or are similar to each other based on homology and/or functionality, although the nucleotides of the specific sequences can be numbered differently. For example, different isoforms of a gene transcript can have similar or conserved portions of nucleotide sequences whose numbering can differ in the respective isoforms based on alternative splicing and/or other modifications. In addition, it is recognized that different numbering systems can be employed when characterizing a nucleic acid or nucleotide sequence (e.g., a gene transcript and whether to begin numbering the sequence from the translation start codon or to include the 5'UTR). Further, it is recognized that the nucleic acid or nucleotide sequence of different variants of a gene or gene transcript can vary. As used herein, however, the regions of the variants that share nucleic acid or nucleotide sequence homology and/or functionality are deemed to "correspond" to one another. For example, a nucleotide sequence of a STAT6 transcript corresponding to nucleotides X to Y of SEQ ID NO: Z ("reference sequence") refers to a STAT6 transcript sequence (e.g., STAT6 pre-mRNA or mRNA) that has an identical sequence or a similar sequence to nucleotides X to Y of SEQ ID NO: Z, wherein X is the start site and Y is the end site. A person of ordinary skill in the art can identify the corresponding X and Y residues in the STAT6 transcript sequence by aligning the STAT6 transcript sequence with SEQ ID NO: Z.

The terms "corresponding nucleotide analog" and "corresponding nucleotide" are intended to indicate that the nucleobase in the nucleotide analog and the naturally occurring nucleotide have the same pairing, or hybridizing, ability. For example, when the 2-deoxyribose unit of the nucleotide is linked to an adenine, the "corresponding nucleotide analog" contains a pentose unit (different from 2-deoxyribose) linked to an adenine.

The annotation of ASO chemistry is as follows Beta-D-oxy LNA nucleotides are designated by OxyB where B designates a nucleotide base such as thymine (T), uridine (U), cytosine (C), 5-methylcytosine (MC), adenine (A) or guanine (G), and thus include OxyA, OxyT, OxyMC, OxyC and OxyG. DNA nucleotides are designated by DNAb, where the lower case b designates a nucleotide base such as thymine (T), uridine (U), cytosine (C), 5-methylcytosine (Mc), adenine (A) or guanine (G), and thus include DNAa, DNAt, DNA and DNAg. The letter M before C or c indicates 5-methylcytosine. The letter "s" indicates a phosphorothioate internucleotide linkage.

The term "ASO Number" or "ASO No." as used herein refers to a unique number given to a nucleotide sequence having the detailed chemical structure of the components, e.g., nucleosides (e.g., DNA), nucleoside analogs (e.g., beta-D-oxy-LNA), nucleobase (e.g., A, T, G, C, U, or MC), and backbone structure (e.g., phosphorothioate or phosphorodiester).

"Potency" is normally expressed as an $IC_{50}$ or $EC_{50}$ value, in μM, nM or pM unless otherwise stated. Potency can also be expressed in terms of percent inhibition. $IC_{50}$ is the median inhibitory concentration of a therapeutic molecule. $EC_{50}$ is the median effective concentration of a therapeutic molecule relative to a vehicle or control (e.g., saline). In functional assays, $IC_{50}$ is the concentration of a therapeutic molecule that reduces a biological response, e.g., transcription of mRNA or protein expression, by 50% of the biological response that is achieved by the therapeutic molecule. In functional assays, $EC_{50}$ is the concentration of a therapeutic molecule that produces 50% of the biological response, e.g., transcription of mRNA or protein expression. $IC_{50}$ or $EC_{50}$ can be calculated by any number of means known in the art.

As used herein, the term "inhibiting," e.g., the expression of STAT6 gene transcript and/or STAT6 protein refers to the ASO reducing the expression of the STAT6 gene transcript and/or STAT6 protein in a cell or a tissue. In some aspects, the term "inhibiting" refers to complete inhibition (100% inhibition or non-detectable level) of STAT6 gene transcript or STAT6 protein. In other aspects, the term "inhibiting" refers to at least 5%, at least 10%, at least 15%, at least 20%, at least 25%, at least 30%, at least 35%, at least 40%, at least 45%, at least 50%, at least 60%, at least 70%, at least 80%, at least 90%, at least 95% or at least 99% inhibition of STAT6 gene transcript and/or STAT6 protein expression in a cell or a tissue.

The term "naturally occurring variant thereof" refers to variants of, e.g., the STAT6 or CEBP/b polypeptide sequence or STAT6 or CEBP/b nucleic acid sequence (e.g., transcript) which exist naturally within the defined taxonomic group, such as mammalian, such as mouse, monkey, and human. Typically, when referring to "naturally occurring variants" of a polynucleotide the term also can encompass any allelic variant of the protein-encoding genomic DNA. For example, STAT6 is encoded by genomic DNA is found at Chromosomal position 1q44 at 247,416,156-247, 449,108 (i.e., nucleotides 247,416,156-247,449,108 of GenBank Accession No. NC_000001.11) by chromosomal translocation or duplication, and the RNA, such as mRNA derived therefrom. “Naturally occurring variants” can also include variants derived from alternative splicing of the mRNA. When referenced to a specific polypeptide sequence, e.g., the term also includes naturally occurring forms of the protein, which can therefore be processed, e.g., by co- or post-translational modifications, such as signal peptide cleavage, proteolytic cleavage, glycosylation, etc.

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8,9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

II. Methods of Treating Neuroimmunological Disorder

Provided herein are methods of treating a neuroimmunological disorder in a subject in need thereof. The method comprises administering to the subject a therapeutically effective amount of the compositions disclosed herein, wherein the composition is capable of up-regulating a STING-mediated immune response in the subject, thereby enhancing the subject’s immune response against the neuroimmunological disorder. In some aspects, the composition is administered intratumorally or intrathecally to the subject.

As used herein, the term “neuroimmunological disorder” refers to diseases and disorders of either the central or peripheral nervous system. The nervous system represents a privileged immune environment that generally dampens inflammatory responses in the brain spinal cord and nerves. This relative low immunoresponsiveness (anergy) is not only a function of the blood brain barrier but also a feature of the resident myeloid cells of the nervous system (e.g., microglia, meningeal macrophages, perivascular macrophages, and choroid plexus macrophages). These cells generally display immunosuppressive phenotypes and are known to become further “immunosilenced” or anergic in the setting of certain pathologies such as cancer or chronic infections. Accordingly, in some aspects, a neuroimmunological disorder can result from an inability of a subject’s immune system to mount an effective immune response against the disorder. In other aspects, a neuroimmunological disorder can result from an aberrant or excessive immune response within the nervous system.

In some aspects, a neuroimmunological disorder that can be treated with the present disclosure comprises a brain tumor or chronic infectious meningitis. In certain aspects, a neuroimmunological disorder is a brain tumor. In some aspects, a neuroimmunological disorder is a chronic infectious meningitis. In certain aspects, a chronic infectious meningitis can be associated with tuberculosis, Lyme disease, fungi, or combinations thereof. In some aspects, a neuroimmunological disorder is associated with neoplastic or infectious lesions within the nervous system compartment.

Also provided herein are methods of preventing metastasis of a brain tumor in a subject. The method comprises administering to the subject a therapeutically effective amount of the compositions disclosed herein, wherein the composition is capable of preventing a brain tumor at one location in the subject from promoting the growth of one or more tumors at another location in the subject. In some aspects, the composition is administered intratumorally or intrathecally in a first tumor in one location, and the composition administered in a first tumor prevents metastasis of one or more tumors at a second location.

In some aspects, administering an EV, e.g., exosome, disclosed herein inhibits and/or reduces growth of a brain tumor in a subject. In some aspects, the growth of a brain tumor (e.g., tumor volume or weight) is reduced by at least about 5%, at least about 10%, at least about 20%, at least about 30%, at least about 40%, at least about 50%, at least about 60%, at least about 70%, at least about 80%, at least about 90%, or about 100% compared to a reference (e.g., tumor volume in a corresponding subject after administration of free STING agonist or an EV, e.g., exosome, without the STING agonist).

As used herein, the term “brain tumor” refers to an abnormal growth of cells within the brain (e.g., within the meninges). Brain tumors can be categorized as primary or secondary brain tumor. “Primary brain tumor” refers to brain tumors that originate within the brain. “Secondary brain tumor” refers to brain tumors that are the result of cancer cells originating at primary sites outside the brain that have metastasized (i.e., spread) to the brain. Unless specified otherwise, the term brain tumor can refer to both primary and secondary brain tumors.

In some aspects, a brain tumor that can be treated with the present disclosure comprises an acoustic neuroma, choroid plexus carcinoma, craniopharyngioma, embryonal tumor, glioma, medulloblastoma, meningioma, pediatric brain tumor, pineoblastoma, pituitary tumor, or combinations thereof.

In certain aspects, a brain tumor that can be treated with the present disclosure comprises a glioma. As used herein, the term “glioma” refers to a type of tumor that starts in the glial cells of the brain or the spine. In some aspects, a glioma can be classified by specific type of cells with which they share histological features. Accordingly, a glioma that can be treated with EVs (e.g., exosomes) disclosed herein can be classified as an ependymoma (ependymal cells), astrocytoma (astrocytes), oligodendroglioma (oligodendrocytes), brainstem glioma (e.g., diffuse intrinsic pontine glioma), optic nerve glioma, mixed glioma, oligoastrocytoma, or any combination thereof. In certain aspects, an astrocytoma comprises glioblastoma multiforme (GBM).

Gliomas disclosed herein can be further categorized according to their grade, which is determined by pathologic evaluation of the tumor. In some aspects, the neuropathological evaluation and diagnostics of brain tumor specimens is performed according to WHO Classification of Tumours of the Central Nervous System. In some aspects, a glioma that can be treated with the present disclosure comprises a low-grade glioma. A “low-grade glioma” [WHO grade II] are well-differentiated (not anaplastic) and tend to exhibit benign tendencies and portend a better prognosis for the patient. However, in some aspects, low-grade gliomas can have a uniform rate of recurrence and increase in grade over time, so should be classified as malignant. In some aspects, a glioma that can be treated comprises a high grade glioma. A “high-grade glioma” [WHO grades III-IV]gliomas are undifferentiated or anaplastic and are malignant and carry a worse prognosis. Of numerous grading systems in use, the most common is the World Health Organization (WHO) grading system for astrocytoma, under which tumors are graded from I (least advanced disease—best prognosis) to IV (most advanced disease-worst prognosis). Non-limiting examples of high-grade gliomas include anaplastic astrocytomas and glioblastoma multiforme.

In some aspects, an EV (e.g., exosome) disclosed herein can be used to treat a glioma grade I, grade II, grade III, grade IV, or combinations thereof, as determined under the WHO grading system. In certain aspects, an EV (e.g., exosome) disclosed herein can be used to treat any type of gliomas.

In some aspects, the glioma treatable by the present methods is a diffuse intrinsic pontine glioma (DIPG), a type of brainstem glioma. Diffuse intrinsic pontine glioma primarily affects children, usually between the ages of 5 and 7. The median survival time with DIPG is under 12 months. Surgery to attempt tumor removal is usually not possible or advisable for DIPG. By their very nature, these tumors invade diffusely throughout the brain stem, growing between normal nerve cells.

In other aspects, the glioma treatable by the present methods is an IDH1 and IDH2-mutated glioma. Patients with glioma carrying mutations in either IDH1 or IDH2 have a relatively favorable survival, compared with patients with glioma with wild-type IDH1/2 genes. In WHO grade III glioma, IDH1/2-mutated glioma have a median prognosis of ~3.5 years, whereas IDH1/2 wild-type glioma perform poor with a median overall survival of 1.5 years. In glioblastoma, the difference is larger.

In some aspects, a neuroimmunological disorder that can be treated with the present disclosure comprises a neoplastic meningitis. As used herein, "neoplastic meningitis" refers to a tumor which has spread from the original tumor site into the dural and leptomeninges, which are thin tissue membranes covering the brain and spinal cord. In some aspects, connective tissue nerve sheaths that extend from the meninges onto and into nerves can also become involved. Neoplastic meningitis is also known as carcinomatous meningitis, leptomeningeal carcinoma, leptomeningeal carcinomatosis, leptomeningeal metastasis, leptomeningeal disease (LMD), leptomeningeal cancer, meningeal carcinomatosis, and meningeal metastasis. In certain aspects, a neoplastic meningitis is caused by leukemia. In some aspects, a neoplastic meningitis is caused by melanoma, breast, lung, gastrointestinal cancer, or combinations thereof. In certain aspects, a neoplastic meningitis is caused by a glioma.

In some aspects, a method for treating a neuroimmunological disorder (e.g., brain tumor) disclosed herein can comprise administering an EV, e.g., exosome, comprising a STING agonist (e.g., encapsulated or expressed on the luminal or exterior surface). In certain aspects, the EV (e.g., exosome) disclosed herein can be used in combination with one or more additional therapeutic agents (e.g., immuno-oncology agents), such that multiple elements of the immune pathway can be targeted. Non-limiting of such combinations include: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking Tregs or other immune suppressing cells (e.g., myeloid-derived suppressor cells); a therapy that stimulates positive immune regulation, e.g., with agonists that stimulate the CD-137, OX-40, and/or CD40 or GITR pathway and/or stimulate T cell effector function; a therapy that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); a therapy that inhibits a metabolic enzyme such as indoleamine dioxygenase (IDO), dioxygenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immuno repressive cytokines.

In some aspects, an immuno-oncology agent that can be used in combination with EVs, e.g., exosomes, disclosed herein comprises an immune checkpoint inhibitor (i.e., blocks signaling through the particular immune checkpoint pathway). Non-limiting examples of immune checkpoint inhibitors that can be used in the present methods comprise a CTLA-4 antagonist (e.g., anti-CTLA-4 antibody), PD-1 antagonist (e.g., anti-PD-1 antibody, anti-PD-L1 antibody), TIM-3 antagonist (e.g., anti-TIM-3 antibody), or combinations thereof.

In some aspects, an immuno-oncology agent comprises an immune checkpoint activator (i.e., promotes signaling through the particular immune checkpoint pathway). In certain aspects, immune checkpoint activator comprises OX40 agonist (e.g., anti-OX40 antibody), LAG-3 agonist (e.g. anti-LAG-3 antibody), 4-1BB (CD137) agonist (e.g., anti-CD137 antibody), GITR agonist (e.g., anti-GITR antibody), or any combination thereof.

In some aspects, EVs, e.g., exosomes, disclosed herein can also be used in combination with one or more additional immunomodulating agents. Such agents can include, for example, chemotherapy drugs, small molecule drugs, or antibodies that stimulate the immune response to a given cancer. In some aspects, the methods described herein are used in combination with a standard of care treatment (e.g., surgery, radiation, and chemotherapy).

In some aspects, a combination of an EV, e.g., exosome, disclosed herein and a second agent discussed herein (e.g., immune checkpoint inhibitor) can be administered concurrently as a single composition in a pharmaceutically acceptable carrier. In other aspects, a combination of an EV, e.g., exosome, and a second agent discussed herein (e.g., immune checkpoint inhibitor) can be administered concurrently as separate compositions. In further aspects, a combination of an EV, e.g., exosome, and a second agent discussed herein (e.g., immune checkpoint inhibitor) can be administered sequentially. In some aspects, an EV, e.g., exosome, is administered prior to the administration of a second agent (e.g., immune checkpoint inhibitor).

In some aspects, the EVs (e.g., exosomes) disclosed herein are administered to a subject via intra-cisterna magna administration. In some aspects, the EVs (e.g., exosomes) disclosed herein are administered to a subject via intracerebroventricular administration. In some aspects, the EVs (e.g., exosomes) disclosed herein are administered to a subject via intracranial administration. In some aspects, intracranial administration comprises administering the composition intracranially into any normal or lesioned part of the brain. In some aspects, intracranial administration comprises administering the composition intracranially via the nasal cavity. In some aspects, intracranial administration comprises administering the composition intracranially via the inner ear.

In some aspects, EVs (e.g., exosomes) disclosed herein are administered to a subject via intrathecal administration.

In some aspects, the EVs are administered via an injection into the spinal canal, or into the subarachnoid space so that it reaches the cerebrospinal fluid (CSF).

In some aspects, the EVs (e.g., exosomes) are administered by intrathecal administration, followed by application of a mechanical convective force to the torso. See, e.g., Verma et al., Alzheimer's Dement. 12:e12030 (2020); which is incorporated by reference herein in its entirety). As such, certain aspects of the present disclosure are directed to methods of administering an EV, e.g., an exosome, to a subject in need thereof, comprising administering the EV, e.g., exosome, to the subject by intrathecal injection, followed by applying a mechanical convective force to the torso of the subject. In some aspects, the mechanical convective force is achieved using a high frequency chest wall or lumbothoracic oscillating respiratory clearance device (e.g., a Smart Vest or Smart Wrap, ELECTROMED INC, New Prague, MN, USA). In some aspects, the mechanical convective force, e.g., the oscillating vest, facilitates spread of the intrathecally dosed EVs, e.g., exosomes, further down the nerve thus allowing for better EV, e.g., exosome, delivery to nerves.

In some aspects, the intra- and trans-compartmental biodistribution of exosomes can be manipulated by exogenous extracorporeal forces acting upon a subject after compartmental delivery of exosomes. This includes the application of mechanical convection, for example by way of applying percussion, vibration, shaking, or massaging of a body compartment or the entire body. Following intrathecal dosing for example, the application of chest wall vibrations by several means including an oscillating mechanical jacket can spread the biodistribution of the EVs, e.g., exosomes along the neuraxis or along cranial and spinal nerves, which can be helpful in the treatment of nerve disorders by drug carrying exosomes.

In some aspects, the application of external mechanical convective forces via an oscillating jacket or other similar means can be used to remove EVs, e.g., exosomes, and other material from the cerebrospinal fluid of the intrathecal space and out to the peripheral circulation. This aspect can help remove endogenous toxic exosomes and other deleterious macromolecules such as beta-amyloid, tau, alpha-synuclein, TDP43, neurofilament and excessive cerebrospinal fluid from the intrathecal space to the periphery for elimination.

In some aspects, exosomes delivered via the intracebroventricular route can be made to translocate throughout the neuraxis by simultaneously incorporating a lumbar puncture and allowing for ventriculo-lumbar perfusion wherein additional fluid is infused into the ventricles after exosome dosing, while allowing the existing neuraxial column of CSF to exit is the lumbar puncture. Ventriculo-lumbar perfusion can allow ICV dosed EVs, e.g., exosomes, to spread along the entire neuraxis and completely cover the subarachnoid space in order to treat leptomeningeal cancer and other diseases.

In some aspects, the application of external extracorporeal focused ultrasound, thermal energy (heat) or cold may be used to manipulate the compartmental pharmacokinetics and drug release properties of exosomes engineered to be sensitive to these phenomena.

In some aspects, the intracompartmental behavior and biodistribution of exosomes engineered to contain paramagnetic material can be manipulated by the external application of magnets or a magnetic field.

Non-limiting examples of other routes of administration that can be used include intravenously, intratumorally, intranasally, periocularly, intraarterially, or combinations thereof.

In some aspects, EVs (e.g., exosomes) disclosed herein can be used to increase the number of NK and/or T cells within a brain tumor. In certain aspects, the number of NK and/or T cells within a brain tumor after the administration of an EV (e.g., exosome) disclosed herein is increased by at least about 5%, at least about 10%, at least about 20%, at least about 30%, at least about 40%, at least about 50%, at least about 60%, at least about 70%, at least about 80%, at least about 90%, at least about 100% or more, compared to a reference (e.g., number of tumor-specific NK and/or T cells within a brain tumor prior to the administration of an EV disclosed herein). In some aspects, the increase in the number of NK and/or T cells within a brain tumor is due to increased recruitment of the NK and/or T cells to the brain tumor. In certain aspects, the increase in the number of NK and/or T cells to the brain tumor can reduce the size of a brain tumor. In certain aspects, the increase in the number of NK and/or T cells to the brain tumor can reduce and/or prevent metastasis of the brain tumor. In some aspects, the NK and/or T cells are specific to the brain tumor.

In some aspects, EVs (e.g., exosome) disclosed herein can be used to increase antigen presentation in situ (e.g., more of the antigen presenting cells present brain tumor antigens to NK and/or T cells). In certain aspects, antigen presentation is increased by at least about 5%, at least about 10%, at least about 20%, at least about 30%, at least about 40%, at least about 50%, at least about 60%, at least about 70%, at least about 80%, at least about 90%, at least about 100% or more, compared to a reference (e.g., amount of antigen presentation within a brain tumor of a subject prior to the administration of an EV disclosed herein). In certain aspects, the increase in antigen presentation in situ can reduce the size of a brain tumor. In certain aspects, the increase in antigen presentation in situ can reduce and/or prevent metastasis of the brain tumor. In some aspects, the increase in antigen presentation in situ can reduce and/or prevent one or more symptoms associated with a neuroimmunological disorder.

In some aspects, EVs (e.g., exosomes) disclosed herein can be used to target the meningeal lymphatic immune system. The meningeal lymphatic system is a network of conventional lymphatic vessels and associated macrophages located parallel to major dural venous sinuses, dural coverings of cerebral arteries and nerve sheaths. This system is responsible for draining the cerebral spinal fluid (CSF), particulate matter and immune cells to specific peripheral lymph nodes that act as sentinel nodes for the nervous system. These lymph nodes include the submandibular, deep cervical and paraspinal nodes. In certain aspects, EVs (e.g., exosomes) disclosed herein can be used to target the macrophages lining the meningeal lymphatics or perivascular regions of the central nervous system. In some aspects, targeting such meningeal and/or perivascular macrophages allows for the regulation of an immune response (e.g., against a brain tumor antigen) within the meninges and the brain.

In some aspects, an EV (e.g., exosome) disclosed herein can re-activate macrophages (e.g., within the nervous system) and/or reverse nervous system anergy. In certain aspects, re-activating macrophages (e.g., within the nervous system) and/or reversing nervous system anergy can help treat a neuroimmunological disorder (e.g., by eradicating neoplastic or infectious lesions within the nervous system).

III. Compositions (Vesicles) with STING Agonist

The innate immune system recognizes pathogen associated molecular patterns (PAMPs) via pattern recognition receptors (PRRs) that induce an immune response. PRRs recognize a variety of pathogen molecules including single and double stranded RNA and DNA. PRRs such as retinoic acid-inducible gene-I (RIG-I)-like receptors (RLRs) and some toll-like receptors (TLRs) recognize RNA ligands. DNA ligands are recognized by cyclic GMP-AMP synthase (cGAS), AIM2 and other TLRs. The TLRs, RLRs, and AIM2 directly interact with other signal cascade adaptor proteins to activate transcription factors, while cGAS produces cGAMP, a cyclic dinucleotide molecule that activates the stimulator of interferon gene (STING) receptor. Both STING and the RLRs activate the adaptor kinase TBK1 which induces activation of transcription factors IRF3, and NF-κB, and result in the production of type I IFNs and pro-inflammatory cytokines.

Cyclic dinucleotides (CDNs) were first identified as bacterial signaling molecules characterized by two 3', 5' phosphodiester bonds, such as in the molecule c-di-GMP. While STING can be activated by bacterial CDNs, the innate immune response in mammalian cells is also mediated by the CDN signaling molecule cGAMP which is produced by cGAS. cGAMP is characterized by a mixed 2', 5' and 3', 5' phosphodiester linkage. Both bacterial and mammalian CDNs directly interact with STING to induce the pro-inflammatory signaling cascade that results in the production of type I IFNs, such as IFNα and IFN-β.

II.A. STING Agonists

STING agonists used in this disclosure can be cyclic dinucleotides (CDNs) or non-cyclic dinucleotide agonists. Cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAIMP), and any analogue thereof, are known to stimulate or enhance an immune or inflammation response in a patient. The CDNs may have 2'2', 2'3', 2'5', 3'3', or 3'5' bonds linking the cyclic dinucleotides, or any combination thereof.

Cyclic purine dinucleotides may be modified via standard organic chemistry techniques to produce analogues of purine dinucleotides. Suitable purine dinucleotides include, but are not limited to, adenine, guanine, inosine, hypoxanthine, xanthine, isoguanine, or any other appropriate purine dinucleotide known in the art. The cyclic dinucleotides may be modified analogues. Any suitable modification known in the art may be used, including, but not limited to, phosphorothioate, biphosphorothioate, fluorinate, and difluorinate modifications.

Non cyclic dinucleotide agonists may also be used, such as 5,6-Dimethylxanthenone-4-acetic acid (DMXAA), or any other non-cyclic dinucleotide agonist known in the art.

It is contemplated that any STING agonist may be used. Among the STING agonists are DMXAA, STING agonist-1, ML RR-S2 CDA, ML RR-S2c-di-GMP, ML-RR-S2 cGAMP, 2'3'-c-di-AM(PS)2, 2'3'-cGAMP, 2'3'-cGAMPdFHS, 3'3'-cGAMP, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 3'3'-cGAMP, c-di-AMP, 2'3'-c-di-AMP, 2'3'-c-di-AM(PS)2, c-di-GMP, 2'3'-c-di-GMP, c-di-IMP, c-di-UMP or any combination thereof. In a preferred aspect, the STING agonist is 3'3'-cAIMPdFSH, alternatively named 3-3 cAIMPdFSH. Additional STING agonists known in the art may also be used.

In other aspects, the STING agonist useful for the present disclosure comprises a compound having the following formula:

CL606

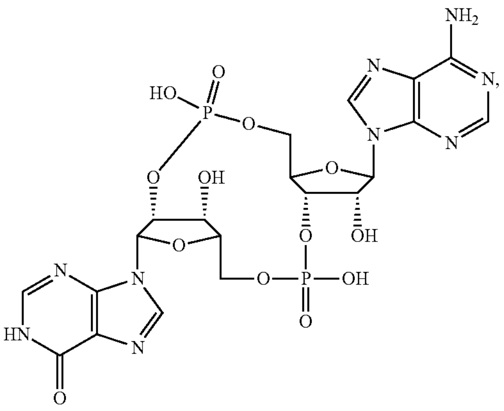

(3′,2′)c-AIMP

CL611

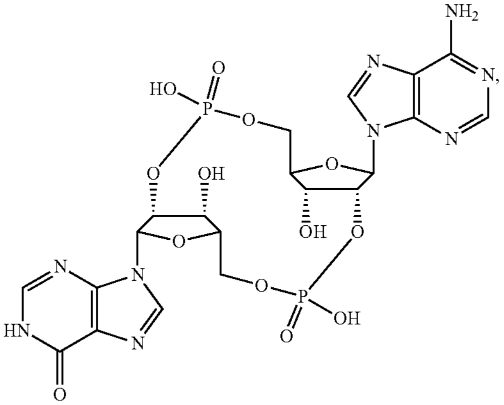

(2′,2′)c-AIMP

CL602

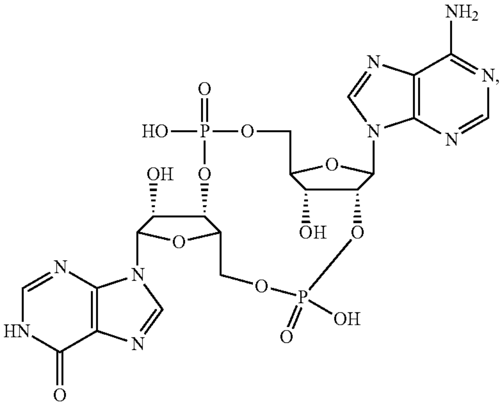

(2′,3′)c-AIMP

-continued
CL655
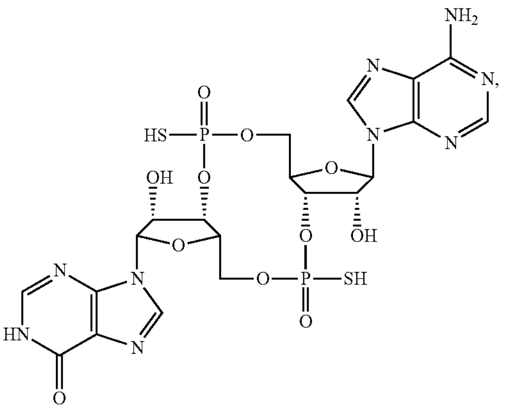
c-AIMP(S)
CL604
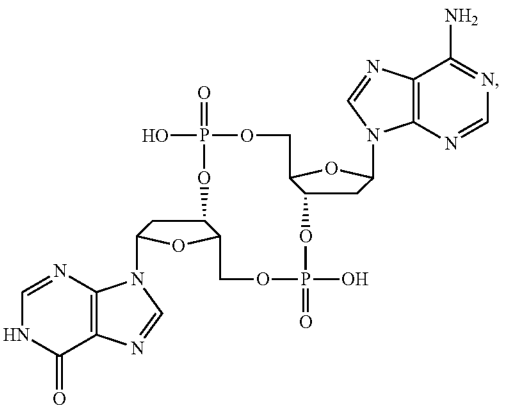
c-(dAMP-dIMP)
CL609
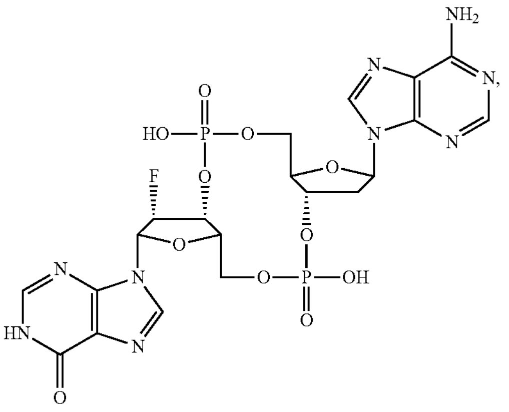
c-(dAMP-2′FdIMP)
-continued
CL614
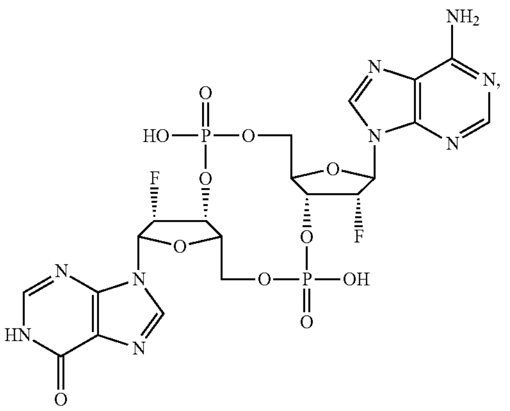
c-(2′FdAMP-2′FdIMP)
CL656
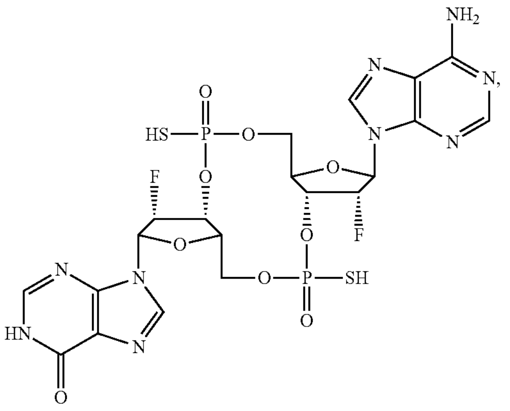
c-[2′Fdamp(S)-2′FdIMP(S)]
CL647
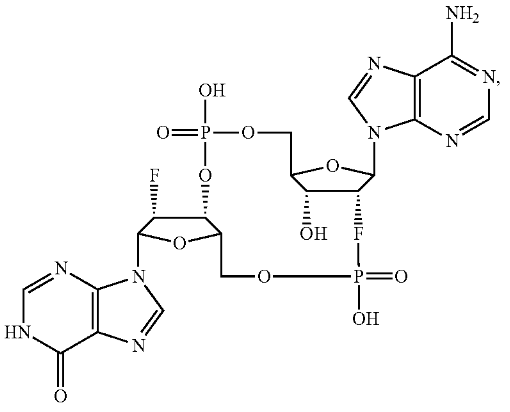
(2′,3′)c-(AMP-2′FdIMP)

-continued

CL626

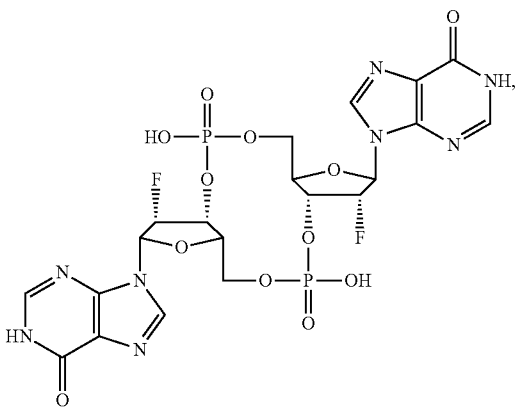

c-di(2′FdIMP)

CL629

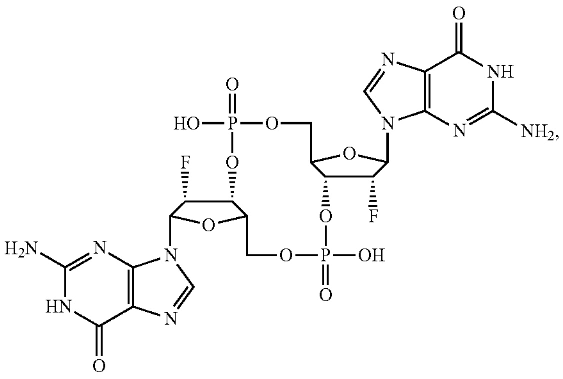

c-di(2′FdGMP)

CL603

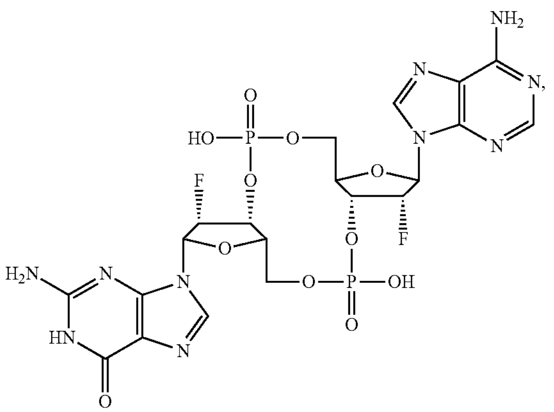

c-(2′FdGMP-2′FdAMP)

-continued

CL632

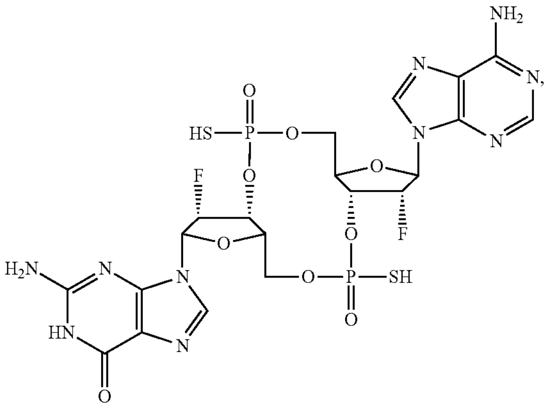

c-[2′FdGMP(S)-2′FdAMP(S)]

CL633

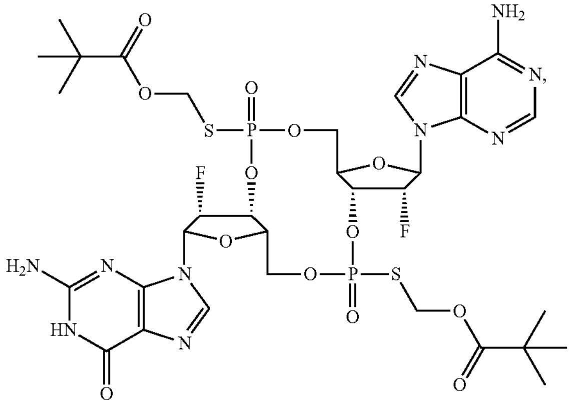

c-[2′FdGMP(S)-2′FdAMP(S)](POM)$_2$

CL659

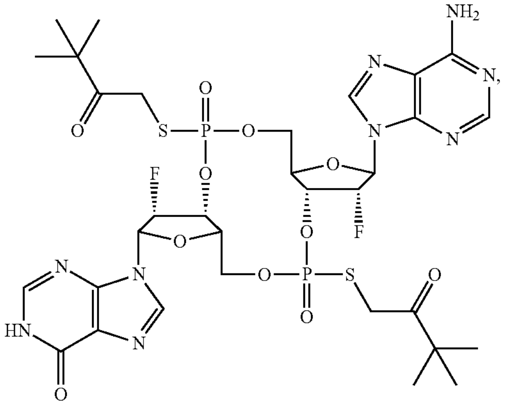

c-[2′FdAMP(S)-2′FdIMP(S)](POM)$_2$ or any pharmaceutically acceptable salts thereof. See WO 2016/096174, the content of which is incorporated herein by reference in its entirety.

In some aspects, the STING agonist useful for the present disclosure comprises a compound disclosed in WO 2014/093936, the content of which is incorporated herein by reference in its entirety.

In some aspects, the STING agonist useful for the present disclosure comprises a compound disclosed in WO 2014/189805, the content of which is incorporated herein by reference in its entirety. In some aspects, the STING agonist useful for the present disclosure comprises a compound disclosed in WO 2015/077354, the content of which is incorporated herein by reference in its entirety. See also Cell reports 11, 1018-1030 (2015). In some aspects, the STING agonist useful for the present disclosure comprises c-di-AMP. c-di-GMP. c-di-IMP. c-AMP-GMP. c-AMP-IMP, and c-GMP-IMP, described in WO 2013/185052 and Sci. Transl. Med. 283,283ra52 (2015), which are incorporated herein by reference in their entireties. In some aspects, the STING agonist useful for the present disclosure comprises a compound disclosed in WO 2014/189806, the content of which is incorporated herein by reference in its entirety. In some aspects, the STING agonist useful for the present disclosure comprises a compound disclosed in WO 2015/185565, the content of which is incorporated herein by reference in its entirety. In some aspects, the STING agonist useful for the present disclosure comprises a compound disclosed in WO 2014/179760, the content of which is incorporated herein by reference in its entirety. In some aspects, the STING agonist useful for the present disclosure comprises a compound disclosed in WO 2014/179335, the content of which is incorporated herein by reference in its entirety. In some aspects, the STING agonist useful for the present disclosure comprises a compound disclosed in WO 2015/017652, the content of which is incorporated herein by reference in its entirety. In some aspects, the STING agonist useful for the present disclosure comprises a compound disclosed in WO 2016/096577, the content of which is incorporated herein by reference in its entirety. In some aspects, the STING agonist useful for the present disclosure comprises a compound disclosed in WO 2016/120305, the content of which is incorporated herein by reference in its entirety. In some aspects, the STING agonist useful for the present disclosure comprises a compound disclosed in WO 2016/145102, the content of which is incorporated herein by reference in its entirety. In some aspects, the STING agonist useful for the present disclosure comprises a compound disclosed in WO 2017/027646, the content of which is incorporated herein by reference in its entirety.

In some aspects, the STING agonist useful for the present disclosure comprises a compound disclosed in WO 2017/075477, the content of which is incorporated herein by reference in its entirety. In some aspects, the STING agonist useful for the present disclosure comprises a compound disclosed in WO 2017/027645, the content of which is incorporated herein by reference in its entirety. In some aspects, the STING agonist useful for the present disclosure comprises a compound disclosed in WO 2018/100558, the content of which is incorporated herein by reference in its entirety. In some aspects, the STING agonist useful for the present disclosure comprises a compound disclosed in WO 2017/175147, the content of which is incorporated herein by reference in its entirety. In some aspects, the STING agonist useful for the present disclosure comprises a compound disclosed in WO 2017/175156, the content of which is incorporated herein by reference in its entirety.

In some aspects, the STING agonist useful for the present disclosure is CL606, CL611, CL602, CL655, CL604, CL609, CL614, CL656, CL647, CL626, CL629, CL603, CL632, CL633, CL659, or a pharmaceutically acceptable salt thereof. In some aspects, the STING agonist useful for the present disclosure is CL606 or a pharmaceutically acceptable salt thereof. In some aspects, the STING agonist useful for the present disclosure is CL611 or a pharmaceutically acceptable salt thereof. In some aspects, the STING agonist useful for the present disclosure is CL602 or a pharmaceutically acceptable salt thereof. In some aspects, the STING agonist useful for the present disclosure is CL655 or a pharmaceutically acceptable salt thereof. In some aspects, the STING agonist useful for the present disclosure is CL604 or a pharmaceutically acceptable salt thereof. In some aspects, the STING agonist useful for the present disclosure is CL609 or a pharmaceutically acceptable salt thereof. In some aspects, the STING agonist useful for the present disclosure is CL614 or a pharmaceutically acceptable salt thereof. In some aspects, the STING agonist useful for the present disclosure is CL656 or a pharmaceutically acceptable salt thereof. In some aspects, the STING agonist useful for the present disclosure is CL647 or a pharmaceutically acceptable salt thereof. In some aspects, the STING agonist useful for the present disclosure is CL626 or a pharmaceutically acceptable salt thereof. In some aspects, the STING agonist useful for the present disclosure is CL629 or a pharmaceutically acceptable salt thereof. In some aspects, the STING agonist useful for the present disclosure is CL603 or a pharmaceutically acceptable salt thereof. In some aspects, the STING agonist useful for the present disclosure is CL632 or a pharmaceutically acceptable salt thereof. In some aspects, the STING agonist useful for the present disclosure is CL633 or a pharmaceutically acceptable salt thereof. In some aspects, the STING agonist useful for the present disclosure is CL659 or a pharmaceutically acceptable salt thereof. See WO 2016/096174A1, which is incorporated herein by reference in its entirety.

In some aspects, the EV, e.g., exosome, comprises a cyclic dinucleotide STING agonist and/or a non-cyclic dinucleotide STING agonist. In some aspects, when several cyclic dinucleotide STING agonist are present on an EV, e.g., exosome, disclosed herein, such STING agonists can be the same or they can be different. In some aspects, when several non-cyclic dinucleotide STING agonist are present, such STING agonists can be the same or they can be different. In some aspects, an EV, e.g., exosome, composition of the present disclosure can comprise two or more populations of EVs, e.g., exosomes, wherein each population of EVs, e.g., exosomes, comprises a different STING agonist or combination thereof.

The STING agonists can also be modified to increase encapsulation of the agonist in an extracellular vesicle or EV (e.g., either unbound in the lumen). In some aspects, the STING agonists are linked to a scaffold moiety, e.g., Scaffold Y. In certain aspects, the modification allows better expression of the STING agonist on the exterior surface of the EV, e.g., exosome, (e.g., linked to a scaffold moiety disclosed herein, e.g., Scaffold X). This modification can include the addition of a lipid binding tag by treating the agonist with a chemical or enzyme, or by physically or chemically altering the polarity or charge of the STING agonist. The STING agonist may be modified by a single treatment, or by a combination of treatments, e.g., adding a lipid binding tag only, or adding a lipid binding tag and altering the polarity. The previous example is meant to be a non-limiting illustrative instance. It is contemplated that any combination of modifications may be practiced. The modification may increase encapsulation of the agonist in the EV by between 2-fold and 10,000 fold, between 10-fold and 1,000 fold, or between 100-fold and 500-fold compared to encapsulation of an unmodified agonist. The modification may increase encapsulation of the agonist in the EV by at least 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800- fold, 900-fold, 1000-fold, 2000-fold, 3000-fold, 4000-fold, 5000-fold, 6000-fold, 7000-fold, 8000-fold, 9000-fold, or 10,000-fold compared to encapsulation of an unmodified agonist.

In some aspects, STING agonists can be modified to allow for better expression of the agonists on the exterior surface of the EV, e.g., exosome, (e.g., linked to a scaffold moiety disclosed herein, e.g., Scaffold X). Any of the modifications described above can be used. The modification may increase encapsulation of the agonist in the EV, e.g., exosome, by about between 2-fold and 10,000 fold, about between 10-fold and 1,000 fold, or about between 100-fold and 500-fold compared to encapsulation of an unmodified agonist. The modification can increase expression of the agonist on the exterior surface of the EV, e.g., exosome, by at least about 2-fold, 5-fold, 10-fold, 20-fold, 30-fold, 40-fold, 50-fold, 60-fold, 70-fold, 80-fold, 90-fold, 100-fold, 200-fold, 300-fold, 400-fold, 500-fold, 600-fold, 700-fold, 800-fold, 900-fold, 1000-fold, 2000-fold, 3000-fold, 4000-fold, 5000-fold, 6000-fold, 7000-fold, 8000-fold, 9000-fold, or 10,000-fold compared to expression of an unmodified agonist.

The concentration of the STING agonist associated with the EV may be about 0.01 μM to 1000 μM. The concentration of the associated STING agonist may be between about 0.01-0.05 μM, 0.05-0.1 μM, 0.1-0.5 μM, 0.5-1 μM, 1-5 μM, 5-10 μM, 10-15 μM, 15-20 μM, 20-25 μM, 25-30 μM, 30-35 μM, 35-40 μM, 45-50 μM, 55-60 μM, 65-70 μM, 70-75 μM, 75-80 μM, 80-85 μM, 85-90 μM, 90-95 μM, 95-100 μM, 100-150 μM, 150-200 μM, 200-250 μM, 250-300 μM, 300-350 μM, 250-400 μM, 400-450 μM, 450-500 μM, 500-550 μM, 550-600 μM, 600-650 μM, 650-700 μM, 700-750 μM, 750-800 μM, 800-850 μM, 805-900 μM, 900-950 μM, or 950-1000 μM. The concentration of the associated STING agonist may be equal to or greater than about 0.01 μM, 0.1 μM, 0.5 μM, 1 μM, 5 μM, 10 μM, 15 μM, 20 μM, 25 μM, 30 μM, 35 μM, 40 μM, 45 μM, 50 μM, 55 μM, 60 μM, 65 μM, 70 μM, 75 μM, 80 μM, 85 μM, 90 μM, 95 μM, 100 μM, 150 μM, 200 μM, 250 μM, 300 μM, 350 μM, 400 μM, 450 μM, 500 μM, 550 μM, 600 μM, 650 μM, 700 μM, 750 μM, 800 μM, 850 μM, 900 μM, 950 μM, or 1000 μM.

III.B. Modified EVs Targeting the Nervous System

In some aspects, an EV, e.g., exosome, disclosed herein can be engineered to adjust its properties, e.g., biodistribution, e.g., via incorporation of immuno-affinity ligands or cognate receptor ligands. For example, EV, e.g., exosomes, disclosed herein can be engineered to direct them to a specific cellular type, e.g., Schwann cells, sensory neurons, motor neurons, or meningeal macrophages, or can be engineered to enhance their migration to a specific compartment, e.g., to the CNS in order to improve intrathecal compartment retention.

In some aspects, an EV, e.g., exosome, comprises (i) a STING agonist disclosed herein and (ii) a bio-distribution modifying agent or targeting moiety. In some aspects, the bio-distribution modifying agent or targeting moiety comprises a single-domain antigen-biding moiety, e.g., a VHH and/or a vNAR. As used here, the terms "bio-distribution modifying agent" and "targeting moiety" are used interchangeably and refer to an agent that can modify the distribution of extracellular vesicles (e.g., exosomes, nanovesicles) in vivo or in vitro (e.g., in a mixed culture of cells of different varieties). In some aspects, the targeting moiety alters the tropism of the EV (e.g., exosome), i.e., the target moiety is a "tropism moiety". As used herein, the term "tropism moiety" refers to a targeting moiety that when expressed on an EV (e.g., exosome) alters and/or enhances the natural movement of the EV. For example, in some aspects, a tropism moiety can promote the EV (e.g., exosome) to be taken up by a particular cell, tissue, or organ.

EVs, e.g., exosomes, exhibit preferential uptake in discrete cell types and tissues, and their tropism can be directed by adding proteins to their surface that interact with receptors on the surface of target cells. The tropism moiety can comprise a biological molecule, such as a protein, a peptide, a lipid, or a carbohydrate, or a synthetic molecule. For example, in some aspects the tropism moiety can comprise an affinity ligand, e.g., an antibody (such as an anti-CD19 nanobody, an anti-CD22 nanobody, an anti-CLEC9A nanobody, or an anti-CD3 nanobody), a VHH domain, a phage display peptide, a fibronectin domain, a camelid nanobody, and/or a vNAR. In some aspects, the tropism moiety can comprise, e.g., a synthetic polymer (e.g., PEG), a natural ligand/molecule (e.g., CD40L, albumin, CD47, CD24, CD55, CD59), and/or a recombinant protein (e.g., XTEN).

In some aspects, a tropism moiety can increase uptake of the EV, e.g., an exosome, by a cell. In some aspects, the tropism moiety that can increase uptake of the EV, e.g., an exosome, by a cell comprises a lymphocyte antigen 75 (also known as DEC205 or CD205), C-type lectin domain family 9 member A (CLEC9A), C-type lectin domain family 6 (CLEC6), C-type lectin domain family 4 member A (also known as DCIR or CLEC4A), Dendritic Cell-Specific Intercellular adhesion molecule-3-Grabbing Non-integrin (also known as DC-SIGN or CD209), lectin-type oxidized LDL receptor 1(LOX-1), macrophage receptor with collagenous structure (MARCO), C-type lectin domain family 12 member A (CLEC12A), C-type lectin domain family 10 member A (CLEC10A), DC-asialoglycoprotein receptor (DC-ASGPR), DC immunoreceptor 2 (DCIR2), Dectin-1, macrophage mannose receptor (MMR), BDCA-2 (CD303, CLEC4C), Dectin-2, BST-2 (CD317), Langerin, CD206, CD11b, CD11c, CD123, CD304, XCR1, AXL, SIGLEC 6, CD209, SIRPA, CX3CR1, GPR182, CD14, CD16, CD32, CD34, CD38, CD10, anti-CD3 antibody, or any combination thereof.

In some aspects, when tropism to the central nervous system is desired, an EV, e.g., exosome, of the present disclosure can comprise a tissue or cell-specific target ligand, which increases EV, e.g., exosome, tropism to a specific central nervous system tissue or cell. In some aspects, the cell is a glial cell. In some aspects, the glial cell is an oligodendrocyte, an astrocyte, an ependymal cell, a microglia cell, a Schwann cell, a satellite glial cell, an olfactory ensheathing cell, or a combination thereof. In some aspects, the cell is a neural stem cell. In some aspects, the cell-specific target ligand, which increases EV, e.g., exosome, tropism to a Schwann cells binds to a Schwann cell surface marker such as Myelin Basic Protein (MBP), Myelin Protein Zero (PO), P75NTR, NCAM, PMP22, or any combination thereof. In some aspects, the cell-specific tropism moiety comprises an antibody or an antigen-binding portion thereof, an aptamer, or an agonist or antagonist of a receptor expressed on the surface of the Schwann cell.

In principle, the EVs, e.g., exosomes of the present disclosure comprising at least one tropism moiety that can direct the EV, e.g., exosome, to a specific target cell or tissue (e.g., a cell in the CNS or a Schwann cell in peripheral nerves) can be administered using any suitable administration method known in the art (e.g., intravenous injection or infusion) since the presence of the tropism moiety will induce a tropism of the EVs, e.g., exosomes, towards the desired target cell or tissue.

In certain aspects, the tropism moiety is linked, e.g., chemically linked via a maleimide moiety, to a scaffold moiety, e.g., a Scaffold X protein or a fragment thereof, on the exterior surface of the EV, e.g., exosome. Tropism can be further improved by the attachment of an anti-phagocytic signal (e.g., CD47 and/or CD24), a half-life extension moiety (e.g., albumin or PEG), or any combination thereof to the external surface of an EV, e.g., exosome, of the present disclosure. In certain aspects, the anti-phagocytic signal or half-life extension moiety is linked, e.g., chemically linked via a maleimide moiety, to a scaffold moiety, e.g., a Scaffold X protein or a fragment thereof, on the exterior surface of the EV, e.g., exosome.

Pharmacokinetics, biodistribution, and in particular tropism and retention in the desired tissue or anatomical location can also be accomplished by selecting the appropriate administration route (e.g., intrathecal administration or intraocular administration to improve tropism to the central nervous system).

In some aspects, the EV, e.g., exosome, comprises at least two different tropism moieties. In some aspects, the EV, e.g., exosome, comprises three different tropism moieties. In some aspects, the EV, e.g., exosome, comprises four different tropism moieties. In some aspects, the EV, e.g., exosome, comprises five or more different tropism moieties. In some aspects, one or more of the tropism moieties increases uptake of the EV, e.g., exosome, by a cell. In some aspects, each tropism moiety is attached to a scaffold moiety, e.g., a Scaffold X protein or a fragment thereof. In some aspects, multiple tropism moieties can be attached to the same scaffold moiety, e.g., a Scaffold X protein or a fragment thereof. In some aspects, several tropism moieties can be attached in tandem to a scaffold moiety, e.g., a Scaffold X protein or a fragment thereof. In some aspects, a tropism moiety disclosed herein or a combination thereof is attached to a scaffold moiety, e.g., a Scaffold X protein or a fragment thereof, via a linker or spacer. In some aspects, a linker or spacer or a combination thereof is interposed between two tropism moieties disclosed herein.

Non-limiting examples of tropism moieties capable of directing EVs, e.g., exosomes, of the present disclosure to different nervous system cell types are disclosed below.

III.B.1. Tropism Moieties Targeting Schwann Cells

In some aspects, a tropism moiety can target a Schwann cell. In some aspects, the tropism moiety that directs an EV, e.g., exosome, disclosed herein to a Schwann cell targets, e.g., a transferrin receptor (TfR), apolipoprotein D (ApoD), Galectin 1 (LGALS1), Myelin proteolipid protein (PLP), Glypican 1, or Syndecan 3. In some aspects, the tropism moiety directing an EV, e.g., exosome, of the present disclosure to a Schwann cell is a transferrin, or a fragment, variant or derivative thereof.

In some aspects, a tropism moiety of the present disclosure targets a transferrin receptor (TfR). Transferrin receptors, e.g., TfR1 or TfR2, are carrier proteins for transferrin. Transferrin receptors import iron by internalizing the transferrin-ion complex through receptor-mediated endocytosis.

TfR1 (see, e.g., UniProt P02786 TFR1_Human) or transferrin receptor 1 (also known as cluster of differentiation 71 or CD71) is expressed on the endothelial cells of the blood-brain barrier (BBB). TfR1 is known to be expressed in a variety of cells such as red blood cells, monocytes, hepatocytes, intestinal cells, and erythroid cells, and is upregulated in rapidly dividing cells such as tumor cells (non small cell lung cancer, colon cancer, and leukemia) as well as in tissue affected by disorders such as acute respiratory distress syndrome (ARDS). TfR2 is primarily expressed in liver and erythroid cells, is found to a lesser extent in lung, spleen and muscle, and has a 45% identity and 66% similarity with TfR1. TfR1 is a transmembrane receptor that forms a homodimer of 760 residues with disulfide bonds and a molecular weight of 90 kDa. Affinity for transferrin varies between the two receptor types, with the affinity for TfR1 being at least 25-30 fold higher than that of TfR2.

Binding to TfR1 allows the transit of large molecules, e.g., antibodies, into the brain. Some TfR1-targeting antibodies have been shown to cross the blood-brain barrier, without interfering with the uptake of iron. Amongst those are the mouse anti rat-TfR antibody OX26 and the rat anti mouse-TfR antibody 8D3. The affinity of the antibody-TfR interaction is important to determine the success of transcytotic transport over endothelial cells of the BBB. Monovalent TfR interaction favors BBB transport due to altered intracellular sorting pathways. Avidity effects of bivalent interactions redirecting transport to the lysosome. Also, reducing TfR binding affinity directly promote dissociation from the TfR which increase brain parenchymal exposure of the TfR binding antibody. See, e.g., U.S. Pat. No. 8,821,943, which is herein incorporated by reference in its entirety. Accordingly, in some aspects, a tropism moiety of the present disclosure can comprise a ligand that can target TfR, e.g., target TfR1, such as transferrin, or an antibody or other binding molecule capable of specifically binding to TfR. In some aspects, the antibody targeting a transferrin receptor is a low affinity anti-transferring receptor antibody (see, e.g., US20190202936A1 which is herein incorporated by reference in its entirety).

In some aspects, the tropism moiety comprises all or a portion (e.g., a binding portion) of a ligand for a transferrin receptor, for example a human transferrin available in GenBank as Accession numbers NM001063, XM002793, XM039847, NM002343 or NM013900, among others, or a variant, fragment, or derivative thereof.

In some aspects, the tropism moiety comprises a transferrin-receptor-targeting moiety, i.e., a targeting moiety directed to a transferrin receptor. Suitable transferrin-receptor-targeting moieties include a transferrin or transferrin variant, such as, but not limited to, a serum transferrin, lacto transferrin (lactoferrin) ovotransferrin, or melanotransferrin. Transferrins are a family of nonheme iron-binding proteins found in vertebrates, including serum transferrins, lacto transferrins (lactoferrins), ovotransferrins, and melanotransferrins. Serum transferrin is a glycoprotein with a molecular weight of about 80 kDa, comprising a single polypeptide chain with two N-linked polysaccharide chains that are branched and terminate in multiple antennae, each with terminal sialic acid residues. There are two main domains, the N domain of about 330 amino acids, and the C domain of about 340 amino acids, each of which is divided into two subdomains, N1 and N2, and C1 and C2. Receptor binding of transferrin occurs through the C domain, regardless of glycosylation.

In some aspects, the tropism moiety is a serum transferrin or transferrin variant such as, but not limited to a hexasialo transferrin, a pentasialo transferrin, a tetrasialo transferrin, a trisialo transferrin, a disialo transferrin, a monosialo transferrin, or an asialo transferrin, or a carbohydrate-deficient transferrin (CDT) such as an asialo, monosialo or disialo transferrin, or a carbohydrate-free transferrin (CFT) such as an asialo transferrin. In some aspects, the tropism moiety is a transferrin variant having the N-terminal domain of transferrin, the C-terminal domain of transferrin, the glycosylation of native transferrin, reduced glycosylation as compared to native (wild-type) transferrin, no glycosylation, at least two N terminal lobes of transferrin, at least two C terminal lobes of transferrin, at least one mutation in the N domain, at least one mutation in the C domain, a mutation wherein the mutant has a weaker binding avidity for transferrin receptor than native transferrin, and/or a mutation wherein the mutant has a stronger binding avidity for transferrin receptor than native transferrin, or any combination of the foregoing.

In some aspects, the tropism moiety targeting a transferrin receptor comprises an anti-trasferrin receptor variable new antigen receptor (vNAR), e.g., a binding domain with a general motif structure (FW1-CDR1-FW2-3-CDR3-FW4). See, e.g., U.S. 2017-0348416, which is herein incorporated by reference in its entirety. vNARs are key component of the adaptive immune system of sharks. At only 11 kDa, these single-domain structures are the smallest IgG-like proteins in the animal kingdom and provide an excellent platform for molecular engineering and biologics drug discovery. vNAR attributes include high affinity for target, ease of expression, stability, solubility, multi-specificity, and increased potential for solid tissue penetration. See Ubah et al. Biochem. Soc. Trans. (2018) 46(6):1559-1565.

In some aspects, the tropism moiety comprises a vNAR domain capable of specifically binding to TfR1, wherein the vNAR domain comprises or consists essentially of a vNAR scaffold with any one CDR1 peptide in Table 1 of U.S. 2017-0348416 in combination with any one CDR3 peptide in Table 1 of U.S. 2017-0348416.

In some aspects, a tropism moiety of the present disclosure targets ApoD. Unlike other lipoproteins, which are mainly produced in the liver, apolipoprotein D is mainly produced in the brain, cerebellum, and peripheral nerves. ApoD is 169 amino acids long, including a secretion peptide signal of 20 amino acids. It contains two glycosylation sites (aspargines 45 and 78) and the molecular weight of the mature protein varies from 20 to 32 kDa. ApoD binds steroid hormones such as progesterone and pregnenolone with a relatively strong affinity, and to estrogen with a weaker affinity. Arachidonic acid (AA) is an ApoD ligand with a much better affinity than that of progesterone or pregnenolone. Other ApoD ligands include E-3-methyl-2-hexenoic acid, retinoic acid, sphingomyelin and sphingolipids. Accordingly, in some aspects, a tropism moiety of the present disclosure comprises a ligand that can target ApoD, e.g., an antibody or other binding molecule capable of specifically binding to ApoD.

In some aspects, a tropism moiety of the present disclosure targets Galectin 1. The galectin-1 protein is 135 amino acids in length. Accordingly, in some aspects, a tropism moiety of the present disclosure comprises a ligand that can target Galectin 1, e.g., an antibody or other binding molecule capable of specifically binding to Galectin 1.

In some aspects, a tropism moiety of the present disclosure targets PLP. PLP is the major myelin protein from the CNS. It plays an important role in the formation or maintenance of the multilamellar structure of myelin. The myelin sheath is a multi-layered membrane, unique to the nervous system that functions as an insulator to greatly increase the efficiency of axonal impulse conduction. PLP is a highly conserved hydrophobic protein of 276 to 280 amino acids which contains four transmembrane segments, two disulfide bonds and which covalently binds lipids (at least six palmitate groups in mammals). Accordingly, in some aspects, a tropism moiety of the present disclosure comprises a ligand that can target PLP, e.g., an antibody or other binding molecule capable of specifically binding to PLP.

In some aspects, a tropism moiety of the present disclosure targets Glypican 1. Accordingly, in some aspects, a tropism moiety of the present disclosure comprises a ligand that can target Glypican 1, e.g, an antibody or other binding molecule capable of specifically binding to Glypican 1. In some aspects, a tropism moiety of the present disclosure targets Syndecan 3. Accordingly, in some aspects, a tropism moiety of the present disclosure comprises a ligand that can target Syndecan 3, e.g., an antibody or other binding molecule capable of specifically binding to Syndecan 3.

III.B.2. Tropism Moieties Targeting Sensory Neurons

In some aspects, a tropism moiety disclosed herein can direct an EV, e.g, exosome, disclosed herein to a sensory neuron. In some aspects, the tropism moiety that directs an EV, e.g, exosome, disclosed herein to a sensory neuron targets a Trk receptor, e.g., TrkA, TrkB, TrkC, or a combination thereof.

Trk (tropomyosin receptor kinase) receptors are a family of tyrosine kinases that regulates synaptic strength and plasticity in the mammalian nervous system. The common ligands of Trk receptors are neurotrophins, a family of growth factors critical to the functioning of the nervous system. The binding of these molecules is highly specific. Each type of neurotrophin has different binding affinity toward its corresponding Trk receptor. Accordingly, in some aspects, the tropism moiety directing an EV, e.g, exosome, disclosed herein to a sensory neuron, comprises a neurotrophin.

Neurotrophins bind to Trk receptors as homodimers. Accordingly, in some aspects, the tropism moiety comprises at least two neurotrophins disclosed herein, e.g., in tandem. In some aspects, the tropism moiety comprises at least two neurotrophins disclosed herein, e.g., in tandem, that are attached to a scaffold protein, for example, Protein X, via a linker. In some aspects, the linker connecting the scaffold protein, e.g., Protein X, to the neurotrophin (e.g., a neurotrophin homodimer) has a length of at least 10 amino acids. In some aspects, the linker connecting the scaffold protein, e.g., Protein X, to the neurotrophin (e.g., a neurotrophin homodimer) has a length of at least about 25 amino acids, about 30 amino acids, about 35 amino acids, about 40 amino acids, about 45 amino acids, or about 50 amino acids.

In some aspects, the neurotrophin is a neurotrophin precursor, i.e., a proneurotrophin, which is later cleaved to produce a mature protein.

Nerve growth factor (NGF) is the first identified and probably the best characterized member of the neurotrophin family. It has prominent effects on developing sensory and sympathetic neurons of the peripheral nervous system. Brain-derived neurotrophic factor (BDNF) has neurotrophic activities similar to NGF, and is expressed mainly in the CNS and has been detected in the heart, lung, skeletal muscle and sciatic nerve in the periphery (Leibrock, J. et al., Nature, 341:149-152 (1989)). Neurotrophin-3 (NT-3) is the third member of the NGF family and is expressed predominantly in a subset of pyramidal and granular neurons of the hippocampus, and has been detected in the cerebellum, cerebral cortex and peripheral tissues such as liver and skeletal muscles (Ernfors, P. et al., Neuron 1: 983-996 (1990)). Neurotrophin-4 (also called NT-415) is the most variable member of the neurotrophin family. Neurotrophin-6 (NT-5) was found in teleost fish and binds to p75 receptor.

In some aspects, the neurotrophin targeting TrkB comprises, e.g., NT-4 or BDNF, or a fragment, variant, or derivative thereof. In some aspects, the neurotrophin targeting TrkA comprises, e.g., NGF or a fragment, variant, or derivative thereof. In some aspects, the neurotrophin targeting TrkC comprises, e.g., NT-3 or a fragment, variant, or derivative thereof.

In some aspects, the tropism moiety comprises brain derived neurotrophic factor (BDNF). In some aspects, the BDNF is a variant of native BDNF, such as a two amino acid carboxyl-truncated variant. In some aspects, the tropism moiety comprises the full-length 119 amino acid sequence of BDNF (HSDPARRGELSVCDSISEWVTAADKKTAVDMSGGTVTVLEKVPVSKGQLKQYFYETK CNFMGYTKEGCRGIDKRHWNSQCRTTQSYVRALTMDSKKRIGWRFIRIDTSCVCTLTIK RGR; SEQ ID NO: 369). In some aspects, a one amino-acid carboxy-truncated variant of BDNF is utilized (amino acids 1-118 of SEQ ID NO: 369).

In some aspects, the tropism moiety comprises a carboxy-truncated variant of the native BDNF, e.g., a variant in which 1, 2, 3, 4, 5, 6, 7, 8, 9, 10, or more than 10 amino acids are absent from the carboxy-terminus of the BDNF. BDNF variants include the complete 119 amino acid BDNF, the 117 or 118 amino acid variant with a truncated carboxyl terminus, variants with a truncated amino terminus, or variants with up to about 20%, about 30, or about 40% change in amino acid composition, as long as the protein variant still binds to the TrkB receptor with high affinity.

In some aspects, the tropism moiety comprises a two amino-acid carboxy-truncated variant of BDNF (amino acids 1-117 of SEQ ID NO: 369). In some aspects, the tropism moiety comprises a three amino-acid carboxy-truncated variant of BDNF (amino acids 1-116 of SEQ ID NO: 369). In some aspects, the tropism moiety comprises a four amino-acid carboxy-truncated variant of BDNF (amino acids 1-115 of SEQ ID NO: 369). In some aspects, the tropism moiety comprises a five amino-acid carboxy-truncated variant of BDNF (amino acids 1-114 of SEQ ID NO: 369). In some aspects, the tropism moiety comprises a BDNF that is at least about 60%, at least about 65%, at least about 70%, at least about 75%, at least about 80%, at least about 85%, at least about 90%, at least about 95%, at least about 99%, or about 100% identical with the sequence of SEQ ID NO: 369, or a truncated version thereof, e.g., the 117 or 118 amino acid variant with a one- or two-amino acid truncated carboxyl terminus, or variants with a truncated amino terminus. See, e.g., U.S. Pat. No. 8,053,569 B2, which is herein incorporated by reference in its entirety.

In some aspects, the tropism moiety comprises nerve growth factor (NGF). In some aspects, the NGF is a variant of native NGF, such as a truncated variant. In some aspects, the tropism moiety comprises the 26-kDa beta subunit of protein, the only component of the 7S NGF complex that is biologically active. In some aspects, the tropism moiety comprises the full-length 120 amino acid sequence of beta NGF (SSSHPIFHRGEFSVCDSVSVWVGDKTTATDIKGKEVMVLGEVNINNSVFKQYFFETKCR DPNPVDSGCRGIDSKHWNSYCTTTHTFVKALTMDGKQAAWRFIRIDTACVCVLSRKAV RRA; SEQ ID NO: 370). In some aspects, the tropism moiety comprises a carboxy-truncated variant of the native NGF, e.g., a variant in which 1, 2, 3, 4, 5, 6, 7, 8, 9, 10, or more than 10 amino acids are absent from the carboxy-terminus of NGF. NGF variants include the complete 120 amino acid NGF, the shorter amino acid variants with a truncated carboxyl terminus, variants with a truncated amino terminus, or variants with up to about 20%, about 30%, or about 40% change in amino acid composition, as long as the tropism moiety still binds to the TrkB receptor with high affinity. In some aspects, the tropism moiety comprises an NGF that is at least about 60%, at least about 65%, at least about 70%, at least about 75%, at least about 80%, at least about 85%, at least about 90%, at least about 95%, at least about 99%, or about 100% identical with the sequence of SEQ ID NO: 370, or a truncated version thereof.

In some aspects, the tropism moiety comprises neurotrophin-3 (NT-3). In some aspects, the NT-3 is a variant of native NT-3, such as a truncated variant. In some aspects, the tropism moiety comprises the full-length 119 amino acid sequence of NT-3 (YAEHKSHRGEYSVCDSESLWVTDKSSAIDIRGHQVTVLGEIKTGNSPVKQYFYETRCKE ARPVKNGCRGIDDKHWNSQCKTSQTYVRALTSENNKLVGWRWIRIDTSCVCALSRKIG RT; SEQ ID NO: 371). In some aspects, the tropism moiety comprises a carboxy-truncated variant of the native NT-3, e.g., a variant in which 1, 2, 3, 4, 5, 6, 7, 8, 9, 10, or more than 10 amino acids are absent from the carboxy-terminus of NT-3. NT-3 variants include the complete 119 amino acid NT-3, the shorter amino acid variants with a truncated carboxyl terminus, variants with a truncated amino terminus, or variants with up to about 20%, about 30%, or about 40% change in amino acid composition, as long as the tropism moiety still binds to the TrkC receptor with high affinity. In some aspects, the tropism moiety comprises an NT-3 that is at least about 60%, at least about 65%, at least about 70%, at least about 75%, at least about 80%, at least about 85%, at least about 90%, at least about 95%, at least about 99%, or about 100% identical with the sequence of SEQ ID NO: 371, or a truncated version thereof.

In some aspects, the tropism moiety comprises neurotrophin-4 (NT-4). In some aspects, the NT-4 is a variant of native NT-4, such as a truncated variant. In some aspects, the tropism moiety comprises the full-length 130 amino acid sequence of NT-4 (GVSETAPASRRGELAVCDAVSGWVTDRRTAVDLRGREVEVLGEVPAAGGSPLRQYFFE TRCKADNAEEGGPGAGGGGCRGVDRRHWVSECKAKQSYVRALTADAQGRVGWRWIR IDTACVCTLLSRTGRA; SEQ ID NO: 372). In some aspects, the tropism moiety comprises a carboxy-truncated variant of the native NT-4, e.g., a variant in which 1, 2, 3, 4, 5, 6, 7, 8, 9, 10, or more than 10 amino acids are absent from the carboxy-terminus of NT-4. NT-4 variants include the complete 130 amino acid NT-4, the shorter amino acid variants with a truncated carboxyl terminus, variants with a truncated amino terminus, or variants with up to about 20%, about 30%, or about 40% change in amino acid composition, as long as the tropism moiety still binds to the TrkB receptor with high affinity. In some aspects, the tropism moiety comprises an NT-4 that is at least about 60%, at least about 65%, at least about 70%, at least about 75%, at least about 80%, at least about 85%, at least about 90%, at least about 95%, at least about 99%, or about 100% identical with the sequence of SEQ ID NO: 372, or a truncated version thereof.

Structure/function relationship studies of NGF and NGF-related recombinant molecules demonstrated that mutations in NGF region 25-36, along with other β-hairpin loop and non-loop regions, significantly influenced NGF/NGF-receptor interactions (Ibanez et al., EMBO J., 10, 2105-2110, (1991)). Small peptides derived from this region have been demonstrated to mimic NGF in binding to Mock receptor and affecting biological responses (LeSauteur et al. J. Biol. Chem. 270, 6564-6569, 1995). Dimers of cyclized peptides corresponding to j-loop regions of NGF were found to act as partial NGF agonists in that they had both survival-promoting and NGF-inhibiting activity while monomer and linear peptides were inactive (Longo et al., J. Neurosci. Res., 48, 1-17, 1997). Accordingly, in some aspects, a tropism moiety of the present disclosure comprises such peptides.

Cyclic peptides have also been designed and synthesized to mimic the 3-loop regions of NGF, BDNF, NT3 and NT-4/5. Certain monomers, dimers or polymers of these cyclic peptides can have a three-dimensional structure, which binds to neurotrophin receptors under physiological conditions. All of these structural analogs of neurotrophins that bind to nerve cell surface receptors and are internalized can serve as the binding agent B of the compound according to the present disclosure to deliver the conjugated therapeutic moiety™ to the nervous system. Accordingly, in some aspects, a tropism moiety of the present disclosure comprises such cyclic peptides or combinations thereof.

In some aspects, antibodies against nerve cell surface receptors that are capable of binding to the receptors and being internalized can also serve as tropism moieties binding to a Trk receptor. For example, monoclonal antibody (MAb) 5C3 is specific for the NGF docking site of the human p140 TrkA receptor, with no cross-reactivity with human TrkB receptor. MAb 5C3 and its Fab mimic the effects of NGF in vitro, and image human Trk-A positive tumors in vivo (Kramer et al., Eur. J. Cancer, 33, 2090-2091, (1997)). Molecular cloning, recombination, mutagenesis and modeling studies of Mab 5C3 variable region indicated that three or less of its complementarity determining regions (CDRs) are relevant for binding to TrkA. Assays with recombinant CDRs and CDR-like synthetic polypeptides demonstrated that they had agonistic bioactivities similar to intact Mab 5C3. Monoclonal antibody MC192 against p75 receptor has also been demonstrated to have neurotrophic effects. Therefore, these antibodies and their functionally equivalent fragments can also serve as tropism moieties of the present disclosure.

In some aspects, peptidomimetics that are synthesized by incorporating unnatural amino acids or other organic molecules can also serve tropism moieties of the present disclosure.

Other neurotrophins are known in the art. Accordingly, in some aspects, the target moiety comprises a neurotrophin selected from the group consisting of fibroblast growth factor (FGF)-2 and other FGFs, erythropoietin (EPO), hepatocyte growth factor (HGF), epidermal growth factor (EGF), transforming growth factor (TGF)-a, TGF-(3, vascular endothelial growth factor (VEGF), interleukin-1 receptor antagonist (IL- lra), ciliary neurotrophic factor (CNTF), glial-derived neurotrophic factor (GDNF), neurturin, platelet-derived growth factor (PDGF), heregulin, neuregulin, artemin, persephin, interleukins, granulocyte-colony stimulating factor (CSF), granulocyte-macrophage-CSF, netrins, cardiotrophin-1, hedgehogs, leukemia inhibitory factor (LIF), midlcine, pleiotrophin, bone morphogenetic proteins (BMPs), netrins, saposins, semaphorins, and stem cell factor (SCF).

In some aspects, the tropism moiety directing an EV, e.g, exosome, disclosed herein to a sensory neuron, comprises a varicella zoster virus (VZV) peptide.

III.B.3. Tropism Moieties Targeting Motor Neurons

In some aspects, a tropism moiety disclosed herein can direct an EV, e.g, exosome, disclosed herein to a motor neuron. In some aspects, the tropism moiety that directs an EV, e.g, exosome, disclosed herein to a motor comprises a Rabies Virus Glycoprotein (RVG) peptide, a Targeted Axonal Import (TAxI) peptide, a P75R peptide, or a Tet-C peptide.

In some aspects, the tropism moiety comprises a Rabies Virus Glycoprotein (RVG) peptide. See, e.g., U.S. Pat. App. Publ. 2014-00294727, which is herein incorporated by reference in its entirety. In some aspects, the RVG peptide comprises amino acid residues 173-202 of the RVG (YTIWMPENPRPGTPCDIFTNSRGKRASNG; SEQ ID NO: 373) or a variant, fragment, or derivative thereof. In some aspects, the tropism moiety is a fragment of SEQ ID NO: 373. Such a fragment of SEQ ID NO: 373 can have, for example, 1, 2, 3, 4, 5, 6, 7, 8, 9, or 10 amino acids deleted from the N-terminal and/or the C-terminal of SEQ ID NO: 373. A functional fragment derived from SEQ ID NO: 373 can be identified by sequentially deleting N- and/or C-terminal amino acids from SEQ ID NO: 373 and assessing the function of the resulting peptide fragment, such as function of the peptide fragment to bind acetylcholine receptor and/or ability to transmit through the blood brain barrier. In some aspects, the tropism moiety comprises a fragment of SEQ ID NO: 373 28, 27, 26, 25, 24, 23, 22, 21, 20, 19, 18, 17, 16 or 15 amino acids in length. In some aspects, the tropism moiety comprises a fragment of SEQ ID NO: 373 less than 15 peptides in length.

A "variant" of a RGV peptide, for example SEQ ID NO: 373, is meant to refer to a molecule substantially similar in structure and function, i.e., where the function is the ability to pass or transit through the BBB, to either the entire molecule, or to a fragment thereof. A variant of an RVG peptide can contain a mutation or modification that differs from a reference amino acid in SEQ ID NO: 373. In some aspects, a variant of SEQ ID NO: 373 is a fragment of SEQ ID NO: 373 as disclosed herein. In some aspects, an RVG variant can be a different isoform of SEQ ID NO: 373 or can comprise different isomer amino acids. Variants can be naturally-occurring, synthetic, recombinant, or chemically modified polynucleotides or polypeptides isolated or generated using methods well known in the art. RVG variants can include conservative or non-conservative amino acid changes. See, e.g., U.S. Pat. No. 9,757,470, which is herein incorporated by reference in its entirety.

In some aspects, the tropism moiety comprises a Targeted Axonal Import (TAxI) peptide. In some aspects, the TAxI peptide is cyclized TAxI peptide of sequence SACQSQSQMRCGGG (SEQ ID NO: 374). See, e.g., Sellers et al. (2016) Proc. Natl. Acad. Sci. USA 113:2514-2519, and U.S. Pat. No. 9,056,892, which are herein incorporated by reference in their entireties. TAxI transport peptides as described herein may be of any length. Typically, the transport peptide will be between 6 and 50 amino acids in length, more typically between 10 and 20 amino acids in length. In some aspects, the TAxI transport peptide comprises the amino acid sequence QSQSQMR (SEQ ID NO: 375), ASGAQAR (SEQ ID NO: 376), PF, or TSTAPEELRLRLTSR (SEQ $D^H$) NO: 377). OptionaHy, the TAxI transport peptide further includes a flanking sequence to facilitate incorporation into a delivery construct or carrier, e.g., a linker. In one aspect, the peptide is flanked with cysteines. In some aspects, the TAxI transport peptide further comprises additional sequence selected to facilitate delivery into nuclei. For example, a peptide that facilitates nuclear delivery is a nuclear localizing signal (NLS). Typically, this signal consists of a few short sequences of positively charged lysines or arginines, such as PPKKRKV (SEQ ID NO: 378). In one aspect, the NLS has the amino acid sequence PKKRKV (SEQ ID NO: 379).

In some aspects, a tropism moiety of the present disclosure comprises a peptide BBB shuttle disclosed in the table below. See, e.g., Oller-Salvia et al. (2016) Chem. Soc. Rev.

45, 4690-4707, and Jafari et al. (2019) Expert Opinion on Drug Delivery 16:583-605 which are herein incorporated by reference in their entireties.

| SEQ ID NO | Peptide | Sequence |
|---|---|---|
| 380 | Angiopep-2 | TFFYGGSRGKRNNFKTEEY-*OH* |
| 381 | ApoB (3371-3409) | SSVIDALQYKLEGTTRLTRK-RGLKLATALSLSNKFVEGS |
| 382 | ApoE $(159\text{-}167)_2$ | $(\text{LRKLRKRLL})_2$ |
| 383 | Peptide-22 | *Ac*-C(&)MPRLRGC(&)-$NH_2$ |
| 384 | THR | THRPPMWSPVWP-$NH_2$ |
| 385 | THR retro-enantio | pwvpswmpprht-$NH_2$ |
| 386 | CRT | C(&)RTIGPSVC(&) |
| 387 | Leptin30 | YQQILTSMPSRNVIQISND-LENLRDLLHVL |
| 388 | RVG29 | YTIWMPENPRPGTPCDIFT-NSRGKRASNG-*OH* |
| 389 | $^{D}$CDX | GreirtGraerwsekf-OH |
| 390 | Apamin | C($\&_1$)NC($\&_2$)KAPETALC($\&_1$)-AR-RC($\&_2$)QQH-$NH_2$ |
| 391 | MiniAp-4 | [Dap](&)KAPETALD(&) |
| 392 | GSH | γ-L-glutamyl-CG-OH |
| 393 | G23 | HLNILSTLWKYRC |
| 394 | g7 | GFtGFLS(*O*-β-Glc)-$NH_2$ |
| 395 | TGN | TGNYKALHPHNG |
| 396 | TAT (47-57) | YGRKKRRQRRR-$NH_2$ |
| 397 | SynB1 | RGGRLSYSRRRFSTSTGR |
| 398 | Diketopiperazines | &(*N*-MePhe)-(*N*-MePhe)Diketo-piperazines |
| 399 | PhPro | $(\text{Phenylproline})_4$-$NH_2$ |

Nomenclature for cyclic peptides (&) is adapted to the 3-letter amino acid code from the one described by Spengler et al-, *Pept. Res.*, 2005, 65, 550-555
[Dap] stands for diaminopropionic acid.

III.C. Scaffold-X-Engineered EVs, e.g., Exosomes

In some aspects, EVs of the present disclosure comprise a membrane modified in its composition. For example, their membrane compositions can be modified by changing the protein, lipid, or glycan content of the membrane.

In some aspects, the surface-engineered EVs are generated by chemical and/or physical methods, such as PEG-induced fusion and/or ultrasonic fusion. In other aspects, the surface-engineered EVs, e.g., exosomes, are generated by genetic engineering. EVs produced from a genetically-modified producer cell or a progeny of the genetically-modified cell can contain modified membrane compositions. In some aspects, surface-engineered EVs, e.g., exosomes, have scaffold moiety (e.g., exosome protein, e.g., Scaffold X) at a higher or lower density (e.g., higher number) or include a variant or a fragment of the scaffold moiety.

For example, surface-engineered EVs (e.g., Scaffold X-engineered EVs) can be produced from a cell (e.g., HEK293 cells) transformed with an exogenous sequence encoding a scaffold moiety (e.g., exosome proteins, e.g., Scaffold X) or a variant or a fragment thereof EVs including scaffold moiety expressed from the exogenous sequence can include modified membrane compositions.

Various modifications or fragments of the scaffold moiety can be used for the aspects of the present disclosure. For example, scaffold moiety modified to have enhanced affinity to a binding agent can be used for generating surface-engineered EVs that can be purified using the binding agent. Scaffold moieties modified to be more effectively targeted to EVs, e.g., exosomes, and/or membranes can be used. Scaffold moieties modified to comprise a minimal fragment required for specific and effective targeting to EVs, e.g., exosomes, membranes can be also used.

In some aspects, a STING agonist disclosed herein is expressed on the surface of an EV, e.g., exosome, as a fusion protein, e.g., fusion protein of a STING agonist to a Scaffold X. For example, the fusion protein can comprise a STING agonist disclosed herein linked to a scaffold moiety (e.g., Scaffold X). In certain aspects, Scaffold X comprises the PTGFRN protein, BSG protein, IGSF2 protein, IGSF3 protein, IGSF8 protein, ITGB1 protein, ITGA4 protein, SLC3A2 protein, ATP transporter protein, or a fragment or a variant thereof.

In some aspects, the surface-engineered EVs, e.g., exosomes (e.g., Scaffold X-engineered EVs, e.g., exosomes) described herein demonstrate superior characteristics compared to EVs, e.g., exosomes, known in the art. For example, surface (e.g., Scaffold X)-engineered contain modified proteins more highly enriched on their surface than naturally occurring EVs, e.g., exosomes, or the EVs, e.g., exosomes, produced using conventional exosome proteins. Moreover, the surface -engineered EVs, e.g., exosomes, (e.g., Scaffold X-engineered EVs, e.g., exosomes) of the present invention can have greater, more specific, or more controlled biological activity compared to naturally occurring EVs, e.g., exosomes, or the EVs, e.g., exosomes, produced using conventional exosome proteins.

In other aspects, the EVs, e.g., exosomes, of the present disclosure contains a STING agonist and a Scaffold X, wherein the STING agonist is linked to the Scaffold X. In some aspects, the EVs, e.g., exosomes, of the present disclosure comprises a STING agonist and a Scaffold X, wherein the STING agonist is not linked to the Scaffold X.

In some aspects, Scaffold X useful for the present disclosure comprises Prostaglandin F2 receptor negative regulator (the PTGFRN polypeptide). Additional examples of Scaffold X that can be used are provided elsewhere in the present disclosure.

III.D. Scaffold-Y-Engineered EVs, e.g., Exosomes

In some aspects, EVs, e.g., exosomes, of the present disclosure comprise an internal space (i.e., lumen) that is different from that of the naturally occurring EVs, e.g., exosomes. For example, the EV, e.g., exosome, can be changed such that the composition in the luminal side of the EV, e.g., exosome, has the protein, lipid, or glycan content different from that of the naturally-occurring EVs, e.g., exosomes.

In some aspects, engineered EVs, e.g., exosomes, can be produced from a cell transformed with an exogenous sequence encoding a scaffold moiety (e.g., exosome proteins, e.g., Scaffold Y) or a modification or a fragment of the scaffold moiety that changes the composition or content of the luminal side of the EV, e.g., exosome. Various modifications or fragments of the exosome protein that can be expressed in the luminal side of the EV, e.g., exosome, can be used for the aspects of the present disclosure.

In some aspects, a STING agonist disclosed herein is in the lumen of the EV, e.g., exosome (i.e., encapsulated). In some aspects, a STING agonist is linked to the luminal surface of the EV, e.g., exosome. As used herein, when a molecule (e.g., antigen or adjuvant) is described as "in the lumen" of the EV, e.g., exosome, it means that the molecule is located within the EV, e.g., exosome (e.g., associated), but is not linked to any molecule on the luminal surface of EVs. In other aspects, a STING agonist is expressed on the luminal surface of the EV, e.g., exosome as a fusion molecule, e.g., fusion molecule of a STING agonist to a scaffold moiety (e.g., Scaffold Y). In certain aspects, Scaffold Y comprises the MARCKS protein, MARCKSL1 protein, BASP1 protein, or any combination thereof.

In other aspects, the EVs, e.g., exosomes, of the present disclosure contain a STING agonist and a Scaffold Y, wherein the STING agonist is linked to Scaffold Y. In some aspects, the EVs, e.g., exosomes, of the present disclosure comprise a STING agonist and a Scaffold Y, wherein the STING agonist is not linked to Scaffold Y.

III.E. Linker

The EVs of the present disclosure can comprises one or more linkers that link the STING agonist to EVs or to a scaffold moiety, e.g., Scaffold X on the exterior surface of the EVs. In some aspects, the STING agonist is linked to the EVs directly or in a scaffold moiety on the EVs by a linker. The linker can be any chemical moiety known in the art.

In some aspects, the term "linker" refers to a peptide or polypeptide sequence (e.g., a synthetic peptide or polypeptide sequence) or to a non-polypeptide. In some aspects, two or more linkers can be linked in tandem. Generally, linkers provide flexibility or prevent/ameliorate steric hindrances. Linkers are not typically cleaved; however in certain aspects, such cleavage can be desirable. Accordingly, in some aspects a linker can comprise one or more protease-cleavable sites, which can be located within the sequence of the linker or flanking the linker at either end of the linker sequence.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect the peptide linker can comprise non-naturally occurring polypeptides which are modified forms of naturally occurring polypeptides (e.g., comprising a mutation such as an addition, substitution or deletion).

Linkers may be susceptible to cleavage ("cleavable linker") thereby facilitating release of the STING Agonist or other payloads. In some aspects, the linker is a "reduction-sensitive linker." In some aspects, the reduction-sensitive linker contains a disulfide bond. In some aspects, the linker is an "acid labile linker." In some aspects, the acid labile linker contains hydrazone. Suitable acid labile linkers also include, for example, a cis-aconitic linker, a hydrazide linker, a thiocarbamoyl linker, or any combination thereof. In some aspects, the linker comprises a non-cleavable liker.

IV. Antisense Oligonucleotides (ASOS)

Certain aspects of the present disclosure are directed to modified exosomes comprising an ASO, wherein the ASO modulates the function of a target gene. In some aspects, the ASO modulates the function of nucleic acid molecules encoding mammalian STAT6, such as the STAT6 nucleic acid, e.g., STAT6 transcript, including STAT6 pre-mRNA, and STAT6 mRNA, or naturally occurring variants of such nucleic acid molecules encoding mammalian STAT6. In some aspects, the ASO modulates the function of nucleic acid molecules encoding mammalian CEBP/b, such as the CEBP/b nucleic acid, e.g., CEBP/b transcript, including CEBP/b pre-mRNA, and CEBP/b mRNA, or naturally occurring variants of such nucleic acid molecules encoding mammalian CEBP/b. The term "ASO" in the context of the present disclosure, refers to a molecule formed by covalent linkage of two or more nucleotides (i.e., an oligonucleotide).

In some aspects, the EV, e.g., the exosome, comprises at least one ASO. In some aspects, the EV, e.g., the exosome, comprises at least two ASOs, e.g., a first ASO comprising a first nucleotide sequence and a second ASO comprising a second nucleotide sequence. In some aspects, the EV, e.g., the exosome, comprises at least three ASOs, at least four ASOs, at least five ASOs, at least six ASOs, or more than six ASOs. In some aspects, each of the first ASO, the second ASO, the third ASO, the fourth ASO, the fifth ASO, the sixth ASO, and/or the ninth ASO is different.

In some aspects, the EV, e.g. the exosome, comprises a first ASO and a second ASO, wherein the first ASO comprises a first nucleotide sequence that is complimentary to a first target sequence in a first transcript, and wherein the second ASO comprises a second nucleotide sequence that is complimentary to a second target sequence in the first transcript. In some aspects, the first target sequence does not overlap with the second target sequence. In some aspects, the first target sequence comprises at least one nucleotide that is within the 5'UTR of the transcript, and the second target sequence does not comprise a nucleotide that is within the 5'UTR. In some aspects, the first target sequence comprises at least one nucleotide that is within the 3'UTR of the transcript, and the second target sequence does not comprise a nucleotide that is within the 3'UTR. In some aspects, the first target sequence comprises at least one nucleotide that is within the 5'UTR of the transcript, and the second target sequence comprises at least one nucleotide that is within the 3'UTR.

In some aspects, the first ASO targets a sequence within an exon-intron junction, and the second ASO targets a sequence within an exon-intron junction. In some aspects, the first ASO targets a sequence within an exon-intron junction, and the second ASO targets a sequence within an exon. In some aspects, the first ASO targets a sequence within an exon-intron junction, and the second ASO targets a sequence within an intron. In some aspects, the first ASO targets a sequence within an exon, and the second ASO targets a sequence within an exon. In some aspects, the first ASO targets a sequence within an intron, and the second ASO targets a sequence within an exon. In some aspects, the first ASO targets a sequence within an intron, and the second ASO targets a sequence within an intron.

In some aspects, the EV, e.g. the exosome, comprises a first ASO and a second ASO, wherein the first ASO comprises a first nucleotide sequence that is complimentary to a first target sequence in a first transcript, and wherein the second ASO comprises a second nucleotide sequence that is complimentary to a second target sequence in a second transcript, wherein the first transcript is not the product of the same gene as the second transcript.

The ASO comprises a contiguous nucleotide sequence of from about 10 to about 30, such as 10-20, 14-20, 16-20, or 15-25, nucleotides in length. In certain aspects, the ASO is 20 nucleotides in length. In certain aspects, the ASO is 18 nucleotides in length. In certain aspects, the ASO is 19 nucleotides in length. In certain aspects, the ASO is 17 nucleotides in length. In certain aspects, the ASO is 16 nucleotides in length. In certain aspects, the ASO is 15 nucleotides in length. The terms "antisense ASO," "antisense oligonucleotide," and "oligomer" as used herein are interchangeable with the term "ASO."

In various aspects, the ASO of the disclosure does not comprise RNA (units). In some aspects, the ASO comprises one or more DNA units. In one aspect, the ASO according to the disclosure is a linear molecule or is synthesized as a linear molecule. In some aspects, the ASO is a single stranded molecule, and does not comprise short regions of, for example, at least 3, 4 or 5 contiguous nucleotides, which are complementary to equivalent regions within the same ASO (i.e. duplexes)—in this regard, the ASO is not (essentially) double stranded. In some aspects, the ASO is essentially not double stranded. In some aspects, the ASO is not a siRNA. In various aspects, the ASO of the disclosure can consist entirely of the contiguous nucleotide region. Thus, in some aspects the ASO is not substantially self-complementary.

In other aspects, the present disclosure includes fragments of ASOs. For example, the disclosure includes at least one nucleotide, at least two contiguous nucleotides, at least three contiguous nucleotides, at least four contiguous nucleotides, at least five contiguous nucleotides, at least six contiguous nucleotides, at least seven contiguous nucleotides, at least eight contiguous nucleotides, or at least nine contiguous nucleotides of the ASOs disclosed herein. Fragments of any of the sequences disclosed herein are contemplated as part of the disclosure.

In some aspects, the ASOs for the present disclosure include a phosphorodiamidate Morpholino oligomer (PMO) or a peptide-conjugated phosphorodiamidate morpholino oligomer (PPMO).

IV.A. The Target

IV.A.1. STAT6

In some aspects, the ASO of the disclosure is capable of down-regulating (e.g., reducing or removing) expression of the STAT6 mRNA or STAT6 protein. In this regard, the ASO of the disclosure can promote differentiation of M2 macrophages and/or decrease the differentiation of M1 macrophages. In particular, some aspects of the present disclosure are directed to ASOs that target one or more regions of the STAT6 pre-mRNA (e.g., intron regions, exon regions, and/or exon-intron junction regions).

Unless indicated otherwise, the term "STAT6," as used herein, can refer to STAT6 from one or more species (e.g., humans, non-human primates, dogs, cats, guinea pigs, rabbits, rats, mice, horses, cattle, and bears).

STAT6 (STAT6) is also known as signal transducer and activator of transcription 6. Synonyms of STAT6/STAT6 are known and include IL-4 STAT; STAT, Interleukin4-Induced; Transcription Factor IL-4 STAT; STAT6B; STAT6C; and D12S1644. The sequence for the human STAT6 gene can be found under publicly available GenBank Accession Number NC_000012.12:c57111413-57095404. The human STAT6 gene is found at chromosome location 12q13.3 at 57111413-57095404, complement.

The sequence for the human STAT6 pre-mRNA transcript corresponds to the reverse complement of residues 57111413-57095404, complement, of chromosome 12q13.3. The STAT6 mRNA sequence is available as GenBank Accession No. NM_001178078.1. The sequence for human STAT6 protein can be found under publicly available Accession Numbers: P42226-1, (canonical sequence), P42226-2, and P42226-3. Each of these is incorporated by reference herein in its entirety.

Natural variants of the human STAT6 gene product are known. For example, natural variants of human STAT6 protein can contain one or more amino acid substitutions selected from: M118R, D419N, and any combination thereof. Additional variants of human STAT6 protein resulting from alternative splicing are also known in the art. STAT6 Isoform 2 (identifier: P42226-2 at UniProt) differs from the canonical sequence as follows: deletion of residues 1-174 and substitution of $_{175}PSE_{177}$ with $_{175}MEQ_{177}$ relative to the canonical sequence. The sequence of STAT6 Isoform 3 (identifier: P42226-3) differs from the canonical sequence as follows: deletion of residues 1-110 relative to the canonical sequence. Therefore, the ASOs of the present disclosure can be designed to reduce or inhibit expression of the natural variants of the STAT6 protein.

An example of a target nucleic acid sequence of the ASOs is STAT6 pre-mRNA. In certain aspects, the "target nucleic acid" comprises an intron of a STAT6 protein-encoding nucleic acids or naturally occurring variants thereof, and RNA nucleic acids derived therefrom, e.g., pre-mRNA. In other aspects, the target nucleic acid comprises an exon region of a STAT6 protein-encoding nucleic acids or naturally occurring variants thereof, and RNA nucleic acids derived therefrom, e.g., pre-mRNA. In yet other aspects, the target nucleic acid comprises an exon-intron junction of a STAT6 protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. In other aspects, the target nucleic acid comprises an untranslated region of a STAT6 protein-encoding nucleic acids or naturally occurring variants thereof, e.g., 5' UTR, 3' UTR, or both.

In some aspects, an ASO of the disclosure hybridizes to a region within the introns of a STAT6 transcript. In certain aspects, an ASO of the disclosure hybridizes to a region within the exons of a STAT6 transcript. In other aspects, an ASO of the disclosure hybridizes to a region within the exon-intron junction of a STAT6 transcript. In some aspects, an ASO of the disclosure hybridizes to a region within a STAT6 transcript (e.g., an intron, exon, or exon-intron junction), wherein the ASO has a design according to formula: 5' A-B-C 3' as described elsewhere herein.

In some aspects, the ASO targets an mRNA encoding a particular isoform of STAT6 protein (e.g., Isoform 1). In some aspects, the ASO targets all isoforms of STAT6 protein. In other aspects, the ASO targets two isoforms (e.g., Isoform 1 and Isoform 2, Isoform 1 and Isoform 3, or Isoform 2 and Isoform 3) of STAT6 protein.

In some aspects, the ASO comprises a contiguous nucleotide sequence (e.g., 10 to 30 nucleotides in length, e.g., 20 nucleotides in length) that are complementary to a nucleic acid sequence within a STAT6 transcript. In some aspects, the ASO comprises a contiguous nucleotide sequence that hybridizes to a nucleic acid sequence, or a region within the sequence, of a STAT6 transcript ("target region"), wherein the nucleic acid sequence corresponds (i) nucleotides 1-700 of the STAT6 transcript; (ii) nucleotides 1000-1500 of the STAT6 transcript; (iii) nucleotides 1500-2000 of the STAT6 transcript; (iv) nucleotides 2000-2500 of the STAT6 transcript; (v) 2500-3000 of the STAT6 transcript; or (vi) 3000-3700 of the STAT6 transcript and wherein, optionally, the ASO has one of the designs described herein or a chemical structure shown elsewhere herein.

In some aspects, the ASO comprises a contiguous nucleotide sequence that hybridizes to a nucleic acid sequence, or a region within the sequence, of a STAT6 transcript ("target region"), wherein the nucleic acid sequence corresponds to (i) nucleotides 413-803 of the STAT6 transcript; (ii) nucleotides 952-1688 of the STAT6 transcript; (iii) nucleotides 1726-2489 of the STAT6 transcript; (iv) nucleotides 2682-2912 of the STAT6 transcript; (v) 2970-3203 of the STAT6 transcript; or (vi) 3331-3561 of the STAT6 transcript and wherein, optionally, the ASO has one of the designs described herein or a chemical structure shown elsewhere herein.

In some aspects, the ASO comprises a contiguous nucleotide sequence that hybridizes to a nucleic acid sequence, or a region within the sequence, of a STAT6 transcript ("target region"), wherein the nucleic acid sequence corresponds to (i) nucleotides 463-753 of the STAT6 transcript; (ii) nucleotides 1002-1638 of the STAT6 transcript; (iii) nucleotides 1776-2439 of the STAT6 transcript; (iv) nucleotides 2682-2862 of the STAT6 transcript; (v) 3020-3153 of the STAT6 transcript; or (vi) 3381-3511 of the STAT6 transcript and wherein, optionally, the ASO has one of the designs described herein or a chemical structure shown elsewhere herein.

In some aspects, the ASO comprises a contiguous nucleotide sequence that hybridizes to a nucleic acid sequence, or a region within the sequence, of a STAT6 transcript ("target region"), wherein the nucleic acid sequence corresponds to (i) nucleotides 503-713 of the STAT6 transcript; (ii) nucleotides 1042-1598 of the STAT6 transcript; (iii) nucleotides 1816-2399 of the STAT6 transcript; (iv) nucleotides 2722-2822 of the STAT6 transcript; (v) 3060-3113 of the STAT6 transcript; or (vi) 3421-3471 of the STAT6 transcript and wherein, optionally, the ASO has one of the designs described herein or a chemical structure shown elsewhere herein.

In some aspects, the target region corresponds to nucleotides 1053-1067 of the STAT6 transcript. In some aspects, the target region corresponds to nucleotides 1359-1373 of the STAT6 transcript. In some aspects, the target region corresponds to nucleotides 1890-1904 of the STAT6 transcript. In some aspects, the target region corresponds to nucleotides 1892-1906 of the STAT6 transcript. In some aspects, the target region corresponds to nucleotides 1915-1929 of the STAT6 transcript. In some aspects, the target region corresponds to nucleotides 1916-1930 of the STAT6 transcript. In some aspects, the target region corresponds to nucleotides 1917-1931 of the STAT6 transcript. In some aspects, the target region corresponds to nucleotides 1918-1932 of the STAT6 transcript. In some aspects, the target region corresponds to nucleotides 1919-1933 of the STAT6 transcript. In some aspects, the target region corresponds to nucleotides 1920-1934 of the STAT6 transcript. In some aspects, the target region corresponds to nucleotides 1937-1951 of the STAT6 transcript. In some aspects, the target region corresponds to nucleotides 1938-1952 of the STAT6 transcript. In some aspects, the target region corresponds to nucleotides 2061-2075 of the STAT6 transcript. In some aspects, the target region corresponds to nucleotides 2062-2076 of the STAT6 transcript. In some aspects, the target region corresponds to nucleotides 2063-2077 of the STAT6 transcript. In some aspects, the target region corresponds to nucleotides 2064-2078 of the STAT6 transcript. In some aspects, the target region corresponds to nucleotides 2066-2080 of the STAT6 transcript. In some aspects, the target region corresponds to nucleotides 2067-2081 of the STAT6 transcript. In some aspects, the target region corresponds to nucleotides 2068-2082 of the STAT6 transcript. In some aspects, the target region corresponds to nucleotides 2352-2366 of the STAT6 transcript. In some aspects, the target region corresponds to nucleotides 3073-3087 of the STAT6 transcript. In some aspects, the target region corresponds to nucleotides 1053-1068 of the STAT6 transcript. In some aspects, the target region corresponds to nucleotides 1054-1069 of the STAT6 transcript. In some aspects, the target region corresponds to nucleotides 1356-1371 of the STAT6 transcript. In some aspects, the target region corresponds to nucleotides 1847-1862 of the STAT6 transcript. In some aspects, the target region corresponds to nucleotides 1886-1901 of the STAT6 transcript. In some aspects, the target region corresponds to nucleotides 1887-1902 of the STAT6 transcript. In some aspects, the target region corresponds to nucleotides 1888-1903 of the STAT6 transcript. In some aspects, the target region corresponds to nucleotides 1889-1904 of the STAT6 transcript. In some aspects, the target region corresponds to nucleotides 1890-1905 of the STAT6 transcript. In some aspects, the target region corresponds to nucleotides 1893-1908 of the STAT6 transcript. In some aspects, the target region corresponds to nucleotides 1917-1932 of the STAT6 transcript. In some aspects, the target region corresponds to nucleotides 1919-1934 of the STAT6 transcript. In some aspects, the target region corresponds to nucleotides 2056-2071 of the STAT6 transcript. In some aspects, the target region corresponds to nucleotides 2060-2075 of the STAT6 transcript. In some aspects, the target region corresponds to nucleotides 2066-2081 of the STAT6 transcript. In some aspects, the target region corresponds to nucleotides 2070-2085 of the STAT6 transcript. In some aspects, the target region corresponds to nucleotides 2351-2366 of the STAT6 transcript. In some aspects, the target region corresponds to nucleotides 2352-2367 of the STAT6 transcript. In some aspects, the target region corresponds to nucleotides 2359-2374 of the STAT6 transcript. In some aspects, the target region corresponds to nucleotides 3633-3648 of the STAT6 transcript. In some aspects, the target region corresponds to nucleotides 673-689 of the STAT6 transcript. In some aspects, the target region corresponds to nucleotides 1052-1068 of the STAT6 transcript. In some aspects, the target region corresponds to nucleotides 1356-1372 of the STAT6 transcript. In some aspects, the target region corresponds to nucleotides 1357-1373 of the STAT6 transcript. In some aspects, the target region corresponds to nucleotides 1359-1375 of the STAT6 transcript. In some aspects, the target region corresponds to nucleotides 1360-1376 of the STAT6 transcript. In some aspects, the target region corresponds to nucleotides 1839-1855 of the STAT6 transcript. In some aspects, the target region corresponds to nucleotides 1848-1864 of the STAT6 transcript. In some aspects, the target region corresponds to nucleotides 1849-1865 of the STAT6 transcript. In some aspects, the target region corresponds to nucleotides 1891-1907 of the STAT6 transcript. In some aspects, the target region corresponds to nucleotides 1915-1931 of the STAT6 transcript. In some aspects, the target region corresponds to nucleotides 1916-1932 of the STAT6 transcript. In some aspects, the target region corresponds to nucleotides 1917-1933 of the STAT6 transcript. In some aspects, the target region corresponds to nucleotides 1938-1954 of the STAT6 transcript. In some aspects, the target region corresponds to nucleotides 1939-1955 of the STAT6 transcript. In some aspects, the target region corresponds to nucleotides 2063-2079 of the STAT6 transcript. In some aspects, the target region corresponds to nucleotides 2064-2080 of the STAT6 transcript. In some aspects, the target region corresponds to nucleotides 2065-2081 of the STAT6 transcript. In some aspects, the target region corresponds to nucleotides 2066-2082 of the STAT6 transcript. In some aspects, the target region corresponds to nucleotides 2068-2084 of the STAT6 transcript. In some aspects, the target region corresponds to nucleotides 2187-2203 of the STAT6 transcript. In some aspects, the target region corresponds to nucleotides 2350-2366 of the STAT6 transcript. In some aspects, the target region corresponds to nucleotides 2351-2367 of the STAT6 transcript. In some aspects, the target region corresponds to nucleotides 2352-2368 of the STAT6 transcript. In some aspects, the target region corresponds to nucleotides 2357-2373 of the STAT6 transcript. In some aspects, the target region corresponds to nucleotides 513-532 of the STAT6 transcript. In some aspects, the target region corresponds to nucleotides 671-690 of the STAT6 transcript. In some aspects, the target region corresponds to nucleotides 1131-1150 of the STAT6 transcript. In some aspects, the target region corresponds to nucleotides 1354-1373 of the STAT6 transcript. In some aspects, the target region corresponds to nucleotides 1355-1374 of the STAT6 transcript. In some aspects, the target region corresponds to nucleotides 1356-1375 of the STAT6 transcript. In some aspects, the target region corresponds to nucleotides 1432-1451 of the STAT6 transcript. In some aspects, the target region corresponds to nucleotides 1555-1574 of the STAT6 transcript. In some aspects, the target region corresponds to nucleotides 1556-1575 of the STAT6 transcript. In some aspects, the target region corresponds to nucleotides 1557-1576 of the STAT6 transcript. In some aspects, the target region corresponds to nucleotides 1558-1577 of the STAT6 transcript. In some aspects, the target region corresponds to nucleotides 1826-1845 of the STAT6 transcript. In some aspects, the target region corresponds to nucleotides 1827-1846 of the STAT6 transcript. In some aspects, the target region corresponds to nucleotides 1833-1852 of the STAT6 transcript. In some aspects, the target region corresponds to nucleotides 1843-1862 of the STAT6 transcript. In some aspects, the target region corresponds to nucleotides 1846-1865 of the STAT6 transcript. In some aspects, the target region corresponds to nucleotides 1847-1866 of the STAT6 transcript. In some aspects, the target region corresponds to nucleotides 1883-1902 of the STAT6 transcript. In some aspects, the target region corresponds to nucleotides 1889-1908 of the STAT6 transcript. In some aspects, the target region corresponds to nucleotides 1890-1909 of the STAT6 transcript. In some aspects, the target region corresponds to nucleotides 1891-1910 of the STAT6 transcript. In some aspects, the target region corresponds to nucleotides 1916-1935 of the STAT6 transcript. In some aspects, the target region corresponds to nucleotides 1917-1936 of the STAT6 transcript. In some aspects, the target region corresponds to nucleotides 2056-2075 of the STAT6 transcript. In some aspects, the target region corresponds to nucleotides 2057-2076 of the STAT6 transcript. In some aspects, the target region corresponds to nucleotides 2060-2079 of the STAT6 transcript. In some aspects, the target region corresponds to nucleotides 2062-2081 of the STAT6 transcript. In some aspects, the target region corresponds to nucleotides 2063-2082 of the STAT6 transcript. In some aspects, the target region corresponds to nucleotides 2065-2084 of the STAT6 transcript. In some aspects, the target region corresponds to nucleotides 2068-2087 of the STAT6 transcript. In some aspects, the target region corresponds to nucleotides 2347-2366 of the STAT6 transcript. In some aspects, the target region corresponds to nucleotides 2348-2367 of the STAT6 transcript. In some aspects, the target region corresponds to nucleotides 2358-2377 of the STAT6 transcript. In some aspects, the target region corresponds to nucleotides 2782-2801 of the STAT6 transcript. In some aspects, the target region corresponds to nucleotides 3070-3089 of the STAT6 transcript. In some aspects, the target region corresponds to nucleotides 3071-3090 of the STAT6 transcript. In some aspects, the target region corresponds to nucleotides 3431-3450 of the STAT6 transcript.

In some aspects, the ASO of the present disclosure hybridizes to multiple target regions within the STAT6 transcript. In some aspects, the ASO hybridizes to two different target regions within the STAT6 transcript. In some aspects, the ASO hybridizes to three different target regions within the STAT6 transcript. In some aspects, the ASOs that hybridizes to multiple regions within the STAT6 transcript are more potent (e.g., having lower EC50) at reducing STAT6 expression compared to ASOs that hybridizes to a single region within the STAT6 transcript.

In some aspects, the ASO of the disclosure is capable of hybridizing to the target nucleic acid (e.g., STAT6 transcript) under physiological condition, i.e., in vivo condition. In some aspects, the ASO of the disclosure is capable of hybridizing to the target nucleic acid (e.g., STAT6 transcript) in vitro. In some aspects, the ASO of the disclosure is capable of hybridizing to the target nucleic acid (e.g., STAT6 transcript) in vitro under stringent conditions. Stringency conditions for hybridization in vitro are dependent on, inter alia, productive cell uptake, RNA accessibility, temperature, free energy of association, salt concentration, and time (see, e.g., Stanley T Crooke, Antisense Drug Technology: Principles, Strategies and Applications, $2^{nd}$ Edition, CRC Press (2007)). Generally, conditions of high to moderate stringency are used for in vitro hybridization to enable hybridization between substantially similar nucleic acids, but not between dissimilar nucleic acids. An example of stringent hybridization conditions includes hybridization in 5λ saline-sodium citrate (SSC) buffer (0.75 M sodium chloride/0.075 M sodium citrate) for 1 hour at 40° C., followed by washing the sample 10 times in 1×SSC at 40° C. and 5 times in 1×SSC buffer at room temperature. In vivo hybridization conditions consist of intracellular conditions (e.g., physiological pH and intracellular ionic conditions) that govern the hybridization of antisense oligonucleotides with target sequences. In vivo conditions can be mimicked in vitro by relatively low stringency conditions. For example, hybridization can be carried out in vitro in 2×SSC (0.3 M sodium chloride/0.03 M sodium citrate), 0.1% SDS at 37° C. A wash solution containing 4×SSC, 0.1% SDS can be used at 37° C., with a final wash in 1×SSC at 45° C.

In some aspects, the ASO of the present disclosure is capable of targeting a STAT6 transcript from one or more species (e.g., humans, non-human primates, dogs, cats, guinea pigs, rabbits, rats, mice, horses, cattle, and bears). In certain aspects, the ASO disclosed herein is capable of targeting both human and rodent (e.g., mice or rats) STAT6 transcript. Accordingly, in some aspects, the ASO is capable of down-regulating (e.g., reducing or removing) expression of the STAT6 mRNA or protein both in humans and in rodents (e.g., mice or rats). In some aspects, any ASO described herein is part of a conjugate, comprising the ASO covalently linked to at least one non-nucleotide or non-polynucleotide.

Certain aspects of the present disclosure are directed to a conjugate comprising an ASO described herein. In certain aspects, the conjugate comprises an ASO covalently attached to at least one non-nucleotide. In certain aspects, the conjugate comprises an ASO covalently attached to at least non-polynucleotide moiety. In some aspects, the non-nucleotide or non-polynucleotide moiety comprises a protein, a fatty acid chain, a sugar residue, a glycoprotein, a polymer, or any combinations thereof.

IV.A.2. CEBP/b

In some aspects, the ASO of the disclosure is capable of down-regulating (e.g., reducing or removing) expression of the CEBP/β mRNA or CEBP/β protein. In this regard, the ASO of the disclosure can promote differentiation of M2 macrophages and/or decrease the differentiation of M1 macrophages. In particular, some aspects of the present disclosure are directed to ASOs that target one or more regions of the CEBP/β pre-mRNA (e.g., intron regions, exon regions, and/or exon-intron junction regions).

Unless indicated otherwise, the term "CEBP/β," as used herein, can refer to CEBP/β from one or more species (e.g., humans, non-human primates, dogs, cats, guinea pigs, rabbits, rats, mice, horses, cattle, and bears).

CEBP/β (CEBP/β) is also known as CCAAT/enhancer-binding protein beta. Synonyms of CEBP/β/CEBP/β are known and include C/EBP beta; •Liver activator protein; LAP; Liver-enriched inhibitory protein; LIP; Nuclear factor NF-IL6; transcription factor 5; TCF-5; CEBPB; CEBPb; CEBPβ; CEBP/B; and TCF5. The sequence for the human CEBP/β gene can be found under publicly available GenBank Accession Number NC_000020.11 (50190583..50192690). The human CEBP/β gene is found at chromosome location 20q13.13 at 50190583-50192690.

The sequence for the human CEBP/β pre-mRNA transcript corresponds to the reverse complement of residues 50190583-50192690 of chromosome 20q13.13. The CEBP/β mRNA sequence is available at GenBank Accession No. NM_001285878.1. The sequence for human CEBP/β protein can be found under publicly available Accession Numbers: P17676, (canonical sequence), P17676-2, and P17676-3. Each of these is incorporated by reference herein in its entirety.

Natural variants of the human CEBP/β gene product are known. For example, natural variants of human CEBP/β protein can contain one or more amino acid substitutions selected from: A241P, A253G, G195S, and any combination thereof. Additional variants of human CEBP/β protein resulting from alternative splicing are also known in the art. CEBP/β Isoform 2 (identifier: P17676-2 at UniProt) differs from the canonical sequence as follows: deletion of residues 1-23 relative to the canonical sequence. The sequence of CEBP/β Isoform 3 (identifier: P17676-3) differs from the canonical sequence as follows: deletion of residues 1-198 relative to the canonical sequence. Therefore, the ASOs of the present disclosure can be designed to reduce or inhibit expression of the natural variants of the protein.

An example of a target nucleic acid sequence of the ASOs is CEBP/β pre-mRNA. In certain aspects, the "target nucleic acid" comprises an intron of a CEBP/β protein-encoding nucleic acids or naturally occurring variants thereof, and RNA nucleic acids derived therefrom, e.g., pre-mRNA. In other aspects, the target nucleic acid comprises an exon region of a CEBP/β protein-encoding nucleic acids or naturally occurring variants thereof, and RNA nucleic acids derived therefrom, e.g., pre-mRNA. In yet other aspects, the target nucleic acid comprises an exon-intron junction of a CEBP/β protein-encoding nucleic acids or naturally occurring variants thereof, and RNA nucleic acids derived therefrom, e.g., pre-mRNA. In some aspects, for example when used in research or diagnostics the "target nucleic acid" can be a cDNA or a synthetic oligonucleotide derived from the above DNA or RNA nucleic acid targets. In other aspects, the target nucleic acid comprises an untranslated region of a CEBP/β protein-encoding nucleic acids or naturally occurring variants thereof, e.g., 5' UTR, 3' UTR, or both.

In some aspects, an ASO of the disclosure hybridizes to a region within the introns of a CEBP/β transcript. In certain aspects, an ASO of the disclosure hybridizes to a region within the exons of a CEBP/β transcript. In other aspects, an ASO of the disclosure hybridizes to a region within the exon-intron junction of a CEBP/β transcript. In some aspects, an ASO of the disclosure hybridizes to a region within a CEBP/β transcript (e.g., an intron, exon, or exon-intron junction) wherein the ASO has a design according to formula: 5' A-B-C 3' as described elsewhere herein.

In some aspects, the ASO targets an mRNA encoding a particular isoform of CEBP/β protein (e.g., Isoform 1). In some aspects, the ASO targets all isoforms of CEBP/β protein. In other aspects, the ASO targets two isoforms (e.g., Isoform 1 and Isoform 2, Isoform 1 and Isoform 3, or Isoform 2 and Isoform 3) of CEBP/β protein.

In some aspects, the ASO comprises a contiguous nucleotide sequence (e.g., 10 to 30 nucleotides in length, e.g., 20 nucleotides in length) that are complementary to a nucleic acid sequence within a CEBP/β transcript. In some aspects, the ASO comprises a contiguous nucleotide sequence that hybridizes to a nucleic acid sequence, or a region within the sequence, of a CEBP/β transcript ("target region"), wherein the nucleic acid sequence corresponds (i) nucleotides 1-600 of the CEBP/β transcript; (ii) nucleotides 100-600 of the CEBP/β transcript; (iii) nucleotides 200-600 of the CEBP/β transcript; (iv) nucleotides 300-600 of the CEBP/β transcript; (v) 400-600 of the CEBP/β transcript, (vi) nucleotides 500-1000 of the CEBP/β transcript; (vii) nucleotides 900-1200 of the CEBP/β transcript; (viii) nucleotides 1000-1300 of the CEBP/β transcript; (ix) nucleotides 1300-1500 of the CEBP/β transcript, and wherein, optionally, the ASO has one of the designs described herein or a chemical structure shown elsewhere herein.

In some aspects, the ASO comprises a contiguous nucleotide sequence that hybridizes to a nucleic acid sequence, or a region within the sequence, of a CEBP/β transcript ("target region"), wherein the nucleic acid sequence corresponds to (i) 439-699 of the CEBP/β transcript; (ii) nucleotides 544-778 of the CEBP/β transcript; (iii) nucleotides 715-750 of the CEBP/β transcript; (iv) nucleotides 886-1126 of the CEBP/β transcript; (v) nucleotides 949-2118 of the CEBP/β transcript; (vi) or 1153-1407 of the CEBP/β transcript and wherein, optionally, the ASO has one of the designs described herein or a chemical structure shown elsewhere herein.

In some aspects, the ASO comprises a contiguous nucleotide sequence that hybridizes to a nucleic acid sequence, or a region within the sequence, of a CEBP/β transcript ("target region"), wherein the nucleic acid sequence corresponds to (i) 489-649 of the CEBP/β transcript; (ii) nucleotides 594-728 of the CEBP/β transcript; (iii) nucleotides 765-700 of the CEBP/β transcript; (iv) nucleotides 936-1076 of the CEBP/β transcript; (v) nucleotides 999-2068 of the CEBP/β transcript; (vi) or 1203-1357 of the CEBP/β transcript and wherein, optionally, the ASO has one of the designs described herein or a chemical structure shown elsewhere herein.

In some aspects, the ASO comprises a contiguous nucleotide sequence that hybridizes to a nucleic acid sequence, or a region within the sequence, of a CEBP/β transcript ("target region"), wherein the nucleic acid sequence corresponds to (i) nucleotides 1355-1487 of the CEBP/β transcript (ii) 529-609 of the CEBP/β transcript; (iii) nucleotides 634-688 of the CEBP/β transcript; (iv) nucleotides 805-700 of the CEBP/β transcript; (v) nucleotides 976-1036 of the CEBP/β transcript; (vi) nucleotides 1039-2028 of the CEBP/β transcript; (vii) 1243-1317 of the CEBP/β transcript or (viii) nucleotides 1395-1447 of the CEBP/β transcript and wherein, optionally, the ASO has one of the designs described herein or a chemical structure shown elsewhere herein.

In some aspects, the target region corresponds to nucleotides 540-554 of the CEBP/β transcript. In some aspects, the target region corresponds to nucleotides 565-579 of the CEBP/β transcript. In some aspects, the target region corresponds to nucleotides 569-583 of the CEBP/β transcript. In some aspects, the target region corresponds to nucleotides 648-662 of the CEBP/βt transcript. In some aspects, the target region corresponds to nucleotides 816-830 of the CEBP/β transcript. In some aspects, the target region corresponds to nucleotides 817-831 of the CEBP/β transcript. In some aspects, the target region corresponds to nucleotides 818-832 of the CEBP/β transcript. In some aspects, the target region corresponds to nucleotides 819-833 of the CEBP/β transcript. In some aspects, the target region corresponds to nucleotides 820-834 of the CEBP/β transcript. In some aspects, the target region corresponds to nucleotides 851-865 of the CEBP/β transcript. In some aspects, the target region corresponds to nucleotides 853-867 of the CEBP/β transcript. In some aspects, the target region corresponds to nucleotides 856-870 of the CEBP/β transcript. In some aspects, the target region corresponds to nucleotides 858-872 of the CEBP/β transcript. In some aspects, the target region corresponds to nucleotides 987-1001 of the CEBP/β transcript. In some aspects, the target region corresponds to nucleotides 1056-1070 of the CEBP/β transcript. In some aspects, the target region corresponds to nucleotides 1064-1078 of the CEBP/β transcript. In some aspects, the target region corresponds to nucleotides 1065-1079 of the CEBP/β transcript. In some aspects, the target region corresponds to nucleotides 1066-1080 of the CEBP/β transcript. In some aspects, the target region corresponds to nucleotides 1071-1085 of the CEBP/β transcript. In some aspects, the target region corresponds to nucleotides 1270-1284 of the CEBP/β transcript. In some aspects, the target region corresponds to nucleotides 1273-1287 of the CEBP/β transcript. In some aspects, the target region corresponds to nucleotides 1274-1288 of the CEBP/β transcript. In some aspects, the target region corresponds to nucleotides 1405-1419 of the CEBP/β transcript. In some aspects, the target region corresponds to nucleotides 1407-1421 of the CEBP/β transcript. In some aspects, the target region corresponds to nucleotides 539-554 of the CEBP/β transcript. In some aspects, the target region corresponds to nucleotides 540-555 of the CEBP/β transcript. In some aspects, the target region corresponds to nucleotides 563-578 of the CEBP/β transcript. In some aspects, the target region corresponds to nucleotides 564-579 of the CEBP/β transcript. In some aspects, the target region corresponds to nucleotides 565-580 of the CEBP/β transcript. In some aspects, the target region corresponds to nucleotides 568-583 of the CEBP/β transcript. In some aspects, the target region corresponds to nucleotides 644-659 of the CEBP/β transcript. In some aspects, the target region corresponds to nucleotides 645-660 of the CEBP/β transcript. In some aspects, the target region corresponds to nucleotides 648-663 of the CEBP/β transcript. In some aspects, the target region corresponds to nucleotides 819-834 of the CEBP/β transcript. In some aspects, the target region corresponds to nucleotides 855-870 of the CEBP/β transcript. In some aspects, the target region corresponds to nucleotides 860-875 of the CEBP/β transcript. In some aspects, the target region corresponds to nucleotides 986-1001 of the CEBP/β transcript. In some aspects, the target region corresponds to nucleotides 987-1002 of the CEBP/β transcript. In some aspects, the target region corresponds to nucleotides 996-1011 of the CEBP/β transcript. In some aspects, the target region corresponds to nucleotides 1049-1064 of the CEBP/β transcript. In some aspects, the target region corresponds to nucleotides 1050-1065 of the CEBP/β transcript. In some aspects, the target region corresponds to nucleotides 1064-1079 of the CEBP/β transcript. In some aspects, the target region corresponds to nucleotides 1065-1080 of the CEBP/β transcript. In some aspects, the target region corresponds to nucleotides 1066-1081 of the CEBP/β transcript. In some aspects, the target region corresponds to nucleotides 1083-1098 of the CEBP/β transcript. In some aspects, the target region corresponds to nucleotides 1088-1103 of the CEBP/β transcript. In some aspects, the target region corresponds to nucleotides 1253-1268 of the CEBP/β transcript. In some aspects, the target region corresponds to nucleotides 1269-1284 of the CEBP/β transcript. In some aspects, the target region corresponds to nucleotides 1272-1287 of the CEBP/β transcript. In some aspects, the target region corresponds to nucleotides 1274-1289 of the CEBP/β transcript. In some aspects, the target region corresponds to nucleotides 539-555 of the CEBP/β transcript. In some aspects, the target region corresponds to nucleotides 564-580 of the CEBP/β transcript. In some aspects, the target region corresponds to nucleotides 565-581 of the CEBP/β transcript. In some aspects, the target region corresponds to nucleotides 567-583 of the CEBP/β transcript. In some aspects, the target region corresponds to nucleotides 647-663 of the CEBP/β transcript. In some aspects, the target region corresponds to nucleotides 648-664 of the CEBP/β transcript. In some aspects, the target region corresponds to nucleotides 815-831 of the CEBP/β transcript. In some aspects, the target region corresponds to nucleotides 818-834 of the CEBP/β transcript. In some aspects, the target region corresponds to nucleotides 820-836 of the CEBP/β transcript. In some aspects, the target region corresponds to nucleotides 854-870 of the CEBP/β transcript. In some aspects, the target region corresponds to nucleotides 855-871 of the CEBP/β transcript. In some aspects, the target region corresponds to nucleotides 859-875 of the CEBP/β transcript. In some aspects, the target region corresponds to nucleotides 1050-1066 of the CEBP/β transcript. In some aspects, the target region corresponds to nucleotides 1053-1069 of the CEBP/β transcript. In some aspects, the target region corresponds to nucleotides 1062-1078 of the CEBP/β transcript. In some aspects, the target region corresponds to nucleotides 1063-1079 of the CEBP/β transcript. In some aspects, the target region corresponds to nucleotides 1064-1080 of the CEBP/β transcript. In some aspects, the target region corresponds to nucleotides 1065-1081 of the CEBP/β transcript. In some aspects, the target region corresponds to nucleotides 1265-1281 of the CEBP/β transcript. In some aspects, the target region corresponds to nucleotides 1270-1286 of the CEBP/β transcript. In some aspects, the target region corresponds to nucleotides 1271-1287 of the CEBP/β transcript. In some aspects, the target region corresponds to nucleotides 1272-1288 of the CEBP/β transcript. In some aspects, the target region corresponds to nucleotides 1274-1290 of the CEBP/β transcript. In some aspects, the target region corresponds to nucleotides 1277-1293 of the CEBP/β transcript. In some aspects, the target region corresponds to nucleotides 564-583 of the CEBP/β transcript. In some aspects, the target region corresponds to nucleotides 565-584 of the CEBP/β transcript. In some aspects, the target region corresponds to nucleotides 818-837 of the CEBP/β transcript. In some aspects, the target region corresponds to nucleotides 1061-1080 of the CEBP/β transcript. In some aspects, the target region corresponds to nucleotides 1062-1081 of the CEBP/β transcript. In some aspects, the target region corresponds to nucleotides 1064-1083 of the CEBP/β transcript. In some aspects, the target region corresponds to nucleotides 1267-1286 of the CEBP/β transcript. In some aspects, the target region corresponds to nucleotides 1272-1291 of the CEBP/β transcript. In some aspects, the target region corresponds to nucleotides 645-664 of the CEBP/β transcript. In some aspects, the target region corresponds to nucleotides 848-867 of the CEBP/β transcript. In some aspects, the target region corresponds to nucleotides 849-868 of the CEBP/β transcript. In some aspects, the target region corresponds to nucleotides 850-869 of the CEBP/β transcript. In some aspects, the target region corresponds to nucleotides 1063-1082 of the CEBP/β transcript. In some aspects, the target region corresponds to nucleotides 1070-1089 of the CEBP/β transcript. In some aspects, the target region corresponds to nucleotides 1071-1090 of the CEBP/β transcript. In some aspects, the target region corresponds to nucleotides 1262-1281 of the CEBP/β transcript. In some aspects, the target region corresponds to nucleotides 1274-1293 of the CEBP/β transcript. In some aspects, the target region corresponds to nucleotides 1275-1294 of the CEBP/β transcript. In some aspects, the target region corresponds to nucleotides 644-663 of the CEBP/β transcript. In some aspects, the target region corresponds to nucleotides 647-666 of the CEBP/β transcript. In some aspects, the target region corresponds to nucleotides 851-870 of the CEBP/β transcript. In some aspects, the target region corresponds to nucleotides 1266-1285 of the CEBP/β transcript. In some aspects, the target region corresponds to nucleotides 1268-1287 of the CEBP/β transcript. In some aspects, the target region corresponds to nucleotides 1270-1289 of the CEBP/β transcript. In some aspects, the target region corresponds to nucleotides 646-665 of the CEBP/β transcript. In some aspects, the target region corresponds to nucleotides 1060-1079 of the CEBP/β transcript. In some aspects, the target region corresponds to nucleotides 1263-1282 of the CEBP/β transcript. In some aspects, the target region corresponds to nucleotides 1269-1288 of the CEBP/β transcript. In some aspects, the target region corresponds to nucleotides 1271-1290 of the CEBP/β transcript.

In some aspects, the ASO of the present disclosure hybridizes to multiple target regions within the CEBP/β transcript. In some aspects, the ASO hybridizes to two different target regions within the CEBP/β transcript. In some aspects, the ASO hybridizes to three different target regions within the CEBP/β transcript. In some aspects, the ASOs that hybridizes to multiple regions within the CEBP/β transcript are more potent (e.g., having lower EC50) at reducing CEBP/β expression compared to ASOs that hybridizes to a single region within the CEBP/β transcript.

In some aspects, the ASO of the disclosure is capable of hybridizing to the target nucleic acid (e.g., CEBP/β transcript)under physiological condition, i.e., in vivo condition. In some aspects, the ASO of the disclosure is capable of hybridizing to the target nucleic acid (e.g., CEBP/β transcript) in vitro. In some aspects, the ASO of the disclosure is capable of hybridizing to the target nucleic acid (e.g., CEBP/β transcript) in vitro under stringent conditions. Stringency conditions for hybridization in vitro are dependent on, inter alia, productive cell uptake, RNA accessibility, temperature, free energy of association, salt concentration, and time (see, e.g., Stanley T Crooke, Antisense Drug Technology: Principles, Strategies and Applications, 2"d Edition, CRC Press (2007)). Generally, conditions of high to moderate stringency are used for in vitro hybridization to enable hybridization between substantially similar nucleic acids, but not between dissimilar nucleic acids. An example of stringent hybridization conditions includes hybridization in 5×saline-sodium citrate (SSC) buffer (0.75 M sodium chloride/0.075 M sodium citrate) for 1 hour at 40° C., followed by washing the sample 10 times in 1×SSC at 40° C. and 5 times in 1×SSC buffer at room temperature. In vivo hybridization conditions consist of intracellular conditions (e.g., physiological pH and intracellular ionic conditions) that govern the hybridization of antisense oligonucleotides with target sequences. In vivo conditions can be mimicked in vitro by relatively low stringency conditions. For example, hybridization can be carried out in vitro in 2×SSC (0.3 M sodium chloride/0.03 M sodium citrate), 0.1% SDS at 37° C. A wash solution containing 4×SSC, 0.1% SDS can be used at 37° C., with a final wash in 1×SSC at 45° C.

In some aspects, the ASO of the present disclosure is capable of targeting a CEBP/β transcript from one or more species (e.g., humans, non-human primates, dogs, cats, guinea pigs, rabbits, rats, mice, horses, cattle, and bears). In certain aspects, the ASO disclosed herein is capable of targeting both human and rodent (e.g., mice or rats) CEBP/β transcript. Accordingly, in some aspects, the ASO is capable of down-regulating (e.g., reducing or removing) expression of the CEBP/β mRNA or protein both in humans and in rodents (e.g., mice or rats). In some aspects, any ASO described herein is part of a conjugate, comprising the ASO covalently linked to at least one non-nucleotide or non-polynucleotide.

Certain aspects of the present disclosure are directed to a conjugate comprising an ASO described herein. In certain aspects, the conjugate comprises an ASO covalently attached to at least one non-nucleotide. In certain aspects, the conjugate comprises an ASO covalently attached to at least non-polynucleotide moiety. In some aspects, the non-nucleotide or non-polynucleotide moiety comprises a protein, a fatty acid chain, a sugar residue, a glycoprotein, a polymer, or any combinations thereof.

IV.B. ASO Sequences

The ASOs of the disclosure comprise a contiguous nucleotide sequence which corresponds to the complement of a region of a target transcript, e.g., STAT6 or CEBP/β.

In certain aspects, the disclosure provides an ASO from 10-30, such as 10-15 nucleotides, 10-20 nucleotides, 10-25 nucleotides in length, or about 20 nucleotides in length, wherein the contiguous nucleotide sequence has at least about 80%, at least about 85%, at least about 90%, at least about 95%, at least about 96%, at least about 97%, at least about 98%, at least about 99%, or about 100% sequence identity to a region within the complement of a target transcript, e.g., STAT6 or CEBP/β, or naturally occurring variant thereof.

The ASO can comprise a contiguous nucleotide sequence which is fully complementary (perfectly complementary) to the equivalent region of a nucleic acid which encodes a target transcript, e.g., STAT6 or CEBP/β. The ASO can comprise a contiguous nucleotide sequence which is fully complementary (perfectly complementary) to a nucleic acid sequence, or a region within the sequence, of a target transcript, e.g., STAT6 or CEBP/β.

The ASO can comprise a contiguous nucleotide sequence which is fully complementary (perfectly complementary) to the equivalent region of a mRNA which encodes a target transcript, e.g., STAT6 or CEBP/β. The ASO can comprise a contiguous nucleotide sequence which is fully complementary (perfectly complementary) to a mRNA sequence, or a region within the sequence, of a target transcript, e.g., STAT6 or CEBP/β.

In some aspects, the ASOs of the disclosure bind to the target nucleic acid sequence and are capable of inhibiting or reducing expression of the transcript by at least 10% or 20% compared to the normal (i.e., control) expression level in the cell, e.g., at least about 30%, at least about 40%, at least about 50%, at least about 60%, at least about 70%, at least about 80%, at least about 90%, at least about 95%, at least about 96%, at least about 97%, at least about 98%, at least about 99%, or about 100% compared to the normal expression level (e.g., expression level in cells that have not been exposed to the ASO).

In some aspects, the ASOs of the disclosure are capable of reducing expression of target mRNA in vitro by at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, or about 100% in target cells when the cells are in contact with the ASO compared to cells that are not in contact with the ASO (e.g., contact with saline).

In some aspects, the ASO can tolerate 1, 2, 3, or 4 (or more) mismatches, when hybridizing to the target sequence and still sufficiently bind to the target to show the desired effect, i.e., down-regulation of the target mRNA and/or protein. Mismatches can, for example, be compensated by increased length of the ASO nucleotide sequence and/or an increased number of nucleotide analogs, which are disclosed elsewhere herein.

In some aspects, the ASO of the disclosure comprises no more than three mismatches when hybridizing to the target sequence. In other aspects, the contiguous nucleotide sequence comprises no more than two mismatches when hybridizing to the target sequence. In other aspects, the contiguous nucleotide sequence comprises no more than one mismatch when hybridizing to the target sequence.

IV.C. ASO Length

The ASOs can comprise a contiguous nucleotide sequence of a total of 10, 11, 12, 13, 14, 15, 16, 17, 18, 19, 20, 21, 22, 23, 24, 25, 26, 27, 28, 29, or 30 contiguous nucleotides in length. It should be understood that when a range is given for an ASO, or contiguous nucleotide sequence length, the range includes the lower and upper lengths provided in the range, for example from (or between) 10-30, includes both 10 and 30.

In some aspects, the ASOs comprise a contiguous nucleotide sequence of a total of about 14-20, 14, 15, 16, 17, 18, 19, or 20 contiguous nucleotides in length. In certain aspects, the ASOs comprise a contiguous nucleotide sequence of a total of about 20 contiguous nucleotides in length. In certain aspects, ASOs of the present disclosure are 14 nucleotides in length. In certain aspects, ASOs of the present disclosure are 15 nucleotides in length. In certain aspects, ASOs of the present disclosure are 16 nucleotides in length. In certain aspects, ASOs of the present disclosure are 17 nucleotides in length. In certain aspects, ASOs of the present disclosure are 18 nucleotides in length. In certain aspects, ASOs of the present disclosure are 19 nucleotides in length.

IV.D. Nucleosides and Nucleoside analogs

In one aspect of the disclosure, the ASOs comprise one or more non-naturally occurring nucleoside analogs. "Nucleoside analogs" as used herein are variants of natural nucleosides, such as DNA or RNA nucleosides, by virtue of modifications in the sugar and/or base moieties. Analogs could in principle be merely "silent" or "equivalent" to the natural nucleosides in the context of the oligonucleotide, i.e. have no functional effect on the way the oligonucleotide works to inhibit target gene expression. Such "equivalent" analogs can nevertheless be useful if, for example, they are easier or cheaper to manufacture, or are more stable to storage or manufacturing conditions, or represent a tag or label. In some aspects, however, the analogs will have a functional effect on the way in which the ASO works to inhibit expression; for example by producing increased binding affinity to the target and/or increased resistance to intracellular nucleases and/or increased ease of transport into the cell. Specific examples of nucleoside analogs are described by e.g. Freier & Altmann; *Nucl. Acid Res.,* 1997, 25, 4429-4443 and Uhlmann; *Curr. Opinion in Drug Development,* 2000, 3(2), 293-213, and in Scheme 1. The ASOs of the present disclosure can contain more than one, more than two, more than three, more than four, more than five, more than six, more than seven, more than eight, more than nine, more than 10, more than 11, more than 12, more than 13, more than 14, more than 15, more than 16, more than 18, more than 19, or more than 20 nucleoside analogs. In some aspects, the nucleoside analogs in the ASOs are the same. In other aspects, the nucleoside analogs in the ASOs are different. The nucleotide analogs in the ASOs can be any one of or combination of the following nucleoside analogs.

In some aspects, the nucleoside analog comprises a 2'-O-alkyl-RNA; 2'-O-methyl RNA (2'-OMe); 2'-alkoxy-RNA; 2'-O-methoxyethyl-RNA (2'-MOE); 2'-amino-DNA; 2'-fluro-RNA; 2'-fluoro-DNA; arabino nucleic acid (ANA); 2'-fluoro-ANA; bicyclic nucleoside analog; or any combination thereof. In some aspects, the nucleoside analog comprises a sugar modified nucleoside. In some aspects, the nucleoside analog comprises a nucleoside comprising a bicyclic sugar. In some aspects, the nucleoside analog comprises an LNA.

In some aspects, the nucleoside analog is selected from the group consisting of constrained ethyl nucleoside (cEt), 2',4'-constrained 2'-O-methoxyethyl (cMOE), α-L-LNA, β-D-LNA, 2'-0,4-C-ethylene-bridged nucleic acids (ENA), amino-LNA, oxy-LNA, thio-LNA, and any combination thereof. In some aspects, the ASO comprises one or more 5'-methyl-cytosine nucleobases.

IV.D.1. Nucleobase

The term nucleobase includes the purine (e.g., adenine and guanine) and pyrimidine (e.g., uracil, thymine and cytosine) moiety present in nucleosides and nucleotides which form hydrogen bonds in nucleic acid hybridization. In the context of the present disclosure, the term nucleobase also encompasses modified nucleobases which may differ from naturally occurring nucleobases, but are functional during nucleic acid hybridization. In some aspects, the nucleobase moiety is modified by modifying or replacing the nucleobase. In this context, "nucleobase" refers to both naturally occurring nucleobases such as adenine, guanine, cytosine, thymidine, uracil, xanthine and hypoxanthine, as well as non-naturally occurring variants. Such variants are for example described in Hirao et al., (2012) *Accounts of Chemical Research* vol 45 page 2055 and Bergstrom (2009) Current Protocols in Nucleic Acid Chemistry Suppl. 37 1.4.1.

In a some aspects, the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl-cytosine, 5-thiozolo-cytosine, 5-propynyl-cytosine, 5-propynyl-uracil, 5-bromouracil, 5-thiazolo-uracil, 2-thio-uracil, 2'thio-thymine, inosine, diaminopurine, 6-aminopurine, 2-aminopurine, 2,6-diaminopurine, and 2-chloro-6-aminopurine.

The nucleobase moieties may be indicated by the letter code for each corresponding nucleobase, e.g., A, T, G, C, or U, wherein each letter may optionally include modified nucleobases of equivalent function. For example, in the exemplified oligonucleotides, the nucleobase moieties are selected from A, T, G, C, and 5-methyl-cytosine. Optionally, for LNA gapmers, 5-methyl-cytosine LNA nucleosides may be used.

IV.D.2. Sugar Modification

The ASO of the disclosure can comprise one or more nucleosides which have a modified sugar moiety, i.e. a modification of the sugar moiety when compared to the ribose sugar moiety found in DNA and RNA. Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradical bridge between the C2' and C4' carbons on the ribose ring (LNA), or an unlinked ribose ring which typically lacks a bond between the C2' and C3' carbons (e.g., UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'—OH group naturally found in RNA nucleosides. Substituents may, for example be introduced at the 2', 3', 4', or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

IV.D.2.a 2' Modified Nucleosides

A 2' sugar modified nucleoside is a nucleoside which has a substituent other than H or —OH at the 2' position (2' substituted nucleoside) or comprises a 2' linked biradical, and includes 2' substituted nucleosides and LNA (2'-4' biradical bridged) nucleosides. For example, the 2' modified sugar may provide enhanced binding affinity (e.g., affinity enhancing 2' sugar modified nucleoside) and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, 2'-Fluro-DNA, arabino nucleic acids (ANA), and 2'-Fluoro-ANA nucleoside. For further examples, please see, e.g., Freier & Altmann; *Nucl. Acid Res.,* 1997, 25, 4429-4443; Uhlmann, *Curr. Opinion in Drug Development,* 2000, 3(2), 293-213; and Deleavey and Damha, Chemistry and Biology 2012, 19, 937. Below are illustrations of some 2' substituted modified nucleosides.

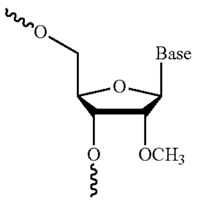
2'-O-Me

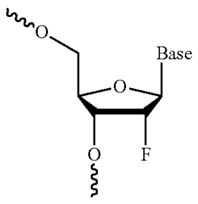
2'F-RNA

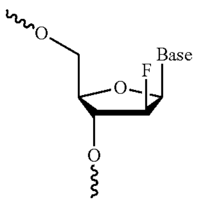
2'F-ANA

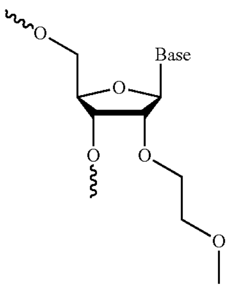
2'-O-MOE

-continued

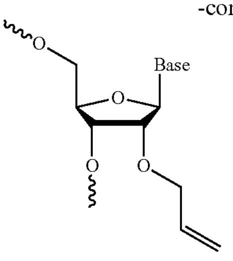

2'-O-Allyl

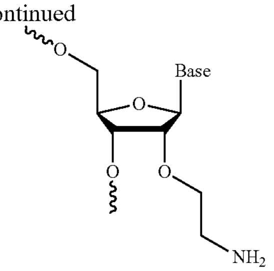

2'-O-Ethylamine

IV.D.2.b Locked Nucleic Acid Nucleosides (LNA).

LNA nucleosides are modified nucleosides which comprise a linker group (referred to as a biradical or a bridge) between C2' and C4' of the ribose sugar ring of a nucleoside (i.e., 2'-4' bridge), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., *Bioorganic & Med. Chem. Lett.* 12, 73-76, Seth et al., *J. Org. Chem.* 2010, Vol 75(5) pp. 1569-81, and Mitsuoka et al., *Nucleic Acids Research* 2009, 37(4), 1225-1238.

In some aspects, the modified nucleoside or the LNA nucleosides of the ASO of the disclosure has a general structure of the formula I or II:

Formula I

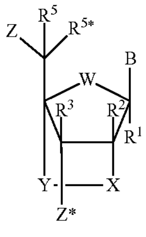

β-D or

Formula II

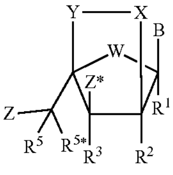

α-L wherein

W is selected from —O—, —S—, —N($R^a$)—, —C($R^aR^b$)—, in particular —O—;

B is a nucleobase or a modified nucleobase moiety;

Z is an internucleoside linkage to an adjacent nucleoside or a 5'-terminal group;

Z* is an internucleoside linkage to an adjacent nucleoside or a 3'-terminal group;

$R^1$, $R^2$, $R^3$, $R^5$ and $R^{5*}$ are independently selected from hydrogen, halogen, alkyl, alkenyl, alkynyl, hydroxy, alkoxy, alkoxyalkyl, alkenyloxy, carboxyl, alkoxycarbonyl, alkylcarbonyl, formyl, azide, heterocycle and aryl; and X, Y, $R^a$ and $R^b$ are as defined herein.

In some aspects, —X—Y—, $R^a$ is hydrogen or alkyl, in particular hydrogen or methyl. In some aspects of —X—Y—, $R^b$ is hydrogen or alkyl, in particular hydrogen or methyl. In other aspects of —X—Y—, one or both of $R^a$ and $R^b$ are hydrogen. In further aspects of —X—Y—, only one of $R^a$ and $R^b$ is hydrogen. In some aspects of —X—Y—, one of $R^a$ and $R^b$ is methyl and the other one is hydrogen. In certain aspects of —X—Y—, $R^a$ and $R^b$ are both methyl at the same time.

In some aspects, —X—, $R^a$ is hydrogen or alkyl, in particular hydrogen or methyl. In some aspects of —X—, $R^b$ is hydrogen or alkyl, in particular hydrogen or methyl. In other aspects of —X—, one or both of $R^a$ and $R^b$ are hydrogen. In certain aspects of —X—, only one of $R^a$ and $R^b$ is hydrogen. In certain aspects of —X—, one of $R^a$ and $R^b$ is methyl and the other one is hydrogen. In other aspects of —X—, $R^a$ and $R^b$ are both methyl at the same time.

In some aspects, —Y—, $R^a$ is hydrogen or alkyl, in particular hydrogen or methyl. In certain aspects of —Y—, R is hydrogen or alkyl, in particular hydrogen or methyl. In other aspects of —Y—, one or both of $R^a$ and $R^b$ are hydrogen. In some aspects of —Y—, only one of $R^a$ and $R^b$ is hydrogen. In other aspects of —Y—, one ofR and $R^b$ is methyl and the other one is hydrogen. In some aspects of —Y—, $R^a$ and $R^b$ are both methyl at the same time.

In some aspects, $R^1$, $R^2$, $R^3$, $R^5$ and R* are independently selected from hydrogen and alkyl, in particular hydrogen and methyl.

In some aspects, $R^1$, $R^2$, $R^3$, $R^5$ and $R^{5*}$ are all hydrogen at the same time.

In some aspects, $R^1$, $R^2$, $R^3$, are all hydrogen at the same time, one of $R^5$ and $R^{5*}$ is hydrogen and the other one is as defined above, in particular alkyl, more particularly methyl.

In some aspects, $R^1$, $R^2$, $R^3$, are all hydrogen at the same time, one of $R^5$ and $R^{5*}$ is hydrogen and the other one is azide.

In some aspects, —X—Y— is —O—$CH_2$—, W is oxygen and $R^1$, $R^2$, $R^3$, $R^5$ and $R^{5*}$ are all hydrogen at the same time. Such LNA nucleosides are disclosed in WO 99/014226, WO 00/66604, WO 98/039352 and WO 2004/046160, which are all hereby incorporated by reference, and include what are commonly known in the art as beta-D-oxy LNA and alpha-L-oxy LNA nucleosides.

In some aspects, —X—Y— is —S—$CH_2$—, W is oxygen and $R^1$, $R^2$, $R^3$, $R^5$ and $R^{5*}$ are all hydrogen at the same time. Such thio LNA nucleosides are disclosed in WO 99/014226 and WO 2004/046160 which are hereby incorporated by reference.

In some aspects, —X—Y— is —NH—$CH_2$—, W is oxygen and $R^1$, $R^2$, $R^3$, $R^5$ and $R^{5*}$ are all hydrogen at the same time. Such amino LNA nucleosides are disclosed in WO 99/014226 and WO 2004/046160, which are hereby incorporated by reference.

In some aspects, —X—Y— is —O—$CH_2CH_2$— or —OCH2$CH_2CH_2$—, W is oxygen, and $R^1$, $R^2$, $R^3$, $R^5$ and $R^{5*}$ are all hydrogen at the same time. Such LNA nucleosides are disclosed in WO 00/047599 and Morita et al., *Bioorganic & Med.Chem. Lett.* 12, 73-76, which are hereby incorporated by reference, and include what are commonly known in the art as 2'-O-4'C-ethylene bridged nucleic acids (ENA).

In some aspects, —X—Y— is —O—$CH_2$—, W is oxygen, $R^1$, $R^2$, $R^3$ are all hydrogen at the same time, one of $R^5$ and $R^{5*}$ is hydrogen and the other one is not hydrogen, such as alkyl, for example methyl. Such 5' substituted LNA nucleosides are disclosed in WO 2007/134181, which is hereby incorporated by reference.

In some aspects, —X—Y— is —O—$CR^aR^b$—, wherein one or both of $R^a$ and $R^b$ are not hydrogen, in particular alkyl such as methyl, W is oxygen, $R^1$, $R^2$, $R^3$ are all hydrogen at the same time, one of $R^5$ and $R^{5*}$ is hydrogen and the other one is not hydrogen, in particular alkyl, for example methyl. Such bis modified LNA nucleosides are disclosed in WO 2010/077578, which is hereby incorporated by reference.

In some aspects, —X—Y— is —O—$CH(CH_2$—O—$CH_3)$— ("2' O-methoxyethyl bicyclic nucleic acid", Seth et al., *J. Org. Chem.* 2010, Vol 75(5) pp. 1569-81).

In some aspects, —X—Y— is —O—$CHR^a$—, W is oxygen and $R^1$, $R^2$, $R^3$, $R^5$ and $R^{5*}$ are all hydrogen at the same time. Such 6'-substituted LNA nucleosides are disclosed in WO 2010/036698 and WO 2007/090071, which are both hereby incorporated by reference. In such 6'-substituted LNA nucleosides, $R^a$ is in particular C1-C6 alkyl, such as methyl.

In some aspects, —X—Y— is —O—$CH(CH_2$—O—$CH_3)$—, W is oxygen and $R^1$, $R^2$, $R^3$, $R^5$ and $R^{5*}$ are all hydrogen at the same time. Such LNA nucleosides are also known in the art as cyclic MOEs (cMOE) and are disclosed in WO 2007/090071.

In some aspects, —X—Y— is —O—$CH(CH_3)$—.

In some aspects, —X—Y— is —O—$CH_2$—O—$CH_2$— (Seth et al., *J. Org. Chem* 2010 op. cit.).

In some aspects, —X—Y— is —O—$CH(CH_3)$—, W is oxygen and $R^1$, $R^2$, $R^3$, $R^5$ and $R^{5*}$ are all hydrogen at the same time. Such 6'-methyl LNA nucleosides are also known in the art as cET nucleosides, and may be either (S)-cET or (R)-cET diastereoisomers, as disclosed in WO 2007/090071 (beta-D) and WO 2010/036698 (alpha-L) which are both hereby incorporated by reference.

In some aspects, —X—Y— is —O—$CR^aR^b$—, wherein neither $R^a$ nor $R^b$ is hydrogen, W is oxygen, and $R^1$, $R^2$, $R^3$, $R^5$ and $R^{5*}$ are all hydrogen at the same time. In certain aspects, $R^a$ and $R^b$ are both alkyl at the same time, in particular both methyl at the same time. Such 6'-di-substituted LNA nucleosides are disclosed in WO 2009/006478 which is hereby incorporated by reference.

In some aspects, —X—Y— is —S—$CHR^a$—, W is oxygen, and $R^1$, $R^2$, $R^3$, $R^5$ and $R^{5*}$ are all hydrogen at the same time. Such 6'-substituted thio LNA nucleosides are disclosed in WO 2011/156202, which is hereby incorporated by reference. In certain aspects of such 6'-substituted thio LNA, $R^a$ is alkyl, in particular methyl.

In some aspects, —X—Y— is —$C(=CH_2)C(R^aR^b)$—, such as, W is oxygen, and $R^1$, $R^2$, $R^3$, $R^5$ and $R^{5*}$ are all hydrogen at the same time. Such vinyl carbo LNA nucleosides are disclosed in WO 2008/154401 and WO 2009/067647, which are both hereby incorporated by reference.

In some aspects, —X—Y— is —$N(OR^a)$—$CH_2$—, W is oxygen and $R^1$, $R^2$, $R^3$, $R^5$ and $R^{5*}$ are all hydrogen at the same time. In some aspects, $R^a$ is alkyl such as methyl. Such LNA nucleosides are also known as N substituted LNAs and are disclosed in WO 2008/150729, which is hereby incorporated by reference.

In some aspects, —X—Y— is —O—$NCH_3$— (Seth et al., *J. Org. Chem* 2010 op. cit.).

In some aspects, —X—Y— is $ON(R^a)$— —$N(R^a)$—O—, —$NR^a$—$CR^aR^b$—$CR^aR^b$—, or —$NR^a$—$CR^aR^b$—, W is oxygen, and $R^1$, $R^2$, $R^3$, $R^5$ and $R^{5*}$ are all hydrogen at the same time. In certain aspects, $R^a$ is alkyl, such as methyl. (Seth et al., *J. Org. Chem* 2010 op. cit.).

In some aspects, $R^5$ and $R^{5*}$ are both hydrogen at the same time. In other aspects, one of $R^5$ and $R^{5*}$ is hydrogen and the other one is alkyl, such as methyl. In such aspects, $R^1$, $R^2$ and $R^3$ can be in particular hydrogen and —X—Y— can be in particular —O—$CH_2$— or —O—$CHC(R^a)_3$, such as —O—$CH(CH_3)$—.

In some aspects, —X—Y— is —$CR^aR^b$—O—$CR^aR^b$—, such as —$CH_2$—O—$CH_2$—, W is oxygen and $R^1$, $R^2$, $R^3$, $R^5$ and $R^{5*}$ are all hydrogen at the same time. In such aspects, $R^a$ can be in particular alkyl such as methyl. Such LNA nucleosides are also known as conformationally restricted nucleotides (CRNs) and are disclosed in WO 2013/036868, which is hereby incorporated by reference.

In some aspects, —X—Y— is —O—$CR^aR^b$—O—$CR^aR^b$—, such as —O—$CH_2$—O—$CH_2$—, W is oxygen and $R^1$, $R^2$, $R^3$, $R^5$ and $R^{5*}$ are all hydrogen at the same time. In certain aspects, $R^a$ can be in particular alkyl such as methyl. Such LNA nucleosides are also known as COC nucleotides and are disclosed in Mitsuoka et al., *Nucleic Acids Research* 2009, 37(4), 1225-1238, which is hereby incorporated by reference.

It will be recognized than, unless specified, the LNA nucleosides may be in the beta-D or alpha-L stereoisoform.

Certain examples of LNA nucleosides are presented in Scheme 1.

Scheme 1

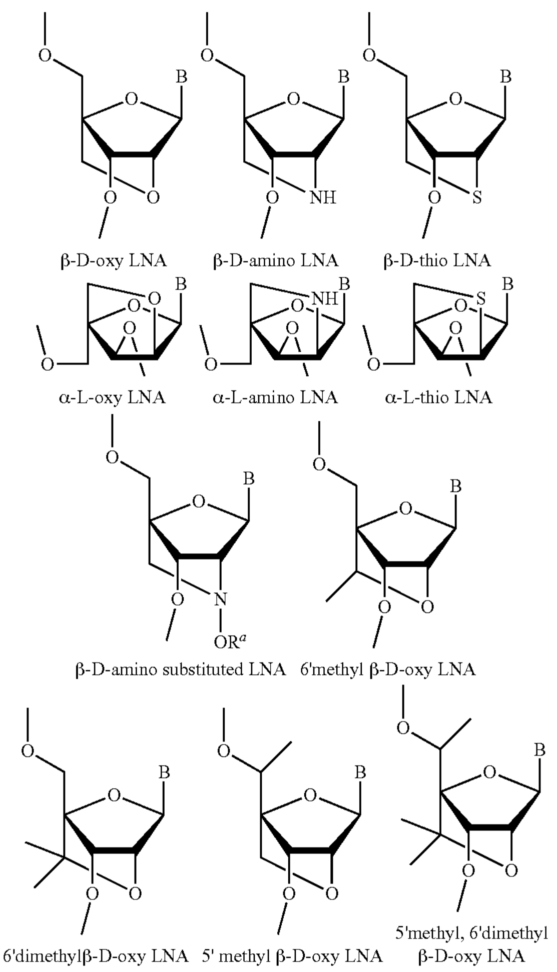

β-D-oxy LNA β-D-amino LNA β-D-thio LNA

α-L-oxy LNA α-L-amino LNA α-L-thio LNA

β-D-amino substituted LNA 6'methyl β-D-oxy LNA

6'dimethylβ-D-oxy LNA 5' methyl β-D-oxy LNA 5'methyl, 6'dimethyl β-D-oxy LNA

-continued

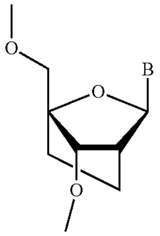

Carbocyclic(vinyl) β-D-LNA

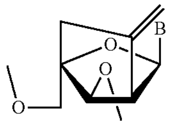

Carbocyclic(vinyl) α-L-LNA

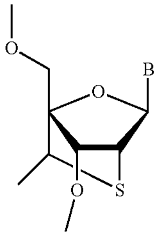

6' methyl thio β-D LNA

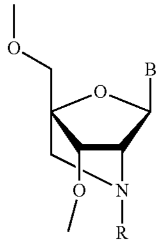

Substituted β-D amino LNA

As illustrated elsewhere, in some aspects of the disclosure the LNA nucleosides in the oligonucleotides are beta-D-oxy-LNA nucleosides.

IV.E. Nuclease Mediated Degradation

Nuclease mediated degradation refers to an oligonucleotide capable of mediating degradation of a complementary nucleotide sequence when forming a duplex with such a sequence.

In some aspects, the oligonucleotide may function via nuclease mediated degradation of the target nucleic acid, where the oligonucleotides of the disclosure are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers.

IV.F. RNase H Activity and Recruitment

The RNase H activity of an antisense oligonucleotide refers to its ability to recruit RNase H when in a duplex with a complementary RNA molecule and induce degradation of the complementary RNA molecule. WO01/23613 provides in vitro methods for determining RNaseH activity, which may be used to determine the ability to recruit RNaseH. Typically, an oligonucleotide is deemed capable of recruiting RNase H if, when provided with a complementary target nucleic acid sequence, it has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers, with phosphorothioate linkages between all monomers in the oligonucleotide, and using the methodology provided by Example 91-95 of WO01/23613.

In some aspects, an oligonucleotide is deemed essentially incapable of recruiting RNaseH if, when provided with the complementary target nucleic acid, the RNaseH initial rate, as measured in pmol/l/min, is less than 20%, such as less than 10%, such as less than 5% of the initial rate determined when using a oligonucleotide having the same base sequence as the oligonucleotide being tested, but containing only DNA monomers, with no 2' substitutions, with phosphorothioate linkages between all monomers in the oligonucleotide, and using the methodology provided by Example 91-95 of WO01/23613.

IV.G. ASO Design

The ASO of the disclosure can comprise a nucleotide sequence which comprises both nucleosides and nucleoside analogs, and can be in the form of a gapmer. Examples of configurations of a gapmer that can be used with the ASO of the disclosure are described in U.S. Patent Appl. Publ. No. 2012/0322851.

The term "gapmer" as used herein refers to an antisense oligonucleotide which comprises a region of RNase H recruiting oligonucleotides (gap) which is flanked 5' and 3' by one or more affinity enhancing modified nucleosides (flanks). The term "LNA gapmer" is a gapmer oligonucleotide wherein at least one of the affinity enhancing modified nucleosides is an LNA nucleoside. The term "mixed wing gapmer" refers to an LNA gapmer wherein the flank regions comprise at least one LNA nucleoside and at least one DNA nucleoside or non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, 2'-Fluro-DNA, arabino nucleic acid (ANA), and 2'-Fluoro-ANA nucleoside(s).

In some aspects, the ASO of the disclosure can be in the form of a mixmer. In some aspects, the ASO of the disclosure can be in the form of a totalmer. In some aspects, in addition to enhancing affinity of the ASO for the target region, some nucleoside analogs also mediate RNase (e.g., RNaseH) binding and cleavage. Since α-L-LNA monomers recruit RNaseH activity to a certain extent, in some aspects, gap regions (e.g., region B as referred to herein) of ASOs containing α-L-LNA monomers consist of fewer monomers recognizable and cleavable by the RNaseH, and more flexibility in the mixmer construction is introduced.

IV.G.1. Gapmer Design

In some aspects, the ASO of the disclosure is a gapmer and comprises a contiguous stretch of nucleotides (e.g., one or more DNA) which is capable of recruiting an RNase, such as RNaseH, referred to herein in as region B (B), wherein region B is flanked at both 5' and 3' by regions of nucleoside analogs 5' and 3' to the contiguous stretch of nucleotides of region B—these regions are referred to as regions A (A) and C (C), respectively. In some aspects, the nucleoside analogs are sugar modified nucleosides (e.g., high affinity sugar modified nucleosides). In certain aspects, the sugar modified nucleosides of regions A and C enhance the affinity of the ASO for the target nucleic acid (i.e., affinity enhancing 2' sugar modified nucleosides). In some aspects, the sugar modified nucleosides are 2' sugar modified nucleosides, such as high affinity 2' sugar modifications, such as LNA and/or 2'-MOE.

In a gapmer, the 5' and 3' most nucleosides of region B are DNA nucleosides, and are positioned adjacent to nucleoside analogs (e.g., high affinity sugar modified nucleosides) of regions A and C, respectively. In some aspects, regions A and C can be further defined by having nucleoside analogs at the end most distant from region B (i.e., at the 5' end of region A and at the 3' end of region C).

In some aspects, the ASOs of the present disclosure comprise a nucleotide sequence of formula (5' to 3') A-B-C, wherein: (A) (5' region or a first wing sequence) comprises at least one nucleoside analog (e.g., 3-5 LNA units); (B) comprises at least four consecutive nucleosides (e.g., 4-24 DNA units), which are capable of recruiting RNase (when formed in a duplex with a complementary RNA molecule, such as the pre-mRNA or mRNA target); and (C) (3' region or a second wing sequence) comprises at least one nucleoside analog (e.g., 3-5 LNA units).

In some aspects, region A comprises 3-5 nucleoside analogs, such as LNA, region B consists of 6-24 (e.g., 6, 7, 8, 9, 10, 11, 12, 13, or 14) DNA units, and region C consists of 3 or 4 nucleoside analogs, such as LNA. Such designs include (A-B-C) 3-14-3, 3-11-3, 3-12-3, 3-13-3, 4-9-4, 4-10-4, 4-11-4, 4-12-4, and 5-10-5. In some aspects, the ASO has a design of LLLDnLLL, LLLLDnLLLL, or LLLLL-DnLLLLL, wherein the L is a nucleoside analog, the D is DNA, and n can be any integer between 4 and 24. In some aspects, n can be any integer between 6 and 14. In some aspects, n can be any integer between 8 and 12. In some aspects, the ASO has a design of LLLMMDnMMLLL, LLLMDnMLLL, LLLLMMDnMMLLLL, LLLL-MDnMLLLL, LLLLLLMMDnMMLLLLL, or LLLLLL-MDnMLLLLL, wherein the D is DNA, n can be any integer between 3 and 15, the L is LNA, and the M is 2'MOE.

Further gapmer designs are disclosed in WO2004/046160, WO 2007/146511, and WO2008/113832, each of which is hereby incorporated by reference in its entirety.

IV.H. Internucleotide Linkages

The monomers of the ASOs described herein are coupled together via linkage groups. Suitably, each monomer is linked to the 3' adjacent monomer via a linkage group.

The person having ordinary skill in the art would understand that, in the context of the present disclosure, the 5' monomer at the end of an ASO does not comprise a 5' linkage group, although it may or may not comprise a 5' terminal group.

In some aspects, the contiguous nucleotide sequence comprises one or more modified internucleoside linkages. The terms "linkage group" or "internucleoside linkage" are intended to mean a group capable of covalently coupling together two nucleosides. Non-limiting examples include phosphate groups and phosphorothioate groups.

The nucleosides of the ASO of the disclosure or contiguous nucleosides sequence thereof are coupled together via linkage groups. Suitably, each nucleoside is linked to the 3' adjacent nucleoside via a linkage group.

In some aspects, the internucleoside linkage is modified from its normal phosphodiester to one that is more resistant to nuclease attack, such as phosphorothioate, which is cleavable by RNaseH, also allows that route of antisense inhibition in reducing the expression of the target gene. In some aspects, at least 75%, at least 80%, at least 85%, at least 90%, at least 91%, at least 92%, at least 93%, at least 94%, at least 95%, at least 96%, at least 97%, at least 98%, at least 99%, or 100% of internucleoside linkages are modified.

V Method of Producing EVs with STING Agonists

V.A. Producer Cells and Modifications

EVs, e.g., exosomes, can be produced from a cell grown in vitro or a body fluid of a subject. When EVs, e.g., exosomes, are produced from in vitro cell culture, various producer cells, e.g., HEK293 cells, can be used. Additional cell types that can be used for the production of the lumen-engineered EVs, e.g., exosomes, described herein include, without limitation, mesenchymal stem cells, T-cells, B-cells, dendritic cells, macrophages, and cancer cell lines. Further examples include: Chinese hamster ovary (CHO) cells, mesenchymal stem cells (MSCs), BJ human foreskin fibroblast cells, fHDF fibroblast cells, AGE.HN® neuronal precursor cells, CAP® amniocyte cells, adipose mesenchymal stem cells, and RPTEC/TERT1 cells. In certain aspects, a producer cell is not a dendritic cell, macrophage, B cell, mast cell, neutrophil, Kupffer-Browicz cell, cell derived from any of these cells, or any combination thereof.

Some aspects may also include genetically modifying the EV, e.g., exosome, to comprise one or more exogenous sequences to produce modified EVs that express exogenous proteins on the vesicle surface. The exogenous sequences can comprise a sequence encoding the EV, e.g., exosome, protein or a modification or a fragment of the EV protein. An extra copy of the sequence encoding the EV, e.g., exosome, protein can be introduced to produce a surface-engineered EV having a higher density of the EV protein. An exogenous sequence encoding a modification or a fragment of the EV, e.g., exosome, protein can be introduced to produce a modified EV containing the modification or the fragment of the EV protein. An exogenous sequence encoding an affinity tag can be introduced to produce a modified EV, e.g., exosome, containing a fusion protein comprising the affinity tag attached to the EV protein.

In some aspects, the exogenous sequence encodes for Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof). In some aspects the modified EV, e.g., exosome, overexpresses Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof). In other aspects, the EV, e.g., exosome, is produced by a cell that overexpresses Scaffold X (e.g., a PTGFRN protein, a BSG protein, an IGSF2 protein, an IGSF3 protein, an IGSF8 protein, an ITGB1 protein, an ITGA4 protein, a SLC3A2 protein, an ATP transporter protein, or a fragment or a variant thereof).

In some aspects, the exogenous sequence encodes for Scaffold Y (e.g., the MARCKS protein, MARCKSL1 protein, BASP1 protein, or a fragment or variant thereof). In some aspects, the modified EV, e.g., exosome, overexpresses Scaffold Y (e.g., the MARCKS protein, MARCKSL1 protein, BASP1 protein, or a fragment or variant thereof). In other aspects, the EV, e.g., exosome, is produced by a cell that overexpresses Scaffold Y (e.g., the MARCKS protein, MARCKSL1 protein, BASP1 protein, or a fragment or variant thereof).

The exogenous sequence may be transiently or stabled expressed in the producer cell or cell line via transfection, transformation, transduction, electroporation, or any other appropriate method of gene delivery or combination thereof known in the art. The exogenous sequence may be integrated into the producer cell genome, or remain extra chromosomal. The exogenous sequence can be transformed as a plasmid. The exogenous sequences can be stably integrated into a genomic sequence of the producer cell, at a targeted site or in a random site. The exogenous sequences can be inserted into a genomic sequence of the producer cell, located within, upstream (5'-end) or downstream (3'-end) of an endogenous sequence encoding the EV, e.g., exosome, protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 CRISPR/Cfpl, CRISPR/C2c1, C2c2, or C2c3, CRISPR/CasY or CasX, TAL-effector nuclease or TALEN, or zinc finger nuclease (ZFN) systems) are within the scope of various aspects.

In some aspects, the producer cell is further modified to comprise an additional exogenous sequence. For example, an additional exogenous sequence can be included to modulate endogenous gene expression, modulate the immune response or immune signaling, or produce an EV, e.g., exosome, including a certain polypeptide as a payload or additional surface expressed ligand. In some aspects, the producer cell can be further modified to comprise an additional exogenous sequence conferring additional functionalities to EVs, e.g., exosomes, for example, specific targeting capabilities, delivery functions, enzymatic functions, increased or decreased half-life in vivo, etc. In some aspects, the producer cell is modified to comprise two exogenous sequences, one encoding the exosome protein or a modification or a fragment of the exosome protein, and the other encoding a protein conferring the additional functionalities to exosomes.

More specifically, the EV, e.g., exosome, of the present can be produced from a cell transformed with a sequence encoding one or more additional exogenous proteins including, but not limited to ligands, cytokines, or antibodies, or any combination thereof. These additional exogenous proteins may enable activation or modulation of additional immune stimulatory signals in combination with the STING agonist. Exemplary additional exogenous proteins contemplated for use include the proteins, ligands, and other molecules described in detail in U.S. Patent Application 62/611,140, which is incorporated herein by reference in its entirety. In some aspects, the EV, e.g., exosome, is further modified with a ligand comprising CD40L, OX40L, or CD27L. In some aspects, the EV, e.g., exosome, is further modified with a cytokine comprising IL-7, IL-12, or IL-15. Any of the one or more exosome proteins described herein can be expressed from a plasmid, an exogenous sequence inserted into the genome or other exogenous nucleic acid such as a synthetic messenger RNA (mRNA).

In some aspects, the EV, e.g., exosome, is further modified to display an antagonistic antibody or an agonistic antibody or a fragment thereof on the EV, e.g., exosome, surface to direct EV uptake, activate, or block cellular pathways to enhance the combinatorial effect of the STING agonist. In some specific aspects, the antibody or fragment thereof is an antibody against DEC205, CLEC9A, CLEC6, DCIR, DC-SIGN, LOX-1, or Langerin. The producer cell may be modified to comprise an additional exogenous sequence encoding for an antagonistic antibody or an agonistic antibody. Alternatively, the antagonistic antibody or agonistic antibody may be covalently linked or conjugated to the EV, e.g., exosome, via any appropriate linking chemistry known in the art. Non-limiting examples of appropriate linking chemistry include amine-reactive groups, carboxyl-reactive groups, sulfhydryl-reactive groups, aldehyde-reactive groups, photoreactive groups, ClickIT chemistry, biotin-streptavidin or other avidin conjugation, or any combination thereof.

V.B. Methods for Encapsulating STING Agonists in EVs

STING agonists can be encapsulated in EVs, e.g., exosomes, via any appropriate technique known in the art. It is contemplated that all known manners of loading biomolecules into EVs, e.g., exosomes, are deemed suitable for use herein. Such techniques include passive diffusion, electroporation, chemical or polymeric transfection, viral transduction, mechanical membrane disruption or mechanical shear, or any combination thereof. The STING agonist and an EV, e.g., exosome, may be incubated in an appropriate buffer during encapsulation.

In one aspect, a STING agonist is encapsulated by an EV, e.g., exosome, by passive diffusion. The STING agonist and the EV, e.g., exosome, may be mixed together and incubated for a time period sufficient for the STING agonist to diffuse through the vesicle lipid bilayer, thereby becoming encapsulated in the EV, e.g., exosome. The STING agonist and the EV, e.g., exosome, may be incubated together for between about 1 to 30 hours, 2 to 24 hours, 4 to 18 hours, 6 to 16 hours, 8 to 14 hours, 10 to 12 hours, 6 to 12 hours, 12 to 20 hours, 14 to 18 hours, or 20 to 30 hours. The STING agonist and the EV, e.g., exosome, may be incubated together for about 2 hours, 4 hours, 6, hours, 8, hours, 10, hours, 12 hours, 14 hours, 16 hours, 18 hours, 20 hours, 22 hours, 24 hours, 26 hours, or 30 hours.

The buffer conditions of the solution of EVs, e.g., exosomes, may also be altered to optimize encapsulation of the STING agonist. In one aspect, the buffer may be a phosphate buffered saline (PBS) with sucrose. PBS is a well-known buffer to those skilled in the art. Additional buffer modifications may also be used, such as shear protectants, viscosity modifiers, and/or solutes that affect vesicle structural properties. Excipients may also be added to improve the efficiency of the STING agonist encapsulation such as membrane softening materials and molecular crowding agents. Other modifications to the buffer may include specific pH ranges and/or concentrations of salts, organic solvents, small molecules, detergents, zwitterions, amino acids, polymers, and/or any combination of the above including multiple concentrations.

The temperature of the solution of EVs, e.g., exosomes, and STING agonists during incubation may be changed to optimize encapsulation of the STING agonist. The temperature may be room temperature. The temperature may be between about 150° C. to 90° C., 15-30° C., 30-50° C., 50-90° C. The temperature may be about 15° C., 20° C., 350 C, 30° C., 350 C, 370° C., 400 C, 450° C., 500 C, 55° C., 60° C., 65° C., 70° C., 75° C., 80° C., 85° C., or 90° C.

The concentration of STING agonist during the incubation of the agonist with the EVs, e.g., exosomes, may also be altered to optimize encapsulation of the STING agonist. The concentration of agonist may be between at least 0.01 mM and 100 mM STING agonist. The concentration of the agonist may be at least 0.01-1 mM, 1-10 mM, 10-50 mM, or 50-100 mM. The concentration of the agonist may be at least 0.01 mM, 0.02 mM, 0.03 mM, 0.04 mM, 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, 10 mM, 15 mM, 20 mM 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM.

The number of extracellular particles incubated with the STING agonist may also be altered to optimize encapsulation of the STING agonist. The number of purified EV, e.g., exosome, particles may be between at least about $10^6$ to at least about $10^{20}$ total particles of purified vesicles. The number of purified particles may be between about $10^8$ to $10^{18}$, $10^{10}$ to $10^{16}$, $10^8$ to $10^{14}$, or $10^{10}$ to $10^{12}$ total particles of purified vesicles. The number of purified particles may be at least about $10^6$, $10^8$, $10^{10}$, $10^{12}$, $10^{14}$, $10^{16}$, 1018, or $10^{20}$ total particles of purified vesicles.

In some aspects, the one or more moieties can be introduced into suitable producer cells using synthetic macromolecules, such as cationic lipids and polymers (Papapetrou et al., *Gene Therapy* 12: S118—S130 (2005)). In some aspects, the cationic lipids form complexes with the one or more moieties through charge interactions. In some of these aspects, the positively charged complexes bind to the negatively charged cell surface and are taken up by the cell by endocytosis. In some other aspects, a cationic polymer can be used to transfect producer cells. In some of these aspects, the cationic polymer is polyethylenimine (PEI). In certain aspects, chemicals such as calcium phosphate, cyclodextrin, or polybrene, can be used to introduce the one or more moieties to the producer cells. The one or more moieties can also be introduced into a producer cell using a physical method such as particle-mediated transfection, "gene gun", biolistics, or particle bombardment technology (Papapetrou et al., *Gene Therapy* 12: S118—S130 (2005)). A reporter gene such as, for example, beta-galactosidase, chloramphenicol acetyltransferase, luciferase, or green fluorescent protein can be used to assess the transfection efficiency of the producer cell.

In some aspects, the producer cell is subjected to several freeze thaw cycles, resulting in cell membrane disruption allowing loading of the one or more moieties.

VC. EV Purification

The EVs, e.g., exosomes, prepared for the present disclosure can be isolated from the producer cells. It is contemplated that all known manners of isolation of EVs, e.g., exosomes, are deemed suitable for use herein. For example, physical properties of EVs, e.g., exosomes, may be employed to separate them from a medium or other source material, including separation on the basis of electrical charge (e.g., electrophoretic separation), size (e.g., filtration, molecular sieving, etc), density (e.g., regular or gradient centrifugation), Svedberg constant (e.g., sedimentation with or without external force, etc). Alternatively, or additionally, isolation may be based on one or more biological properties, and include methods that may employ surface markers (e.g., for precipitation, reversible binding to solid phase, FACS separation, specific ligand binding, non-specific ligand binding, etc.). In yet further contemplated methods, the EVs, e.g., exosomes, may also be fused using chemical and/or physical methods, including PEG-induced fusion and/or ultrasonic fusion.

The EVs, e.g., exosomes, may also be purified after incubation with the STING agonist to remove free, unencapsulated STING agonist from the composition. All manners of previously disclosed methods are also deemed suitable for use herein, including separation on the basis of physical or biological properties of EVs, e.g., exosomes.

Isolation, purification, and enrichment can be done in a general and non-selective manner (typically including serial centrifugation). Alternatively, isolation, purification, and enrichment can be done in a more specific and selective manner (e.g., using producer cell-specific surface markers). For example, specific surface markers may be used in immunoprecipitation, FACS sorting, affinity purification, bead-bound ligands for magnetic separation etc.

In some aspects, size exclusion chromatography can be utilized to isolate or purify the EVs, e.g., exosomes. Size exclusion chromatography techniques are known in the art. Exemplary, non-limiting techniques are provided herein. In some aspects, a void volume fraction is isolated and comprises the EVs, e.g., exosomes, of interest. In some aspects, for example, density gradient centrifugation can be utilized to further isolate the EVs, e.g., exosomes. Still further, in some aspects, it can be desirable to further separate the producer cell-derived EVs, e.g., exosomes, from EVs of other origin. For example, the producer cell-derived EVs, e.g., exosomes, can be separated from non-producer cell-derived EVs, e.g., exosomes, by immunosorbent capture using an antigen antibody specific for the producer cell.

In some aspects, the isolation of EVs, e.g., exosomes, may involve size exclusion chromatography or ion chromatography, such as anion exchange, cation exchange, or mixed mode chromatography. In some aspects, the isolation of EVs, e.g., exosomes, may involve desalting, dialysis, tangential flow filtration, ultrafiltration, or diafiltration, or any combination thereof0. In some aspects, the isolation of EVs, e.g., exosomes, may involve combinations of methods that include, but are not limited to, differential centrifugation, size-based membrane filtration, concentration and/or rate zonal centrifugation. In some aspects, the isolation of EVs, e.g., exosomes, may involve one or more centrifugation steps. The centrifugation may be performed at about 50,000 to 150,000×g. The centrifugation may be performed at about 50,000×g, 75,000×g, 100,000×g, 125,000×g, or 150,000×g.

VI. Pharmaceutical Compositions

Provided herein are pharmaceutical compositions comprising EVs, e.g., exosomes, that are suitable for administration to a subject. The pharmaceutical compositions generally comprise a plurality of EVs, e.g., exosomes, comprising a STING agonist (e.g., encapsulated or expressed on the luminal or exterior surface) and a pharmaceutically-acceptable excipient or carrier in a form suitable for administration to a subject. Pharmaceutically-acceptable excipients or carriers are determined in part by the particular composition being administered, as well as by the particular method used to administer the composition. Accordingly, there is a wide variety of suitable formulations of pharmaceutical compositions comprising a plurality of EVs, e.g., exosomes. (See, e.g., Remington's Pharmaceutical Sciences, Mack Publishing Co., Easton, Pa. 18th ed. (1990)). The pharmaceutical compositions are generally formulated sterile and in full compliance with all Good Manufacturing Practice (GMP) regulations of the U.S. Food and Drug Administration.

In some aspects, the pharmaceutical composition comprises one or more STING agonist and the EVs, e.g., exosomes, described herein. In certain aspects, the EVs, e.g., exosomes, are co-administered with of one or more additional therapeutic agents, in a pharmaceutically acceptable carrier. In some aspects, the pharmaceutical composition comprising the EV, e.g., exosome is administered prior to administration of the additional therapeutic agents. In other aspects, the pharmaceutical composition comprising the EV, e.g., exosome is administered after the administration of the additional therapeutic agents. In further aspects, the pharmaceutical composition comprising the EV, e.g., exosome is administered concurrently with the additional therapeutic agents.

Pharmaceutically-acceptable excipients include excipients that are generally safe (GRAS), non-toxic, and desirable, including excipients that are acceptable for veterinary use as well as for human pharmaceutical use.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the EVs, e.g., exosomes, described herein, use thereof in the compositions is contemplated. Supplementary therapeutic agents may also be incorporated into the compositions. Typically, a pharmaceutical composition is formulated to be compatible with its intended route of administration. The EVs, e.g., exosomes, for the present methods can be administered intrathecally. The EVs, e.g., exosomes, can optionally be administered in combination with other therapeutic agents that are at least partly effective in treating the disease, disorder or condition for which the EVs, e.g., exosomes, are intended.

Solutions or suspensions can include the following components: a sterile diluent such as water, saline solution, fixed oils, polyethylene glycols, glycerin, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, sodium chloride can be added to the composition. Prolonged absorption of the injectable compositions can be brought about by including in the composition a compound which delays absorption, e.g., aluminum monostearate and gelatin.

VI. Kits

Also provided herein are kits comprising one or more exosomes described herein. In some aspects, provided herein is a pharmaceutical pack or kit comprising one or more containers filled with one or more of the ingredients of the pharmaceutical compositions described herein, such as one or more exosomes provided herein, optional an instruction for use. In some aspects, the kits contain a pharmaceutical composition described herein and any prophylactic or therapeutic agent, such as those described herein.

EXAMPLES

The following examples are provided for illustrative purposes only, and are not to be construed as limiting the scope or content of the invention in any way. The practice of the current invention will employ, unless otherwise indicated, conventional methods of protein chemistry, biochemistry, recombinant DNA techniques and pharmacology, within the skill of the art. Such techniques are explained fully in the literature. See, e.g., T.E. Creighton, Proteins: Structures and Molecular Properties (W.H. Freeman and Company, 1993); Green & Sambrook et al., Molecular Cloning: A Laboratory Manual, 4th Edition (Cold Spring Harbor Laboratory Press, 2012); Colowick & Kaplan, Methods In Enzymology (Academic Press); Remington: The Science and Practice of Pharmacy, 22nd Edition (Pharmaceutical Press, 2012); Sundberg & Carey, Advanced Organic Chemistry: Parts A and B, 5th Edition (Springer, 2007).

Example 1: Construction of Exosomes

To generate the EVs (e.g., exosomes) disclosed herein, the following methods will be used.

Exosome Purification

HEK293SF cells will be grown to high density in chemically defined medium for 7 days. Conditioned cell culture media will be collected and centrifuged at 300-800×g for 5 minutes at room temperature to remove cells and large debris. Media supernatant will be then supplemented with 1000 U/L BENZONASE® and incubated at 37° C. for 1 hour in a water bath. Supernatant will be collected and centrifuged at 16,000×g for 30 minutes at 4° C. to remove residual cell debris and other large contaminants. Supernatant will be then ultracentrifuged at 133,900×g for 3 hours at 4° C. to pellet the exosomes. Supernatant will be discarded and any residual media will be aspirated from the bottom of the tube. The pellet will be resuspended in 200-1000 μL PBS (—Ca —Mg).

To further enrich exosome populations, the pellet will be processed via density gradient purification (sucrose or OPTIPREP™). For sucrose gradient purification, the exosome pellet will be layered on top of a sucrose gradient as defined in Table 4 below.

TABLE 4

| WORKING PERCENTAGE (%) | 65% STOCK VOL. (ML) | MILLI-Q VOL. (ML) |
|---|---|---|
| 50 | 3.85 | 1.15 |
| 40 | 3.08 | 1.92 |
| 25 | 1.92 | 3.08 |
| 10 | 0.46 | 2.54 |

The gradient will be spun at 200,000×g for 16 hours at 4° C. in a 12 mL Ultra-Clear (344059) tube placed in a SW 41 Ti rotor to separate the exosome fraction.

The exosome layer will be gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet will be resuspended in a minimal volume of PBS (~200 μL) and stored at 4° C.

For OPTIPREP™ gradient, a 3-tier sterile gradient will be prepared with equal volumes of 10%, 30%, and 45% OPTIPREP™ in a 12 mL Ultra-Clear (344059) tube for a SW 41 Ti rotor. The pellet will be added to the OPTIPREP™ gradient and ultracentrifuged at 200,000×g for 16 hours at 4° C. to separate the exosome fraction. The exosome layer will be then gently collected from the top ~3 mL of the tube.

The exosome fraction will be diluted in ~32 mL PBS in a 38.5 mL Ultra-Clear (344058) tube and ultracentrifuged at 133,900×g for 3 hours at 4° C. to pellet the purified exosomes. The pelleted exosomes will be then resuspended in a minimal volume of PBS (~200 μL) and stored at 4° C.

Encapsulation of STING Agonist 1 mM STING agonist including ML RR-S2 CDA ammonium salt (MedChem Express, Cat. No. HY—12885B) and (3-3 cAIMPdFSH; InvivoGen, Cat. No. tlrl-nacairs) will be incubated with purified exosomes (1E12 total particles) in 300 ul of PBS at 37° C. overnight. The mixture will be then washed twice in PBS and purified by ultra-centrifugation at 100,000×g.

Quantification of the Cyclic Dinucleotide STING Agonist
Sample Preparation for LC-MS Analysis All samples will be suspended in either phosphate-buffered saline (PBS) buffer or PBS and 5% sucrose. Prior to analysis, the particle concentration (P/mL) will be measured by Nanoparticle Tracking Analysis (NTA) on the NanoSight NS300. All standards and samples will be prepared such that each injection contains a virtually identical number of particles. This will be achieved through a combination of diluting samples and spiking exosomes into standards to reach a final concentration of 1.0–4.0E+11 P/mL, depending on the initial particle concentrations of the samples.

Standard curves will be prepared by spiking a known concentration of STING agonist into PBS buffer, then preparing additional standards through serial dilution. Separate standards will be typically prepared such that the final concentrations (after all sample preparation steps) were 25, 50, 250, 500, 1250, 2500, and 5000 nM STING agonist. First, 75.0 μL of each appropriately diluted sample and each matrix-matched standard will be prepared in a separate 1.5 mL microcentrifuge tube. Next, 25.0 μL of exosome lysis buffer (60 mM Tris, 400 mM GdmCl, 100 mM EDTA, 20 mM TCEP, 1.0% Triton X-100) will be added to each tube, then all tubes will be vortexed to mix and will be briefly centrifuged to settle. Finally, 1.0 μL of concentrated Proteinase K enzyme solution (Dako, reference S3004) will be added to each tube, and again all tubes will be vortexed and then will be briefly centrifuged, which will be followed by incubation at 55° C. for 60 minutes. Prior to injection on the LC-MS, samples will be allowed to cool to room temperature and will be transferred to HPLC vials.

LC-MS analysis 20.0 μL of standards and samples will be injected neat into an UltiMate 3000 RSCLnano (Thermo Fisher Scientific) low flow chromatography system without cleanup. Separation of analytes will be performed using a Phenomenex Kinetex EVO C18 core-shell analytical column (50×2.1 mm, 2.6 μm particle size, 100 Å pore size) and the loading pumps delivering a gradient of mobile phase A (MPA:water, 0.1% formic acid) and mobile phase B (MPB:acetonitrile, 0.1% formic acid) at a flowrate of 500 μL/min. The gradient will begin at 2% MPB, which will be held for 2 minutes to load and desalt the STING agonist analyte. The percentage MPB then will be increased from 2-30% over 3 minutes to elute the STING agonist analyte. The percentage MPB then will be increased from 30-95% over 1 minute, held at 95% for 3 minutes, decreased from 95-2% over 1 minute, and then held at 2% for another 3 minutes to re-equilibrate the column.

Mass analyses will be performed with a Q Exactive Basic (Thermo Fisher Scientific) mass spectrometer with the Ion Max source and a HESI-II probe operating in negative ion mode, and mass spectra will be collected using Full MS—SIM mode scanning from 500-800 Da with an AGC target of 1E+6 ions, a maximum injection time of 200 ms, and a resolution of 35,000. STING agonist quantitation will be performed using the monoisotopic −1 STING agonist peak by selectively extracting all ions within the m/z range from 688.97-689.13 Da, and then integrating the resulting peak at a retention time between 3.80-3.90 minutes. The concentration of STING agonist in a given sample will be determined by comparing the STING agonist peak area in that sample to STING agonist peak areas generated by standards, which is typical of relative quantitation.

Example 2: Analysis of Exosome Tropism after Intrathecal Administration

One of the limitations of treating a neuroimmunological disorder (e.g., brain tumor) is the inability of many treatment regimens to cross the blood-brain barrier. Accordingly, the ability of EVs (e.g., exosomes) to target the brain after intrathecal administration was assessed. Briefly, 89Zrf-labeled exosomes were administered to animals via intrathecal dosing. Then, the uptake of the exosomes within different regions of the central nervous system was assessed using both PET scan and autogradiogram. Immunofluorescence microscopy was also used for a more detailed analysis of the cells responsible for the exosome uptake.

As shown in FIG. 1A, after intrathecal administration, there was significant uptake of the exosomes within the meningeal lymphatics of the central nervous system. Immunofluorescence analysis showed that the exosome uptake was observed primarily within the M2 macrophages (CD206+) and the lymphatic endothelial cells (LYVE1+) (see FIG. 1B-1G). These results suggest that intrathecal delivery of EVs (e.g., exosomes) disclosed herein could be a viable treatment option for brain tumors, such as glioma and neoplastic meningitis.

Example 3: Efficacy of Exosomes Comprising a STING Agonist in Treating Glioma To evaluate the anti-cancer effects of the EVs (e.g., exosomes) disclosed herein, an animal model of glioblastoma will be used (e.g., GL261, GL26, CT-2A, and P560), such as those described in Oh, T., et al., *J Transl Med* 29(12):107 (2014). After tumor induction, the animals will be treated with one of the following: (i) PBS alone, (ii) soluble STING agonist, (iii) exosomes loaded with a STING agonist (e.g., such as those disclosed herein). Different routes of administration will also be tested (e.g., intrathecal, intravenous, intraperitoneal). The animals will be periodically monitored and both tumor size and survival of the animals will be assessed. Some of the animals will also be sacrificed, and the anti-tumor response in different tissues will be assessed.

Figure 3A:
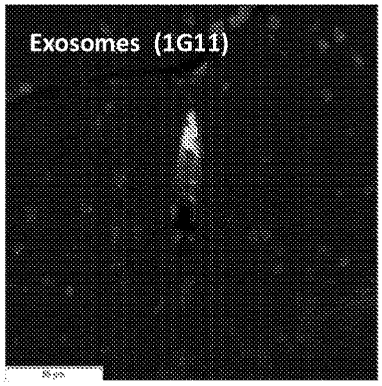
FIGS. 3A-3M are images showing expression of IFN-β along penetrating cerebellar cortex arterioles at two hours (FIGS. 3A-3C) and within macrophages in the periphery of a glioblastoma multiforme tumor (FIGS. 3D-3M).
Figure 3B:
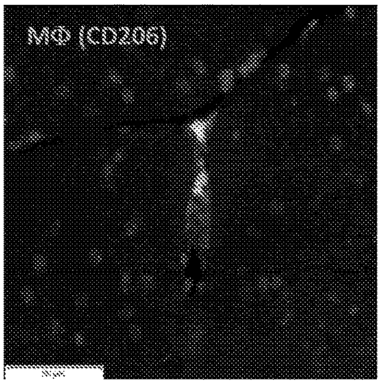
Figure 3C:
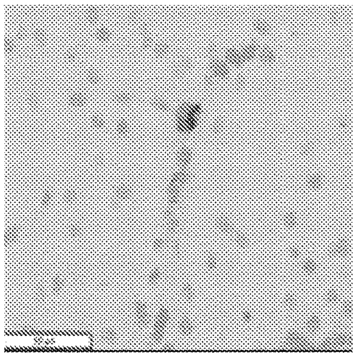
Figure 3D:
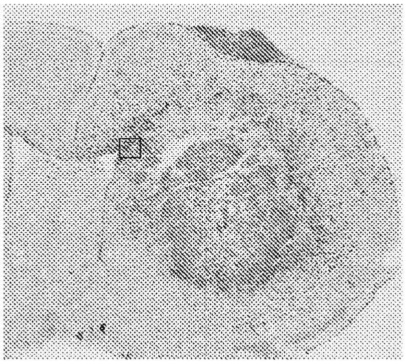
Figure 3E:
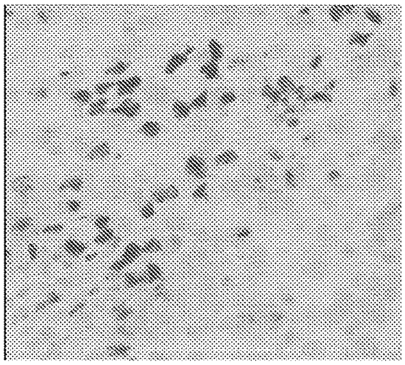
Figure 3F:
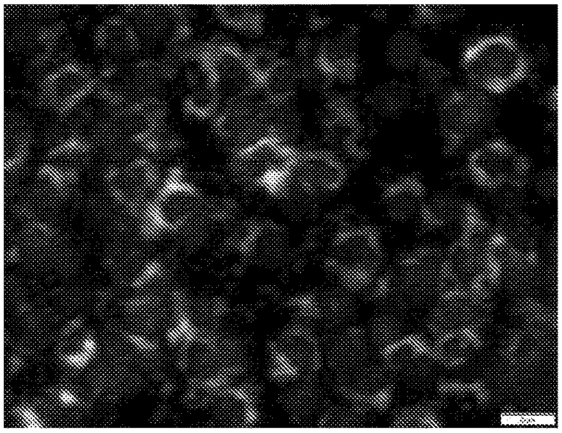
Figure 3G:
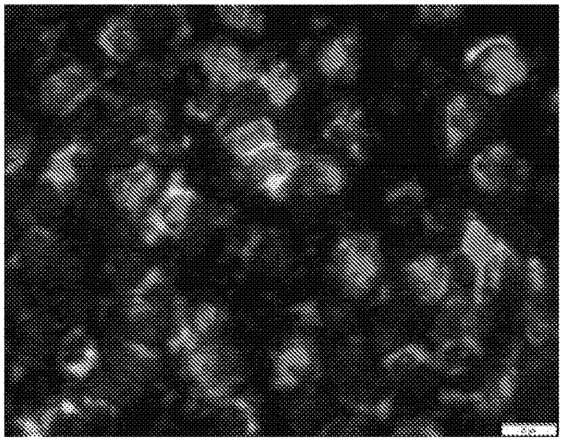
Figure 3H:
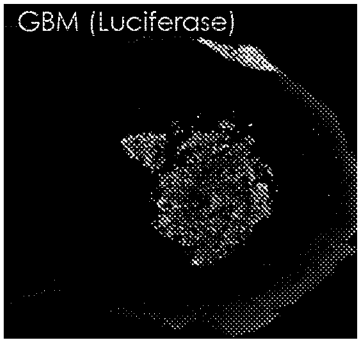
Figure 3I:
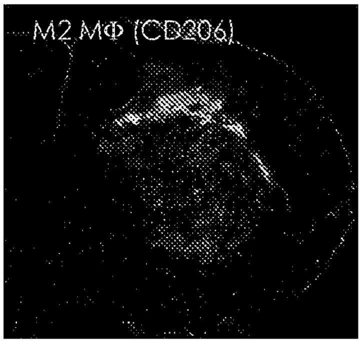
Figure 3J:
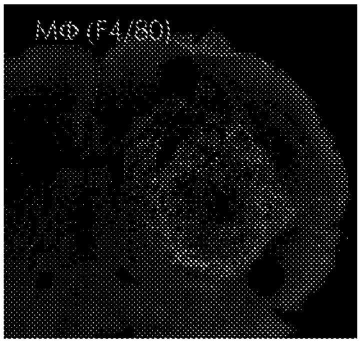
Figure 3K:
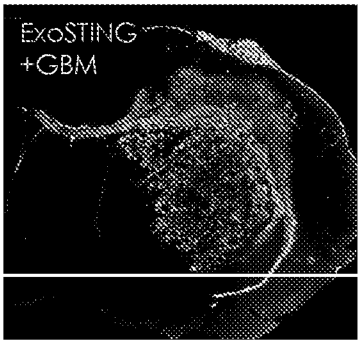
Figure 3L:
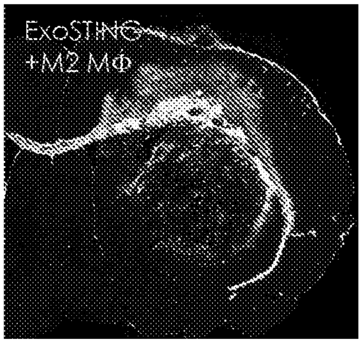
Figure 3M:
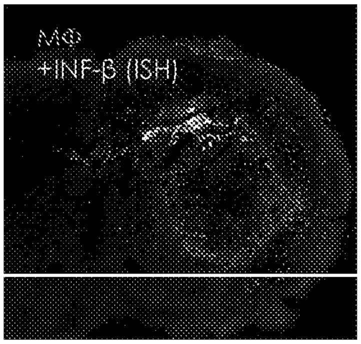
Figure 4A:
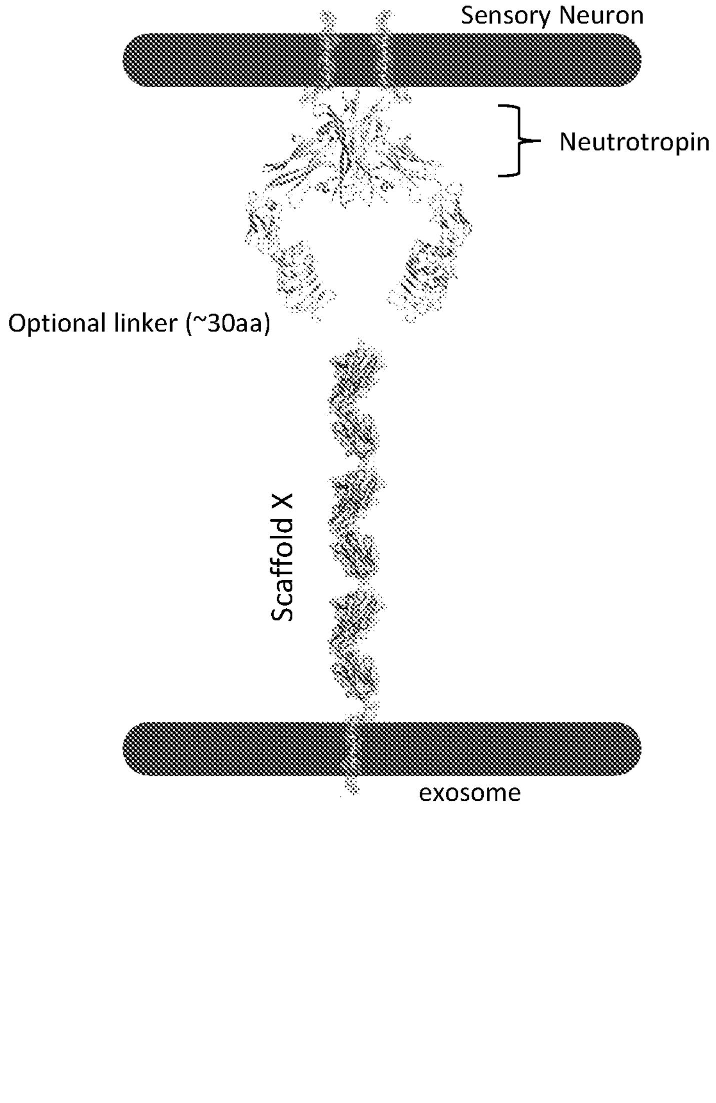
FIG. 4A shows a schematic diagram of exemplary extracellular vesicle (e.g., exosome) targeting Trks using neurotrophin-Scaffold X fusion construct that can be expressed along with a STING agonist. Neurotrophins bind to Trk receptors as a homo dimer and allow the EV to target a sensory neuron.
Figure 4B:
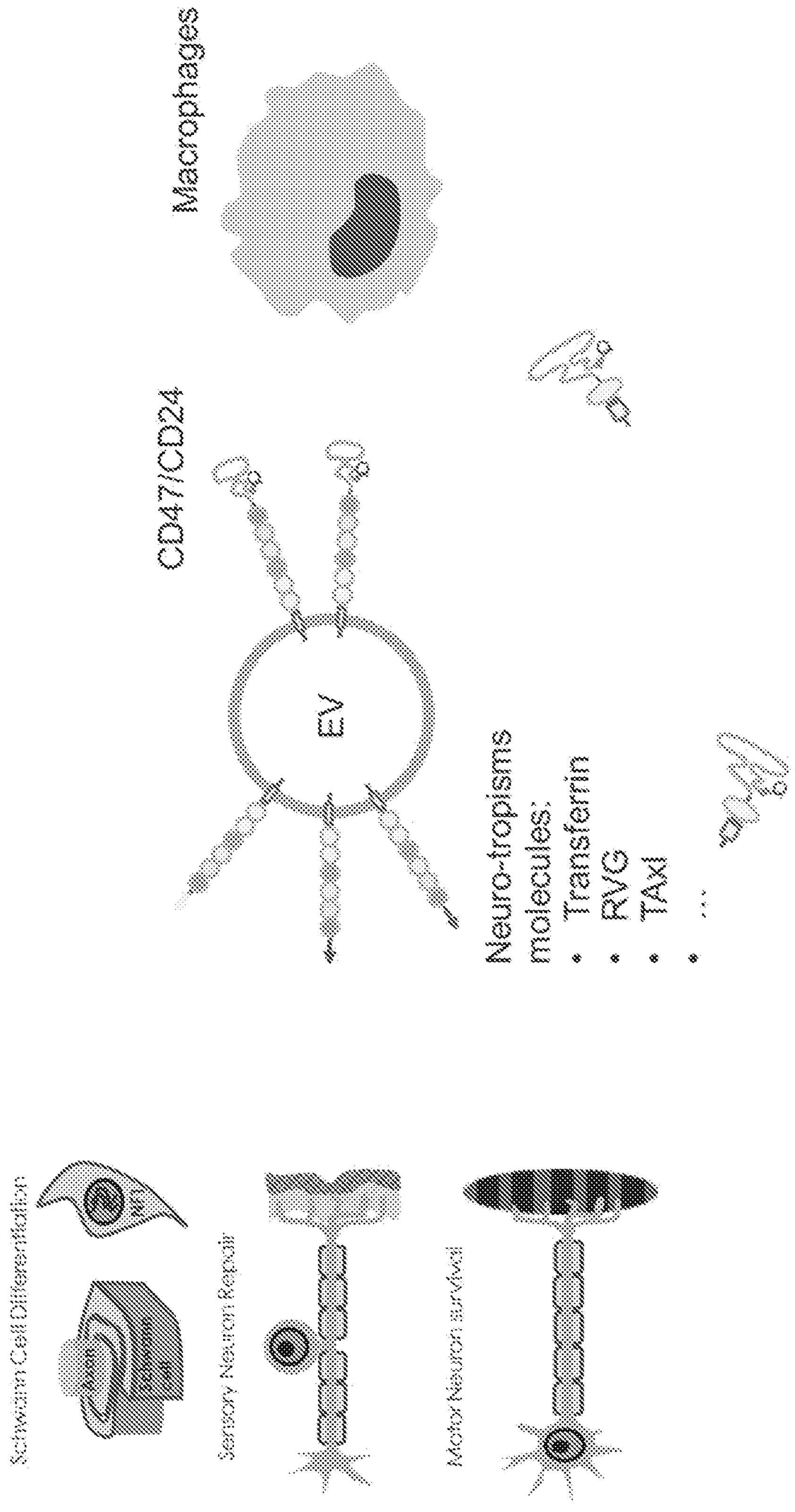
FIG. 4B shows a schematic diagram of exemplary extracellular vesicle (e.g., exosome) having (i) neuro-tropism as well as (ii) an anti-phagocytic signal, e.g., CD47 and/or CD24, on the exterior surface of the EV that can be expressed along with (iii) a STING agonist.

Example 4: Targeted Delivery of Exosomes Comprising a STING Agonist in a Mouse GBM Model Mice were administered exosomes comprising a STING agonist by intrathecal or intra-tumor delivery and assayed for IFN-β expression. Following intrathecal delivery, IFN-β expression was observed by in situ hybridization in meningeal macrophages (FIGS. 2A-2E). Exosomes comprising a STING agonist further induced IFN-β along penetrating cerebellar cortex arterioles at two-hours post administration (FIGS. 3A-3C). Targeted delivery of exosomes comprising a STING agonist into glioblastomas in mice induced IFN-β in tumor infiltrating macrophages (FIGS. 3D-3M).

These experiments will be repeated using exosomes carrying antisense oligonucleotides (ASOs), including ASOs targeting transcription factors, including STAT6 and CEBP/p. Macrophage activation will be measured as well as efficacy in treating glioblastoma multiforme (GBM) and leptomeningeal cancer disease (LMB).

Example 5—Construction and Characterization of Exosomes Surface-Loaded with CD47

Figure 5A:
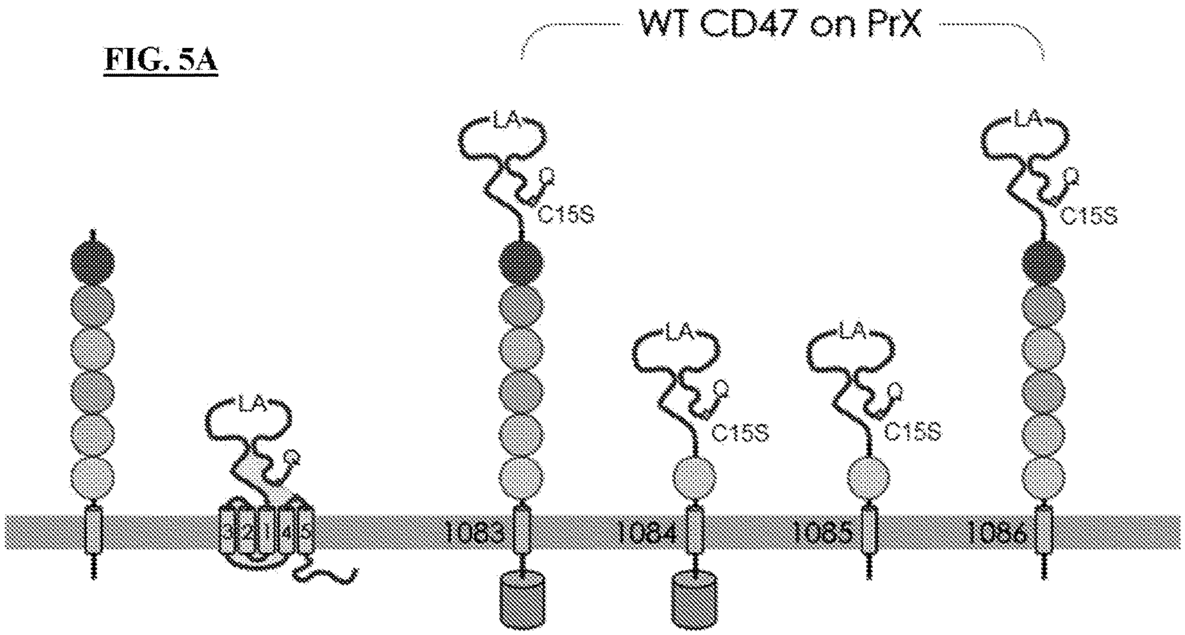
FIGS. 5A-5D are schematic drawings of various CD47-Scaffold X fusion constructs that can be loaded on the extracellular vesicles described herein.
Figure 5B:
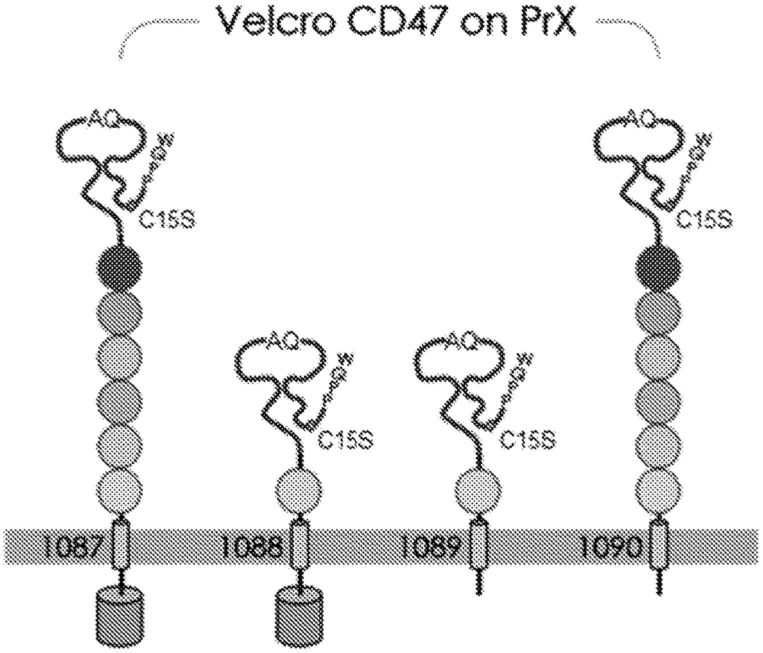
Figure 5C:
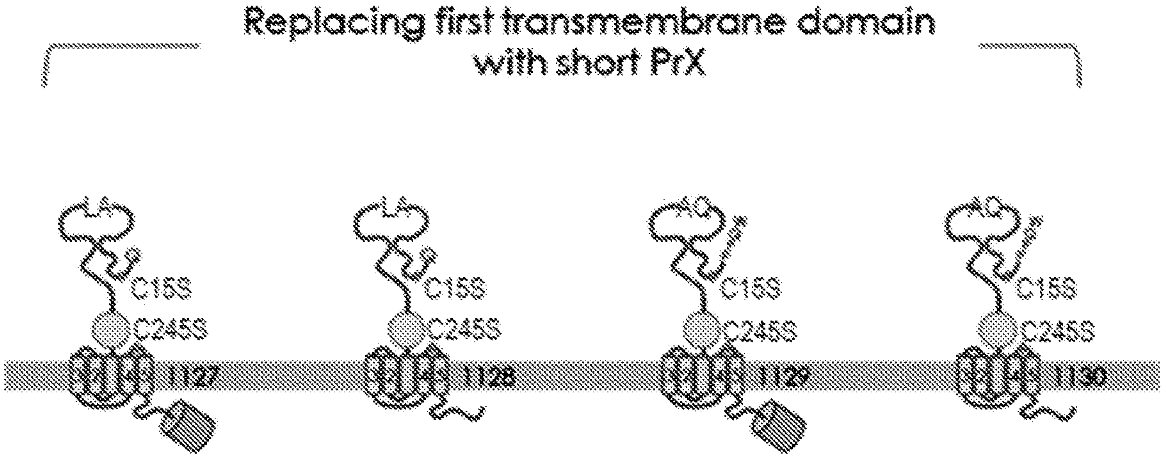
Figure 5D:
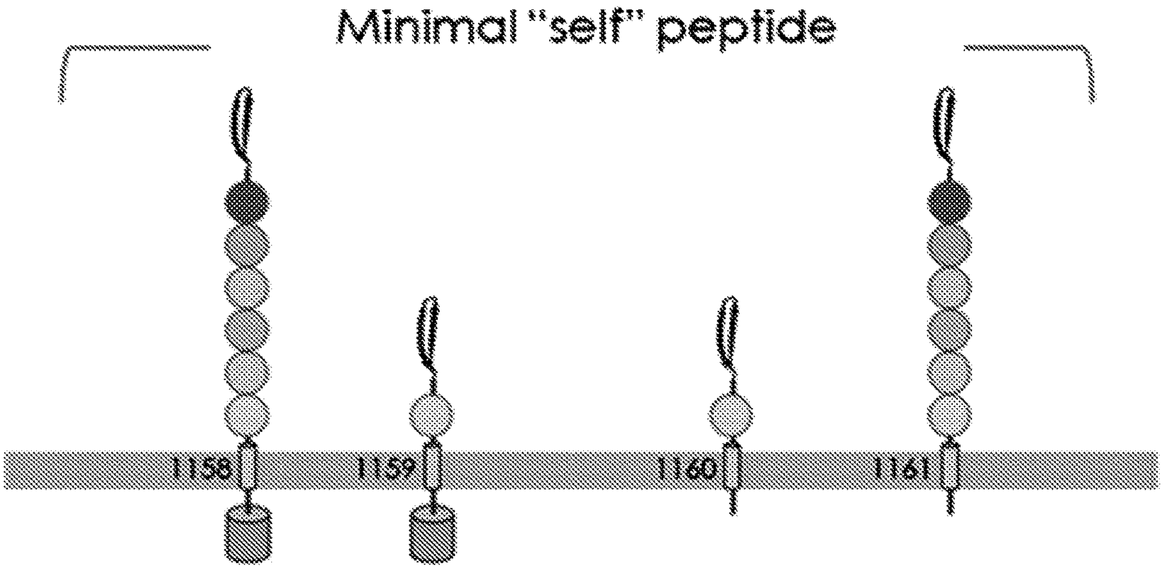
Figure 6:
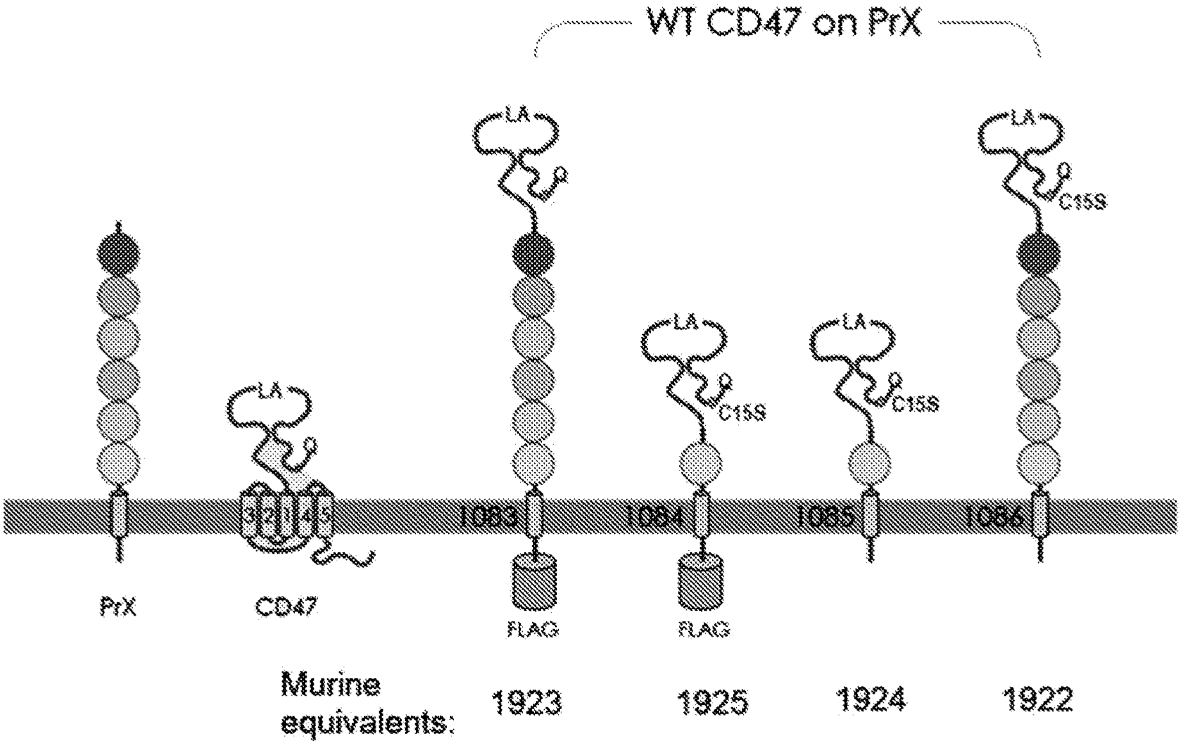
FIG. 6 shows the expression of exemplary mouse CD47-Scaffold X fusion constructs that can be expressed on the surface of modified exosomes described herein. The constructs comprises the extracellular domain of wild-type murine CD47 (with a C15S substitution) fused to either a flag-tagged (1923 and 1925) or non-flag-tagged (1924 and 1922) full length Scaffold X (1923 and 1922) or a truncated Scaffold X (1925 and 1924).

In order to minimize the uptake of administered exosomes by native myeloid cells, various constructs were created to load human CD47 or a fragment thereof on the surface of exosomes. The extracellular domain of human wild type CD47, having a C15S substitution, or Velcro-CD47 was fused to Scaffold X or a fragment thereof and expressed in exosome-producing cells (FIGS. 5A-5B). In addition, exosomes were produced expressing a modified CD47 having a truncated Scaffold X protein inserted in the first domain of human wild type CD47, having a C15S substitution, or Velcro-CD47 (FIG. 5C). Further exosomes were generated expressing a minimal "self" peptide (GNYTCEVTELTREGETIIELK; SEQ ID NO: 400) fused to Scaffold X or a fragment thereof (FIG. 1D; see, e.g., Rodriguez et al., Science 339:971-75 (February 2013)).

Exosomes loaded with each construct were assayed for CD47 expression by ELISA using an anti-CD47 antibody targeted to a specific epitope of CD47 or by binding to SIRPα using a SIRPα (human) signaling reporter cell bioassay (DiscoverX) or using Octet analysis. Because the ELISA antibody recognized a specific epitope of CD47, some constructs were not recognized in the ELISA experiments. The results of each method of assaying CD47 expression are summarized in Table 5.

TABLE 5

Summary of CD47 Exosome Expression Assays

| Construct | ELISA | Bioassay | Octet |
|---|---|---|---|
| 1083 | Y | | Y |
| 1084 | Y | Y | Y |
| 1085 | Y | Y | Y |
| 1086 | Y | | Y |
| 1087 | | | Y |
| 1088 | | Y | Y |
| 1089 | Y | Y | Y |
| 1090 | Y | | Y |
| 1127 | Y | Low | Y |
| 1128 | | Y | Y |
| 1129 | | Low | Y |
| 1130 | | Y | Y |
| 1158 | | Low | Y |
| 1159 | | Low | Y |
| 1160 | | Low | Y |
| 1161 | | Low | Y |
| PrX | | | |

Example 6—ExoSTING Efficacy in Syngeneic GL261-Luc Gliobastoma Multiform Model The efficacy of exoSTING treatment in a syngeneic GL261-Luc glioblastoma multiforme model was assessed. Briefly, $5\times10^5$ GL261-LUC cells were administered via a 10 μl intra-striatal stereotactic injection to the mice. Tumor presence was confirmed by T1-weighted (T1W) MRI scan 15 days later. Four days after the MRI scan, when tumors were approximately 80-100 $mm^3$, stereotactic coordinates were used to administer 5 μl (~120 ng) ExoSTING every 72 hours for 3 total injections to some of the animals. The other animals (i.e., control) were treated with one of the following: (i) PrX exosomes (i.e., comprising Scaffold X alone), (ii) phosphate buffered saline (PBS), (iii) an anti-PD-L1 antibody, or (iv) Temozolamide (TMZ). Anti-PDL-1 mAb was dosed twice weekly for 2 weeks (IOmpk IV). Phosphate buffered saline (PBS) alone and Temozolomide (TMZ) alone were dosed twice weekly for 2 weeks (30mpk IP). Mice were then followed for survival end-point.

Figure 7A:
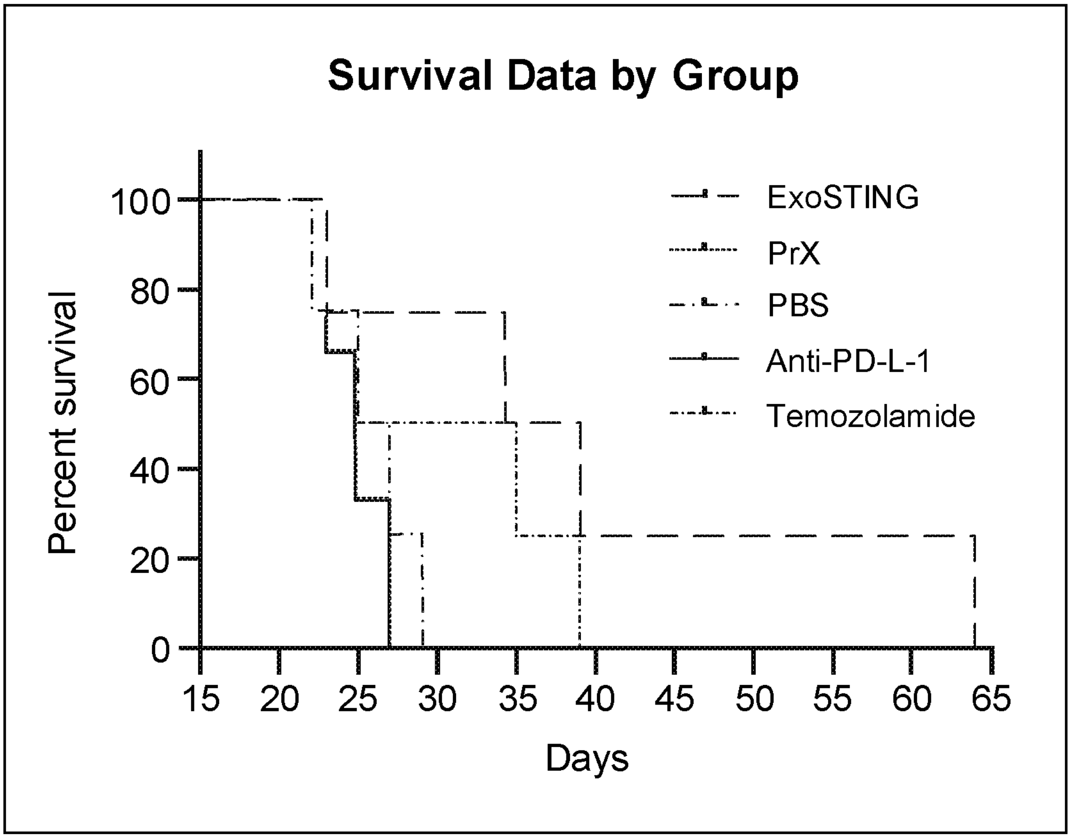
FIGS. 7A-7B show ExoSTING efficacy in a syngeneic GL261-Luc glioblastoma multiform model.
Figure 7B:
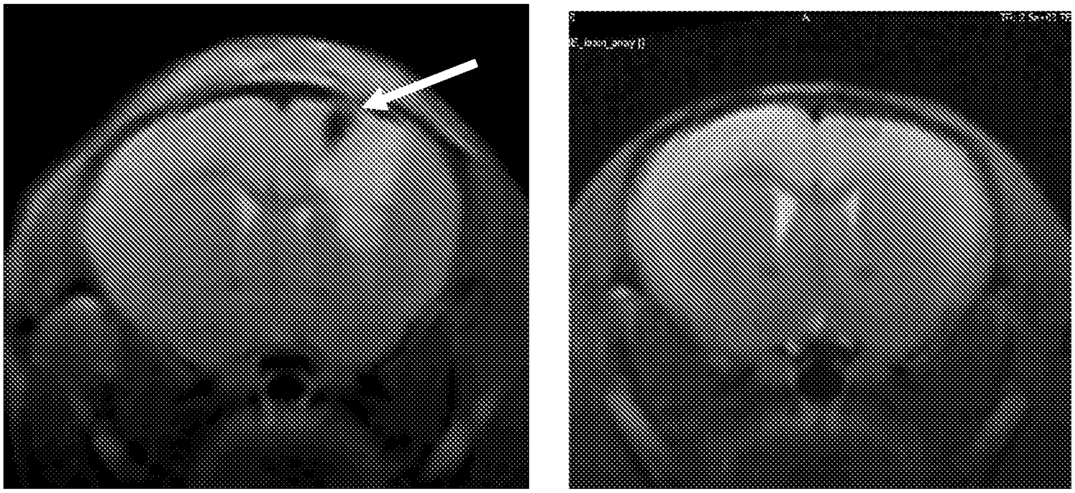

As shown in FIG. 7A, animals from the different control groups (i.e., treated with either exosome alone, PBS only, or Temozolamide alone) all succumbed to the tumor by about day 40 post tumor induction. In contrast, some of the animals treated with the exoSTING survived as far out as about day 65 post tumor induction. The MRI scan shown in FIG. 7B confirms the reduced tumor burden observed in the exoSTING treated animals.

Collectively, the above data demonstrates that the exosomes described in the present disclosure (comprising a STING agonist) are capable of treating certain tumors.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

The present disclosure provides, inter alia, compositions of exosomes encapsulating STING agonists for use as therapeutics, e.g., in treating brain tumor. The present disclosure also provides methods of producing exosomes encapsulating STING agonists and methods of administering such exosomes as therapeutics, e.g., in treating brain tumor. While various specific aspects have been illustrated and described, the above specification is not restrictive. It will be appreciated that various changes can be made without departing from the spirit and scope of the invention(s). Many variations will become apparent to those skilled in the art upon review of this specification.

The invention claimed is:

1. A method of treating a glioblastoma multiforme in a subject in need thereof comprising administering to the subject a composition comprising an extracellular vesicle EV and a stimulator of interferon genes protein STING agonist, wherein the EV overexpresses a Scaffold X protein selected from the group consisting of: prostaglandin F2 receptor negative regulator PTGFRN, basigin BSG, immunoglobulin superfamily member 2 IGSF2, immunoglobulin superfamily member 3 IGSF3, immunoglobulin superfamily member 8 IGSF8, integrin beta-1 ITGB1, integrin alpha-4 ITGA4, 4F2 cell-surface antigen heavy chain SLC3A2, ATP transporter protein, and wherein the Scaffold X protein is a whole protein or a fragment thereof.

2. The method of claim 1, wherein the composition is administered intrathecally or intratumorally.

3. The method of claim 1, wherein the extracellular vesicle is an exosome.

4. The method of claim 1, wherein the STING agonist is associated with the extracellular vesicle.

5. The method of claim 1, wherein the Scaffold X protein is prostaglandin F2 receptor negative regulator PTGFRN or a fragment thereof.

6. The method of claim 5, wherein the STING agonist is linked to the PTGFRN protein or fragment thereof, optionally by a linker.

7. The method of claim 1, wherein the extracellular vesicle is produced by a cell that overexpresses a PTGFRN protein.

8. The method of claim 1, wherein the extracellular vesicle further comprises a ligand, a cytokine, or an antibody.

9. The method of claim 8, wherein the antibody comprises an antagonistic antibody and/or an agonistic antibody.

10. The method of claim 1, wherein the STING agonist is a cyclic dinucleotide or a non-cyclic dinucleotide.

11. The method of claim 1, wherein the STING agonist comprises a lipid-binding tag.

12. The method of claim 1, wherein the concentration of the STING agonist associated with the extracellular vesicle is about 0.01 μM to 100 μM.

13. The method of claim 1, wherein the STING agonist is selected from the group consisting of:
CL606
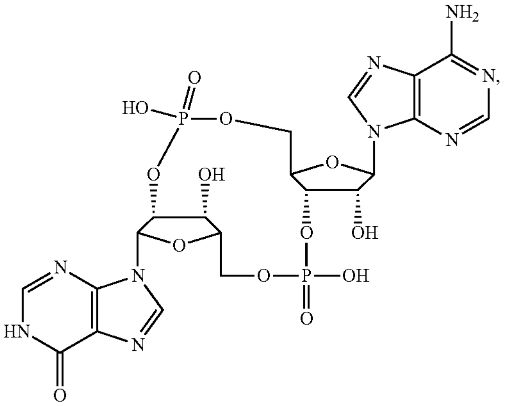
(3',2')c-AIMP
CL611
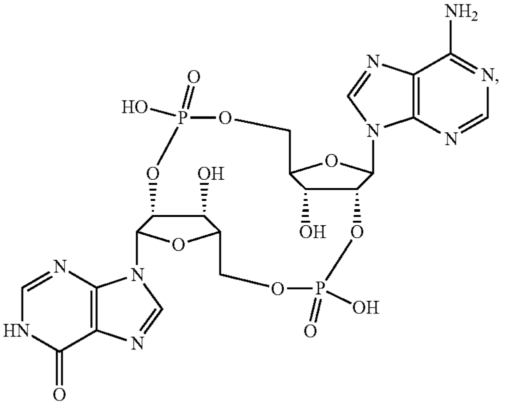
(2',2')c-AIMP
CL602
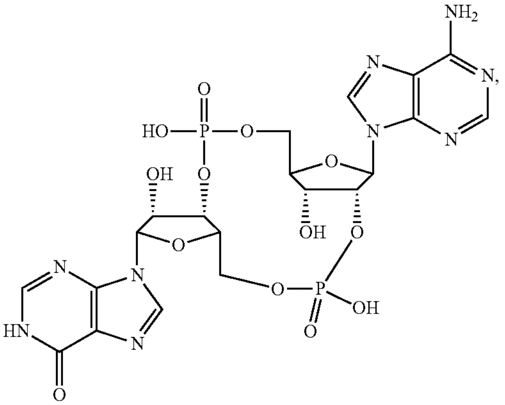
(2',3')c-AIMP
-continued
CL655
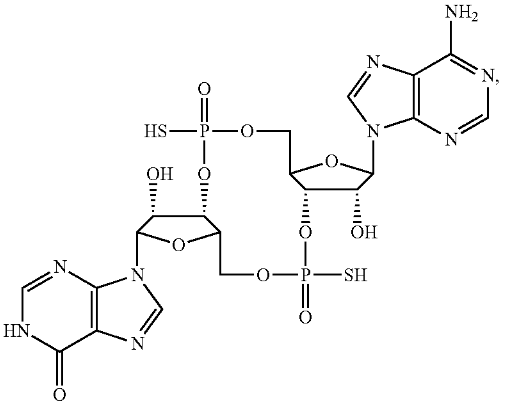
c-AIMP(S)
CL604
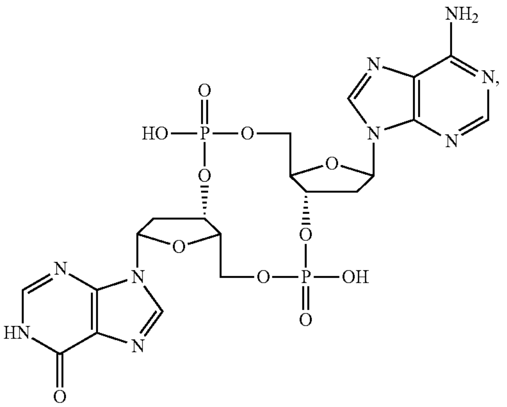
c-(dAMP-dIMP)
CL609
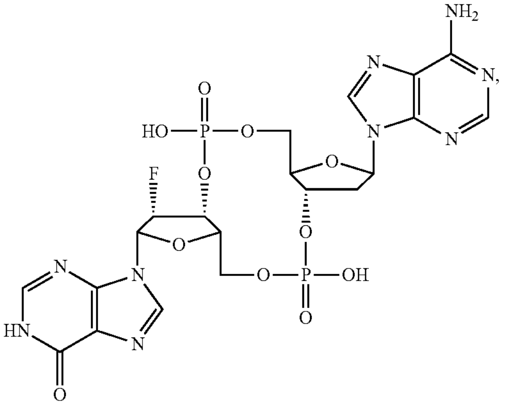
c-(dAMP-2'FdIMP)

-continued
CL614
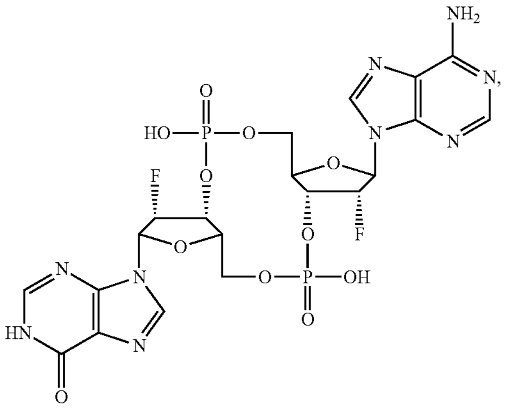
c-(2'FdAMP-2'FdIMP)
CL656
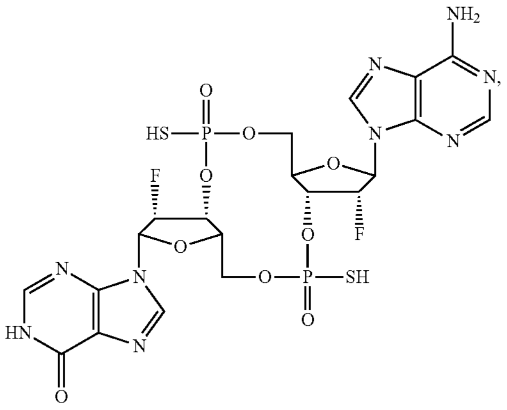
c-[2'FdAMP(S)-2'FdIMP(S)]
CL647
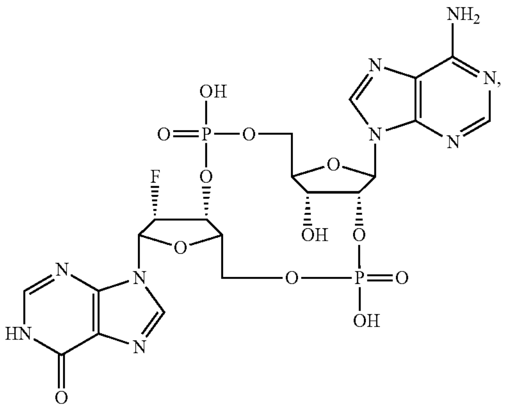
(2',3')c-(AMP-2'FdIMP)
-continued
CL626
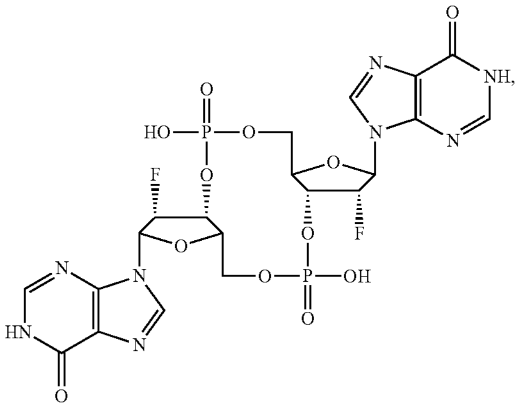
c-di(2'FdIMP)
CL629
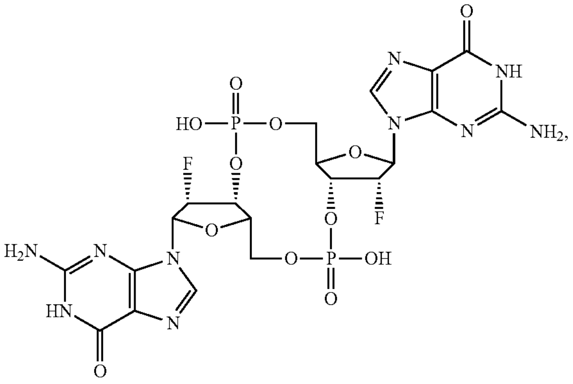
c-di(2'FdGMP)
CL603
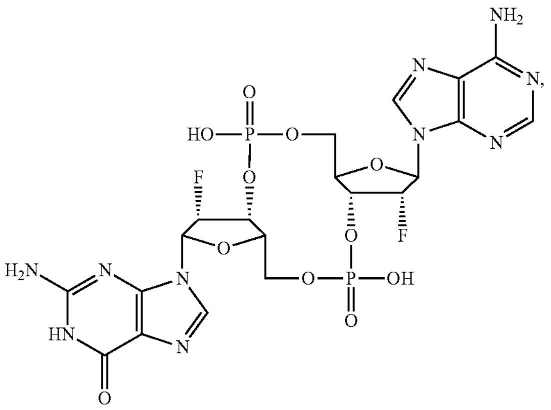
c-(2'FdGMP-2'FdAMP)

-continued

CL632

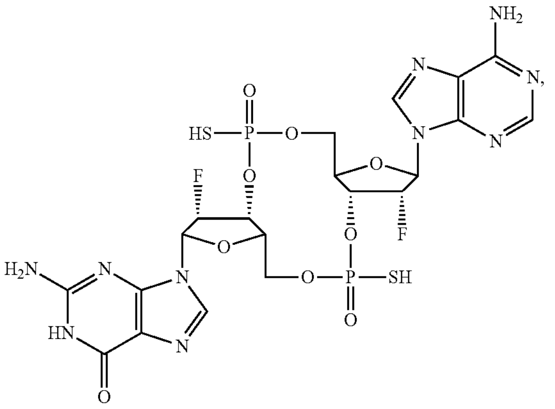

c-[2'FdGMP(S)-2'FdAMP(S)]

CL633

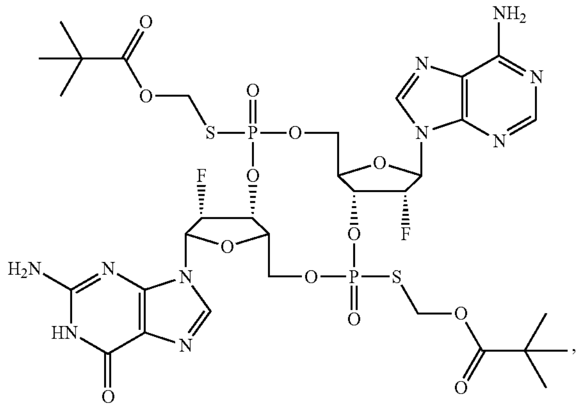

c-[2'FdGMP(S)-2'FdAMP(S)](POM)$_2$

-continued

CL659

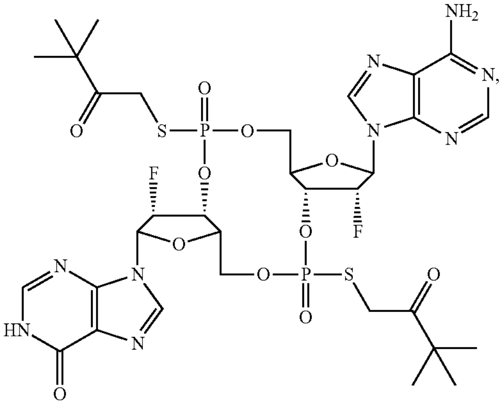

c-[2'FdAMP(S)-2'FdIMP(S)](POM)$_2$ and a pharmaceutically acceptable salt thereof.

14. The method of claim 13, wherein the STING agonist is in the lumen of the extracellular vesicle and is not linked to a scaffold moiety.

15. The method of claim 14, wherein the composition further comprises a pharmaceutically acceptable carrier.

16. The method of claim 1, wherein the administering induces or modulates an immune response and/or an inflammatory response in the subject.

17. The method of claim 1, further comprising administering an additional therapeutic agent.

18. The method of claim 17, wherein the additional therapeutic agent is an antibody or antigen-binding fragment thereof or an IL-12 moiety.

19. A kit comprising a composition which comprises an extracellular vesicle and a STING agonist and instructions for use according to the method of claim 1.

20. The method of claim 1, wherein the extracellular vesicle further comprises one or more antisense oligonucleotides ASO.

21. The method of claim 1, wherein the EV comprises an anti-phagocytic signal on the exterior surface of the EV.

22. The method of claim 1, wherein the EV further comprises one or more tropism moieties that alters the distribution of the EV in a particular cell, tissue or organ.

* * * * *

SEQUENCE LISTING

```
<160> NUMBER OF SEQ ID NOS: 400

<210> SEQ ID NO 1
<211> LENGTH: 879
<212> TYPE: PRT
<213> ORGANISM: Artificial Sequence
<220> FEATURE:
<223> OTHER INFORMATION: Synthetic: PTGFRN Protein

<400> SEQUENCE: 1

Met Gly Arg Leu Ala Ser Arg Pro Leu Leu Leu Ala Leu Leu Ser Leu
1               5                   10                  15

Ala Leu Cys Arg Gly Arg Val Val Arg Val Pro Thr Ala Thr Leu Val
            20                  25                  30
```

-continued

```
Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
        115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Pro Ser Leu Ser Leu Arg
145                 150                 155                 160

Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
            180                 185                 190

Arg Arg Ser Val Leu Ala Leu Thr His Glu Gly Arg Phe His Pro Gly
        195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
        275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
        355                 360                 365

Gly Tyr Tyr Tyr Cys His Val Ser Leu Trp Ala Pro Gly His Asn Arg
    370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                405                 410                 415

Val Pro Gly Phe Ala Asp Asp Pro Thr Glu Leu Ala Cys Arg Val Val
            420                 425                 430

Asp Thr Lys Ser Gly Glu Ala Asn Val Arg Phe Thr Val Ser Trp Tyr
        435                 440                 445

Tyr Arg Met Asn Arg Arg Ser Asp Asn Val Val Thr Ser Glu Leu Leu
```

-continued

```
    450                 455                 460

Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
            500                 505                 510

Tyr Tyr Cys Val Val Ser Ala Trp Thr Lys Gln Arg Asn Asn Ser Trp
        515                 520                 525

Val Lys Ser Lys Asp Val Phe Ser Lys Pro Val Asn Ile Phe Trp Ala
    530                 535                 540

Leu Glu Asp Ser Val Leu Val Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
            580                 585                 590

Val Gly Asp Leu Ser Ser Pro Asn Glu Thr Lys Tyr Ile Ile Ser Leu
        595                 600                 605

Asp Gln Asp Ser Val Val Lys Leu Glu Asn Trp Thr Asp Ala Ser Arg
    610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
            660                 665                 670

Thr Ser Leu Ser Asn Pro Ile Glu Ile Asp Phe Gln Thr Ser Gly Pro
        675                 680                 685

Ile Phe Asn Ala Ser Val His Ser Asp Thr Pro Ser Val Ile Arg Gly
    690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
    770                 775                 780

Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Cys Lys Lys Glu Val Gln
    850                 855                 860

Glu Thr Arg Arg Glu Arg Arg Arg Leu Met Ser Met Glu Met Asp
865                 870                 875
```

<210> SEQ ID NO 2
<211> LENGTH: 731
<212> TYPE: PRT
<213> ORGANISM: Artificial Sequence
<220> FEATURE:
<223> OTHER INFORMATION: Synthetic: PTGFRN Protein Fragment #1

<400> SEQUENCE: 2

```
Pro Ser Ala Arg Pro Pro Pro Ser Leu Ser Leu Arg Glu Gly Glu Pro
1               5                   10                  15

Phe Glu Leu Arg Cys Thr Ala Ala Ser Ala Ser Pro Leu His Thr His
            20                  25                  30

Leu Ala Leu Leu Trp Glu Val His Arg Gly Pro Ala Arg Arg Ser Val
        35                  40                  45

Leu Ala Leu Thr His Glu Gly Arg Phe His Pro Gly Leu Gly Tyr Glu
    50                  55                  60

Gln Arg Tyr His Ser Gly Asp Val Arg Leu Asp Thr Val Gly Ser Asp
65                  70                  75                  80

Ala Tyr Arg Leu Ser Val Ser Arg Ala Leu Ser Ala Asp Gln Gly Ser
                85                  90                  95

Tyr Arg Cys Ile Val Ser Glu Trp Ile Ala Glu Gln Gly Asn Trp Gln
            100                 105                 110

Glu Ile Gln Glu Lys Ala Val Glu Val Ala Thr Val Val Ile Gln Pro
        115                 120                 125

Ser Val Leu Arg Ala Ala Val Pro Lys Asn Val Ser Val Ala Glu Gly
    130                 135                 140

Lys Glu Leu Asp Leu Thr Cys Asn Ile Thr Thr Asp Arg Ala Asp Asp
145                 150                 155                 160

Val Arg Pro Glu Val Thr Trp Ser Phe Ser Arg Met Pro Asp Ser Thr
                165                 170                 175

Leu Pro Gly Ser Arg Val Leu Ala Arg Leu Asp Arg Asp Ser Leu Val
            180                 185                 190

His Ser Ser Pro His Val Ala Leu Ser His Val Asp Ala Arg Ser Tyr
        195                 200                 205

His Leu Leu Val Arg Asp Val Ser Lys Glu Asn Ser Gly Tyr Tyr Tyr
    210                 215                 220

Cys His Val Ser Leu Trp Ala Pro Gly His Asn Arg Ser Trp His Lys
225                 230                 235                 240

Val Ala Glu Ala Val Ser Ser Pro Ala Gly Val Gly Val Thr Trp Leu
                245                 250                 255

Glu Pro Asp Tyr Gln Val Tyr Leu Asn Ala Ser Lys Val Pro Gly Phe
            260                 265                 270

Ala Asp Asp Pro Thr Glu Leu Ala Cys Arg Val Val Asp Thr Lys Ser
        275                 280                 285

Gly Glu Ala Asn Val Arg Phe Thr Val Ser Trp Tyr Tyr Arg Met Asn
    290                 295                 300

Arg Arg Ser Asp Asn Val Val Thr Ser Glu Leu Leu Ala Val Met Asp
305                 310                 315                 320

Gly Asp Trp Thr Leu Lys Tyr Gly Glu Arg Ser Lys Gln Arg Ala Gln
                325                 330                 335

Asp Gly Asp Phe Ile Phe Ser Lys Glu His Thr Asp Thr Phe Asn Phe
            340                 345                 350

Arg Ile Gln Arg Thr Thr Glu Glu Asp Arg Gly Asn Tyr Tyr Cys Val
        355                 360                 365
```

```
Val Ser Ala Trp Thr Lys Gln Arg Asn Asn Ser Trp Val Lys Ser Lys
    370                 375                 380

Asp Val Phe Ser Lys Pro Val Asn Ile Phe Trp Ala Leu Glu Asp Ser
385                 390                 395                 400

Val Leu Val Val Lys Ala Arg Gln Pro Lys Pro Phe Phe Ala Ala Gly
                405                 410                 415

Asn Thr Phe Glu Met Thr Cys Lys Val Ser Ser Lys Asn Ile Lys Ser
            420                 425                 430

Pro Arg Tyr Ser Val Leu Ile Met Ala Glu Lys Pro Val Gly Asp Leu
        435                 440                 445

Ser Ser Pro Asn Glu Thr Lys Tyr Ile Ile Ser Leu Asp Gln Asp Ser
    450                 455                 460

Val Val Lys Leu Glu Asn Trp Thr Asp Ala Ser Arg Val Asp Gly Val
465                 470                 475                 480

Val Leu Glu Lys Val Gln Glu Asp Glu Phe Arg Tyr Arg Met Tyr Gln
                485                 490                 495

Thr Gln Val Ser Asp Ala Gly Leu Tyr Arg Cys Met Val Thr Ala Trp
            500                 505                 510

Ser Pro Val Arg Gly Ser Leu Trp Arg Glu Ala Ala Thr Ser Leu Ser
        515                 520                 525

Asn Pro Ile Glu Ile Asp Phe Gln Thr Ser Gly Pro Ile Phe Asn Ala
    530                 535                 540

Ser Val His Ser Asp Thr Pro Ser Val Ile Arg Gly Asp Leu Ile Lys
545                 550                 555                 560

Leu Phe Cys Ile Ile Thr Val Glu Gly Ala Ala Leu Asp Pro Asp Asp
                565                 570                 575

Met Ala Phe Asp Val Ser Trp Phe Ala Val His Ser Phe Gly Leu Asp
            580                 585                 590

Lys Ala Pro Val Leu Leu Ser Ser Leu Asp Arg Lys Gly Ile Val Thr
        595                 600                 605

Thr Ser Arg Arg Asp Trp Lys Ser Asp Leu Ser Leu Glu Arg Val Ser
    610                 615                 620

Val Leu Glu Phe Leu Leu Gln Val His Gly Ser Glu Asp Gln Asp Phe
625                 630                 635                 640

Gly Asn Tyr Tyr Cys Ser Val Thr Pro Trp Val Lys Ser Pro Thr Gly
                645                 650                 655

Ser Trp Gln Lys Glu Ala Glu Ile His Ser Lys Pro Val Phe Ile Thr
            660                 665                 670

Val Lys Met Asp Val Leu Asn Ala Phe Lys Tyr Pro Leu Leu Ile Gly
        675                 680                 685

Val Gly Leu Ser Thr Val Ile Gly Leu Leu Ser Cys Leu Ile Gly Tyr
    690                 695                 700

Cys Ser Ser His Trp Cys Cys Lys Lys Glu Val Gln Glu Thr Arg Arg
705                 710                 715                 720

Glu Arg Arg Arg Leu Met Ser Met Glu Met Asp
                725                 730
```

<210> SEQ ID NO 3
<211> LENGTH: 611
<212> TYPE: PRT
<213> ORGANISM: Artificial Sequence
<220> FEATURE:
<223> OTHER INFORMATION: Synthetic: PTGFRN Protein Fragment #2

<400> SEQUENCE: 3

-continued

```
Val Ala Thr Val Val Ile Gln Pro Ser Val Leu Arg Ala Ala Val Pro
1               5                   10                  15

Lys Asn Val Ser Val Ala Glu Gly Lys Glu Leu Asp Leu Thr Cys Asn
            20                  25                  30

Ile Thr Thr Asp Arg Ala Asp Asp Val Arg Pro Glu Val Thr Trp Ser
        35                  40                  45

Phe Ser Arg Met Pro Asp Ser Thr Leu Pro Gly Ser Arg Val Leu Ala
    50                  55                  60

Arg Leu Asp Arg Asp Ser Leu Val His Ser Ser Pro His Val Ala Leu
65                  70                  75                  80

Ser His Val Asp Ala Arg Ser Tyr His Leu Leu Val Arg Asp Val Ser
                85                  90                  95

Lys Glu Asn Ser Gly Tyr Tyr Tyr Cys His Val Ser Leu Trp Ala Pro
            100                 105                 110

Gly His Asn Arg Ser Trp His Lys Val Ala Glu Ala Val Ser Ser Pro
        115                 120                 125

Ala Gly Val Gly Val Thr Trp Leu Glu Pro Asp Tyr Gln Val Tyr Leu
    130                 135                 140

Asn Ala Ser Lys Val Pro Gly Phe Ala Asp Asp Pro Thr Glu Leu Ala
145                 150                 155                 160

Cys Arg Val Val Asp Thr Lys Ser Gly Glu Ala Asn Val Arg Phe Thr
                165                 170                 175

Val Ser Trp Tyr Tyr Arg Met Asn Arg Arg Ser Asp Asn Val Val Thr
            180                 185                 190

Ser Glu Leu Leu Ala Val Met Asp Gly Asp Trp Thr Leu Lys Tyr Gly
        195                 200                 205

Glu Arg Ser Lys Gln Arg Ala Gln Asp Gly Asp Phe Ile Phe Ser Lys
    210                 215                 220

Glu His Thr Asp Thr Phe Asn Phe Arg Ile Gln Arg Thr Thr Glu Glu
225                 230                 235                 240

Asp Arg Gly Asn Tyr Tyr Cys Val Val Ser Ala Trp Thr Lys Gln Arg
                245                 250                 255

Asn Asn Ser Trp Val Lys Ser Lys Asp Val Phe Ser Lys Pro Val Asn
            260                 265                 270

Ile Phe Trp Ala Leu Glu Asp Ser Val Leu Val Val Lys Ala Arg Gln
        275                 280                 285

Pro Lys Pro Phe Phe Ala Ala Gly Asn Thr Phe Glu Met Thr Cys Lys
    290                 295                 300

Val Ser Ser Lys Asn Ile Lys Ser Pro Arg Tyr Ser Val Leu Ile Met
305                 310                 315                 320

Ala Glu Lys Pro Val Gly Asp Leu Ser Ser Pro Asn Glu Thr Lys Tyr
                325                 330                 335

Ile Ile Ser Leu Asp Gln Asp Ser Val Val Lys Leu Glu Asn Trp Thr
            340                 345                 350

Asp Ala Ser Arg Val Asp Gly Val Val Leu Glu Lys Val Gln Glu Asp
        355                 360                 365

Glu Phe Arg Tyr Arg Met Tyr Gln Thr Gln Val Ser Asp Ala Gly Leu
    370                 375                 380

Tyr Arg Cys Met Val Thr Ala Trp Ser Pro Val Arg Gly Ser Leu Trp
385                 390                 395                 400

Arg Glu Ala Ala Thr Ser Leu Ser Asn Pro Ile Glu Ile Asp Phe Gln
                405                 410                 415
```

-continued

```
Thr Ser Gly Pro Ile Phe Asn Ala Ser Val His Ser Asp Thr Pro Ser
            420                 425                 430

Val Ile Arg Gly Asp Leu Ile Lys Leu Phe Cys Ile Ile Thr Val Glu
        435                 440                 445

Gly Ala Ala Leu Asp Pro Asp Asp Met Ala Phe Asp Val Ser Trp Phe
    450                 455                 460

Ala Val His Ser Phe Gly Leu Asp Lys Ala Pro Val Leu Leu Ser Ser
465                 470                 475                 480

Leu Asp Arg Lys Gly Ile Val Thr Thr Ser Arg Arg Asp Trp Lys Ser
                485                 490                 495

Asp Leu Ser Leu Glu Arg Val Ser Val Leu Glu Phe Leu Leu Gln Val
            500                 505                 510

His Gly Ser Glu Asp Gln Asp Phe Gly Asn Tyr Tyr Cys Ser Val Thr
        515                 520                 525

Pro Trp Val Lys Ser Pro Thr Gly Ser Trp Gln Lys Glu Ala Glu Ile
    530                 535                 540

His Ser Lys Pro Val Phe Ile Thr Val Lys Met Asp Val Leu Asn Ala
545                 550                 555                 560

Phe Lys Tyr Pro Leu Leu Ile Gly Val Gly Leu Ser Thr Val Ile Gly
                565                 570                 575

Leu Leu Ser Cys Leu Ile Gly Tyr Cys Ser Ser His Trp Cys Cys Lys
            580                 585                 590

Lys Glu Val Gln Glu Thr Arg Arg Glu Arg Arg Arg Leu Met Ser Met
        595                 600                 605

Glu Met Asp
    610


<210> SEQ ID NO 4
<211> LENGTH: 485
<212> TYPE: PRT
<213> ORGANISM: Artificial Sequence
<220> FEATURE:
<223> OTHER INFORMATION: Synthetic: PTGFRN Protein Fragment #3

<400> SEQUENCE: 4

Ser Pro Ala Gly Val Gly Val Thr Trp Leu Glu Pro Asp Tyr Gln Val
1               5                   10                  15

Tyr Leu Asn Ala Ser Lys Val Pro Gly Phe Ala Asp Asp Pro Thr Glu
            20                  25                  30

Leu Ala Cys Arg Val Val Asp Thr Lys Ser Gly Glu Ala Asn Val Arg
        35                  40                  45

Phe Thr Val Ser Trp Tyr Tyr Arg Met Asn Arg Arg Ser Asp Asn Val
    50                  55                  60

Val Thr Ser Glu Leu Leu Ala Val Met Asp Gly Asp Trp Thr Leu Lys
65                  70                  75                  80

Tyr Gly Glu Arg Ser Lys Gln Arg Ala Gln Asp Gly Asp Phe Ile Phe
                85                  90                  95

Ser Lys Glu His Thr Asp Thr Phe Asn Phe Arg Ile Gln Arg Thr Thr
            100                 105                 110

Glu Glu Asp Arg Gly Asn Tyr Tyr Cys Val Val Ser Ala Trp Thr Lys
        115                 120                 125

Gln Arg Asn Asn Ser Trp Val Lys Ser Lys Asp Val Phe Ser Lys Pro
    130                 135                 140

Val Asn Ile Phe Trp Ala Leu Glu Asp Ser Val Leu Val Val Lys Ala
145                 150                 155                 160
```

-continued

```
Arg Gln Pro Lys Pro Phe Phe Ala Ala Gly Asn Thr Phe Glu Met Thr
                165                 170                 175

Cys Lys Val Ser Ser Lys Asn Ile Lys Ser Pro Arg Tyr Ser Val Leu
            180                 185                 190

Ile Met Ala Glu Lys Pro Val Gly Asp Leu Ser Ser Pro Asn Glu Thr
        195                 200                 205

Lys Tyr Ile Ile Ser Leu Asp Gln Asp Ser Val Val Lys Leu Glu Asn
    210                 215                 220

Trp Thr Asp Ala Ser Arg Val Asp Gly Val Val Leu Glu Lys Val Gln
225                 230                 235                 240

Glu Asp Glu Phe Arg Tyr Arg Met Tyr Gln Thr Gln Val Ser Asp Ala
                245                 250                 255

Gly Leu Tyr Arg Cys Met Val Thr Ala Trp Ser Pro Val Arg Gly Ser
            260                 265                 270

Leu Trp Arg Glu Ala Ala Thr Ser Leu Ser Asn Pro Ile Glu Ile Asp
        275                 280                 285

Phe Gln Thr Ser Gly Pro Ile Phe Asn Ala Ser Val His Ser Asp Thr
    290                 295                 300

Pro Ser Val Ile Arg Gly Asp Leu Ile Lys Leu Phe Cys Ile Ile Thr
305                 310                 315                 320

Val Glu Gly Ala Ala Leu Asp Pro Asp Asp Met Ala Phe Asp Val Ser
                325                 330                 335

Trp Phe Ala Val His Ser Phe Gly Leu Asp Lys Ala Pro Val Leu Leu
            340                 345                 350

Ser Ser Leu Asp Arg Lys Gly Ile Val Thr Thr Ser Arg Arg Asp Trp
        355                 360                 365

Lys Ser Asp Leu Ser Leu Glu Arg Val Ser Val Leu Glu Phe Leu Leu
    370                 375                 380

Gln Val His Gly Ser Glu Asp Gln Asp Phe Gly Asn Tyr Tyr Cys Ser
385                 390                 395                 400

Val Thr Pro Trp Val Lys Ser Pro Thr Gly Ser Trp Gln Lys Glu Ala
                405                 410                 415

Glu Ile His Ser Lys Pro Val Phe Ile Thr Val Lys Met Asp Val Leu
            420                 425                 430

Asn Ala Phe Lys Tyr Pro Leu Leu Ile Gly Val Gly Leu Ser Thr Val
        435                 440                 445

Ile Gly Leu Leu Ser Cys Leu Ile Gly Tyr Cys Ser Ser His Trp Cys
    450                 455                 460

Cys Lys Lys Glu Val Gln Glu Thr Arg Arg Glu Arg Arg Arg Leu Met
465                 470                 475                 480

Ser Met Glu Met Asp
                485
```

<210> SEQ ID NO 5
<211> LENGTH: 343
<212> TYPE: PRT
<213> ORGANISM: Artificial Sequence
<220> FEATURE:
<223> OTHER INFORMATION: Synthetic: PTGFRN Protein Fragment #4

<400> SEQUENCE: 5

```
Lys Pro Val Asn Ile Phe Trp Ala Leu Glu Asp Ser Val Leu Val Val
1               5                   10                  15

Lys Ala Arg Gln Pro Lys Pro Phe Phe Ala Ala Gly Asn Thr Phe Glu
            20                  25                  30
```

-continued

```
Met Thr Cys Lys Val Ser Ser Lys Asn Ile Lys Ser Pro Arg Tyr Ser
        35                  40                  45

Val Leu Ile Met Ala Glu Lys Pro Val Gly Asp Leu Ser Ser Pro Asn
    50                  55                  60

Glu Thr Lys Tyr Ile Ile Ser Leu Asp Gln Asp Ser Val Val Lys Leu
65                  70                  75                  80

Glu Asn Trp Thr Asp Ala Ser Arg Val Asp Gly Val Val Leu Glu Lys
                85                  90                  95

Val Gln Glu Asp Glu Phe Arg Tyr Arg Met Tyr Gln Thr Gln Val Ser
            100                 105                 110

Asp Ala Gly Leu Tyr Arg Cys Met Val Thr Ala Trp Ser Pro Val Arg
        115                 120                 125

Gly Ser Leu Trp Arg Glu Ala Ala Thr Ser Leu Ser Asn Pro Ile Glu
    130                 135                 140

Ile Asp Phe Gln Thr Ser Gly Pro Ile Phe Asn Ala Ser Val His Ser
145                 150                 155                 160

Asp Thr Pro Ser Val Ile Arg Gly Asp Leu Ile Lys Leu Phe Cys Ile
                165                 170                 175

Ile Thr Val Glu Gly Ala Ala Leu Asp Pro Asp Asp Met Ala Phe Asp
            180                 185                 190

Val Ser Trp Phe Ala Val His Ser Phe Gly Leu Asp Lys Ala Pro Val
        195                 200                 205

Leu Leu Ser Ser Leu Asp Arg Lys Gly Ile Val Thr Thr Ser Arg Arg
    210                 215                 220

Asp Trp Lys Ser Asp Leu Ser Leu Glu Arg Val Ser Val Leu Glu Phe
225                 230                 235                 240

Leu Leu Gln Val His Gly Ser Glu Asp Gln Asp Phe Gly Asn Tyr Tyr
                245                 250                 255

Cys Ser Val Thr Pro Trp Val Lys Ser Pro Thr Gly Ser Trp Gln Lys
            260                 265                 270

Glu Ala Glu Ile His Ser Lys Pro Val Phe Ile Thr Val Lys Met Asp
        275                 280                 285

Val Leu Asn Ala Phe Lys Tyr Pro Leu Leu Ile Gly Val Gly Leu Ser
    290                 295                 300

Thr Val Ile Gly Leu Leu Ser Cys Leu Ile Gly Tyr Cys Ser Ser His
305                 310                 315                 320

Trp Cys Cys Lys Lys Glu Val Gln Glu Thr Arg Arg Glu Arg Arg Arg
                325                 330                 335

Leu Met Ser Met Glu Met Asp
            340
```

<210> SEQ ID NO 6
<211> LENGTH: 217
<212> TYPE: PRT
<213> ORGANISM: Artificial Sequence
<220> FEATURE:
<223> OTHER INFORMATION: Synthetic: PTGFRN Protein Fragment #5

<400> SEQUENCE: 6

```
Val Arg Gly Ser Leu Trp Arg Glu Ala Ala Thr Ser Leu Ser Asn Pro
1               5                   10                  15

Ile Glu Ile Asp Phe Gln Thr Ser Gly Pro Ile Phe Asn Ala Ser Val
            20                  25                  30

His Ser Asp Thr Pro Ser Val Ile Arg Gly Asp Leu Ile Lys Leu Phe
        35                  40                  45
```

```
Cys Ile Ile Thr Val Glu Gly Ala Ala Leu Asp Pro Asp Asp Met Ala
    50                  55                  60

Phe Asp Val Ser Trp Phe Ala Val His Ser Phe Gly Leu Asp Lys Ala
65                  70                  75                  80

Pro Val Leu Leu Ser Ser Leu Asp Arg Lys Gly Ile Val Thr Thr Ser
                85                  90                  95

Arg Arg Asp Trp Lys Ser Asp Leu Ser Leu Glu Arg Val Ser Val Leu
            100                 105                 110

Glu Phe Leu Leu Gln Val His Gly Ser Glu Asp Gln Asp Phe Gly Asn
        115                 120                 125

Tyr Tyr Cys Ser Val Thr Pro Trp Val Lys Ser Pro Thr Gly Ser Trp
    130                 135                 140

Gln Lys Glu Ala Glu Ile His Ser Lys Pro Val Phe Ile Thr Val Lys
145                 150                 155                 160

Met Asp Val Leu Asn Ala Phe Lys Tyr Pro Leu Leu Ile Gly Val Gly
                165                 170                 175

Leu Ser Thr Val Ile Gly Leu Leu Ser Cys Leu Ile Gly Tyr Cys Ser
            180                 185                 190

Ser His Trp Cys Cys Lys Lys Glu Val Gln Glu Thr Arg Arg Glu Arg
        195                 200                 205

Arg Arg Leu Met Ser Met Glu Met Asp
    210                 215


<210> SEQ ID NO 7
<211> LENGTH: 66
<212> TYPE: PRT
<213> ORGANISM: Artificial Sequence
<220> FEATURE:
<223> OTHER INFORMATION: Synthetic: PTGFRN Protein Fragment #6

<400> SEQUENCE: 7

Ser Lys Pro Val Phe Ile Thr Val Lys Met Asp Val Leu Asn Ala Phe
1               5                   10                  15

Lys Tyr Pro Leu Leu Ile Gly Val Gly Leu Ser Thr Val Ile Gly Leu
            20                  25                  30

Leu Ser Cys Leu Ile Gly Tyr Cys Ser Ser His Trp Cys Cys Lys Lys
        35                  40                  45

Glu Val Gln Glu Thr Arg Arg Glu Arg Arg Arg Leu Met Ser Met Glu
    50                  55                  60

Met Asp
65


<210> SEQ ID NO 8
<211> LENGTH: 21
<212> TYPE: PRT
<213> ORGANISM: Artificial Sequence
<220> FEATURE:
<223> OTHER INFORMATION: Synthetic: PTGFRN Protein - Signal Peptide

<400> SEQUENCE: 8

Met Gly Arg Leu Ala Ser Arg Pro Leu Leu Leu Ala Leu Leu Ser Leu
1               5                   10                  15

Ala Leu Cys Arg Gly
            20


<210> SEQ ID NO 9
<211> LENGTH: 385
<212> TYPE: PRT
<213> ORGANISM: Artificial Sequence
```

-continued

```
<220> FEATURE:
<223> OTHER INFORMATION: Synthetic: BSG Protein

<400> SEQUENCE: 9

Met Ala Ala Ala Leu Phe Val Leu Leu Gly Phe Ala Leu Leu Gly Thr
1               5                   10                  15

His Gly Ala Ser Gly Ala Ala Gly Phe Val Gln Ala Pro Leu Ser Gln
            20                  25                  30

Gln Arg Trp Val Gly Gly Ser Val Glu Leu His Cys Glu Ala Val Gly
        35                  40                  45

Ser Pro Val Pro Glu Ile Gln Trp Trp Phe Glu Gly Gln Gly Pro Asn
    50                  55                  60

Asp Thr Cys Ser Gln Leu Trp Asp Gly Ala Arg Leu Asp Arg Val His
65                  70                  75                  80

Ile His Ala Thr Tyr His Gln His Ala Ala Ser Thr Ile Ser Ile Asp
                85                  90                  95

Thr Leu Val Glu Glu Asp Thr Gly Thr Tyr Glu Cys Arg Ala Ser Asn
            100                 105                 110

Asp Pro Asp Arg Asn His Leu Thr Arg Ala Pro Arg Val Lys Trp Val
        115                 120                 125

Arg Ala Gln Ala Val Val Leu Val Leu Glu Pro Gly Thr Val Phe Thr
    130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190

Asp Ser Asp Asp Gln Trp Gly Glu Tyr Ser Cys Val Phe Leu Pro Glu
        195                 200                 205

Pro Met Gly Thr Ala Asn Ile Gln Leu His Gly Pro Pro Arg Val Lys
    210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
            260                 265                 270

Arg Phe Phe Val Ser Ser Ser Gln Gly Arg Ser Glu Leu His Ile Glu
        275                 280                 285

Asn Leu Asn Met Glu Ala Asp Pro Gly Gln Tyr Arg Cys Asn Gly Thr
    290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
            340                 345                 350

Asp Val Leu Asp Asp Asp Asp Ala Gly Ser Ala Pro Leu Lys Ser Ser
        355                 360                 365

Gly Gln His Gln Asn Asp Lys Gly Lys Asn Val Arg Gln Arg Asn Ser
    370                 375                 380

Ser
385
```

<210> SEQ ID NO 10
<211> LENGTH: 247
<212> TYPE: PRT
<213> ORGANISM: Artificial Sequence
<220> FEATURE:
<223> OTHER INFORMATION: Synthetic: BSG Protein Fragment #1

<400> SEQUENCE: 10

```
Pro Gly Thr Val Phe Thr Thr Val Glu Asp Leu Gly Ser Lys Ile Leu
1               5                   10                  15

Leu Thr Cys Ser Leu Asn Asp Ser Ala Thr Glu Val Thr Gly His Arg
            20                  25                  30

Trp Leu Lys Gly Gly Val Val Leu Lys Glu Asp Ala Leu Pro Gly Gln
        35                  40                  45

Lys Thr Glu Phe Lys Val Asp Ser Asp Asp Gln Trp Gly Glu Tyr Ser
    50                  55                  60

Cys Val Phe Leu Pro Glu Pro Met Gly Thr Ala Asn Ile Gln Leu His
65                  70                  75                  80

Gly Pro Pro Arg Val Lys Ala Val Lys Ser Ser Glu His Ile Asn Glu
                85                  90                  95

Gly Glu Thr Ala Met Leu Val Cys Lys Ser Glu Ser Val Pro Pro Val
            100                 105                 110

Thr Asp Trp Ala Trp Tyr Lys Ile Thr Asp Ser Glu Asp Lys Ala Leu
        115                 120                 125

Met Asn Gly Ser Glu Ser Arg Phe Phe Val Ser Ser Ser Gln Gly Arg
    130                 135                 140

Ser Glu Leu His Ile Glu Asn Leu Asn Met Glu Ala Asp Pro Gly Gln
145                 150                 155                 160

Tyr Arg Cys Asn Gly Thr Ser Ser Lys Gly Ser Asp Gln Ala Ile Ile
                165                 170                 175

Thr Leu Arg Val Arg Ser His Leu Ala Ala Leu Trp Pro Phe Leu Gly
            180                 185                 190

Ile Val Ala Glu Val Leu Val Leu Val Thr Ile Ile Phe Ile Tyr Glu
        195                 200                 205

Lys Arg Arg Lys Pro Glu Asp Val Leu Asp Asp Asp Asp Ala Gly Ser
    210                 215                 220

Ala Pro Leu Lys Ser Ser Gly Gln His Gln Asn Asp Lys Gly Lys Asn
225                 230                 235                 240

Val Arg Gln Arg Asn Ser Ser
                245
```

<210> SEQ ID NO 11
<211> LENGTH: 168
<212> TYPE: PRT
<213> ORGANISM: Artificial Sequence
<220> FEATURE:
<223> OTHER INFORMATION: Synthetic: BSG Protein Fragment #2

<400> SEQUENCE: 11

```
His Gly Pro Pro Arg Val Lys Ala Val Lys Ser Ser Glu His Ile Asn
1               5                   10                  15

Glu Gly Glu Thr Ala Met Leu Val Cys Lys Ser Glu Ser Val Pro Pro
            20                  25                  30

Val Thr Asp Trp Ala Trp Tyr Lys Ile Thr Asp Ser Glu Asp Lys Ala
        35                  40                  45

Leu Met Asn Gly Ser Glu Ser Arg Phe Phe Val Ser Ser Ser Gln Gly
```

```
    50                  55                  60

Arg Ser Glu Leu His Ile Glu Asn Leu Asn Met Glu Ala Asp Pro Gly
65                  70                  75                  80

Gln Tyr Arg Cys Asn Gly Thr Ser Ser Lys Gly Ser Asp Gln Ala Ile
                85                  90                  95

Ile Thr Leu Arg Val Arg Ser His Leu Ala Ala Leu Trp Pro Phe Leu
            100                 105                 110

Gly Ile Val Ala Glu Val Leu Val Leu Val Thr Ile Ile Phe Ile Tyr
        115                 120                 125

Glu Lys Arg Arg Lys Pro Glu Asp Val Leu Asp Asp Asp Asp Ala Gly
    130                 135                 140

Ser Ala Pro Leu Lys Ser Ser Gly Gln His Gln Asn Asp Lys Gly Lys
145                 150                 155                 160

Asn Val Arg Gln Arg Asn Ser Ser
                165


<210> SEQ ID NO 12
<211> LENGTH: 66
<212> TYPE: PRT
<213> ORGANISM: Artificial Sequence
<220> FEATURE:
<223> OTHER INFORMATION: Synthetic: BSG Protein Fragment #3

<400> SEQUENCE: 12

Ser His Leu Ala Ala Leu Trp Pro Phe Leu Gly Ile Val Ala Glu Val
1               5                   10                  15

Leu Val Leu Val Thr Ile Ile Phe Ile Tyr Glu Lys Arg Arg Lys Pro
            20                  25                  30

Glu Asp Val Leu Asp Asp Asp Asp Ala Gly Ser Ala Pro Leu Lys Ser
        35                  40                  45

Ser Gly Gln His Gln Asn Asp Lys Gly Lys Asn Val Arg Gln Arg Asn
    50                  55                  60

Ser Ser
65


<210> SEQ ID NO 13
<211> LENGTH: 18
<212> TYPE: PRT
<213> ORGANISM: Artificial Sequence
<220> FEATURE:
<223> OTHER INFORMATION: Synthetic: BSG Protein - Signal Peptide

<400> SEQUENCE: 13

Met Ala Ala Ala Leu Phe Val Leu Leu Gly Phe Ala Leu Leu Gly Thr
1               5                   10                  15

His Gly


<210> SEQ ID NO 14
<211> LENGTH: 613
<212> TYPE: PRT
<213> ORGANISM: Artificial Sequence
<220> FEATURE:
<223> OTHER INFORMATION: Synthetic: IGSF8

<400> SEQUENCE: 14

Met Gly Ala Leu Arg Pro Thr Leu Leu Pro Pro Ser Leu Pro Leu Leu
1               5                   10                  15

Leu Leu Leu Met Leu Gly Met Gly Cys Trp Ala Arg Glu Val Leu Val
            20                  25                  30
```

```
Pro Glu Gly Pro Leu Tyr Arg Val Ala Gly Thr Ala Val Ser Ile Ser
        35                  40                  45

Cys Asn Val Thr Gly Tyr Glu Gly Pro Ala Gln Gln Asn Phe Glu Trp
    50                  55                  60

Phe Leu Tyr Arg Pro Glu Ala Pro Asp Thr Ala Leu Gly Ile Val Ser
65                  70                  75                  80

Thr Lys Asp Thr Gln Phe Ser Tyr Ala Val Phe Lys Ser Arg Val Val
                85                  90                  95

Ala Gly Glu Val Gln Val Gln Arg Leu Gln Gly Asp Ala Val Val Leu
            100                 105                 110

Lys Ile Ala Arg Leu Gln Ala Gln Asp Ala Gly Ile Tyr Glu Cys His
        115                 120                 125

Thr Pro Ser Thr Asp Thr Arg Tyr Leu Gly Ser Tyr Ser Gly Lys Val
    130                 135                 140

Glu Leu Arg Val Leu Pro Asp Val Leu Gln Val Ser Ala Ala Pro Pro
145                 150                 155                 160

Gly Pro Arg Gly Arg Gln Ala Pro Thr Ser Pro Pro Arg Met Thr Val
                165                 170                 175

His Glu Gly Gln Glu Leu Ala Leu Gly Cys Leu Ala Arg Thr Ser Thr
            180                 185                 190

Gln Lys His Thr His Leu Ala Val Ser Phe Gly Arg Ser Val Pro Glu
        195                 200                 205

Ala Pro Val Gly Arg Ser Thr Leu Gln Glu Val Val Gly Ile Arg Ser
    210                 215                 220

Asp Leu Ala Val Glu Ala Gly Ala Pro Tyr Ala Glu Arg Leu Ala Ala
225                 230                 235                 240

Gly Glu Leu Arg Leu Gly Lys Glu Gly Thr Asp Arg Tyr Arg Met Val
                245                 250                 255

Val Gly Gly Ala Gln Ala Gly Asp Ala Gly Thr Tyr His Cys Thr Ala
            260                 265                 270

Ala Glu Trp Ile Gln Asp Pro Asp Gly Ser Trp Ala Gln Ile Ala Glu
        275                 280                 285

Lys Arg Ala Val Leu Ala His Val Asp Val Gln Thr Leu Ser Ser Gln
    290                 295                 300

Leu Ala Val Thr Val Gly Pro Gly Glu Arg Arg Ile Gly Pro Gly Glu
305                 310                 315                 320

Pro Leu Glu Leu Leu Cys Asn Val Ser Gly Ala Leu Pro Pro Ala Gly
                325                 330                 335

Arg His Ala Ala Tyr Ser Val Gly Trp Glu Met Ala Pro Ala Gly Ala
            340                 345                 350

Pro Gly Pro Gly Arg Leu Val Ala Gln Leu Asp Thr Glu Gly Val Gly
        355                 360                 365

Ser Leu Gly Pro Gly Tyr Glu Gly Arg His Ile Ala Met Glu Lys Val
    370                 375                 380

Ala Ser Arg Thr Tyr Arg Leu Arg Leu Glu Ala Ala Arg Pro Gly Asp
385                 390                 395                 400

Ala Gly Thr Tyr Arg Cys Leu Ala Lys Ala Tyr Val Arg Gly Ser Gly
                405                 410                 415

Thr Arg Leu Arg Glu Ala Ala Ser Ala Arg Ser Arg Pro Leu Pro Val
            420                 425                 430

His Val Arg Glu Glu Gly Val Val Leu Glu Ala Val Ala Trp Leu Ala
        435                 440                 445

Gly Gly Thr Val Tyr Arg Gly Glu Thr Ala Ser Leu Leu Cys Asn Ile
```

```
    450                 455                 460

Ser Val Arg Gly Gly Pro Pro Gly Leu Arg Leu Ala Ala Ser Trp Trp
465                 470                 475                 480

Val Glu Arg Pro Glu Asp Gly Glu Leu Ser Ser Val Pro Ala Gln Leu
                485                 490                 495

Val Gly Gly Val Gly Gln Asp Gly Val Ala Glu Leu Gly Val Arg Pro
            500                 505                 510

Gly Gly Gly Pro Val Ser Val Glu Leu Val Gly Pro Arg Ser His Arg
        515                 520                 525

Leu Arg Leu His Ser Leu Gly Pro Glu Asp Glu Gly Val Tyr His Cys
    530                 535                 540

Ala Pro Ser Ala Trp Val Gln His Ala Asp Tyr Ser Trp Tyr Gln Ala
545                 550                 555                 560

Gly Ser Ala Arg Ser Gly Pro Val Thr Val Tyr Pro Tyr Met His Ala
                565                 570                 575

Leu Asp Thr Leu Phe Val Pro Leu Leu Val Gly Thr Gly Val Ala Leu
            580                 585                 590

Val Thr Gly Ala Thr Val Leu Gly Thr Ile Thr Cys Cys Phe Met Lys
        595                 600                 605

Arg Leu Arg Lys Arg
    610


<210> SEQ ID NO 15
<211> LENGTH: 456
<212> TYPE: PRT
<213> ORGANISM: Artificial Sequence
<220> FEATURE:
<223> OTHER INFORMATION: Synthetic: IGSF8 Protein Fragment #1

<400> SEQUENCE: 15

Ala Pro Pro Gly Pro Arg Gly Arg Gln Ala Pro Thr Ser Pro Pro Arg
1               5                   10                  15

Met Thr Val His Glu Gly Gln Glu Leu Ala Leu Gly Cys Leu Ala Arg
            20                  25                  30

Thr Ser Thr Gln Lys His Thr His Leu Ala Val Ser Phe Gly Arg Ser
        35                  40                  45

Val Pro Glu Ala Pro Val Gly Arg Ser Thr Leu Gln Glu Val Val Gly
    50                  55                  60

Ile Arg Ser Asp Leu Ala Val Glu Ala Gly Ala Pro Tyr Ala Glu Arg
65                  70                  75                  80

Leu Ala Ala Gly Glu Leu Arg Leu Gly Lys Glu Gly Thr Asp Arg Tyr
                85                  90                  95

Arg Met Val Val Gly Gly Ala Gln Ala Gly Asp Ala Gly Thr Tyr His
            100                 105                 110

Cys Thr Ala Ala Glu Trp Ile Gln Asp Pro Asp Gly Ser Trp Ala Gln
        115                 120                 125

Ile Ala Glu Lys Arg Ala Val Leu Ala His Val Asp Val Gln Thr Leu
    130                 135                 140

Ser Ser Gln Leu Ala Val Thr Val Gly Pro Gly Glu Arg Arg Ile Gly
145                 150                 155                 160

Pro Gly Glu Pro Leu Glu Leu Leu Cys Asn Val Ser Gly Ala Leu Pro
                165                 170                 175

Pro Ala Gly Arg His Ala Ala Tyr Ser Val Gly Trp Glu Met Ala Pro
            180                 185                 190

Ala Gly Ala Pro Gly Pro Gly Arg Leu Val Ala Gln Leu Asp Thr Glu
```

-continued

```
        195                 200                 205

Gly Val Gly Ser Leu Gly Pro Gly Tyr Glu Gly Arg His Ile Ala Met
    210                 215                 220

Glu Lys Val Ala Ser Arg Thr Tyr Arg Leu Arg Leu Glu Ala Ala Arg
225                 230                 235                 240

Pro Gly Asp Ala Gly Thr Tyr Arg Cys Leu Ala Lys Ala Tyr Val Arg
                245                 250                 255

Gly Ser Gly Thr Arg Leu Arg Glu Ala Ala Ser Ala Arg Ser Arg Pro
            260                 265                 270

Leu Pro Val His Val Arg Glu Glu Gly Val Val Leu Glu Ala Val Ala
        275                 280                 285

Trp Leu Ala Gly Gly Thr Val Tyr Arg Gly Glu Thr Ala Ser Leu Leu
    290                 295                 300

Cys Asn Ile Ser Val Arg Gly Gly Pro Pro Gly Leu Arg Leu Ala Ala
305                 310                 315                 320

Ser Trp Trp Val Glu Arg Pro Glu Asp Gly Glu Leu Ser Ser Val Pro
                325                 330                 335

Ala Gln Leu Val Gly Gly Val Gly Gln Asp Gly Val Ala Glu Leu Gly
            340                 345                 350

Val Arg Pro Gly Gly Gly Pro Val Ser Val Glu Leu Val Gly Pro Arg
        355                 360                 365

Ser His Arg Leu Arg Leu His Ser Leu Gly Pro Glu Asp Glu Gly Val
    370                 375                 380

Tyr His Cys Ala Pro Ser Ala Trp Val Gln His Ala Asp Tyr Ser Trp
385                 390                 395                 400

Tyr Gln Ala Gly Ser Ala Arg Ser Gly Pro Val Thr Val Tyr Pro Tyr
                405                 410                 415

Met His Ala Leu Asp Thr Leu Phe Val Pro Leu Leu Val Gly Thr Gly
            420                 425                 430

Val Ala Leu Val Thr Gly Ala Thr Val Leu Gly Thr Ile Thr Cys Cys
        435                 440                 445

Phe Met Lys Arg Leu Arg Lys Arg
    450                 455


<210> SEQ ID NO 16
<211> LENGTH: 320
<212> TYPE: PRT
<213> ORGANISM: Artificial Sequence
<220> FEATURE:
<223> OTHER INFORMATION: Synthetic: IGSF8 Protein Fragment #2

<400> SEQUENCE: 16

Ala His Val Asp Val Gln Thr Leu Ser Ser Gln Leu Ala Val Thr Val
1               5                   10                  15

Gly Pro Gly Glu Arg Arg Ile Gly Pro Gly Glu Pro Leu Glu Leu Leu
            20                  25                  30

Cys Asn Val Ser Gly Ala Leu Pro Pro Ala Gly Arg His Ala Ala Tyr
        35                  40                  45

Ser Val Gly Trp Glu Met Ala Pro Ala Gly Ala Pro Gly Pro Gly Arg
    50                  55                  60

Leu Val Ala Gln Leu Asp Thr Glu Gly Val Gly Ser Leu Gly Pro Gly
65                  70                  75                  80

Tyr Glu Gly Arg His Ile Ala Met Glu Lys Val Ala Ser Arg Thr Tyr
                85                  90                  95

Arg Leu Arg Leu Glu Ala Ala Arg Pro Gly Asp Ala Gly Thr Tyr Arg
```

```
            100                 105                 110

Cys Leu Ala Lys Ala Tyr Val Arg Gly Ser Gly Thr Arg Leu Arg Glu
        115                 120                 125

Ala Ala Ser Ala Arg Ser Arg Pro Leu Pro Val His Val Arg Glu Glu
    130                 135                 140

Gly Val Val Leu Glu Ala Val Ala Trp Leu Ala Gly Gly Thr Val Tyr
145                 150                 155                 160

Arg Gly Glu Thr Ala Ser Leu Leu Cys Asn Ile Ser Val Arg Gly Gly
                165                 170                 175

Pro Pro Gly Leu Arg Leu Ala Ala Ser Trp Trp Val Glu Arg Pro Glu
            180                 185                 190

Asp Gly Glu Leu Ser Ser Val Pro Ala Gln Leu Val Gly Gly Val Gly
        195                 200                 205

Gln Asp Gly Val Ala Glu Leu Gly Val Arg Pro Gly Gly Gly Pro Val
    210                 215                 220

Ser Val Glu Leu Val Gly Pro Arg Ser His Arg Leu Arg Leu His Ser
225                 230                 235                 240

Leu Gly Pro Glu Asp Glu Gly Val Tyr His Cys Ala Pro Ser Ala Trp
                245                 250                 255

Val Gln His Ala Asp Tyr Ser Trp Tyr Gln Ala Gly Ser Ala Arg Ser
            260                 265                 270

Gly Pro Val Thr Val Tyr Pro Tyr Met His Ala Leu Asp Thr Leu Phe
        275                 280                 285

Val Pro Leu Leu Val Gly Thr Gly Val Ala Leu Val Thr Gly Ala Thr
    290                 295                 300

Val Leu Gly Thr Ile Thr Cys Cys Phe Met Lys Arg Leu Arg Lys Arg
305                 310                 315                 320


<210> SEQ ID NO 17
<211> LENGTH: 179
<212> TYPE: PRT
<213> ORGANISM: Artificial Sequence
<220> FEATURE:
<223> OTHER INFORMATION: Synthetic: IGSF8 Protein Fragment #3

<400> SEQUENCE: 17

Arg Glu Glu Gly Val Val Leu Glu Ala Val Ala Trp Leu Ala Gly Gly
1               5                   10                  15

Thr Val Tyr Arg Gly Glu Thr Ala Ser Leu Leu Cys Asn Ile Ser Val
            20                  25                  30

Arg Gly Gly Pro Pro Gly Leu Arg Leu Ala Ala Ser Trp Trp Val Glu
        35                  40                  45

Arg Pro Glu Asp Gly Glu Leu Ser Ser Val Pro Ala Gln Leu Val Gly
    50                  55                  60

Gly Val Gly Gln Asp Gly Val Ala Glu Leu Gly Val Arg Pro Gly Gly
65                  70                  75                  80

Gly Pro Val Ser Val Glu Leu Val Gly Pro Arg Ser His Arg Leu Arg
                85                  90                  95

Leu His Ser Leu Gly Pro Glu Asp Glu Gly Val Tyr His Cys Ala Pro
            100                 105                 110

Ser Ala Trp Val Gln His Ala Asp Tyr Ser Trp Tyr Gln Ala Gly Ser
        115                 120                 125

Ala Arg Ser Gly Pro Val Thr Val Tyr Pro Tyr Met His Ala Leu Asp
    130                 135                 140

Thr Leu Phe Val Pro Leu Leu Val Gly Thr Gly Val Ala Leu Val Thr
```

-continued

```
145                 150                 155                 160

Gly Ala Thr Val Leu Gly Thr Ile Thr Cys Cys Phe Met Lys Arg Leu
                165                 170                 175

Arg Lys Arg


<210> SEQ ID NO 18
<211> LENGTH: 24
<212> TYPE: PRT
<213> ORGANISM: Artificial Sequence
<220> FEATURE:
<223> OTHER INFORMATION: Synthetic: IGSF8 Protein Fragment #4

<400> SEQUENCE: 18

Val Ala Leu Val Thr Gly Ala Thr Val Leu Gly Thr Ile Thr Cys Cys
1               5                   10                  15

Phe Met Lys Arg Leu Arg Lys Arg
            20


<210> SEQ ID NO 19
<211> LENGTH: 27
<212> TYPE: PRT
<213> ORGANISM: Artificial Sequence
<220> FEATURE:
<223> OTHER INFORMATION: Synthetic: IGSF8 Protein - Signal Peptide

<400> SEQUENCE: 19

Met Gly Ala Leu Arg Pro Thr Leu Leu Pro Pro Ser Leu Pro Leu Leu
1               5                   10                  15

Leu Leu Leu Met Leu Gly Met Gly Cys Trp Ala
            20                  25


<210> SEQ ID NO 20
<211> LENGTH: 1195
<212> TYPE: PRT
<213> ORGANISM: Artificial Sequence
<220> FEATURE:
<223> OTHER INFORMATION: Synthetic: Scaffold X Protein

<400> SEQUENCE: 20

Met Lys Cys Phe Phe Pro Val Leu Ser Cys Leu Ala Val Leu Gly Val
1               5                   10                  15

Val Ser Ala Gln Arg Gln Val Thr Val Gln Glu Gly Pro Leu Tyr Arg
            20                  25                  30

Thr Glu Gly Ser His Ile Thr Ile Trp Cys Asn Val Ser Gly Tyr Gln
        35                  40                  45

Gly Pro Ser Glu Gln Asn Phe Gln Trp Ser Ile Tyr Leu Pro Ser Ser
    50                  55                  60

Pro Glu Arg Glu Val Gln Ile Val Ser Thr Met Asp Ser Ser Phe Pro
65                  70                  75                  80

Tyr Ala Ile Tyr Thr Gln Arg Val Arg Gly Gly Lys Ile Phe Ile Glu
                85                  90                  95

Arg Val Gln Gly Asn Ser Thr Leu Leu His Ile Thr Asp Leu Gln Ala
            100                 105                 110

Arg Asp Ala Gly Glu Tyr Glu Cys His Thr Pro Ser Thr Asp Lys Gln
        115                 120                 125

Tyr Phe Gly Ser Tyr Ser Ala Lys Met Asn Leu Val Val Ile Pro Asp
    130                 135                 140

Ser Leu Gln Thr Thr Ala Met Pro Gln Thr Leu His Arg Val Glu Gln
145                 150                 155                 160
```

-continued

```
Asp Pro Leu Glu Leu Thr Cys Glu Val Ala Ser Glu Thr Ile Gln His
                165                 170                 175

Ser His Leu Ser Val Ala Trp Leu Arg Gln Lys Val Gly Glu Lys Pro
            180                 185                 190

Val Glu Val Ile Ser Leu Ser Arg Asp Phe Met Leu His Ser Ser Ser
        195                 200                 205

Glu Tyr Ala Gln Arg Gln Ser Leu Gly Glu Val Arg Leu Asp Lys Leu
    210                 215                 220

Gly Arg Thr Thr Phe Arg Leu Thr Ile Phe His Leu Gln Pro Ser Asp
225                 230                 235                 240

Gln Gly Glu Phe Tyr Cys Glu Ala Ala Glu Trp Ile Gln Asp Pro Asp
                245                 250                 255

Gly Ser Trp Tyr Ala Met Thr Arg Lys Arg Ser Glu Gly Ala Val Val
            260                 265                 270

Asn Val Gln Pro Thr Asp Lys Glu Phe Thr Val Arg Leu Glu Thr Glu
        275                 280                 285

Lys Arg Leu His Thr Val Gly Glu Pro Val Glu Phe Arg Cys Ile Leu
    290                 295                 300

Glu Ala Gln Asn Val Pro Asp Arg Tyr Phe Ala Val Ser Trp Ala Phe
305                 310                 315                 320

Asn Ser Ser Leu Ile Ala Thr Met Gly Pro Asn Ala Val Pro Val Leu
                325                 330                 335

Asn Ser Glu Phe Ala His Arg Glu Ala Arg Gly Gln Leu Lys Val Ala
            340                 345                 350

Lys Glu Ser Asp Ser Val Phe Val Leu Lys Ile Tyr His Leu Arg Gln
        355                 360                 365

Glu Asp Ser Gly Lys Tyr Asn Cys Arg Val Thr Glu Arg Glu Lys Thr
    370                 375                 380

Val Thr Gly Glu Phe Ile Asp Lys Glu Ser Lys Arg Pro Lys Asn Ile
385                 390                 395                 400

Pro Ile Ile Val Leu Pro Leu Lys Ser Ser Ile Ser Val Glu Val Ala
                405                 410                 415

Ser Asn Ala Ser Val Ile Leu Glu Gly Glu Asp Leu Arg Phe Ser Cys
            420                 425                 430

Ser Val Arg Thr Ala Gly Arg Pro Gln Gly Arg Phe Ser Val Ile Trp
        435                 440                 445

Gln Leu Val Asp Arg Gln Asn Arg Arg Ser Asn Ile Met Trp Leu Asp
    450                 455                 460

Arg Asp Gly Thr Val Gln Pro Gly Ser Ser Tyr Trp Glu Arg Ser Ser
465                 470                 475                 480

Phe Gly Gly Val Gln Met Glu Gln Val Gln Pro Asn Ser Phe Ser Leu
                485                 490                 495

Gly Ile Phe Asn Ser Arg Lys Glu Asp Glu Gly Gln Tyr Glu Cys His
            500                 505                 510

Val Thr Glu Trp Val Arg Ala Val Asp Gly Glu Trp Gln Ile Val Gly
        515                 520                 525

Glu Arg Arg Ala Ser Thr Pro Ile Ser Ile Thr Ala Leu Glu Met Gly
    530                 535                 540

Phe Ala Val Thr Ala Ile Ser Arg Thr Pro Gly Val Thr Tyr Ser Asp
545                 550                 555                 560

Ser Phe Asp Leu Gln Cys Ile Ile Lys Pro His Tyr Pro Ala Trp Val
                565                 570                 575

Pro Val Ser Val Thr Trp Arg Phe Gln Pro Val Gly Thr Val Glu Phe
```

-continued

```
            580                 585                 590

His Asp Leu Val Thr Phe Thr Arg Asp Gly Gly Val Gln Trp Gly Asp
        595                 600                 605

Arg Ser Ser Ser Phe Arg Thr Arg Thr Ala Ile Glu Lys Ala Glu Ser
    610                 615                 620

Ser Asn Asn Val Arg Leu Ser Ile Ser Arg Ala Ser Asp Thr Glu Ala
625                 630                 635                 640

Gly Lys Tyr Gln Cys Val Ala Glu Leu Trp Arg Lys Asn Tyr Asn Asn
                645                 650                 655

Thr Trp Thr Arg Leu Ala Glu Arg Thr Ser Asn Leu Leu Glu Ile Arg
            660                 665                 670

Val Leu Gln Pro Val Thr Lys Leu Gln Val Ser Lys Ser Lys Arg Thr
        675                 680                 685

Leu Thr Leu Val Glu Asn Lys Pro Ile Gln Leu Asn Cys Ser Val Lys
    690                 695                 700

Ser Gln Thr Ser Gln Asn Ser His Phe Ala Val Leu Trp Tyr Val His
705                 710                 715                 720

Lys Pro Ser Asp Ala Asp Gly Lys Leu Ile Leu Lys Thr Thr His Asn
                725                 730                 735

Ser Ala Phe Glu Tyr Gly Thr Tyr Ala Glu Glu Glu Gly Leu Arg Ala
            740                 745                 750

Arg Leu Gln Phe Glu Arg His Val Ser Gly Gly Leu Phe Ser Leu Thr
        755                 760                 765

Val Gln Arg Ala Glu Val Ser Asp Ser Gly Ser Tyr Tyr Cys His Val
    770                 775                 780

Glu Glu Trp Leu Leu Ser Pro Asn Tyr Ala Trp Tyr Lys Leu Ala Glu
785                 790                 795                 800

Glu Val Ser Gly Arg Thr Glu Val Thr Val Lys Gln Pro Asp Ser Arg
                805                 810                 815

Leu Arg Leu Ser Gln Ala Gln Gly Asn Leu Ser Val Leu Glu Thr Arg
            820                 825                 830

Gln Val Gln Leu Glu Cys Val Val Leu Asn Arg Thr Ser Ile Thr Ser
        835                 840                 845

Gln Leu Met Val Glu Trp Phe Val Trp Lys Pro Asn His Pro Glu Arg
    850                 855                 860

Glu Thr Val Ala Arg Leu Ser Arg Asp Ala Thr Phe His Tyr Gly Glu
865                 870                 875                 880

Gln Ala Ala Lys Asn Asn Leu Lys Gly Arg Leu His Leu Glu Ser Pro
                885                 890                 895

Ser Pro Gly Val Tyr Arg Leu Phe Ile Gln Asn Val Ala Val Gln Asp
            900                 905                 910

Ser Gly Thr Tyr Ser Cys His Val Glu Glu Trp Leu Pro Ser Pro Ser
        915                 920                 925

Gly Met Trp Tyr Lys Arg Ala Glu Asp Thr Ala Gly Gln Thr Ala Leu
    930                 935                 940

Thr Val Met Arg Pro Asp Ala Ser Leu Gln Val Asp Thr Val Val Pro
945                 950                 955                 960

Asn Ala Thr Val Ser Glu Lys Ala Ala Phe Gln Leu Asp Cys Ser Ile
                965                 970                 975

Val Ser Arg Ser Ser Gln Asp Ser Arg Phe Ala Val Ala Trp Tyr Ser
            980                 985                 990

Leu Arg Thr Lys Ala Gly Gly Lys  Arg Ser Ser Pro Gly  Leu Glu Glu
        995                 1000                 1005
```

Gln Glu Glu Glu Arg Glu Glu Glu Glu Glu Glu Glu Glu Asp Asp
1010 1015 1020

Asp Asp Asp Asp Pro Thr Glu Arg Thr Ala Leu Leu Ser Val Gly
1025 1030 1035

Pro Asp Ala Val Phe Gly Pro Glu Gly Ser Pro Trp Glu Gly Arg
1040 1045 1050

Leu Arg Phe Gln Arg Leu Ser Pro Val Leu Tyr Arg Leu Thr Val
1055 1060 1065

Leu Gln Ala Ser Pro Gln Asp Thr Gly Asn Tyr Ser Cys His Val
1070 1075 1080

Glu Glu Trp Leu Pro Ser Pro Gln Lys Glu Trp Tyr Arg Leu Thr
1085 1090 1095

Glu Glu Glu Ser Ala Pro Ile Gly Ile Arg Val Leu Asp Thr Ser
1100 1105 1110

Pro Thr Leu Gln Ser Ile Ile Cys Ser Asn Asp Ala Leu Phe Tyr
1115 1120 1125

Phe Val Phe Phe Tyr Pro Phe Pro Ile Phe Gly Ile Leu Ile Ile
1130 1135 1140

Thr Ile Leu Leu Val Arg Phe Lys Ser Arg Asn Ser Ser Lys Asn
1145 1150 1155

Ser Asp Gly Lys Asn Gly Val Pro Leu Leu Trp Ile Lys Glu Pro
1160 1165 1170

His Leu Asn Tyr Ser Pro Thr Cys Leu Glu Pro Pro Val Leu Ser
1175 1180 1185

Ile His Pro Gly Ala Ile Asp
1190 1195

<210> SEQ ID NO 21
<211> LENGTH: 748
<212> TYPE: PRT
<213> ORGANISM: Artificial Sequence
<220> FEATURE:
<223> OTHER INFORMATION: Synthetic: Scaffold X Protein

<400> SEQUENCE: 21

Met Asn Leu Gln Pro Ile Phe Trp Ile Gly Leu Ile Ser Ser Val Cys
1 5 10 15

Cys Val Phe Ala Gln Thr Asp Glu Asn Arg Cys Leu Lys Ala Asn Ala
20 25 30

Lys Ser Cys Gly Glu Cys Ile Gln Ala Gly Pro Asn Cys Gly Trp Cys
35 40 45

Thr Asn Ser Thr Phe Leu Gln Glu Gly Met Pro Thr Ser Ala Arg Cys
50 55 60

Asp Asp Leu Glu Ala Leu Lys Lys Lys Gly Cys Pro Pro Asp Asp Ile
65 70 75 80

Glu Asn Pro Arg Gly Ser Lys Asp Ile Lys Lys Asn Lys Asn Val Thr
85 90 95

Asn Arg Ser Lys Gly Thr Ala Glu Lys Leu Lys Pro Glu Asp Ile Thr
100 105 110

Gln Ile Gln Pro Gln Gln Leu Val Leu Arg Leu Arg Ser Gly Glu Pro
115 120 125

Gln Thr Phe Thr Leu Lys Phe Lys Arg Ala Glu Asp Tyr Pro Ile Asp
130 135 140

Leu Tyr Tyr Leu Met Asp Leu Ser Tyr Ser Met Lys Asp Asp Leu Glu
145 150 155 160

```
Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
    370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
    450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
    530                 535                 540

Asn Glu Ile Tyr Ser Gly Ala Ser Asn Gly Gln Ile Cys Asn Gly Arg
545                 550                 555                 560

Gly Ile Cys Glu Cys Gly Val Cys Lys Cys Thr Asp Pro Lys Phe Gln
                565                 570                 575
```

```
Gly Gln Thr Cys Glu Met Cys Gln Thr Cys Leu Gly Val Cys Ala Glu
            580                 585                 590

His Lys Glu Cys Val Gln Cys Arg Ala Phe Asn Lys Gly Glu Lys Lys
        595                 600                 605

Asp Thr Cys Thr Gln Glu Cys Ser Tyr Phe Asn Ile Thr Lys Val Glu
    610                 615                 620

Ser Arg Asp Lys Leu Pro Gln Pro Val Gln Pro Asp Pro Val Ser His
625                 630                 635                 640

Cys Lys Glu Lys Asp Val Asp Asp Cys Trp Phe Tyr Phe Thr Tyr Ser
                645                 650                 655

Val Asn Gly Asn Asn Glu Val Met Val His Val Val Glu Asn Pro Glu
            660                 665                 670

Cys Pro Thr Gly Pro Asp Ile Ile Pro Ile Val Ala Gly Val Val Ala
        675                 680                 685

Gly Ile Val Leu Ile Gly Leu Ala Leu Leu Leu Ile Trp Lys Leu Leu
    690                 695                 700

Met Ile Ile His Asp Arg Arg Glu Phe Ala Lys Phe Glu Lys Glu Lys
705                 710                 715                 720

Met Asn Ala Lys Trp Asp Thr Gly Glu Asn Pro Ile Tyr Lys Ser Ala
                725                 730                 735

Val Thr Thr Val Val Asn Pro Lys Tyr Glu Gly Lys
            740                 745
```

<210> SEQ ID NO 22
<211> LENGTH: 1032
<212> TYPE: PRT
<213> ORGANISM: Artificial Sequence
<220> FEATURE:
<223> OTHER INFORMATION: Synthetic: Scaffold X Protein

<400> SEQUENCE: 22

```
Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
            20                  25                  30

Pro Tyr Asn Val Asp Thr Glu Ser Ala Leu Leu Tyr Gln Gly Pro His
        35                  40                  45

Asn Thr Leu Phe Gly Tyr Ser Val Val Leu His Ser His Gly Ala Asn
    50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190
```

-continued

```
Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
        355                 360                 365

Gly Glu Ser Ile Val Asn Leu Gly Asp Ile Asp Asn Asp Gly Phe Glu
    370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415

Arg Ile Glu Gly Leu Gln Ile Ser Lys Ser Leu Ser Met Phe Gly Gln
            420                 425                 430

Ser Ile Ser Gly Gln Ile Asp Ala Asp Asn Asn Gly Tyr Val Asp Val
        435                 440                 445

Ala Val Gly Ala Phe Arg Ser Asp Ser Ala Val Leu Leu Arg Thr Arg
    450                 455                 460

Pro Val Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
        515                 520                 525

Ser Pro Pro Arg Phe Tyr Phe Ser Ser Asn Gly Thr Ser Asp Val Ile
    530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
            580                 585                 590

Thr Glu Glu Phe Pro Pro Leu Gln Pro Ile Leu Gln Gln Lys Lys Glu
        595                 600                 605

Lys Asp Ile Met Lys Lys Thr Ile Asn Phe Ala Arg Phe Cys Ala His
```

-continued

```
    610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
                645                 650                 655

Leu Met Leu Asn Val Ser Leu Phe Asn Ala Gly Asp Asp Ala Tyr Glu
            660                 665                 670

Thr Thr Leu His Val Lys Leu Pro Val Gly Leu Tyr Phe Ile Lys Ile
        675                 680                 685

Leu Glu Leu Glu Glu Lys Gln Ile Asn Cys Glu Val Thr Asp Asn Ser
    690                 695                 700

Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
            740                 745                 750

Glu Glu Glu Met Asp Asn Leu Lys His Ser Arg Val Thr Val Ala Ile
        755                 760                 765

Pro Leu Lys Tyr Glu Val Lys Leu Thr Val His Gly Phe Val Asn Pro
    770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
            820                 825                 830

Ser Pro Gln Thr Asp Lys Leu Phe Asn Ile Leu Asp Val Gln Thr Thr
        835                 840                 845

Thr Gly Glu Cys His Phe Glu Asn Tyr Gln Arg Val Cys Ala Leu Glu
    850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
            900                 905                 910

Ala Ser Val His Ile Gln Leu Glu Gly Arg Pro Ser Ile Leu Glu Met
        915                 920                 925

Asp Glu Thr Ser Ala Leu Lys Phe Glu Ile Arg Ala Thr Gly Phe Pro
    930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Ser Leu Leu Leu Gly Leu Ile Val Leu
            980                 985                 990

Leu Leu Ile Ser Tyr Val Met Trp  Lys Ala Gly Phe Phe  Lys Arg Gln
        995                 1000                1005

Tyr Lys  Ser Ile Leu Gln Glu  Glu Asn Arg Arg Asp  Ser Trp Ser
    1010                1015                1020

Tyr Ile  Asn Ser Lys Ser Asn  Asp Asp
    1025                1030
```

<210> SEQ ID NO 23
<211> LENGTH: 630
<212> TYPE: PRT
<213> ORGANISM: Artificial Sequence
<220> FEATURE:
<223> OTHER INFORMATION: Synthetic: Scaffold X Protein

<400> SEQUENCE: 23

Met Glu Leu Gln Pro Pro Glu Ala Ser Ile Ala Val Val Ser Ile Pro
1 5 10 15

Arg Gln Leu Pro Gly Ser His Ser Glu Ala Gly Val Gln Gly Leu Ser
20 25 30

Ala Gly Asp Asp Ser Glu Leu Gly Ser His Cys Val Ala Gln Thr Gly
35 40 45

Leu Glu Leu Leu Ala Ser Gly Asp Pro Leu Pro Ser Ala Ser Gln Asn
50 55 60

Ala Glu Met Ile Glu Thr Gly Ser Asp Cys Val Thr Gln Ala Gly Leu
65 70 75 80

Gln Leu Leu Ala Ser Ser Asp Pro Pro Ala Leu Ala Ser Lys Asn Ala
85 90 95

Glu Val Thr Gly Thr Met Ser Gln Asp Thr Glu Val Asp Met Lys Glu
100 105 110

Val Glu Leu Asn Glu Leu Glu Pro Glu Lys Gln Pro Met Asn Ala Ala
115 120 125

Ser Gly Ala Ala Met Ser Leu Ala Gly Ala Glu Lys Asn Gly Leu Val
130 135 140

Lys Ile Lys Val Ala Glu Asp Glu Ala Glu Ala Ala Ala Ala Ala Lys
145 150 155 160

Phe Thr Gly Leu Ser Lys Glu Glu Leu Leu Lys Val Ala Gly Ser Pro
165 170 175

Gly Trp Val Arg Thr Arg Trp Ala Leu Leu Leu Leu Phe Trp Leu Gly
180 185 190

Trp Leu Gly Met Leu Ala Gly Ala Val Val Ile Ile Val Arg Ala Pro
195 200 205

Arg Cys Arg Glu Leu Pro Ala Gln Lys Trp Trp His Thr Gly Ala Leu
210 215 220

Tyr Arg Ile Gly Asp Leu Gln Ala Phe Gln Gly His Gly Ala Gly Asn
225 230 235 240

Leu Ala Gly Leu Lys Gly Arg Leu Asp Tyr Leu Ser Ser Leu Lys Val
245 250 255

Lys Gly Leu Val Leu Gly Pro Ile His Lys Asn Gln Lys Asp Asp Val
260 265 270

Ala Gln Thr Asp Leu Leu Gln Ile Asp Pro Asn Phe Gly Ser Lys Glu
275 280 285

Asp Phe Asp Ser Leu Leu Gln Ser Ala Lys Lys Lys Ser Ile Arg Val
290 295 300

Ile Leu Asp Leu Thr Pro Asn Tyr Arg Gly Glu Asn Ser Trp Phe Ser
305 310 315 320

Thr Gln Val Asp Thr Val Ala Thr Lys Val Lys Asp Ala Leu Glu Phe
325 330 335

Trp Leu Gln Ala Gly Val Asp Gly Phe Gln Val Arg Asp Ile Glu Asn
340 345 350

Leu Lys Asp Ala Ser Ser Phe Leu Ala Glu Trp Gln Asn Ile Thr Lys
355 360 365

```
Gly Phe Ser Glu Asp Arg Leu Leu Ile Ala Gly Thr Asn Ser Ser Asp
    370                 375                 380

Leu Gln Gln Ile Leu Ser Leu Leu Glu Ser Asn Lys Asp Leu Leu Leu
385                 390                 395                 400

Thr Ser Ser Tyr Leu Ser Asp Ser Gly Ser Thr Gly Glu His Thr Lys
                405                 410                 415

Ser Leu Val Thr Gln Tyr Leu Asn Ala Thr Gly Asn Arg Trp Cys Ser
            420                 425                 430

Trp Ser Leu Ser Gln Ala Arg Leu Leu Thr Ser Phe Leu Pro Ala Gln
        435                 440                 445

Leu Leu Arg Leu Tyr Gln Leu Met Leu Phe Thr Leu Pro Gly Thr Pro
    450                 455                 460

Val Phe Ser Tyr Gly Asp Glu Ile Gly Leu Asp Ala Ala Ala Leu Pro
465                 470                 475                 480

Gly Gln Pro Met Glu Ala Pro Val Met Leu Trp Asp Glu Ser Ser Phe
                485                 490                 495

Pro Asp Ile Pro Gly Ala Val Ser Ala Asn Met Thr Val Lys Gly Gln
            500                 505                 510

Ser Glu Asp Pro Gly Ser Leu Leu Ser Leu Phe Arg Arg Leu Ser Asp
        515                 520                 525

Gln Arg Ser Lys Glu Arg Ser Leu Leu His Gly Asp Phe His Ala Phe
    530                 535                 540

Ser Ala Gly Pro Gly Leu Phe Ser Tyr Ile Arg His Trp Asp Gln Asn
545                 550                 555                 560

Glu Arg Phe Leu Val Val Leu Asn Phe Gly Asp Val Gly Leu Ser Ala
                565                 570                 575

Gly Leu Gln Ala Ser Asp Leu Pro Ala Ser Ala Ser Leu Pro Ala Lys
            580                 585                 590

Ala Asp Leu Leu Leu Ser Thr Gln Pro Gly Arg Glu Glu Gly Ser Pro
        595                 600                 605

Leu Glu Leu Glu Arg Leu Lys Leu Glu Pro His Glu Gly Leu Leu Leu
    610                 615                 620

Arg Phe Pro Tyr Ala Ala
625                 630
```

<210> SEQ ID NO 24
<211> LENGTH: 1023
<212> TYPE: PRT
<213> ORGANISM: Artificial Sequence
<220> FEATURE:
<223> OTHER INFORMATION: Synthetic: ATP transporter proteins

<400> SEQUENCE: 24

```
Met Gly Lys Gly Val Gly Arg Asp Lys Tyr Glu Pro Ala Ala Val Ser
1               5                   10                  15

Glu Gln Gly Asp Lys Lys Gly Lys Lys Gly Lys Lys Asp Arg Asp Met
            20                  25                  30

Asp Glu Leu Lys Lys Glu Val Ser Met Asp Asp His Lys Leu Ser Leu
        35                  40                  45

Asp Glu Leu His Arg Lys Tyr Gly Thr Asp Leu Ser Arg Gly Leu Thr
    50                  55                  60

Ser Ala Arg Ala Ala Glu Ile Leu Ala Arg Asp Gly Pro Asn Ala Leu
65                  70                  75                  80

Thr Pro Pro Pro Thr Thr Pro Glu Trp Ile Lys Phe Cys Arg Gln Leu
                85                  90                  95
```

-continued

```
Phe Gly Gly Phe Ser Met Leu Leu Trp Ile Gly Ala Ile Leu Cys Phe
            100                 105                 110

Leu Ala Tyr Ser Ile Gln Ala Ala Thr Glu Glu Glu Pro Gln Asn Asp
        115                 120                 125

Asn Leu Tyr Leu Gly Val Val Leu Ser Ala Val Val Ile Ile Thr Gly
    130                 135                 140

Cys Phe Ser Tyr Tyr Gln Glu Ala Lys Ser Ser Lys Ile Met Glu Ser
145                 150                 155                 160

Phe Lys Asn Met Val Pro Gln Gln Ala Leu Val Ile Arg Asn Gly Glu
                165                 170                 175

Lys Met Ser Ile Asn Ala Glu Glu Val Val Val Gly Asp Leu Val Glu
            180                 185                 190

Val Lys Gly Gly Asp Arg Ile Pro Ala Asp Leu Arg Ile Ile Ser Ala
        195                 200                 205

Asn Gly Cys Lys Val Asp Asn Ser Ser Leu Thr Gly Glu Ser Glu Pro
    210                 215                 220

Gln Thr Arg Ser Pro Asp Phe Thr Asn Glu Asn Pro Leu Glu Thr Arg
225                 230                 235                 240

Asn Ile Ala Phe Phe Ser Thr Asn Cys Val Glu Gly Thr Ala Arg Gly
                245                 250                 255

Ile Val Val Tyr Thr Gly Asp Arg Thr Val Met Gly Arg Ile Ala Thr
            260                 265                 270

Leu Ala Ser Gly Leu Glu Gly Gly Gln Thr Pro Ile Ala Ala Glu Ile
        275                 280                 285

Glu His Phe Ile His Ile Ile Thr Gly Val Ala Val Phe Leu Gly Val
    290                 295                 300

Ser Phe Phe Ile Leu Ser Leu Ile Leu Glu Tyr Thr Trp Leu Glu Ala
305                 310                 315                 320

Val Ile Phe Leu Ile Gly Ile Ile Val Ala Asn Val Pro Glu Gly Leu
                325                 330                 335

Leu Ala Thr Val Thr Val Cys Leu Thr Leu Thr Ala Lys Arg Met Ala
            340                 345                 350

Arg Lys Asn Cys Leu Val Lys Asn Leu Glu Ala Val Glu Thr Leu Gly
        355                 360                 365

Ser Thr Ser Thr Ile Cys Ser Asp Lys Thr Gly Thr Leu Thr Gln Asn
    370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                405                 410                 415

Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
        435                 440                 445

Gly Asp Ala Ser Glu Ser Ala Leu Leu Lys Cys Ile Glu Leu Cys Cys
    450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
            500                 505                 510
```

```
Arg Ile Leu Asp Arg Cys Ser Ser Ile Leu Leu His Gly Lys Glu Gln
        515                 520                 525

Pro Leu Asp Glu Glu Leu Lys Asp Ala Phe Gln Asn Ala Tyr Leu Glu
    530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
            580                 585                 590

Asp Pro Pro Arg Ala Ala Val Pro Asp Ala Val Gly Lys Cys Arg Ser
        595                 600                 605

Ala Gly Ile Lys Val Ile Met Val Thr Gly Asp His Pro Ile Thr Ala
    610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
        675                 680                 685

Val Phe Ala Arg Thr Ser Pro Gln Gln Lys Leu Ile Ile Val Glu Gly
    690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
        755                 760                 765

Phe Asp Asn Leu Lys Lys Ser Ile Ala Tyr Thr Leu Thr Ser Asn Ile
    770                 775                 780

Pro Glu Ile Thr Pro Phe Leu Ile Phe Ile Ile Ala Asn Ile Pro Leu
785                 790                 795                 800

Pro Leu Gly Thr Val Thr Ile Leu Cys Ile Asp Leu Gly Thr Asp Met
                805                 810                 815

Val Pro Ala Ile Ser Leu Ala Tyr Glu Gln Ala Glu Ser Asp Ile Met
            820                 825                 830

Lys Arg Gln Pro Arg Asn Pro Lys Thr Asp Lys Leu Val Asn Glu Arg
        835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Asp Arg Trp Ile Asn
                885                 890                 895

Asp Val Glu Asp Ser Tyr Gly Gln Gln Trp Thr Tyr Glu Gln Arg Lys
            900                 905                 910

Ile Val Glu Phe Thr Cys His Thr Ala Phe Phe Val Ser Ile Val Val
        915                 920                 925

Val Gln Trp Ala Asp Leu Val Ile Cys Lys Thr Arg Arg Asn Ser Val
```

-continued

```
    930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                965                 970                 975

Ala Leu Arg Met Tyr Pro Leu Lys Pro Thr Trp Trp Phe Cys Ala Phe
            980                 985                 990

Pro Tyr Ser Leu Leu Ile Phe Val  Tyr Asp Glu Val Arg  Lys Leu Ile
        995                 1000                1005

Ile Arg  Arg Arg Pro Gly Gly  Trp Val Glu Lys Glu  Thr Tyr Tyr
    1010                1015                1020


<210> SEQ ID NO 25
<211> LENGTH: 240
<212> TYPE: PRT
<213> ORGANISM: Artificial Sequence
<220> FEATURE:
<223> OTHER INFORMATION: Synthetic: ATP transporter proteins

<400> SEQUENCE: 25

Met Gly Arg Gly Ala Gly Arg Glu Tyr Ser Pro Ala Ala Thr Thr Ala
1               5                   10                  15

Glu Asn Gly Gly Gly Lys Lys Lys Gln Lys Glu Lys Glu Leu Asp Glu
            20                  25                  30

Leu Lys Lys Glu Val Ala Met Asp Asp His Lys Leu Ser Leu Asp Glu
        35                  40                  45

Leu Gly Arg Lys Tyr Gln Val Asp Leu Ser Lys Gly Leu Thr Asn Gln
    50                  55                  60

Arg Ala Gln Asp Val Leu Ala Arg Asp Gly Pro Asn Ala Leu Thr Pro
65                  70                  75                  80

Pro Pro Thr Thr Pro Glu Trp Val Lys Phe Cys Arg Gln Leu Phe Gly
                85                  90                  95

Gly Phe Ser Ile Leu Leu Trp Ile Gly Ala Ile Leu Cys Phe Leu Ala
            100                 105                 110

Tyr Gly Ile Gln Ala Ala Met Glu Asp Glu Pro Ser Asn Asp Asn Leu
        115                 120                 125

Tyr Leu Gly Val Val Leu Ala Ala Val Val Ile Val Thr Gly Cys Phe
    130                 135                 140

Ser Tyr Tyr Gln Glu Ala Lys Ser Ser Lys Ile Met Asp Ser Phe Lys
145                 150                 155                 160

Asn Met Val Pro Gln Gln Ala Leu Val Ile Arg Glu Gly Glu Lys Met
                165                 170                 175

Gln Ile Asn Ala Glu Glu Val Val Val Gly Asp Leu Val Glu Val Lys
            180                 185                 190

Gly Gly Asp Arg Val Pro Ala Asp Leu Arg Ile Ile Ser Ser His Gly
        195                 200                 205

Cys Lys Val Asp Asn Ser Ser Leu Thr Gly Glu Ser Glu Pro Gln Thr
    210                 215                 220

Arg Ser Pro Glu Phe Thr His Glu Asn Pro Leu Glu Thr Arg Asn Ile
225                 230                 235                 240


<210> SEQ ID NO 26
<211> LENGTH: 780
<212> TYPE: PRT
<213> ORGANISM: Artificial Sequence
<220> FEATURE:
<223> OTHER INFORMATION: Synthetic: ATP transporter proteins
```

<400> SEQUENCE: 26

```
Cys Phe Phe Ser Thr Asn Cys Val Glu Gly Thr Ala Arg Gly Ile Val
1               5                   10                  15

Ile Ala Thr Gly Asp Arg Thr Val Met Gly Arg Ile Ala Thr Leu Ala
            20                  25                  30

Ser Gly Leu Glu Val Gly Arg Thr Pro Ile Ala Met Glu Ile Glu His
        35                  40                  45

Phe Ile Gln Leu Ile Thr Gly Val Ala Val Phe Leu Gly Val Ser Phe
    50                  55                  60

Phe Val Leu Ser Leu Ile Leu Gly Tyr Ser Trp Leu Glu Ala Val Ile
65                  70                  75                  80

Phe Leu Ile Gly Ile Ile Val Ala Asn Val Pro Glu Gly Leu Leu Ala
                85                  90                  95

Thr Val Thr Val Cys Leu Thr Leu Thr Ala Lys Arg Met Ala Arg Lys
            100                 105                 110

Asn Cys Leu Val Lys Asn Leu Glu Ala Val Glu Thr Leu Gly Ser Thr
        115                 120                 125

Ser Thr Ile Cys Ser Asp Lys Thr Gly Thr Leu Thr Gln Asn Arg Met
    130                 135                 140

Thr Val Ala His Met Trp Phe Asp Asn Gln Ile His Glu Ala Asp Thr
145                 150                 155                 160

Thr Glu Asp Gln Ser Gly Ala Thr Phe Asp Lys Arg Ser Pro Thr Trp
                165                 170                 175

Thr Ala Leu Ser Arg Ile Ala Gly Leu Cys Asn Arg Ala Val Phe Lys
            180                 185                 190

Ala Gly Gln Glu Asn Ile Ser Val Ser Lys Arg Asp Thr Ala Gly Asp
        195                 200                 205

Ala Ser Glu Ser Ala Leu Leu Lys Cys Ile Glu Leu Ser Cys Gly Ser
    210                 215                 220

Val Arg Lys Met Arg Asp Arg Asn Pro Lys Val Ala Glu Ile Pro Phe
225                 230                 235                 240

Asn Ser Thr Asn Lys Tyr Gln Leu Ser Ile His Glu Arg Glu Asp Ser
                245                 250                 255

Pro Gln Ser His Val Leu Val Met Lys Gly Ala Pro Glu Arg Ile Leu
            260                 265                 270

Asp Arg Cys Ser Thr Ile Leu Val Gln Gly Lys Glu Ile Pro Leu Asp
        275                 280                 285

Lys Glu Met Gln Asp Ala Phe Gln Asn Ala Tyr Met Glu Leu Gly Gly
    290                 295                 300

Leu Gly Glu Arg Val Leu Gly Phe Cys Gln Leu Asn Leu Pro Ser Gly
305                 310                 315                 320

Lys Phe Pro Arg Gly Phe Lys Phe Asp Thr Asp Glu Leu Asn Phe Pro
                325                 330                 335

Thr Glu Lys Leu Cys Phe Val Gly Leu Met Ser Met Ile Asp Pro Pro
            340                 345                 350

Arg Ala Ala Val Pro Asp Ala Val Gly Lys Cys Arg Ser Ala Gly Ile
        355                 360                 365

Lys Val Ile Met Val Thr Gly Asp His Pro Ile Thr Ala Lys Ala Ile
    370                 375                 380

Ala Lys Gly Val Gly Ile Ile Ser Glu Gly Asn Glu Thr Val Glu Asp
385                 390                 395                 400

Ile Ala Ala Arg Leu Asn Ile Pro Met Ser Gln Val Asn Pro Arg Glu
```

```
                405                 410                 415

Ala Lys Ala Cys Val Val His Gly Ser Asp Leu Lys Asp Met Thr Ser
            420                 425                 430

Glu Gln Leu Asp Glu Ile Leu Lys Asn His Thr Glu Ile Val Phe Ala
        435                 440                 445

Arg Thr Ser Pro Gln Gln Lys Leu Ile Ile Val Glu Gly Cys Gln Arg
    450                 455                 460

Gln Gly Ala Ile Val Ala Val Thr Gly Asp Gly Val Asn Asp Ser Pro
465                 470                 475                 480

Ala Leu Lys Lys Ala Asp Ile Gly Ile Ala Met Gly Ile Ser Gly Ser
                485                 490                 495

Asp Val Ser Lys Gln Ala Ala Asp Met Ile Leu Leu Asp Asp Asn Phe
            500                 505                 510

Ala Ser Ile Val Thr Gly Val Glu Glu Gly Arg Leu Ile Phe Asp Asn
        515                 520                 525

Leu Lys Lys Ser Ile Ala Tyr Thr Leu Thr Ser Asn Ile Pro Glu Ile
    530                 535                 540

Thr Pro Phe Leu Leu Phe Ile Ile Ala Asn Ile Pro Leu Pro Leu Gly
545                 550                 555                 560

Thr Val Thr Ile Leu Cys Ile Asp Leu Gly Thr Asp Met Val Pro Ala
                565                 570                 575

Ile Ser Leu Ala Tyr Glu Ala Ala Glu Ser Asp Ile Met Lys Arg Gln
            580                 585                 590

Pro Arg Asn Ser Gln Thr Asp Lys Leu Val Asn Glu Arg Leu Ile Ser
        595                 600                 605

Met Ala Tyr Gly Gln Ile Gly Met Ile Gln Ala Leu Gly Gly Phe Phe
    610                 615                 620

Thr Tyr Phe Val Ile Leu Ala Glu Asn Gly Phe Leu Pro Ser Arg Leu
625                 630                 635                 640

Leu Gly Ile Arg Leu Asp Trp Asp Asp Arg Thr Met Asn Asp Leu Glu
                645                 650                 655

Asp Ser Tyr Gly Gln Glu Trp Thr Tyr Glu Gln Arg Lys Val Val Glu
            660                 665                 670

Phe Thr Cys His Thr Ala Phe Phe Ala Ser Ile Val Val Val Gln Trp
        675                 680                 685

Ala Asp Leu Ile Ile Cys Lys Thr Arg Arg Asn Ser Val Phe Gln Gln
    690                 695                 700

Gly Met Lys Asn Lys Ile Leu Ile Phe Gly Leu Leu Glu Glu Thr Ala
705                 710                 715                 720

Leu Ala Ala Phe Leu Ser Tyr Cys Pro Gly Met Gly Val Ala Leu Arg
                725                 730                 735

Met Tyr Pro Leu Lys Val Thr Trp Trp Phe Cys Ala Phe Pro Tyr Ser
            740                 745                 750

Leu Leu Ile Phe Ile Tyr Asp Glu Val Arg Lys Leu Ile Leu Arg Arg
        755                 760                 765

Tyr Pro Gly Gly Trp Val Glu Lys Glu Thr Tyr Tyr
    770                 775                 780


<210> SEQ ID NO 27
<211> LENGTH: 1026
<212> TYPE: PRT
<213> ORGANISM: Artificial Sequence
<220> FEATURE:
<223> OTHER INFORMATION: Synthetic: ATP transporter proteins
```

<400> SEQUENCE: 27

```
Met Gly Ser Gly Gly Ser Asp Ser Tyr Arg Ile Ala Thr Ser Gln Asp
1               5                   10                  15

Lys Lys Asp Asp Lys Asp Ser Pro Lys Lys Asn Lys Gly Lys Glu Arg
            20                  25                  30

Arg Asp Leu Asp Asp Leu Lys Lys Glu Val Ala Met Thr Glu His Lys
        35                  40                  45

Met Ser Val Glu Glu Val Cys Arg Lys Tyr Asn Thr Asp Cys Val Gln
    50                  55                  60

Gly Leu Thr His Ser Lys Ala Gln Glu Ile Leu Ala Arg Asp Gly Pro
65                  70                  75                  80

Asn Ala Leu Thr Pro Pro Pro Thr Thr Pro Glu Trp Val Lys Phe Cys
                85                  90                  95

Arg Gln Leu Phe Gly Gly Phe Ser Ile Leu Leu Trp Ile Gly Ala Ile
            100                 105                 110

Leu Cys Phe Leu Ala Tyr Gly Ile Gln Ala Gly Thr Glu Asp Asp Pro
        115                 120                 125

Ser Gly Asp Asn Leu Tyr Leu Gly Ile Val Leu Ala Ala Val Val Ile
    130                 135                 140

Ile Thr Gly Cys Phe Ser Tyr Tyr Gln Glu Ala Lys Ser Ser Lys Ile
145                 150                 155                 160

Met Glu Ser Phe Lys Asn Met Val Pro Gln Gln Ala Leu Val Ile Arg
                165                 170                 175

Glu Gly Glu Lys Met Gln Val Asn Ala Glu Glu Val Val Val Gly Asp
            180                 185                 190

Leu Val Glu Ile Lys Gly Gly Asp Arg Val Pro Ala Asp Leu Arg Ile
        195                 200                 205

Ile Ser Ala His Gly Cys Lys Val Asp Asn Ser Ser Leu Thr Gly Glu
    210                 215                 220

Ser Glu Pro Gln Thr Arg Ser Pro Asp Cys Thr His Asp Asn Pro Leu
225                 230                 235                 240

Glu Thr Arg Asn Ile Thr Phe Phe Ser Thr Asn Cys Val Glu Gly Thr
                245                 250                 255

Ala Arg Gly Val Val Val Ala Thr Gly Asp Arg Thr Val Met Gly Arg
            260                 265                 270

Ile Ala Thr Leu Ala Ser Gly Leu Glu Val Gly Lys Thr Pro Ile Ala
        275                 280                 285

Ile Glu Ile Glu His Phe Ile Gln Leu Ile Thr Gly Val Ala Val Phe
    290                 295                 300

Leu Gly Val Ser Phe Phe Ile Leu Ser Leu Ile Leu Gly Tyr Thr Trp
305                 310                 315                 320

Leu Glu Ala Val Ile Phe Leu Ile Gly Ile Ile Val Ala Asn Val Pro
                325                 330                 335

Glu Gly Leu Leu Ala Thr Val Thr Val Cys Leu Thr Leu Thr Ala Lys
            340                 345                 350

Arg Met Ala Arg Lys Asn Cys Leu Val Lys Asn Leu Glu Ala Val Glu
        355                 360                 365

Thr Leu Gly Ser Thr Ser Thr Ile Cys Ser Asp Lys Thr Gly Thr Leu
    370                 375                 380

Thr Gln Asn Arg Met Thr Val Ala His Met Trp Phe Asp Asn Gln Ile
385                 390                 395                 400

His Glu Ala Asp Thr Thr Glu Asp Gln Ser Gly Thr Ser Phe Asp Lys
                405                 410                 415
```

-continued

```
Ser Ser His Thr Trp Val Ala Leu Ser His Ile Ala Gly Leu Cys Asn
            420                 425                 430

Arg Ala Val Phe Lys Gly Gly Gln Asp Asn Ile Pro Val Leu Lys Arg
        435                 440                 445

Asp Val Ala Gly Asp Ala Ser Glu Ser Ala Leu Leu Lys Cys Ile Glu
    450                 455                 460

Leu Ser Ser Gly Ser Val Lys Leu Met Arg Glu Arg Asn Lys Lys Val
465                 470                 475                 480

Ala Glu Ile Pro Phe Asn Ser Thr Asn Lys Tyr Gln Leu Ser Ile His
                485                 490                 495

Glu Thr Glu Asp Pro Asn Asp Asn Arg Tyr Leu Leu Val Met Lys Gly
            500                 505                 510

Ala Pro Glu Arg Ile Leu Asp Arg Cys Ser Thr Ile Leu Leu Gln Gly
        515                 520                 525

Lys Glu Gln Pro Leu Asp Glu Glu Met Lys Glu Ala Phe Gln Asn Ala
    530                 535                 540

Tyr Leu Glu Leu Gly Gly Leu Gly Glu Arg Val Leu Gly Phe Cys His
545                 550                 555                 560

Tyr Tyr Leu Pro Glu Glu Gln Phe Pro Lys Gly Phe Ala Phe Asp Cys
                565                 570                 575

Asp Asp Val Asn Phe Thr Thr Asp Asn Leu Cys Phe Val Gly Leu Met
            580                 585                 590

Ser Met Ile Asp Pro Pro Arg Ala Ala Val Pro Asp Ala Val Gly Lys
        595                 600                 605

Cys Arg Ser Ala Gly Ile Lys Val Ile Met Val Thr Gly Asp His Pro
    610                 615                 620

Ile Thr Ala Lys Ala Ile Ala Lys Gly Val Gly Ile Ile Ser Glu Gly
625                 630                 635                 640

Asn Glu Thr Val Glu Asp Ile Ala Ala Arg Leu Asn Ile Pro Val Ser
                645                 650                 655

Gln Val Asn Pro Arg Asp Ala Lys Ala Cys Val Ile His Gly Thr Asp
            660                 665                 670

Leu Lys Asp Phe Thr Ser Glu Gln Ile Asp Glu Ile Leu Gln Asn His
        675                 680                 685

Thr Glu Ile Val Phe Ala Arg Thr Ser Pro Gln Gln Lys Leu Ile Ile
    690                 695                 700

Val Glu Gly Cys Gln Arg Gln Gly Ala Ile Val Ala Val Thr Gly Asp
705                 710                 715                 720

Gly Val Asn Asp Ser Pro Ala Leu Lys Lys Ala Asp Ile Gly Val Ala
                725                 730                 735

Met Gly Ile Ala Gly Ser Asp Val Ser Lys Gln Ala Ala Asp Met Ile
            740                 745                 750

Leu Leu Asp Asp Asn Phe Ala Ser Ile Val Thr Gly Val Glu Glu Gly
        755                 760                 765

Arg Leu Ile Phe Asp Asn Leu Lys Lys Ser Ile Ala Tyr Thr Leu Thr
    770                 775                 780

Ser Asn Ile Pro Glu Ile Thr Pro Phe Leu Leu Phe Ile Met Ala Asn
785                 790                 795                 800

Ile Pro Leu Pro Leu Gly Thr Ile Thr Ile Leu Cys Ile Asp Leu Gly
                805                 810                 815

Thr Asp Met Val Pro Ala Ile Ser Leu Ala Tyr Glu Ala Ala Glu Ser
            820                 825                 830
```

```
Asp Ile Met Lys Arg Gln Pro Arg Asn Pro Arg Thr Asp Lys Leu Val
        835                 840                 845

Asn Glu Arg Leu Ile Ser Met Ala Tyr Gly Gln Ile Gly Met Ile Gln
    850                 855                 860

Ala Leu Gly Gly Phe Phe Ser Tyr Phe Val Ile Leu Ala Glu Asn Gly
865                 870                 875                 880

Phe Leu Pro Gly Asn Leu Val Gly Ile Arg Leu Asn Trp Asp Asp Arg
                885                 890                 895

Thr Val Asn Asp Leu Glu Asp Ser Tyr Gly Gln Gln Trp Thr Tyr Glu
            900                 905                 910

Gln Arg Lys Val Val Glu Phe Thr Cys His Thr Ala Phe Phe Val Ser
        915                 920                 925

Ile Val Val Val Gln Trp Ala Asp Leu Ile Ile Cys Lys Thr Arg Arg
    930                 935                 940

Asn Ser Val Phe Gln Gln Gly Met Lys Asn Lys Ile Leu Ile Phe Gly
945                 950                 955                 960

Leu Phe Glu Glu Thr Ala Leu Ala Ala Phe Leu Ser Tyr Cys Pro Gly
                965                 970                 975

Met Asp Val Ala Leu Arg Met Tyr Pro Leu Lys Pro Ser Trp Trp Phe
            980                 985                 990

Cys Ala Phe Pro Tyr Ser Phe Leu  Ile Phe Val Tyr Asp  Glu Ile Arg
        995                 1000                1005

Lys Leu  Ile Leu Arg Arg Asn  Pro Gly Gly Trp Val  Glu Lys Glu
    1010                1015                1020

Thr Tyr  Tyr
    1025


<210> SEQ ID NO 28
<211> LENGTH: 1029
<212> TYPE: PRT
<213> ORGANISM: Artificial Sequence
<220> FEATURE:
<223> OTHER INFORMATION: Synthetic: ATP transporter proteins

<400> SEQUENCE: 28

Met Gly Leu Trp Gly Lys Lys Gly Thr Val Ala Pro His Asp Gln Ser
1               5                   10                  15

Pro Arg Arg Arg Pro Lys Lys Gly Leu Ile Lys Lys Lys Met Val Lys
            20                  25                  30

Arg Glu Lys Gln Lys Arg Asn Met Glu Glu Leu Lys Lys Glu Val Val
        35                  40                  45

Met Asp Asp His Lys Leu Thr Leu Glu Glu Leu Ser Thr Lys Tyr Ser
    50                  55                  60

Val Asp Leu Thr Lys Gly His Ser His Gln Arg Ala Lys Glu Ile Leu
65                  70                  75                  80

Thr Arg Gly Gly Pro Asn Thr Val Thr Pro Pro Pro Thr Thr Pro Glu
                85                  90                  95

Trp Val Lys Phe Cys Lys Gln Leu Phe Gly Gly Phe Ser Leu Leu Leu
            100                 105                 110

Trp Thr Gly Ala Ile Leu Cys Phe Val Ala Tyr Ser Ile Gln Ile Tyr
        115                 120                 125

Phe Asn Glu Glu Pro Thr Lys Asp Asn Leu Tyr Leu Ser Ile Val Leu
    130                 135                 140

Ser Val Val Val Ile Val Thr Gly Cys Phe Ser Tyr Tyr Gln Glu Ala
145                 150                 155                 160
```

-continued

```
Lys Ser Ser Lys Ile Met Glu Ser Phe Lys Asn Met Val Pro Gln Gln
                165                 170                 175

Ala Leu Val Ile Arg Gly Gly Glu Lys Met Gln Ile Asn Val Gln Glu
            180                 185                 190

Val Val Leu Gly Asp Leu Val Glu Ile Lys Gly Gly Asp Arg Val Pro
        195                 200                 205

Ala Asp Leu Arg Leu Ile Ser Ala Gln Gly Cys Lys Val Asp Asn Ser
    210                 215                 220

Ser Leu Thr Gly Glu Ser Glu Pro Gln Ser Arg Ser Pro Asp Phe Thr
225                 230                 235                 240

His Glu Asn Pro Leu Glu Thr Arg Asn Ile Cys Phe Phe Ser Thr Asn
                245                 250                 255

Cys Val Glu Gly Thr Ala Arg Gly Ile Val Ile Ala Thr Gly Asp Ser
            260                 265                 270

Thr Val Met Gly Arg Ile Ala Ser Leu Thr Ser Gly Leu Ala Val Gly
        275                 280                 285

Gln Thr Pro Ile Ala Ala Glu Ile Glu His Phe Ile His Leu Ile Thr
    290                 295                 300

Val Val Ala Val Phe Leu Gly Val Thr Phe Phe Ala Leu Ser Leu Leu
305                 310                 315                 320

Leu Gly Tyr Gly Trp Leu Glu Ala Ile Ile Phe Leu Ile Gly Ile Ile
                325                 330                 335

Val Ala Asn Val Pro Glu Gly Leu Leu Ala Thr Val Thr Val Cys Leu
            340                 345                 350

Thr Leu Thr Ala Lys Arg Met Ala Arg Lys Asn Cys Leu Val Lys Asn
        355                 360                 365

Leu Glu Ala Val Glu Thr Leu Gly Ser Thr Ser Thr Ile Cys Ser Asp
    370                 375                 380

Lys Thr Gly Thr Leu Thr Gln Asn Arg Met Thr Val Ala His Met Trp
385                 390                 395                 400

Phe Asp Met Thr Val Tyr Glu Ala Asp Thr Thr Glu Glu Gln Thr Gly
                405                 410                 415

Lys Thr Phe Thr Lys Ser Ser Asp Thr Trp Phe Met Leu Ala Arg Ile
            420                 425                 430

Ala Gly Leu Cys Asn Arg Ala Asp Phe Lys Ala Asn Gln Glu Ile Leu
        435                 440                 445

Pro Ile Ala Lys Arg Ala Thr Thr Gly Asp Ala Ser Glu Ser Ala Leu
    450                 455                 460

Leu Lys Phe Ile Glu Gln Ser Tyr Ser Ser Val Ala Glu Met Arg Glu
465                 470                 475                 480

Lys Asn Pro Lys Val Ala Glu Ile Pro Phe Asn Ser Thr Asn Lys Tyr
                485                 490                 495

Gln Met Ser Ile His Leu Arg Glu Asp Ser Ser Gln Thr His Val Leu
            500                 505                 510

Met Met Lys Gly Ala Pro Glu Arg Ile Leu Glu Phe Cys Ser Thr Phe
        515                 520                 525

Leu Leu Asn Gly Gln Glu Tyr Ser Met Asn Asp Glu Met Lys Glu Ala
    530                 535                 540

Phe Gln Asn Ala Tyr Leu Glu Leu Gly Gly Leu Gly Glu Arg Val Leu
545                 550                 555                 560

Gly Phe Cys Phe Leu Asn Leu Pro Ser Ser Phe Ser Lys Gly Phe Pro
                565                 570                 575

Phe Asn Thr Asp Glu Ile Asn Phe Pro Met Asp Asn Leu Cys Phe Val
```

```
            580                 585                 590

Gly Leu Ile Ser Met Ile Asp Pro Pro Arg Ala Ala Val Pro Asp Ala
        595                 600                 605

Val Ser Lys Cys Arg Ser Ala Gly Ile Lys Val Ile Met Val Thr Gly
    610                 615                 620

Asp His Pro Ile Thr Ala Lys Ala Ile Ala Lys Gly Val Gly Ile Ile
625                 630                 635                 640

Ser Glu Gly Thr Glu Thr Ala Glu Glu Val Ala Ala Arg Leu Lys Ile
                645                 650                 655

Pro Ile Ser Lys Val Asp Ala Ser Ala Ala Lys Ala Ile Val Val His
            660                 665                 670

Gly Ala Glu Leu Lys Asp Ile Gln Ser Lys Gln Leu Asp Gln Ile Leu
        675                 680                 685

Gln Asn His Pro Glu Ile Val Phe Ala Arg Thr Ser Pro Gln Gln Lys
    690                 695                 700

Leu Ile Ile Val Glu Gly Cys Gln Arg Leu Gly Ala Val Val Ala Val
705                 710                 715                 720

Thr Gly Asp Gly Val Asn Asp Ser Pro Ala Leu Lys Lys Ala Asp Ile
                725                 730                 735

Gly Ile Ala Met Gly Ile Ser Gly Ser Asp Val Ser Lys Gln Ala Ala
            740                 745                 750

Asp Met Ile Leu Leu Asp Asp Asn Phe Ala Ser Ile Val Thr Gly Val
        755                 760                 765

Glu Glu Gly Arg Leu Ile Phe Asp Asn Leu Lys Lys Ser Ile Met Tyr
    770                 775                 780

Thr Leu Thr Ser Asn Ile Pro Glu Ile Thr Pro Phe Leu Met Phe Ile
785                 790                 795                 800

Ile Leu Gly Ile Pro Leu Pro Leu Gly Thr Ile Thr Ile Leu Cys Ile
                805                 810                 815

Asp Leu Gly Thr Asp Met Val Pro Ala Ile Ser Leu Ala Tyr Glu Ser
            820                 825                 830

Ala Glu Ser Asp Ile Met Lys Arg Leu Pro Arg Asn Pro Lys Thr Asp
        835                 840                 845

Asn Leu Val Asn His Arg Leu Ile Gly Met Ala Tyr Gly Gln Ile Gly
    850                 855                 860

Met Ile Gln Ala Leu Ala Gly Phe Phe Thr Tyr Phe Val Ile Leu Ala
865                 870                 875                 880

Glu Asn Gly Phe Arg Pro Val Asp Leu Leu Gly Ile Arg Leu His Trp
                885                 890                 895

Glu Asp Lys Tyr Leu Asn Asp Leu Glu Asp Ser Tyr Gly Gln Gln Trp
            900                 905                 910

Thr Tyr Glu Gln Arg Lys Val Val Glu Phe Thr Cys Gln Thr Ala Phe
        915                 920                 925

Phe Val Thr Ile Val Val Val Gln Trp Ala Asp Leu Ile Ile Ser Lys
    930                 935                 940

Thr Arg Arg Asn Ser Leu Phe Gln Gln Gly Met Arg Asn Lys Val Leu
945                 950                 955                 960

Ile Phe Gly Ile Leu Glu Glu Thr Leu Leu Ala Ala Phe Leu Ser Tyr
                965                 970                 975

Thr Pro Gly Met Asp Val Ala Leu Arg Met Tyr Pro Leu Lys Ile Thr
            980                 985                 990

Trp Trp Leu Cys Ala Ile Pro Tyr  Ser Ile Leu Ile Phe  Val Tyr Asp
        995                 1000                1005
```

Glu Ile Arg Lys Leu Leu Ile Arg Gln His Pro Asp Gly Trp Val
1010 1015 1020

Glu Arg Glu Thr Tyr Tyr
1025

<210> SEQ ID NO 29
<211> LENGTH: 279
<212> TYPE: PRT
<213> ORGANISM: Artificial Sequence
<220> FEATURE:
<223> OTHER INFORMATION: Synthetic: ATP transporter proteins

<400> SEQUENCE: 29

Met Thr Lys Asn Glu Lys Lys Ser Leu Asn Gln Ser Leu Ala Glu Trp
1 5 10 15

Lys Leu Phe Ile Tyr Asn Pro Thr Thr Gly Glu Phe Leu Gly Arg Thr
20 25 30

Ala Lys Ser Trp Gly Leu Ile Leu Leu Phe Tyr Leu Val Phe Tyr Gly
35 40 45

Phe Leu Ala Ala Leu Phe Ser Phe Thr Met Trp Val Met Leu Gln Thr
50 55 60

Leu Asn Asp Glu Val Pro Lys Tyr Arg Asp Gln Ile Pro Ser Pro Gly
65 70 75 80

Leu Met Val Phe Pro Lys Pro Val Thr Ala Leu Glu Tyr Thr Phe Ser
85 90 95

Arg Ser Asp Pro Thr Ser Tyr Ala Gly Tyr Ile Glu Asp Leu Lys Lys
100 105 110

Phe Leu Lys Pro Tyr Thr Leu Glu Glu Gln Lys Asn Leu Thr Val Cys
115 120 125

Pro Asp Gly Ala Leu Phe Glu Gln Lys Gly Pro Val Tyr Val Ala Cys
130 135 140

Gln Phe Pro Ile Ser Leu Leu Gln Ala Cys Ser Gly Met Asn Asp Pro
145 150 155 160

Asp Phe Gly Tyr Ser Gln Gly Asn Pro Cys Ile Leu Val Lys Met Asn
165 170 175

Arg Ile Ile Gly Leu Lys Pro Glu Gly Val Pro Arg Ile Asp Cys Val
180 185 190

Ser Lys Asn Glu Asp Ile Pro Asn Val Ala Val Tyr Pro His Asn Gly
195 200 205

Met Ile Asp Leu Lys Tyr Phe Pro Tyr Tyr Gly Lys Lys Leu His Val
210 215 220

Gly Tyr Leu Gln Pro Leu Val Ala Val Gln Val Ser Phe Ala Pro Asn
225 230 235 240

Asn Thr Gly Lys Glu Val Thr Val Glu Cys Lys Ile Asp Gly Ser Ala
245 250 255

Asn Leu Lys Ser Gln Asp Asp Arg Asp Lys Phe Leu Gly Arg Val Met
260 265 270

Phe Lys Ile Thr Ala Arg Ala
275

<210> SEQ ID NO 30
<211> LENGTH: 1258
<212> TYPE: PRT
<213> ORGANISM: Artificial Sequence
<220> FEATURE:
<223> OTHER INFORMATION: Synthetic: ATP transporter proteins

<400> SEQUENCE: 30

```
Met Gly Asp Met Ala Asn Asn Ser Val Ala Tyr Ser Gly Val Lys Asn
1               5                   10                  15

Ser Leu Lys Glu Ala Asn His Asp Gly Asp Phe Gly Ile Thr Leu Ala
            20                  25                  30

Glu Leu Arg Ala Leu Met Glu Leu Arg Ser Thr Asp Ala Leu Arg Lys
        35                  40                  45

Ile Gln Glu Ser Tyr Gly Asp Val Tyr Gly Ile Cys Thr Lys Leu Lys
    50                  55                  60

Thr Ser Pro Asn Glu Gly Leu Ser Gly Asn Pro Ala Asp Leu Glu Arg
65                  70                  75                  80

Arg Glu Ala Val Phe Gly Lys Asn Phe Ile Pro Pro Lys Lys Pro Lys
                85                  90                  95

Thr Phe Leu Gln Leu Val Trp Glu Ala Leu Gln Asp Val Thr Leu Ile
            100                 105                 110

Ile Leu Glu Ile Ala Ala Ile Val Ser Leu Gly Leu Ser Phe Tyr Gln
        115                 120                 125

Pro Pro Glu Gly Asp Asn Ala Leu Cys Gly Glu Val Ser Val Gly Glu
    130                 135                 140

Glu Glu Gly Glu Gly Glu Thr Gly Trp Ile Glu Gly Ala Ala Ile Leu
145                 150                 155                 160

Leu Ser Val Val Cys Val Val Leu Val Thr Ala Phe Asn Asp Trp Ser
                165                 170                 175

Lys Glu Lys Gln Phe Arg Gly Leu Gln Ser Arg Ile Glu Gln Glu Gln
            180                 185                 190

Lys Phe Thr Val Ile Arg Gly Gly Gln Val Ile Gln Ile Pro Val Ala
        195                 200                 205

Asp Ile Thr Val Gly Asp Ile Ala Gln Val Lys Tyr Gly Asp Leu Leu
    210                 215                 220

Pro Ala Asp Gly Ile Leu Ile Gln Gly Asn Asp Leu Lys Ile Asp Glu
225                 230                 235                 240

Ser Ser Leu Thr Gly Glu Ser Asp His Val Lys Lys Ser Leu Asp Lys
                245                 250                 255

Asp Pro Leu Leu Leu Ser Gly Thr His Val Met Glu Gly Ser Gly Arg
            260                 265                 270

Met Val Val Thr Ala Val Gly Val Asn Ser Gln Thr Gly Ile Ile Phe
        275                 280                 285

Thr Leu Leu Gly Ala Gly Gly Glu Glu Glu Glu Lys Lys Asp Glu Lys
    290                 295                 300

Lys Lys Glu Lys Lys Asn Lys Lys Gln Asp Gly Ala Ile Glu Asn Arg
305                 310                 315                 320

Asn Lys Ala Lys Ala Gln Asp Gly Ala Ala Met Glu Met Gln Pro Leu
                325                 330                 335

Lys Ser Glu Glu Gly Gly Asp Gly Asp Glu Lys Asp Lys Lys Lys Ala
            340                 345                 350

Asn Leu Pro Lys Lys Glu Lys Ser Val Leu Gln Gly Lys Leu Thr Lys
        355                 360                 365

Leu Ala Val Gln Ile Gly Lys Ala Gly Leu Leu Met Ser Ala Ile Thr
    370                 375                 380

Val Ile Ile Leu Val Leu Tyr Phe Val Ile Asp Thr Phe Trp Val Gln
385                 390                 395                 400

Lys Arg Pro Trp Leu Ala Glu Cys Thr Pro Ile Tyr Ile Gln Tyr Phe
                405                 410                 415
```

-continued

```
Val Lys Phe Phe Ile Ile Gly Val Thr Val Leu Val Val Ala Val Pro
            420                 425                 430

Glu Gly Leu Pro Leu Ala Val Thr Ile Ser Leu Ala Tyr Ser Val Lys
        435                 440                 445

Lys Met Met Lys Asp Asn Asn Leu Val Arg His Leu Asp Ala Cys Glu
    450                 455                 460

Thr Met Gly Asn Ala Thr Ala Ile Cys Ser Asp Lys Thr Gly Thr Leu
465                 470                 475                 480

Thr Met Asn Arg Met Thr Val Val Gln Ala Tyr Ile Asn Glu Lys His
                485                 490                 495

Tyr Lys Lys Val Pro Glu Pro Glu Ala Ile Pro Pro Asn Ile Leu Ser
            500                 505                 510

Tyr Leu Val Thr Gly Ile Ser Val Asn Cys Ala Tyr Thr Ser Lys Ile
        515                 520                 525

Leu Pro Pro Glu Lys Glu Gly Gly Leu Pro Arg His Val Gly Asn Lys
    530                 535                 540

Thr Glu Cys Ala Leu Leu Gly Leu Leu Leu Asp Leu Lys Arg Asp Tyr
545                 550                 555                 560

Gln Asp Val Arg Asn Glu Ile Pro Glu Glu Ala Leu Tyr Lys Val Tyr
                565                 570                 575

Thr Phe Asn Ser Val Arg Lys Ser Met Ser Thr Val Leu Lys Asn Ser
            580                 585                 590

Asp Gly Ser Tyr Arg Ile Phe Ser Lys Gly Ala Ser Glu Ile Ile Leu
        595                 600                 605

Lys Lys Cys Phe Lys Ile Leu Ser Ala Asn Gly Glu Ala Lys Val Phe
    610                 615                 620

Arg Pro Arg Asp Arg Asp Asp Ile Val Lys Thr Val Ile Glu Pro Met
625                 630                 635                 640

Ala Ser Glu Gly Leu Arg Thr Ile Cys Leu Ala Phe Arg Asp Phe Pro
                645                 650                 655

Ala Gly Glu Pro Glu Pro Glu Trp Asp Asn Glu Asn Asp Ile Val Thr
            660                 665                 670

Gly Leu Thr Cys Ile Ala Val Val Gly Ile Glu Asp Pro Val Arg Pro
        675                 680                 685

Glu Val Pro Asp Ala Ile Lys Lys Cys Gln Arg Ala Gly Ile Thr Val
    690                 695                 700

Arg Met Val Thr Gly Asp Asn Ile Asn Thr Ala Arg Ala Ile Ala Thr
705                 710                 715                 720

Lys Cys Gly Ile Leu His Pro Gly Glu Asp Phe Leu Cys Leu Glu Gly
                725                 730                 735

Lys Asp Phe Asn Arg Arg Ile Arg Asn Glu Lys Gly Glu Ile Glu Gln
            740                 745                 750

Glu Arg Ile Asp Lys Ile Trp Pro Lys Leu Arg Val Leu Ala Arg Ser
        755                 760                 765

Ser Pro Thr Asp Lys His Thr Leu Val Lys Gly Ile Ile Asp Ser Thr
    770                 775                 780

Val Ser Asp Gln Arg Gln Val Val Ala Val Thr Gly Asp Gly Thr Asn
785                 790                 795                 800

Asp Gly Pro Ala Leu Lys Lys Ala Asp Val Gly Phe Ala Met Gly Ile
                805                 810                 815

Ala Gly Thr Asp Val Ala Lys Glu Ala Ser Asp Ile Ile Leu Thr Asp
            820                 825                 830
```

```
Asp Asn Phe Thr Ser Ile Val Lys Ala Val Met Trp Gly Arg Asn Val
        835                 840                 845

Tyr Asp Ser Ile Ser Lys Phe Leu Gln Phe Gln Leu Thr Val Asn Val
    850                 855                 860

Val Ala Val Ile Val Ala Phe Thr Gly Ala Cys Ile Thr Gln Asp Ser
865                 870                 875                 880

Pro Leu Lys Ala Val Gln Met Leu Trp Val Asn Leu Ile Met Asp Thr
                885                 890                 895

Leu Ala Ser Leu Ala Leu Ala Thr Glu Pro Pro Thr Glu Ser Leu Leu
            900                 905                 910

Leu Arg Lys Pro Tyr Gly Arg Asn Lys Pro Leu Ile Ser Arg Thr Met
        915                 920                 925

Met Lys Asn Ile Leu Gly His Ala Phe Tyr Gln Leu Val Val Val Phe
    930                 935                 940

Thr Leu Leu Phe Ala Gly Glu Lys Phe Phe Asp Ile Asp Ser Gly Arg
945                 950                 955                 960

Asn Ala Pro Leu His Ala Pro Pro Ser Glu His Tyr Thr Ile Val Phe
                965                 970                 975

Asn Thr Phe Val Leu Met Gln Leu Phe Asn Glu Ile Asn Ala Arg Lys
            980                 985                 990

Ile His Gly Glu Arg Asn Val Phe  Glu Gly Ile Phe Asn  Asn Ala Ile
        995                 1000                 1005

Phe Cys  Thr Ile Val Leu Gly  Thr Phe Val Val Gln  Ile Ile Ile
    1010                 1015                 1020

Val Gln  Phe Gly Gly Lys Pro  Phe Ser Cys Ser Glu  Leu Ser Ile
    1025                 1030                 1035

Glu Gln  Trp Leu Trp Ser Ile  Phe Leu Gly Met Gly  Thr Leu Leu
    1040                 1045                 1050

Trp Gly  Gln Leu Ile Ser Thr  Ile Pro Thr Ser Arg  Leu Lys Phe
    1055                 1060                 1065

Leu Lys  Glu Ala Gly His Gly  Thr Gln Lys Glu Glu  Ile Pro Glu
    1070                 1075                 1080

Glu Glu  Leu Ala Glu Asp Val  Glu Glu Ile Asp His  Ala Glu Arg
    1085                 1090                 1095

Glu Leu  Arg Arg Gly Gln Ile  Leu Trp Phe Arg Gly  Leu Asn Arg
    1100                 1105                 1110

Ile Gln  Thr Gln Met Asp Val  Val Asn Ala Phe Gln  Ser Gly Ser
    1115                 1120                 1125

Ser Ile  Gln Gly Ala Leu Arg  Arg Gln Pro Ser Ile  Ala Ser Gln
    1130                 1135                 1140

His His  Asp Val Thr Asn Ile  Ser Thr Pro Thr His  Ile Arg Val
    1145                 1150                 1155

Val Asn  Ala Phe Arg Ser Ser  Leu Tyr Glu Gly Leu  Glu Lys Pro
    1160                 1165                 1170

Glu Ser  Arg Ser Ser Ile His  Asn Phe Met Thr His  Pro Glu Phe
    1175                 1180                 1185

Arg Ile  Glu Asp Ser Glu Pro  His Ile Pro Leu Ile  Asp Asp Thr
    1190                 1195                 1200

Asp Ala  Glu Asp Asp Ala Pro  Thr Lys Arg Asn Ser  Ser Pro Pro
    1205                 1210                 1215

Pro Ser  Pro Asn Lys Asn Asn  Asn Ala Val Asp Ser  Gly Ile His
    1220                 1225                 1230

Leu Thr  Ile Glu Met Asn Lys  Ser Ala Thr Ser Ser  Ser Pro Gly
```

1235 1240 1245

Ser Pro Leu His Ser Leu Glu Thr Ser Leu
1250 1255

<210> SEQ ID NO 31
<211> LENGTH: 1272
<212> TYPE: PRT
<213> ORGANISM: Artificial Sequence
<220> FEATURE:
<223> OTHER INFORMATION: Synthetic: ATP transporter proteins

<400> SEQUENCE: 31

Met Gly Asp Met Thr Asn Ser Asp Phe Tyr Ser Lys Asn Gln Arg Asn
1 5 10 15

Glu Ser Ser His Gly Gly Glu Phe Gly Cys Thr Met Glu Glu Leu Arg
20 25 30

Ser Leu Met Glu Leu Arg Gly Thr Glu Ala Val Val Lys Ile Lys Glu
35 40 45

Thr Tyr Gly Asp Thr Glu Ala Ile Cys Arg Arg Leu Lys Thr Ser Pro
50 55 60

Val Glu Gly Leu Pro Gly Thr Ala Pro Asp Leu Glu Lys Arg Lys Gln
65 70 75 80

Ile Phe Gly Gln Asn Phe Ile Pro Pro Lys Lys Pro Lys Thr Phe Leu
85 90 95

Gln Leu Val Trp Glu Ala Leu Gln Asp Val Thr Leu Ile Ile Leu Glu
100 105 110

Ile Ala Ala Ile Ile Ser Leu Gly Leu Ser Phe Tyr His Pro Pro Gly
115 120 125

Glu Gly Asn Glu Gly Cys Ala Thr Ala Gln Gly Gly Ala Glu Asp Glu
130 135 140

Gly Glu Ala Glu Ala Gly Trp Ile Glu Gly Ala Ala Ile Leu Leu Ser
145 150 155 160

Val Ile Cys Val Val Leu Val Thr Ala Phe Asn Asp Trp Ser Lys Glu
165 170 175

Lys Gln Phe Arg Gly Leu Gln Ser Arg Ile Glu Gln Glu Gln Lys Phe
180 185 190

Thr Val Val Arg Ala Gly Gln Val Val Gln Ile Pro Val Ala Glu Ile
195 200 205

Val Val Gly Asp Ile Ala Gln Val Lys Tyr Gly Asp Leu Leu Pro Ala
210 215 220

Asp Gly Leu Phe Ile Gln Gly Asn Asp Leu Lys Ile Asp Glu Ser Ser
225 230 235 240

Leu Thr Gly Glu Ser Asp Gln Val Arg Lys Ser Val Asp Lys Asp Pro
245 250 255

Met Leu Leu Ser Gly Thr His Val Met Glu Gly Ser Gly Arg Met Leu
260 265 270

Val Thr Ala Val Gly Val Asn Ser Gln Thr Gly Ile Ile Phe Thr Leu
275 280 285

Leu Gly Ala Gly Gly Glu Glu Glu Glu Lys Lys Asp Lys Lys Gly Val
290 295 300

Lys Lys Gly Asp Gly Leu Gln Leu Pro Ala Ala Asp Gly Ala Ala Ala
305 310 315 320

Ser Asn Ala Ala Asp Ser Ala Asn Ala Ser Leu Val Asn Gly Lys Met
325 330 335

Gln Asp Gly Asn Val Asp Ala Ser Gln Ser Lys Ala Lys Gln Gln Asp

```
            340                 345                 350

Gly Ala Ala Ala Met Glu Met Gln Pro Leu Lys Ser Ala Glu Gly Gly
        355                 360                 365

Asp Ala Asp Asp Arg Lys Lys Ala Ser Met His Lys Lys Glu Lys Ser
    370                 375                 380

Val Leu Gln Gly Lys Leu Thr Lys Leu Ala Val Gln Ile Gly Lys Ala
385                 390                 395                 400

Gly Leu Val Met Ser Ala Ile Thr Val Ile Ile Leu Val Leu Tyr Phe
                405                 410                 415

Thr Val Asp Thr Phe Val Val Asn Lys Lys Pro Trp Leu Pro Glu Cys
            420                 425                 430

Thr Pro Val Tyr Val Gln Tyr Phe Val Lys Phe Phe Ile Ile Gly Val
        435                 440                 445

Thr Val Leu Val Val Ala Val Pro Glu Gly Leu Pro Leu Ala Val Thr
    450                 455                 460

Ile Ser Leu Ala Tyr Ser Val Lys Lys Met Met Lys Asp Asn Asn Leu
465                 470                 475                 480

Val Arg His Leu Asp Ala Cys Glu Thr Met Gly Asn Ala Thr Ala Ile
                485                 490                 495

Cys Ser Asp Lys Thr Gly Thr Leu Thr Thr Asn Arg Met Thr Val Val
            500                 505                 510

Gln Ala Tyr Val Gly Asp Val His Tyr Lys Glu Ile Pro Asp Pro Ser
        515                 520                 525

Ser Ile Asn Thr Lys Thr Met Glu Leu Leu Ile Asn Ala Ile Ala Ile
    530                 535                 540

Asn Ser Ala Tyr Thr Thr Lys Ile Leu Pro Pro Glu Lys Glu Gly Ala
545                 550                 555                 560

Leu Pro Arg Gln Val Gly Asn Lys Thr Glu Cys Gly Leu Leu Gly Phe
                565                 570                 575

Val Leu Asp Leu Lys Gln Asp Tyr Glu Pro Val Arg Ser Gln Met Pro
            580                 585                 590

Glu Glu Lys Leu Tyr Lys Val Tyr Thr Phe Asn Ser Val Arg Lys Ser
        595                 600                 605

Met Ser Thr Val Ile Lys Leu Pro Asp Glu Ser Phe Arg Met Tyr Ser
    610                 615                 620

Lys Gly Ala Ser Glu Ile Val Leu Lys Lys Cys Cys Lys Ile Leu Asn
625                 630                 635                 640

Gly Ala Gly Glu Pro Arg Val Phe Arg Pro Arg Asp Arg Asp Glu Met
                645                 650                 655

Val Lys Lys Val Ile Glu Pro Met Ala Cys Asp Gly Leu Arg Thr Ile
            660                 665                 670

Cys Val Ala Tyr Arg Asp Phe Pro Ser Ser Pro Glu Pro Asp Trp Asp
        675                 680                 685

Asn Glu Asn Asp Ile Leu Asn Glu Leu Thr Cys Ile Cys Val Val Gly
    690                 695                 700

Ile Glu Asp Pro Val Arg Pro Glu Val Pro Glu Ala Ile Arg Lys Cys
705                 710                 715                 720

Gln Arg Ala Gly Ile Thr Val Arg Met Val Thr Gly Asp Asn Ile Asn
                725                 730                 735

Thr Ala Arg Ala Ile Ala Ile Lys Cys Gly Ile Ile His Pro Gly Glu
            740                 745                 750

Asp Phe Leu Cys Leu Glu Gly Lys Glu Phe Asn Arg Arg Ile Arg Asn
        755                 760                 765
```

```
Glu Lys Gly Glu Ile Glu Gln Glu Arg Ile Asp Lys Ile Trp Pro Lys
    770                 775                 780

Leu Arg Val Leu Ala Arg Ser Ser Pro Thr Asp Lys His Thr Leu Val
785                 790                 795                 800

Lys Gly Ile Ile Asp Ser Thr His Thr Glu Gln Arg Gln Val Val Ala
                805                 810                 815

Val Thr Gly Asp Gly Thr Asn Asp Gly Pro Ala Leu Lys Lys Ala Asp
            820                 825                 830

Val Gly Phe Ala Met Gly Ile Ala Gly Thr Asp Val Ala Lys Glu Ala
        835                 840                 845

Ser Asp Ile Ile Leu Thr Asp Asp Asn Phe Ser Ser Ile Val Lys Ala
    850                 855                 860

Val Met Trp Gly Arg Asn Val Tyr Asp Ser Ile Ser Lys Phe Leu Gln
865                 870                 875                 880

Phe Gln Leu Thr Val Asn Val Val Ala Val Ile Val Ala Phe Thr Gly
                885                 890                 895

Ala Cys Ile Thr Gln Asp Ser Pro Leu Lys Ala Val Gln Met Leu Trp
            900                 905                 910

Val Asn Leu Ile Met Asp Thr Phe Ala Ser Leu Ala Leu Ala Thr Glu
        915                 920                 925

Pro Pro Thr Glu Thr Leu Leu Leu Arg Lys Pro Tyr Gly Arg Asn Lys
    930                 935                 940

Pro Leu Ile Ser Arg Thr Met Met Lys Asn Ile Leu Gly His Ala Val
945                 950                 955                 960

Tyr Gln Leu Ala Leu Ile Phe Thr Leu Leu Phe Val Gly Glu Lys Met
                965                 970                 975

Phe Gln Ile Asp Ser Gly Arg Asn Ala Pro Leu His Ser Pro Pro Ser
            980                 985                 990

Glu His Tyr Thr Ile Ile Phe Asn  Thr Phe Val Met Met  Gln Leu Phe
        995                 1000                 1005

Asn Glu  Ile Asn Ala Arg Lys  Ile His Gly Glu Arg  Asn Val Phe
    1010                 1015                 1020

Asp Gly  Ile Phe Arg Asn Pro  Ile Phe Cys Thr Ile  Val Leu Gly
    1025                 1030                 1035

Thr Phe  Ala Ile Gln Ile Val  Ile Val Gln Phe Gly  Gly Lys Pro
    1040                 1045                 1050

Phe Ser  Cys Ser Pro Leu Gln  Leu Asp Gln Trp Met  Trp Cys Ile
    1055                 1060                 1065

Phe Ile  Gly Leu Gly Glu Leu  Val Trp Gly Gln Val  Ile Ala Thr
    1070                 1075                 1080

Ile Pro  Thr Ser Arg Leu Lys  Phe Leu Lys Glu Ala  Gly Arg Leu
    1085                 1090                 1095

Thr Gln  Lys Glu Glu Ile Pro  Glu Glu Glu Leu Asn  Glu Asp Val
    1100                 1105                 1110

Glu Glu  Ile Asp His Ala Glu  Arg Glu Leu Arg Arg  Gly Gln Ile
    1115                 1120                 1125

Leu Trp  Phe Arg Gly Leu Asn  Arg Ile Gln Thr Gln  Ile Glu Val
    1130                 1135                 1140

Val Asn  Thr Phe Lys Ser Gly  Ala Ser Phe Gln Gly  Ala Leu Arg
    1145                 1150                 1155

Arg Gln  Ser Ser Val Thr Ser  Gln Ser Gln Asp Ile  Arg Val Val
    1160                 1165                 1170
```

Lys Ala Phe Arg Ser Ser Leu Tyr Glu Gly Leu Glu Lys Pro Glu
1175 1180 1185

Ser Arg Thr Ser Ile His Asn Phe Met Ala His Pro Glu Phe Arg
1190 1195 1200

Ile Glu Asp Ser Gln Pro His Ile Pro Leu Ile Asp Asp Thr Asp
1205 1210 1215

Leu Glu Glu Asp Ala Ala Leu Lys Gln Asn Ser Ser Pro Pro Ser
1220 1225 1230

Ser Leu Asn Lys Asn Asn Ser Ala Ile Asp Ser Gly Ile Asn Leu
1235 1240 1245

Thr Thr Asp Thr Ser Lys Ser Ala Thr Ser Ser Ser Pro Gly Ser
1250 1255 1260

Pro Ile His Ser Leu Glu Thr Ser Leu
1265 1270

<210> SEQ ID NO 32
<211> LENGTH: 874
<212> TYPE: PRT
<213> ORGANISM: Artificial Sequence
<220> FEATURE:
<223> OTHER INFORMATION: Synthetic: ATP transporter proteins

<400> SEQUENCE: 32

Met Gly Asp Met Ala Asn Ser Ser Ile Glu Phe His Pro Lys Pro Gln
1 5 10 15

Gln Gln Arg Asp Val Pro Gln Ala Gly Gly Phe Gly Cys Thr Leu Ala
20 25 30

Glu Leu Arg Thr Leu Met Glu Leu Arg Gly Ala Glu Ala Leu Gln Lys
35 40 45

Ile Glu Glu Ala Tyr Gly Asp Val Ser Gly Leu Cys Arg Arg Leu Lys
50 55 60

Thr Ser Pro Thr Glu Gly Leu Ala Asp Asn Thr Asn Asp Leu Glu Lys
65 70 75 80

Arg Arg Gln Ile Tyr Gly Gln Asn Phe Ile Pro Pro Lys Gln Pro Lys
85 90 95

Thr Phe Leu Gln Leu Val Trp Glu Ala Leu Gln Asp Val Thr Leu Ile
100 105 110

Ile Leu Glu Val Ala Ala Ile Val Ser Leu Gly Leu Ser Phe Tyr Ala
115 120 125

Pro Pro Gly Glu Glu Ser Glu Ala Cys Gly Asn Val Ser Gly Gly Ala
130 135 140

Glu Asp Glu Gly Glu Ala Glu Ala Gly Trp Ile Glu Gly Ala Ala Ile
145 150 155 160

Leu Leu Ser Val Ile Cys Val Val Leu Val Thr Ala Phe Asn Asp Trp
165 170 175

Ser Lys Glu Lys Gln Phe Arg Gly Leu Gln Ser Arg Ile Glu Gln Glu
180 185 190

Gln Lys Phe Thr Val Ile Arg Asn Gly Gln Leu Leu Gln Val Pro Val
195 200 205

Ala Ala Leu Val Val Gly Asp Ile Ala Gln Val Lys Tyr Gly Asp Leu
210 215 220

Leu Pro Ala Asp Gly Val Leu Ile Gln Ala Asn Asp Leu Lys Ile Asp
225 230 235 240

Glu Ser Ser Leu Thr Gly Glu Ser Asp His Val Arg Lys Ser Ala Asp
245 250 255

-continued

```
Lys Asp Pro Met Leu Leu Ser Gly Thr His Val Met Glu Gly Ser Gly
            260                 265                 270

Arg Met Val Val Thr Ala Val Gly Val Asn Ser Gln Thr Gly Ile Ile
        275                 280                 285

Phe Thr Leu Leu Gly Ala Gly Gly Glu Glu Glu Glu Lys Lys Asp Lys
    290                 295                 300

Lys Gly Lys Gln Gln Asp Gly Ala Met Glu Ser Ser Gln Thr Lys Ala
305                 310                 315                 320

Lys Lys Gln Asp Gly Ala Val Ala Met Glu Met Gln Pro Leu Lys Ser
                325                 330                 335

Ala Glu Gly Gly Glu Met Glu Glu Arg Glu Lys Lys Lys Ala Asn Ala
            340                 345                 350

Pro Lys Lys Glu Lys Ser Val Leu Gln Gly Lys Leu Thr Lys Leu Ala
        355                 360                 365

Val Gln Ile Gly Lys Ala Gly Leu Val Met Ser Ala Ile Thr Val Ile
    370                 375                 380

Ile Leu Val Leu Tyr Phe Val Ile Glu Thr Phe Val Val Glu Gly Arg
385                 390                 395                 400

Thr Trp Leu Ala Glu Cys Thr Pro Val Tyr Val Gln Tyr Phe Val Lys
                405                 410                 415

Phe Phe Ile Ile Gly Val Thr Val Leu Val Val Ala Val Pro Glu Gly
            420                 425                 430

Leu Pro Leu Ala Val Thr Ile Ser Leu Ala Tyr Ser Val Lys Lys Met
        435                 440                 445

Met Lys Asp Asn Asn Leu Val Arg His Leu Asp Ala Cys Glu Thr Met
    450                 455                 460

Gly Asn Ala Thr Ala Ile Cys Ser Asp Lys Thr Gly Thr Leu Thr Thr
465                 470                 475                 480

Asn Arg Met Thr Val Val Gln Ser Tyr Leu Gly Asp Thr His Tyr Lys
                485                 490                 495

Glu Ile Pro Ala Pro Ser Ala Leu Thr Pro Lys Ile Leu Asp Leu Leu
            500                 505                 510

Val His Ala Ile Ser Ile Asn Ser Ala Tyr Thr Thr Lys Ile Leu Pro
        515                 520                 525

Pro Glu Lys Glu Gly Ala Leu Pro Arg Gln Val Gly Asn Lys Thr Glu
    530                 535                 540

Cys Ala Leu Leu Gly Phe Val Leu Asp Leu Lys Arg Asp Phe Gln Pro
545                 550                 555                 560

Val Arg Glu Gln Ile Pro Glu Asp Lys Leu Tyr Lys Val Tyr Thr Phe
                565                 570                 575

Asn Ser Val Arg Lys Ser Met Ser Thr Val Ile Arg Met Pro Asp Gly
            580                 585                 590

Gly Phe Arg Leu Phe Ser Lys Gly Ala Ser Glu Ile Leu Leu Lys Lys
        595                 600                 605

Cys Thr Asn Ile Leu Asn Ser Asn Gly Glu Leu Arg Gly Phe Arg Pro
    610                 615                 620

Arg Asp Arg Asp Asp Met Val Arg Lys Ile Ile Glu Pro Met Ala Cys
625                 630                 635                 640

Asp Gly Leu Arg Thr Ile Cys Ile Ala Tyr Arg Asp Phe Ser Ala Gly
                645                 650                 655

Gln Glu Pro Asp Trp Asp Asn Glu Asn Glu Val Val Gly Asp Leu Thr
            660                 665                 670

Cys Ile Ala Val Val Gly Ile Glu Asp Pro Val Arg Pro Glu Val Pro
```

```
        675                 680                 685

Glu Ala Ile Arg Lys Cys Gln Arg Ala Gly Ile Thr Val Arg Met Val
    690                 695                 700

Thr Gly Asp Asn Ile Asn Thr Ala Arg Ala Ile Ala Ala Lys Cys Gly
705                 710                 715                 720

Ile Ile Gln Pro Gly Glu Asp Phe Leu Cys Leu Glu Gly Lys Glu Phe
                725                 730                 735

Asn Arg Arg Ile Arg Asn Glu Lys Gly Glu Ile Glu Gln Glu Arg Leu
            740                 745                 750

Asp Lys Val Trp Pro Lys Leu Arg Val Leu Ala Arg Ser Ser Pro Thr
        755                 760                 765

Asp Lys His Thr Leu Val Lys Gly Ile Ile Asp Ser Thr Thr Gly Glu
    770                 775                 780

Gln Arg Gln Val Val Ala Val Thr Gly Asp Gly Thr Asn Asp Gly Pro
785                 790                 795                 800

Ala Leu Lys Lys Ala Asp Val Gly Phe Ala Met Gly Ile Ala Gly Thr
                805                 810                 815

Asp Val Ala Lys Glu Ala Ser Asp Ile Ile Leu Thr Asp Asp Asn Phe
            820                 825                 830

Thr Ser Ile Val Lys Ala Val Met Trp Gly Arg Asn Val Tyr Asp Ser
        835                 840                 845

Ile Ser Lys Phe Leu Gln Phe Gln Leu Thr Val Asn Val Val Ala Val
    850                 855                 860

Ile Val Ala Phe Thr Gly Ala Cys Ile Thr
865                 870


<210> SEQ ID NO 33
<211> LENGTH: 192
<212> TYPE: PRT
<213> ORGANISM: Artificial Sequence
<220> FEATURE:
<223> OTHER INFORMATION: Synthetic: PTGFRN Protein Fragment #7

<400> SEQUENCE: 33

Gly Pro Ile Phe Asn Ala Ser Val His Ser Asp Thr Pro Ser Val Ile
1               5                   10                  15

Arg Gly Asp Leu Ile Lys Leu Phe Cys Ile Ile Thr Val Glu Gly Ala
            20                  25                  30

Ala Leu Asp Pro Asp Asp Met Ala Phe Asp Val Ser Trp Phe Ala Val
        35                  40                  45

His Ser Phe Gly Leu Asp Lys Ala Pro Val Leu Leu Ser Ser Leu Asp
    50                  55                  60

Arg Lys Gly Ile Val Thr Thr Ser Arg Arg Asp Trp Lys Ser Asp Leu
65                  70                  75                  80

Ser Leu Glu Arg Val Ser Val Leu Glu Phe Leu Leu Gln Val His Gly
                85                  90                  95

Ser Glu Asp Gln Asp Phe Gly Asn Tyr Tyr Cys Ser Val Thr Pro Trp
            100                 105                 110

Val Lys Ser Pro Thr Gly Ser Trp Gln Lys Glu Ala Glu Ile His Ser
        115                 120                 125

Lys Pro Val Phe Ile Thr Val Lys Met Asp Val Leu Asn Ala Phe Lys
    130                 135                 140

Tyr Pro Leu Leu Ile Gly Val Gly Leu Ser Thr Val Ile Gly Leu Leu
145                 150                 155                 160

Ser Cys Leu Ile Gly Tyr Cys Ser Ser His Trp Cys Cys Lys Lys Glu
```

165 170 175

Val Gln Glu Thr Arg Arg Glu Arg Arg Arg Leu Met Ser Met Glu Met
180 185 190

<210> SEQ ID NO 34
<211> LENGTH: 1021
<212> TYPE: PRT
<213> ORGANISM: Artificial Sequence
<220> FEATURE:
<223> OTHER INFORMATION: Synthetic: IGSF2

<400> SEQUENCE: 34

Met Ala Gly Ile Ser Tyr Val Ala Ser Phe Phe Leu Leu Leu Thr Lys
1 5 10 15

Leu Ser Ile Gly Gln Arg Glu Val Thr Val Gln Lys Gly Pro Leu Phe
20 25 30

Arg Ala Glu Gly Tyr Pro Val Ser Ile Gly Cys Asn Val Thr Gly His
35 40 45

Gln Gly Pro Ser Glu Gln His Phe Gln Trp Ser Val Tyr Leu Pro Thr
50 55 60

Asn Pro Thr Gln Glu Val Gln Ile Ile Ser Thr Lys Asp Ala Ala Phe
65 70 75 80

Ser Tyr Ala Val Tyr Thr Gln Arg Val Arg Ser Gly Asp Val Tyr Val
85 90 95

Glu Arg Val Gln Gly Asn Ser Val Leu Leu His Ile Ser Lys Leu Gln
100 105 110

Met Lys Asp Ala Gly Glu Tyr Glu Cys His Thr Pro Asn Thr Asp Glu
115 120 125

Lys Tyr Tyr Gly Ser Tyr Ser Ala Lys Thr Asn Leu Ile Val Ile Pro
130 135 140

Asp Thr Leu Ser Ala Thr Met Ser Ser Gln Thr Leu Gly Lys Glu Glu
145 150 155 160

Gly Glu Pro Leu Ala Leu Thr Cys Glu Ala Ser Lys Ala Thr Ala Gln
165 170 175

His Thr His Leu Ser Val Thr Trp Tyr Leu Thr Gln Asp Gly Gly Gly
180 185 190

Ser Gln Ala Thr Glu Ile Ile Ser Leu Ser Lys Asp Phe Ile Leu Val
195 200 205

Pro Gly Pro Leu Tyr Thr Glu Arg Phe Ala Ala Ser Asp Val Gln Leu
210 215 220

Asn Lys Leu Gly Pro Thr Thr Phe Arg Leu Ser Ile Glu Arg Leu Gln
225 230 235 240

Ser Ser Asp Gln Gly Gln Leu Phe Cys Glu Ala Thr Glu Trp Ile Gln
245 250 255

Asp Pro Asp Glu Thr Trp Met Phe Ile Thr Lys Lys Gln Thr Asp Gln
260 265 270

Thr Thr Leu Arg Ile Gln Pro Ala Val Lys Asp Phe Gln Val Asn Ile
275 280 285

Thr Ala Asp Ser Leu Phe Ala Glu Gly Lys Pro Leu Glu Leu Val Cys
290 295 300

Leu Val Val Ser Ser Gly Arg Asp Pro Gln Leu Gln Gly Ile Trp Phe
305 310 315 320

Phe Asn Gly Thr Glu Ile Ala His Ile Asp Ala Gly Gly Val Leu Gly
325 330 335

Leu Lys Asn Asp Tyr Lys Glu Arg Ala Ser Gln Gly Glu Leu Gln Val

```
            340                 345                 350

Ser Lys Leu Gly Pro Lys Ala Phe Ser Leu Lys Ile Phe Ser Leu Gly
        355                 360                 365

Pro Glu Asp Glu Gly Ala Tyr Arg Cys Val Val Ala Glu Val Met Lys
    370                 375                 380

Thr Arg Thr Gly Ser Trp Gln Val Leu Gln Arg Lys Gln Ser Pro Asp
385                 390                 395                 400

Ser His Val His Leu Arg Lys Pro Ala Ala Arg Ser Val Val Met Ser
                405                 410                 415

Thr Lys Asn Lys Gln Gln Val Val Trp Glu Gly Glu Thr Leu Ala Phe
            420                 425                 430

Leu Cys Lys Ala Gly Gly Ala Glu Ser Pro Leu Ser Val Ser Trp Trp
        435                 440                 445

His Ile Pro Arg Asp Gln Thr Gln Pro Glu Phe Val Ala Gly Met Gly
    450                 455                 460

Gln Asp Gly Ile Val Gln Leu Gly Ala Ser Tyr Gly Val Pro Ser Tyr
465                 470                 475                 480

His Gly Asn Thr Arg Leu Glu Lys Met Asp Trp Ala Thr Phe Gln Leu
                485                 490                 495

Glu Ile Thr Phe Thr Ala Ile Thr Asp Ser Gly Thr Tyr Glu Cys Arg
            500                 505                 510

Val Ser Glu Lys Ser Arg Asn Gln Ala Arg Asp Leu Ser Trp Thr Gln
        515                 520                 525

Lys Ile Ser Val Thr Val Lys Ser Leu Glu Ser Ser Leu Gln Val Ser
    530                 535                 540

Leu Met Ser Arg Gln Pro Gln Val Met Leu Thr Asn Thr Phe Asp Leu
545                 550                 555                 560

Ser Cys Val Val Arg Ala Gly Tyr Ser Asp Leu Lys Val Pro Leu Thr
                565                 570                 575

Val Thr Trp Gln Phe Gln Pro Ala Ser Ser His Ile Phe His Gln Leu
            580                 585                 590

Ile Arg Ile Thr His Asn Gly Thr Ile Glu Trp Gly Asn Phe Leu Ser
        595                 600                 605

Arg Phe Gln Lys Lys Thr Lys Val Ser Gln Ser Leu Phe Arg Ser Gln
    610                 615                 620

Leu Leu Val His Asp Ala Thr Glu Glu Glu Thr Gly Val Tyr Gln Cys
625                 630                 635                 640

Glu Val Glu Val Tyr Asp Arg Asn Ser Leu Tyr Asn Asn Arg Pro Pro
                645                 650                 655

Arg Ala Ser Ala Ile Ser His Pro Leu Arg Ile Ala Val Thr Leu Pro
            660                 665                 670

Glu Ser Lys Leu Lys Val Asn Ser Arg Ser Gln Val Gln Glu Leu Ser
        675                 680                 685

Ile Asn Ser Asn Thr Asp Ile Glu Cys Ser Ile Leu Ser Arg Ser Asn
    690                 695                 700

Gly Asn Leu Gln Leu Ala Ile Ile Trp Tyr Phe Ser Pro Val Ser Thr
705                 710                 715                 720

Asn Ala Ser Trp Leu Lys Ile Leu Glu Met Asp Gln Thr Asn Val Ile
                725                 730                 735

Lys Thr Gly Asp Glu Phe His Thr Pro Gln Arg Lys Gln Lys Phe His
            740                 745                 750

Thr Glu Lys Val Ser Gln Asp Leu Phe Gln Leu His Ile Leu Asn Val
        755                 760                 765
```

```
Glu Asp Ser Asp Arg Gly Lys Tyr His Cys Ala Val Glu Glu Trp Leu
    770                 775                 780

Leu Ser Thr Asn Gly Thr Trp His Lys Leu Gly Glu Lys Lys Ser Gly
785                 790                 795                 800

Leu Thr Glu Leu Lys Leu Lys Pro Thr Gly Ser Lys Val Arg Val Ser
                805                 810                 815

Lys Val Tyr Trp Thr Glu Asn Val Thr Glu His Arg Glu Val Ala Ile
            820                 825                 830

Arg Cys Ser Leu Glu Ser Val Gly Ser Ser Ala Thr Leu Tyr Ser Val
        835                 840                 845

Met Trp Tyr Trp Asn Arg Glu Asn Ser Gly Ser Lys Leu Leu Val His
    850                 855                 860

Leu Gln His Asp Gly Leu Leu Glu Tyr Gly Glu Glu Gly Leu Arg Arg
865                 870                 875                 880

His Leu His Cys Tyr Arg Ser Ser Ser Thr Asp Phe Val Leu Lys Leu
                885                 890                 895

His Gln Val Glu Met Glu Asp Ala Gly Met Tyr Trp Cys Arg Val Ala
            900                 905                 910

Glu Trp Gln Leu His Gly His Pro Ser Lys Trp Ile Asn Gln Ala Ser
        915                 920                 925

Asp Glu Ser Gln Arg Met Val Leu Thr Val Leu Pro Ser Glu Pro Thr
    930                 935                 940

Leu Pro Ser Arg Ile Cys Ser Ser Ala Pro Leu Leu Tyr Phe Leu Phe
945                 950                 955                 960

Ile Cys Pro Phe Val Leu Leu Leu Leu Leu Leu Ile Ser Leu Leu Cys
                965                 970                 975

Leu Tyr Trp Lys Ala Arg Lys Leu Ser Thr Leu Arg Ser Asn Thr Arg
            980                 985                 990

Lys Glu Lys Ala Leu Trp Val Asp  Leu Lys Glu Ala Gly  Gly Val Thr
        995                 1000                1005

Thr Asn  Arg Arg Glu Asp Glu  Glu Glu Asp Glu Gly  Asn
    1010                1015                1020
```

<210> SEQ ID NO 35
<211> LENGTH: 20
<212> TYPE: PRT
<213> ORGANISM: Artificial Sequence
<220> FEATURE:
<223> OTHER INFORMATION: Synthetic: IGSF2 Protein - Signal Peptide

<400> SEQUENCE: 35

```
Met Ala Gly Ile Ser Tyr Val Ala Ser Phe Phe Leu Leu Leu Thr Lys
1               5                   10                  15

Leu Ser Ile Gly
            20
```

<210> SEQ ID NO 36
<211> LENGTH: 20
<212> TYPE: DNA
<213> ORGANISM: Artificial Sequence
<220> FEATURE:
<223> OTHER INFORMATION: Synthetic: CRISPR926045_CR

<400> SEQUENCE: 36
cgttggcagt ccgccttaac 20

<210> SEQ ID NO 37

<211> LENGTH: 20
<212> TYPE: DNA
<213> ORGANISM: Artificial Sequence
<220> FEATURE:
<223> OTHER INFORMATION: Synthetic: CRISPR926054_CR

<400> SEQUENCE: 37
catagtcact gacgttgcag 20

<210> SEQ ID NO 38
<211> LENGTH: 20
<212> TYPE: DNA
<213> ORGANISM: Artificial Sequence
<220> FEATURE:
<223> OTHER INFORMATION: Synthetic: CRISPR926055_CR

<400> SEQUENCE: 38
ttgtggagct tgcaagcacc 20

<210> SEQ ID NO 39
<211> LENGTH: 20
<212> TYPE: DNA
<213> ORGANISM: Artificial Sequence
<220> FEATURE:
<223> OTHER INFORMATION: Synthetic: CRISPR926071_CR

<400> SEQUENCE: 39
gttctttatg tggagctcca 20

<210> SEQ ID NO 40
<211> LENGTH: 20
<212> TYPE: DNA
<213> ORGANISM: Artificial Sequence
<220> FEATURE:
<223> OTHER INFORMATION: Synthetic: TMgRNA5.1.97

<400> SEQUENCE: 40
tatcccttgc tgatcggcgt 20

<210> SEQ ID NO 41
<211> LENGTH: 20
<212> TYPE: DNA
<213> ORGANISM: Artificial Sequence
<220> FEATURE:
<223> OTHER INFORMATION: Synthetic: TMgRNA3.7.87

<400> SEQUENCE: 41
gctgcagtac ccgatgagac 20

<210> SEQ ID NO 42
<211> LENGTH: 38
<212> TYPE: PRT
<213> ORGANISM: Artificial Sequence
<220> FEATURE:
<223> OTHER INFORMATION: Synthetic: PTGFRN_IgV6 (#451)

<400> SEQUENCE: 42

```
Glu His Ser Ala Gly Gly Gly Gly Ser Asp Tyr Lys Asp Asp Asp Asp
1               5                   10                  15

Lys Gly Gly Gly Gly Ser Leu Ser Asn Pro Ile Glu Ile Asp Phe Gln
            20                  25                  30

Thr Ser Gly Pro Ile Phe
        35
```

<210> SEQ ID NO 43

-continued

<211> LENGTH: 34
<212> TYPE: PRT
<213> ORGANISM: Artificial Sequence
<220> FEATURE:
<223> OTHER INFORMATION: Synthetic: PTGFRN_IgV6 Mutant

<400> SEQUENCE: 43

Glu His Ser Ala Gly Gly Gly Gly Ser Asp Tyr Lys Asp Asp Asp Asp
1 5 10 15

Lys Gly Gly Gly Gly Ser Ile Glu Ile Asp Phe Gln Thr Ser Gly Pro
20 25 30

Ile Phe

<210> SEQ ID NO 44
<211> LENGTH: 30
<212> TYPE: PRT
<213> ORGANISM: Artificial Sequence
<220> FEATURE:
<223> OTHER INFORMATION: Synthetic: PTGFRN_IgV6 Mutant

<400> SEQUENCE: 44

Glu His Ser Ala Gly Gly Gly Gly Ser Asp Tyr Lys Asp Asp Asp Asp
1 5 10 15

Lys Gly Gly Gly Gly Ser Phe Gln Thr Ser Gly Pro Ile Phe
20 25 30

<210> SEQ ID NO 45
<211> LENGTH: 26
<212> TYPE: PRT
<213> ORGANISM: Artificial Sequence
<220> FEATURE:
<223> OTHER INFORMATION: Synthetic: PTGFRN_IgV6 Mutant

<400> SEQUENCE: 45

Glu His Ser Ala Gly Gly Gly Gly Ser Asp Tyr Lys Asp Asp Asp Asp
1 5 10 15

Lys Gly Gly Gly Gly Ser Gly Pro Ile Phe
20 25

<210> SEQ ID NO 46
<211> LENGTH: 42
<212> TYPE: PRT
<213> ORGANISM: Artificial Sequence
<220> FEATURE:
<223> OTHER INFORMATION: Synthetic: PTGFRN Cleavage Site

<400> SEQUENCE: 46

Phe Ile Thr Val Lys Met Asp Thr Leu Asp Pro Arg Ser Phe Leu Leu
1 5 10 15

Arg Asn Pro Asn Asp Lys Tyr Glu Pro Phe Trp Glu Asp Glu Glu Lys
20 25 30

Asn Glu Ser Gly Ser Asp Lys Thr His Thr
35 40

<210> SEQ ID NO 47
<211> LENGTH: 879
<212> TYPE: PRT
<213> ORGANISM: Artificial Sequence
<220> FEATURE:
<223> OTHER INFORMATION: Synthetic: MARCKS

<400> SEQUENCE: 47

Met Gly Arg Leu Ala Ser Arg Pro Leu Leu Leu Ala Leu Leu Ser Leu
1 5 10 15

```
Ala Leu Cys Arg Gly Arg Val Val Arg Val Pro Thr Ala Thr Leu Val
            20                  25                  30

Arg Val Val Gly Thr Glu Leu Val Ile Pro Cys Asn Val Ser Asp Tyr
        35                  40                  45

Asp Gly Pro Ser Glu Gln Asn Phe Asp Trp Ser Phe Ser Ser Leu Gly
    50                  55                  60

Ser Ser Phe Val Glu Leu Ala Ser Thr Trp Glu Val Gly Phe Pro Ala
65                  70                  75                  80

Gln Leu Tyr Gln Glu Arg Leu Gln Arg Gly Glu Ile Leu Leu Arg Arg
                85                  90                  95

Thr Ala Asn Asp Ala Val Glu Leu His Ile Lys Asn Val Gln Pro Ser
            100                 105                 110

Asp Gln Gly His Tyr Lys Cys Ser Thr Pro Ser Thr Asp Ala Thr Val
        115                 120                 125

Gln Gly Asn Tyr Glu Asp Thr Val Gln Val Lys Val Leu Ala Asp Ser
    130                 135                 140

Leu His Val Gly Pro Ser Ala Arg Pro Pro Pro Ser Leu Ser Leu Arg
145                 150                 155                 160

Glu Gly Glu Pro Phe Glu Leu Arg Cys Thr Ala Ala Ser Ala Ser Pro
                165                 170                 175

Leu His Thr His Leu Ala Leu Leu Trp Glu Val His Arg Gly Pro Ala
            180                 185                 190

Arg Arg Ser Val Leu Ala Leu Thr His Glu Gly Arg Phe His Pro Gly
        195                 200                 205

Leu Gly Tyr Glu Gln Arg Tyr His Ser Gly Asp Val Arg Leu Asp Thr
    210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                245                 250                 255

Gly Asn Trp Gln Glu Ile Gln Glu Lys Ala Val Glu Val Ala Thr Val
            260                 265                 270

Val Ile Gln Pro Ser Val Leu Arg Ala Ala Val Pro Lys Asn Val Ser
        275                 280                 285

Val Ala Glu Gly Lys Glu Leu Asp Leu Thr Cys Asn Ile Thr Thr Asp
    290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                325                 330                 335

Asp Ser Leu Val His Ser Ser Pro His Val Ala Leu Ser His Val Asp
            340                 345                 350

Ala Arg Ser Tyr His Leu Leu Val Arg Asp Val Ser Lys Glu Asn Ser
        355                 360                 365

Gly Tyr Tyr Tyr Cys His Val Ser Leu Trp Ala Pro Gly His Asn Arg
    370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                405                 410                 415

Val Pro Gly Phe Ala Asp Asp Pro Thr Glu Leu Ala Cys Arg Val Val
            420                 425                 430
```

```
Asp Thr Lys Ser Gly Glu Ala Asn Val Arg Phe Thr Val Ser Trp Tyr
        435                 440                 445

Tyr Arg Met Asn Arg Arg Ser Asp Asn Val Val Thr Ser Glu Leu Leu
    450                 455                 460

Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
            500                 505                 510

Tyr Tyr Cys Val Val Ser Ala Trp Thr Lys Gln Arg Asn Asn Ser Trp
        515                 520                 525

Val Lys Ser Lys Asp Val Phe Ser Lys Pro Val Asn Ile Phe Trp Ala
    530                 535                 540

Leu Glu Asp Ser Val Leu Val Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
            580                 585                 590

Val Gly Asp Leu Ser Ser Pro Asn Glu Thr Lys Tyr Ile Ile Ser Leu
        595                 600                 605

Asp Gln Asp Ser Val Val Lys Leu Glu Asn Trp Thr Asp Ala Ser Arg
    610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
            660                 665                 670

Thr Ser Leu Ser Asn Pro Ile Glu Ile Asp Phe Gln Thr Ser Gly Pro
        675                 680                 685

Ile Phe Asn Ala Ser Val His Ser Asp Thr Pro Ser Val Ile Arg Gly
    690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
    770                 775                 780

Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Cys Lys Lys Glu Val Gln
```

850 855 860

Glu Thr Arg Arg Glu Arg Arg Arg Leu Met Ser Met Glu Met Asp
865 870 875

<210> SEQ ID NO 48
<211> LENGTH: 192
<212> TYPE: PRT
<213> ORGANISM: Artificial Sequence
<220> FEATURE:
<223> OTHER INFORMATION: Synthetic: MARCKSL1

<400> SEQUENCE: 48

Gly Pro Ile Phe Asn Ala Ser Val His Ser Asp Thr Pro Ser Val Ile
1 5 10 15

Arg Gly Asp Leu Ile Lys Leu Phe Cys Ile Ile Thr Val Glu Gly Ala
20 25 30

Ala Leu Asp Pro Asp Asp Met Ala Phe Asp Val Ser Trp Phe Ala Val
35 40 45

His Ser Phe Gly Leu Asp Lys Ala Pro Val Leu Leu Ser Ser Leu Asp
50 55 60

Arg Lys Gly Ile Val Thr Thr Ser Arg Arg Asp Trp Lys Ser Asp Leu
65 70 75 80

Ser Leu Glu Arg Val Ser Val Leu Glu Phe Leu Leu Gln Val His Gly
85 90 95

Ser Glu Asp Gln Asp Phe Gly Asn Tyr Tyr Cys Ser Val Thr Pro Trp
100 105 110

Val Lys Ser Pro Thr Gly Ser Trp Gln Lys Glu Ala Glu Ile His Ser
115 120 125

Lys Pro Val Phe Ile Thr Val Lys Met Asp Val Leu Asn Ala Phe Lys
130 135 140

Tyr Pro Leu Leu Ile Gly Val Gly Leu Ser Thr Val Ile Gly Leu Leu
145 150 155 160

Ser Cys Leu Ile Gly Tyr Cys Ser Ser His Trp Cys Cys Lys Lys Glu
165 170 175

Val Gln Glu Thr Arg Arg Glu Arg Arg Arg Leu Met Ser Met Glu Met
180 185 190

<210> SEQ ID NO 49
<211> LENGTH: 385
<212> TYPE: PRT
<213> ORGANISM: Artificial Sequence
<220> FEATURE:
<223> OTHER INFORMATION: Synthetic: BASP1

<400> SEQUENCE: 49

Met Ala Ala Ala Leu Phe Val Leu Leu Gly Phe Ala Leu Leu Gly Thr
1 5 10 15

His Gly Ala Ser Gly Ala Ala Gly Phe Val Gln Ala Pro Leu Ser Gln
20 25 30

Gln Arg Trp Val Gly Gly Ser Val Glu Leu His Cys Glu Ala Val Gly
35 40 45

Ser Pro Val Pro Glu Ile Gln Trp Trp Phe Glu Gly Gln Gly Pro Asn
50 55 60

Asp Thr Cys Ser Gln Leu Trp Asp Gly Ala Arg Leu Asp Arg Val His
65 70 75 80

Ile His Ala Thr Tyr His Gln His Ala Ala Ser Thr Ile Ser Ile Asp
85 90 95

-continued

```
Thr Leu Val Glu Glu Asp Thr Gly Thr Tyr Glu Cys Arg Ala Ser Asn
            100                 105                 110

Asp Pro Asp Arg Asn His Leu Thr Arg Ala Pro Arg Val Lys Trp Val
        115                 120                 125

Arg Ala Gln Ala Val Val Leu Val Leu Glu Pro Gly Thr Val Phe Thr
    130                 135                 140

Thr Val Glu Asp Leu Gly Ser Lys Ile Leu Leu Thr Cys Ser Leu Asn
145                 150                 155                 160

Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190

Asp Ser Asp Asp Gln Trp Gly Glu Tyr Ser Cys Val Phe Leu Pro Glu
        195                 200                 205

Pro Met Gly Thr Ala Asn Ile Gln Leu His Gly Pro Pro Arg Val Lys
    210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
            260                 265                 270

Arg Phe Phe Val Ser Ser Ser Gln Gly Arg Ser Glu Leu His Ile Glu
        275                 280                 285

Asn Leu Asn Met Glu Ala Asp Pro Gly Gln Tyr Arg Cys Asn Gly Thr
    290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
            340                 345                 350

Asp Val Leu Asp Asp Asp Asp Ala Gly Ser Ala Pro Leu Lys Ser Ser
        355                 360                 365

Gly Gln His Gln Asn Asp Lys Gly Lys Asn Val Arg Gln Arg Asn Ser
    370                 375                 380

Ser
385


<210> SEQ ID NO 50

<400> SEQUENCE: 50

000


<210> SEQ ID NO 51

<400> SEQUENCE: 51

000


<210> SEQ ID NO 52

<400> SEQUENCE: 52

000
```

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

-continued

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

-continued

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

-continued

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277
<211> LENGTH: 29
<212> TYPE: PRT
<213> ORGANISM: Artificial Sequence
<220> FEATURE:
<223> OTHER INFORMATION: Synthetic: Scaffold Y Fragment

<400> SEQUENCE: 277

Gly Ala Lys Lys Ser Lys Lys Arg Phe Ser Phe Lys Lys Ser Phe Lys
1 5 10 15

```
Leu Ser Gly Phe Ser Phe Lys Lys Asn Lys Lys Glu Ala
            20                  25


<210> SEQ ID NO 278
<211> LENGTH: 28
<212> TYPE: PRT
<213> ORGANISM: Artificial Sequence
<220> FEATURE:
<223> OTHER INFORMATION: Synthetic: Scaffold Y Fragment

<400> SEQUENCE: 278

Gly Ala Lys Lys Ser Lys Lys Arg Phe Ser Phe Lys Lys Ser Phe Lys
1               5                   10                  15

Leu Ser Gly Phe Ser Phe Lys Lys Asn Lys Lys Glu
            20                  25


<210> SEQ ID NO 279
<211> LENGTH: 27
<212> TYPE: PRT
<213> ORGANISM: Artificial Sequence
<220> FEATURE:
<223> OTHER INFORMATION: Synthetic: Scaffold Y Fragment

<400> SEQUENCE: 279

Gly Ala Lys Lys Ser Lys Lys Arg Phe Ser Phe Lys Lys Ser Phe Lys
1               5                   10                  15

Leu Ser Gly Phe Ser Phe Lys Lys Asn Lys Lys
            20                  25


<210> SEQ ID NO 280
<211> LENGTH: 26
<212> TYPE: PRT
<213> ORGANISM: Artificial Sequence
<220> FEATURE:
<223> OTHER INFORMATION: Synthetic: Scaffold Y Fragment

<400> SEQUENCE: 280

Gly Ala Lys Lys Ser Lys Lys Arg Phe Ser Phe Lys Lys Ser Phe Lys
1               5                   10                  15

Leu Ser Gly Phe Ser Phe Lys Lys Asn Lys
            20                  25


<210> SEQ ID NO 281
<211> LENGTH: 25
<212> TYPE: PRT
<213> ORGANISM: Artificial Sequence
<220> FEATURE:
<223> OTHER INFORMATION: Synthetic: Scaffold Y Fragment

<400> SEQUENCE: 281

Gly Ala Lys Lys Ser Lys Lys Arg Phe Ser Phe Lys Lys Ser Phe Lys
1               5                   10                  15

Leu Ser Gly Phe Ser Phe Lys Lys Asn
            20                  25


<210> SEQ ID NO 282
<211> LENGTH: 24
<212> TYPE: PRT
<213> ORGANISM: Artificial Sequence
<220> FEATURE:
<223> OTHER INFORMATION: Synthetic: Scaffold Y Fragment

<400> SEQUENCE: 282

Gly Ala Lys Lys Ser Lys Lys Arg Phe Ser Phe Lys Lys Ser Phe Lys
1               5                   10                  15
```

Leu Ser Gly Phe Ser Phe Lys Lys
20

<210> SEQ ID NO 283
<211> LENGTH: 23
<212> TYPE: PRT
<213> ORGANISM: Artificial Sequence
<220> FEATURE:
<223> OTHER INFORMATION: Synthetic: Scaffold Y Fragment

<400> SEQUENCE: 283

Gly Ala Lys Lys Ser Lys Lys Arg Phe Ser Phe Lys Lys Ser Phe Lys
1 5 10 15

Leu Ser Gly Phe Ser Phe Lys
20

<210> SEQ ID NO 284
<211> LENGTH: 22
<212> TYPE: PRT
<213> ORGANISM: Artificial Sequence
<220> FEATURE:
<223> OTHER INFORMATION: Synthetic: Scaffold Y Fragment

<400> SEQUENCE: 284

Gly Ala Lys Lys Ser Lys Lys Arg Phe Ser Phe Lys Lys Ser Phe Lys
1 5 10 15

Leu Ser Gly Phe Ser Phe
20

<210> SEQ ID NO 285
<211> LENGTH: 21
<212> TYPE: PRT
<213> ORGANISM: Artificial Sequence
<220> FEATURE:
<223> OTHER INFORMATION: Synthetic: Scaffold Y Fragment

<400> SEQUENCE: 285

Gly Ala Lys Lys Ser Lys Lys Arg Phe Ser Phe Lys Lys Ser Phe Lys
1 5 10 15

Leu Ser Gly Phe Ser
20

<210> SEQ ID NO 286
<211> LENGTH: 20
<212> TYPE: PRT
<213> ORGANISM: Artificial Sequence
<220> FEATURE:
<223> OTHER INFORMATION: Synthetic: Scaffold Y Fragment

<400> SEQUENCE: 286

Gly Ala Lys Lys Ser Lys Lys Arg Phe Ser Phe Lys Lys Ser Phe Lys
1 5 10 15

Leu Ser Gly Phe
20

<210> SEQ ID NO 287
<211> LENGTH: 19
<212> TYPE: PRT
<213> ORGANISM: Artificial Sequence
<220> FEATURE:
<223> OTHER INFORMATION: Synthetic: Scaffold Y Fragment

<400> SEQUENCE: 287

Gly Ala Lys Lys Ser Lys Lys Arg Phe Ser Phe Lys Lys Ser Phe Lys 1 5 10 15

Leu Ser Gly

<210> SEQ ID NO 288
<211> LENGTH: 18
<212> TYPE: PRT
<213> ORGANISM: Artificial Sequence
<220> FEATURE:
<223> OTHER INFORMATION: Synthetic: Scaffold Y Fragment

<400> SEQUENCE: 288

Gly Ala Lys Lys Ser Lys Lys Arg Phe Ser Phe Lys Lys Ser Phe Lys
1 5 10 15

Leu Ser

<210> SEQ ID NO 289
<211> LENGTH: 17
<212> TYPE: PRT
<213> ORGANISM: Artificial Sequence
<220> FEATURE:
<223> OTHER INFORMATION: Synthetic: Scaffold Y Fragment

<400> SEQUENCE: 289

Gly Ala Lys Lys Ser Lys Lys Arg Phe Ser Phe Lys Lys Ser Phe Lys
1 5 10 15

Leu

<210> SEQ ID NO 290
<211> LENGTH: 16
<212> TYPE: PRT
<213> ORGANISM: Artificial Sequence
<220> FEATURE:
<223> OTHER INFORMATION: Synthetic: Scaffold Y Fragment

<400> SEQUENCE: 290

Gly Ala Lys Lys Ser Lys Lys Arg Phe Ser Phe Lys Lys Ser Phe Lys
1 5 10 15

<210> SEQ ID NO 291
<211> LENGTH: 15
<212> TYPE: PRT
<213> ORGANISM: Artificial Sequence
<220> FEATURE:
<223> OTHER INFORMATION: Synthetic: Scaffold Y Fragment

<400> SEQUENCE: 291

Gly Ala Lys Lys Ser Lys Lys Arg Phe Ser Phe Lys Lys Ser Phe
1 5 10 15

<210> SEQ ID NO 292
<211> LENGTH: 13
<212> TYPE: PRT
<213> ORGANISM: Artificial Sequence
<220> FEATURE:
<223> OTHER INFORMATION: Synthetic: Scaffold Y Fragment

<400> SEQUENCE: 292

Gly Ala Lys Lys Ser Lys Lys Arg Phe Ser Phe Lys Lys
1 5 10

<210> SEQ ID NO 293
<211> LENGTH: 12
<212> TYPE: PRT
<213> ORGANISM: Artificial Sequence
<220> FEATURE:

-continued

<223> OTHER INFORMATION: Synthetic: Scaffold Y Fragment

<400> SEQUENCE: 293

Gly Ala Lys Lys Ser Lys Lys Arg Phe Ser Phe Lys
1 5 10

<210> SEQ ID NO 294
<211> LENGTH: 11
<212> TYPE: PRT
<213> ORGANISM: Artificial Sequence
<220> FEATURE:
<223> OTHER INFORMATION: Synthetic: Scaffold Y Fragment

<400> SEQUENCE: 294

Gly Ala Lys Lys Ser Lys Lys Arg Phe Ser Phe
1 5 10

<210> SEQ ID NO 295
<211> LENGTH: 10
<212> TYPE: PRT
<213> ORGANISM: Artificial Sequence
<220> FEATURE:
<223> OTHER INFORMATION: Synthetic: Scaffold Y Fragment

<400> SEQUENCE: 295

Gly Ala Lys Lys Ser Lys Lys Arg Phe Ser
1 5 10

<210> SEQ ID NO 296
<211> LENGTH: 9
<212> TYPE: PRT
<213> ORGANISM: Artificial Sequence
<220> FEATURE:
<223> OTHER INFORMATION: Synthetic: Scaffold Y Fragment

<400> SEQUENCE: 296

Gly Ala Lys Lys Ser Lys Lys Arg Phe
1 5

<210> SEQ ID NO 297
<211> LENGTH: 8
<212> TYPE: PRT
<213> ORGANISM: Artificial Sequence
<220> FEATURE:
<223> OTHER INFORMATION: Synthetic: Scaffold Y Fragment

<400> SEQUENCE: 297

Gly Ala Lys Lys Ser Lys Lys Arg
1 5

<210> SEQ ID NO 298
<211> LENGTH: 7
<212> TYPE: PRT
<213> ORGANISM: Artificial Sequence
<220> FEATURE:
<223> OTHER INFORMATION: Synthetic: Scaffold Y Fragment

<400> SEQUENCE: 298

Gly Ala Lys Lys Ser Lys Lys
1 5

<210> SEQ ID NO 299
<211> LENGTH: 29
<212> TYPE: PRT
<213> ORGANISM: Artificial Sequence
<220> FEATURE:
<223> OTHER INFORMATION: Synthetic: Scaffold Y Fragment

<400> SEQUENCE: 299

Gly Ala Lys Lys Ala Lys Lys Arg Phe Ser Phe Lys Lys Ser Phe Lys
1 5 10 15

Leu Ser Gly Phe Ser Phe Lys Lys Asn Lys Lys Glu Ala
20 25

<210> SEQ ID NO 300
<211> LENGTH: 28
<212> TYPE: PRT
<213> ORGANISM: Artificial Sequence
<220> FEATURE:
<223> OTHER INFORMATION: Synthetic: Scaffold Y Fragment

<400> SEQUENCE: 300

Gly Ala Lys Lys Ala Lys Lys Arg Phe Ser Phe Lys Lys Ser Phe Lys
1 5 10 15

Leu Ser Gly Phe Ser Phe Lys Lys Asn Lys Lys Glu
20 25

<210> SEQ ID NO 301
<211> LENGTH: 27
<212> TYPE: PRT
<213> ORGANISM: Artificial Sequence
<220> FEATURE:
<223> OTHER INFORMATION: Synthetic: Scaffold Y Fragment

<400> SEQUENCE: 301

Gly Ala Lys Lys Ala Lys Lys Arg Phe Ser Phe Lys Lys Ser Phe Lys
1 5 10 15

Leu Ser Gly Phe Ser Phe Lys Lys Asn Lys Lys
20 25

<210> SEQ ID NO 302
<211> LENGTH: 26
<212> TYPE: PRT
<213> ORGANISM: Artificial Sequence
<220> FEATURE:
<223> OTHER INFORMATION: Synthetic: Scaffold Y Fragment

<400> SEQUENCE: 302

Gly Ala Lys Lys Ala Lys Lys Arg Phe Ser Phe Lys Lys Ser Phe Lys
1 5 10 15

Leu Ser Gly Phe Ser Phe Lys Lys Asn Lys
20 25

<210> SEQ ID NO 303
<211> LENGTH: 25
<212> TYPE: PRT
<213> ORGANISM: Artificial Sequence
<220> FEATURE:
<223> OTHER INFORMATION: Synthetic: Scaffold Y Fragment

<400> SEQUENCE: 303

Gly Ala Lys Lys Ala Lys Lys Arg Phe Ser Phe Lys Lys Ser Phe Lys
1 5 10 15

Leu Ser Gly Phe Ser Phe Lys Lys Asn
20 25

<210> SEQ ID NO 304
<211> LENGTH: 24
<212> TYPE: PRT
<213> ORGANISM: Artificial Sequence
<220> FEATURE:

```
<223> OTHER INFORMATION: Synthetic: Scaffold Y Fragment

<400> SEQUENCE: 304

Gly Ala Lys Lys Ala Lys Lys Arg Phe Ser Phe Lys Lys Ser Phe Lys
1               5                   10                  15

Leu Ser Gly Phe Ser Phe Lys Lys
            20


<210> SEQ ID NO 305
<211> LENGTH: 23
<212> TYPE: PRT
<213> ORGANISM: Artificial Sequence
<220> FEATURE:
<223> OTHER INFORMATION: Synthetic: Scaffold Y Fragment

<400> SEQUENCE: 305

Gly Ala Lys Lys Ala Lys Lys Arg Phe Ser Phe Lys Lys Ser Phe Lys
1               5                   10                  15

Leu Ser Gly Phe Ser Phe Lys
            20


<210> SEQ ID NO 306
<211> LENGTH: 22
<212> TYPE: PRT
<213> ORGANISM: Artificial Sequence
<220> FEATURE:
<223> OTHER INFORMATION: Synthetic: Scaffold Y Fragment

<400> SEQUENCE: 306

Gly Ala Lys Lys Ala Lys Lys Arg Phe Ser Phe Lys Lys Ser Phe Lys
1               5                   10                  15

Leu Ser Gly Phe Ser Phe
            20


<210> SEQ ID NO 307
<211> LENGTH: 21
<212> TYPE: PRT
<213> ORGANISM: Artificial Sequence
<220> FEATURE:
<223> OTHER INFORMATION: Synthetic: Scaffold Y Fragment

<400> SEQUENCE: 307

Gly Ala Lys Lys Ala Lys Lys Arg Phe Ser Phe Lys Lys Ser Phe Lys
1               5                   10                  15

Leu Ser Gly Phe Ser
            20


<210> SEQ ID NO 308
<211> LENGTH: 20
<212> TYPE: PRT
<213> ORGANISM: Artificial Sequence
<220> FEATURE:
<223> OTHER INFORMATION: Synthetic: Scaffold Y Fragment

<400> SEQUENCE: 308

Gly Ala Lys Lys Ala Lys Lys Arg Phe Ser Phe Lys Lys Ser Phe Lys
1               5                   10                  15

Leu Ser Gly Phe
            20


<210> SEQ ID NO 309
<211> LENGTH: 19
<212> TYPE: PRT
<213> ORGANISM: Artificial Sequence
```

<220> FEATURE:
<223> OTHER INFORMATION: Synthetic: Scaffold Y Fragment

<400> SEQUENCE: 309

Gly Ala Lys Lys Ala Lys Lys Arg Phe Ser Phe Lys Lys Ser Phe Lys
1 5 10 15

Leu Ser Gly

<210> SEQ ID NO 310
<211> LENGTH: 18
<212> TYPE: PRT
<213> ORGANISM: Artificial Sequence
<220> FEATURE:
<223> OTHER INFORMATION: Synthetic: Scaffold Y Fragment

<400> SEQUENCE: 310

Gly Ala Lys Lys Ala Lys Lys Arg Phe Ser Phe Lys Lys Ser Phe Lys
1 5 10 15

Leu Ser

<210> SEQ ID NO 311
<211> LENGTH: 17
<212> TYPE: PRT
<213> ORGANISM: Artificial Sequence
<220> FEATURE:
<223> OTHER INFORMATION: Synthetic: Scaffold Y Fragment

<400> SEQUENCE: 311

Gly Ala Lys Lys Ala Lys Lys Arg Phe Ser Phe Lys Lys Ser Phe Lys
1 5 10 15

Leu

<210> SEQ ID NO 312
<211> LENGTH: 16
<212> TYPE: PRT
<213> ORGANISM: Artificial Sequence
<220> FEATURE:
<223> OTHER INFORMATION: Synthetic: Scaffold Y Fragment

<400> SEQUENCE: 312

Gly Ala Lys Lys Ala Lys Lys Arg Phe Ser Phe Lys Lys Ser Phe Lys
1 5 10 15

<210> SEQ ID NO 313
<211> LENGTH: 15
<212> TYPE: PRT
<213> ORGANISM: Artificial Sequence
<220> FEATURE:
<223> OTHER INFORMATION: Synthetic: Scaffold Y Fragment

<400> SEQUENCE: 313

Gly Ala Lys Lys Ala Lys Lys Arg Phe Ser Phe Lys Lys Ser Phe
1 5 10 15

<210> SEQ ID NO 314
<211> LENGTH: 14
<212> TYPE: PRT
<213> ORGANISM: Artificial Sequence
<220> FEATURE:
<223> OTHER INFORMATION: Synthetic: Scaffold Y Fragment

<400> SEQUENCE: 314

Gly Ala Lys Lys Ala Lys Lys Arg Phe Ser Phe Lys Lys Ser
1 5 10

<210> SEQ ID NO 315
<211> LENGTH: 13
<212> TYPE: PRT
<213> ORGANISM: Artificial Sequence
<220> FEATURE:
<223> OTHER INFORMATION: Synthetic: Scaffold Y Fragment

<400> SEQUENCE: 315

Gly Ala Lys Lys Ala Lys Lys Arg Phe Ser Phe Lys Lys
1 5 10

<210> SEQ ID NO 316
<211> LENGTH: 12
<212> TYPE: PRT
<213> ORGANISM: Artificial Sequence
<220> FEATURE:
<223> OTHER INFORMATION: Synthetic: Scaffold Y Fragment

<400> SEQUENCE: 316

Gly Ala Lys Lys Ala Lys Lys Arg Phe Ser Phe Lys
1 5 10

<210> SEQ ID NO 317
<211> LENGTH: 11
<212> TYPE: PRT
<213> ORGANISM: Artificial Sequence
<220> FEATURE:
<223> OTHER INFORMATION: Synthetic: Scaffold Y Fragment

<400> SEQUENCE: 317

Gly Ala Lys Lys Ala Lys Lys Arg Phe Ser Phe
1 5 10

<210> SEQ ID NO 318
<211> LENGTH: 10
<212> TYPE: PRT
<213> ORGANISM: Artificial Sequence
<220> FEATURE:
<223> OTHER INFORMATION: Synthetic: Scaffold Y Fragment

<400> SEQUENCE: 318

Gly Ala Lys Lys Ala Lys Lys Arg Phe Ser
1 5 10

<210> SEQ ID NO 319
<211> LENGTH: 9
<212> TYPE: PRT
<213> ORGANISM: Artificial Sequence
<220> FEATURE:
<223> OTHER INFORMATION: Synthetic: Scaffold Y Fragment

<400> SEQUENCE: 319

Gly Ala Lys Lys Ala Lys Lys Arg Phe
1 5

<210> SEQ ID NO 320
<211> LENGTH: 8
<212> TYPE: PRT
<213> ORGANISM: Artificial Sequence
<220> FEATURE:
<223> OTHER INFORMATION: Synthetic: Scaffold Y Fragment

<400> SEQUENCE: 320

Gly Ala Lys Lys Ala Lys Lys Arg
1 5

<210> SEQ ID NO 321
<211> LENGTH: 7
<212> TYPE: PRT
<213> ORGANISM: Artificial Sequence
<220> FEATURE:
<223> OTHER INFORMATION: Synthetic: Scaffold Y Fragment

<400> SEQUENCE: 321

```
Gly Ala Lys Lys Ala Lys Lys
1               5
```

<210> SEQ ID NO 322
<211> LENGTH: 28
<212> TYPE: PRT
<213> ORGANISM: Artificial Sequence
<220> FEATURE:
<223> OTHER INFORMATION: Synthetic: Scaffold Y Fragment

<400> SEQUENCE: 322

```
Gly Ala Gln Glu Ser Lys Lys Lys Lys Lys Lys Arg Phe Ser Phe Lys
1               5                   10                  15

Lys Ser Phe Lys Leu Ser Gly Phe Ser Phe Lys Lys
            20                  25
```

<210> SEQ ID NO 323
<211> LENGTH: 27
<212> TYPE: PRT
<213> ORGANISM: Artificial Sequence
<220> FEATURE:
<223> OTHER INFORMATION: Synthetic: Scaffold Y Fragment

<400> SEQUENCE: 323

```
Gly Ala Gln Glu Ser Lys Lys Lys Lys Lys Lys Arg Phe Ser Phe Lys
1               5                   10                  15

Lys Ser Phe Lys Leu Ser Gly Phe Ser Phe Lys
            20                  25
```

<210> SEQ ID NO 324
<211> LENGTH: 26
<212> TYPE: PRT
<213> ORGANISM: Artificial Sequence
<220> FEATURE:
<223> OTHER INFORMATION: Synthetic: Scaffold Y Fragment

<400> SEQUENCE: 324

```
Gly Ala Gln Glu Ser Lys Lys Lys Lys Lys Lys Arg Phe Ser Phe Lys
1               5                   10                  15

Lys Ser Phe Lys Leu Ser Gly Phe Ser Phe
            20                  25
```

<210> SEQ ID NO 325
<211> LENGTH: 25
<212> TYPE: PRT
<213> ORGANISM: Artificial Sequence
<220> FEATURE:
<223> OTHER INFORMATION: Synthetic: Scaffold Y Fragment

<400> SEQUENCE: 325

```
Gly Ala Gln Glu Ser Lys Lys Lys Lys Lys Lys Arg Phe Ser Phe Lys
1               5                   10                  15

Lys Ser Phe Lys Leu Ser Gly Phe Ser
            20                  25
```

<210> SEQ ID NO 326
<211> LENGTH: 24

-continued

<212> TYPE: PRT
<213> ORGANISM: Artificial Sequence
<220> FEATURE:
<223> OTHER INFORMATION: Synthetic: Scaffold Y Fragment

<400> SEQUENCE: 326

Gly Ala Gln Glu Ser Lys Lys Lys Lys Lys Lys Arg Phe Ser Phe Lys
1 5 10 15

Lys Ser Phe Lys Leu Ser Gly Phe
20

<210> SEQ ID NO 327
<211> LENGTH: 23
<212> TYPE: PRT
<213> ORGANISM: Artificial Sequence
<220> FEATURE:
<223> OTHER INFORMATION: Synthetic: Scaffold Y Fragment

<400> SEQUENCE: 327

Gly Ala Gln Glu Ser Lys Lys Lys Lys Lys Lys Arg Phe Ser Phe Lys
1 5 10 15

Lys Ser Phe Lys Leu Ser Gly
20

<210> SEQ ID NO 328
<211> LENGTH: 22
<212> TYPE: PRT
<213> ORGANISM: Artificial Sequence
<220> FEATURE:
<223> OTHER INFORMATION: Synthetic: Scaffold Y Fragment

<400> SEQUENCE: 328

Gly Ala Gln Glu Ser Lys Lys Lys Lys Lys Lys Arg Phe Ser Phe Lys
1 5 10 15

Lys Ser Phe Lys Leu Ser
20

<210> SEQ ID NO 329
<211> LENGTH: 21
<212> TYPE: PRT
<213> ORGANISM: Artificial Sequence
<220> FEATURE:
<223> OTHER INFORMATION: Synthetic: Scaffold Y Fragment

<400> SEQUENCE: 329

Gly Ala Gln Glu Ser Lys Lys Lys Lys Lys Lys Arg Phe Ser Phe Lys
1 5 10 15

Lys Ser Phe Lys Leu
20

<210> SEQ ID NO 330
<211> LENGTH: 20
<212> TYPE: PRT
<213> ORGANISM: Artificial Sequence
<220> FEATURE:
<223> OTHER INFORMATION: Synthetic: Scaffold Y Fragment

<400> SEQUENCE: 330

Gly Ala Gln Glu Ser Lys Lys Lys Lys Lys Lys Arg Phe Ser Phe Lys
1 5 10 15

Lys Ser Phe Lys
20

<210> SEQ ID NO 331

<211> LENGTH: 19
<212> TYPE: PRT
<213> ORGANISM: Artificial Sequence
<220> FEATURE:
<223> OTHER INFORMATION: Synthetic: Scaffold Y Fragment

<400> SEQUENCE: 331

Gly Ala Gln Glu Ser Lys Lys Lys Lys Lys Lys Arg Phe Ser Phe Lys
1 5 10 15

Lys Ser Phe

<210> SEQ ID NO 332
<211> LENGTH: 18
<212> TYPE: PRT
<213> ORGANISM: Artificial Sequence
<220> FEATURE:
<223> OTHER INFORMATION: Synthetic: Scaffold Y Fragment

<400> SEQUENCE: 332

Gly Ala Gln Glu Ser Lys Lys Lys Lys Lys Lys Arg Phe Ser Phe Lys
1 5 10 15

Lys Ser

<210> SEQ ID NO 333
<211> LENGTH: 17
<212> TYPE: PRT
<213> ORGANISM: Artificial Sequence
<220> FEATURE:
<223> OTHER INFORMATION: Synthetic: Scaffold Y Fragment

<400> SEQUENCE: 333

Gly Ala Gln Glu Ser Lys Lys Lys Lys Lys Lys Arg Phe Ser Phe Lys
1 5 10 15

Lys

<210> SEQ ID NO 334
<211> LENGTH: 16
<212> TYPE: PRT
<213> ORGANISM: Artificial Sequence
<220> FEATURE:
<223> OTHER INFORMATION: Synthetic: Scaffold Y Fragment

<400> SEQUENCE: 334

Gly Ala Gln Glu Ser Lys Lys Lys Lys Lys Lys Arg Phe Ser Phe Lys
1 5 10 15

<210> SEQ ID NO 335
<211> LENGTH: 15
<212> TYPE: PRT
<213> ORGANISM: Artificial Sequence
<220> FEATURE:
<223> OTHER INFORMATION: Synthetic: Scaffold Y Fragment

<400> SEQUENCE: 335

Gly Ala Gln Glu Ser Lys Lys Lys Lys Lys Lys Arg Phe Ser Phe
1 5 10 15

<210> SEQ ID NO 336
<211> LENGTH: 14
<212> TYPE: PRT
<213> ORGANISM: Artificial Sequence
<220> FEATURE:
<223> OTHER INFORMATION: Synthetic: Scaffold Y Fragment

<400> SEQUENCE: 336

Gly Ala Gln Glu Ser Lys Lys Lys Lys Lys Lys Arg Phe Ser
1 5 10

<210> SEQ ID NO 337
<211> LENGTH: 13
<212> TYPE: PRT
<213> ORGANISM: Artificial Sequence
<220> FEATURE:
<223> OTHER INFORMATION: Synthetic: Scaffold Y Fragment

<400> SEQUENCE: 337

Gly Ala Gln Glu Ser Lys Lys Lys Lys Lys Lys Arg Phe
1 5 10

<210> SEQ ID NO 338
<211> LENGTH: 12
<212> TYPE: PRT
<213> ORGANISM: Artificial Sequence
<220> FEATURE:
<223> OTHER INFORMATION: Synthetic: Scaffold Y Fragment

<400> SEQUENCE: 338

Gly Ala Gln Glu Ser Lys Lys Lys Lys Lys Lys Arg
1 5 10

<210> SEQ ID NO 339
<211> LENGTH: 11
<212> TYPE: PRT
<213> ORGANISM: Artificial Sequence
<220> FEATURE:
<223> OTHER INFORMATION: Synthetic: Scaffold Y Fragment

<400> SEQUENCE: 339

Gly Ala Gln Glu Ser Lys Lys Lys Lys Lys Lys
1 5 10

<210> SEQ ID NO 340
<211> LENGTH: 10
<212> TYPE: PRT
<213> ORGANISM: Artificial Sequence
<220> FEATURE:
<223> OTHER INFORMATION: Synthetic: Scaffold Y Fragment

<400> SEQUENCE: 340

Gly Ala Gln Glu Ser Lys Lys Lys Lys Lys
1 5 10

<210> SEQ ID NO 341
<211> LENGTH: 9
<212> TYPE: PRT
<213> ORGANISM: Artificial Sequence
<220> FEATURE:
<223> OTHER INFORMATION: Synthetic: Scaffold Y Fragment

<400> SEQUENCE: 341

Gly Ala Gln Glu Ser Lys Lys Lys Lys
1 5

<210> SEQ ID NO 342
<211> LENGTH: 8
<212> TYPE: PRT
<213> ORGANISM: Artificial Sequence
<220> FEATURE:
<223> OTHER INFORMATION: Synthetic: Scaffold Y Fragment

<400> SEQUENCE: 342

Gly Ala Gln Glu Ser Lys Lys Lys 1 5

<210> SEQ ID NO 343
<211> LENGTH: 7
<212> TYPE: PRT
<213> ORGANISM: Artificial Sequence
<220> FEATURE:
<223> OTHER INFORMATION: Synthetic: Scaffold Y Fragment

<400> SEQUENCE: 343

Gly Ala Gln Glu Ser Lys Lys
1 5

<210> SEQ ID NO 344
<211> LENGTH: 30
<212> TYPE: PRT
<213> ORGANISM: Artificial Sequence
<220> FEATURE:
<223> OTHER INFORMATION: Synthetic: Scaffold Y Fragment

<400> SEQUENCE: 344

Gly Ser Gln Ser Ser Lys Lys Lys Lys Lys Lys Phe Ser Phe Lys Lys
1 5 10 15

Pro Phe Lys Leu Ser Gly Leu Ser Phe Lys Arg Asn Arg Lys
20 25 30

<210> SEQ ID NO 345
<211> LENGTH: 29
<212> TYPE: PRT
<213> ORGANISM: Artificial Sequence
<220> FEATURE:
<223> OTHER INFORMATION: Synthetic: Scaffold Y Fragment

<400> SEQUENCE: 345

Gly Ser Gln Ser Ser Lys Lys Lys Lys Lys Lys Phe Ser Phe Lys Lys
1 5 10 15

Pro Phe Lys Leu Ser Gly Leu Ser Phe Lys Arg Asn Arg
20 25

<210> SEQ ID NO 346
<211> LENGTH: 28
<212> TYPE: PRT
<213> ORGANISM: Artificial Sequence
<220> FEATURE:
<223> OTHER INFORMATION: Synthetic: Scaffold Y Fragment

<400> SEQUENCE: 346

Gly Ser Gln Ser Ser Lys Lys Lys Lys Lys Lys Phe Ser Phe Lys Lys
1 5 10 15

Pro Phe Lys Leu Ser Gly Leu Ser Phe Lys Arg Asn
20 25

<210> SEQ ID NO 347
<211> LENGTH: 27
<212> TYPE: PRT
<213> ORGANISM: Artificial Sequence
<220> FEATURE:
<223> OTHER INFORMATION: Synthetic: Scaffold Y Fragment

<400> SEQUENCE: 347

Gly Ser Gln Ser Ser Lys Lys Lys Lys Lys Lys Phe Ser Phe Lys Lys
1 5 10 15

Pro Phe Lys Leu Ser Gly Leu Ser Phe Lys Arg
20 25

<210> SEQ ID NO 348
<211> LENGTH: 26
<212> TYPE: PRT
<213> ORGANISM: Artificial Sequence
<220> FEATURE:
<223> OTHER INFORMATION: Synthetic: Scaffold Y Fragment

<400> SEQUENCE: 348

```
Gly Ser Gln Ser Ser Lys Lys Lys Lys Lys Lys Phe Ser Phe Lys Lys
1               5                   10                  15

Pro Phe Lys Leu Ser Gly Leu Ser Phe Lys
            20                  25
```

<210> SEQ ID NO 349
<211> LENGTH: 25
<212> TYPE: PRT
<213> ORGANISM: Artificial Sequence
<220> FEATURE:
<223> OTHER INFORMATION: Synthetic: Scaffold Y Fragment

<400> SEQUENCE: 349

```
Gly Ser Gln Ser Ser Lys Lys Lys Lys Lys Lys Phe Ser Phe Lys Lys
1               5                   10                  15

Pro Phe Lys Leu Ser Gly Leu Ser Phe
            20                  25
```

<210> SEQ ID NO 350
<211> LENGTH: 24
<212> TYPE: PRT
<213> ORGANISM: Artificial Sequence
<220> FEATURE:
<223> OTHER INFORMATION: Synthetic: Scaffold Y Fragment

<400> SEQUENCE: 350

```
Gly Ser Gln Ser Ser Lys Lys Lys Lys Lys Lys Phe Ser Phe Lys Lys
1               5                   10                  15

Pro Phe Lys Leu Ser Gly Leu Ser
            20
```

<210> SEQ ID NO 351
<211> LENGTH: 23
<212> TYPE: PRT
<213> ORGANISM: Artificial Sequence
<220> FEATURE:
<223> OTHER INFORMATION: Synthetic: Scaffold Y Fragment

<400> SEQUENCE: 351

```
Gly Ser Gln Ser Ser Lys Lys Lys Lys Lys Lys Phe Ser Phe Lys Lys
1               5                   10                  15

Pro Phe Lys Leu Ser Gly Leu
            20
```

<210> SEQ ID NO 352
<211> LENGTH: 22
<212> TYPE: PRT
<213> ORGANISM: Artificial Sequence
<220> FEATURE:
<223> OTHER INFORMATION: Synthetic: Scaffold Y Fragment

<400> SEQUENCE: 352

```
Gly Ser Gln Ser Ser Lys Lys Lys Lys Lys Lys Phe Ser Phe Lys Lys
1               5                   10                  15

Pro Phe Lys Leu Ser Gly
            20
```

<210> SEQ ID NO 353
<211> LENGTH: 21
<212> TYPE: PRT
<213> ORGANISM: Artificial Sequence
<220> FEATURE:
<223> OTHER INFORMATION: Synthetic: Scaffold Y Fragment

<400> SEQUENCE: 353

Gly Ser Gln Ser Ser Lys Lys Lys Lys Lys Lys Phe Ser Phe Lys Lys
1               5                   10                  15

Pro Phe Lys Leu Ser
            20

<210> SEQ ID NO 354
<211> LENGTH: 20
<212> TYPE: PRT
<213> ORGANISM: Artificial Sequence
<220> FEATURE:
<223> OTHER INFORMATION: Synthetic: Scaffold Y Fragment

<400> SEQUENCE: 354

Gly Ser Gln Ser Ser Lys Lys Lys Lys Lys Lys Phe Ser Phe Lys Lys
1               5                   10                  15

Pro Phe Lys Leu
            20

<210> SEQ ID NO 355
<211> LENGTH: 19
<212> TYPE: PRT
<213> ORGANISM: Artificial Sequence
<220> FEATURE:
<223> OTHER INFORMATION: Synthetic: Scaffold Y Fragment

<400> SEQUENCE: 355

Gly Ser Gln Ser Ser Lys Lys Lys Lys Lys Lys Phe Ser Phe Lys Lys
1               5                   10                  15

Pro Phe Lys

<210> SEQ ID NO 356
<211> LENGTH: 18
<212> TYPE: PRT
<213> ORGANISM: Artificial Sequence
<220> FEATURE:
<223> OTHER INFORMATION: Synthetic: Scaffold Y Fragment

<400> SEQUENCE: 356

Gly Ser Gln Ser Ser Lys Lys Lys Lys Lys Lys Phe Ser Phe Lys Lys
1               5                   10                  15

Pro Phe

<210> SEQ ID NO 357
<211> LENGTH: 17
<212> TYPE: PRT
<213> ORGANISM: Artificial Sequence
<220> FEATURE:
<223> OTHER INFORMATION: Synthetic: Scaffold Y Fragment

<400> SEQUENCE: 357

Gly Ser Gln Ser Ser Lys Lys Lys Lys Lys Lys Phe Ser Phe Lys Lys
1               5                   10                  15

Pro

-continued

<210> SEQ ID NO 358
<211> LENGTH: 16
<212> TYPE: PRT
<213> ORGANISM: Artificial Sequence
<220> FEATURE:
<223> OTHER INFORMATION: Synthetic: Scaffold Y Fragment

<400> SEQUENCE: 358

Gly Ser Gln Ser Ser Lys Lys Lys Lys Lys Lys Phe Ser Phe Lys Lys
1 5 10 15

<210> SEQ ID NO 359
<211> LENGTH: 15
<212> TYPE: PRT
<213> ORGANISM: Artificial Sequence
<220> FEATURE:
<223> OTHER INFORMATION: Synthetic: Scaffold Y Fragment

<400> SEQUENCE: 359

Gly Ser Gln Ser Ser Lys Lys Lys Lys Lys Lys Phe Ser Phe Lys
1 5 10 15

<210> SEQ ID NO 360
<211> LENGTH: 14
<212> TYPE: PRT
<213> ORGANISM: Artificial Sequence
<220> FEATURE:
<223> OTHER INFORMATION: Synthetic: Scaffold Y Fragment

<400> SEQUENCE: 360

Gly Ser Gln Ser Ser Lys Lys Lys Lys Lys Lys Phe Ser Phe
1 5 10

<210> SEQ ID NO 361
<211> LENGTH: 13
<212> TYPE: PRT
<213> ORGANISM: Artificial Sequence
<220> FEATURE:
<223> OTHER INFORMATION: Synthetic: Scaffold Y Fragment

<400> SEQUENCE: 361

Gly Ser Gln Ser Ser Lys Lys Lys Lys Lys Lys Phe Ser
1 5 10

<210> SEQ ID NO 362
<211> LENGTH: 12
<212> TYPE: PRT
<213> ORGANISM: Artificial Sequence
<220> FEATURE:
<223> OTHER INFORMATION: Synthetic: Scaffold Y Fragment

<400> SEQUENCE: 362

Gly Ser Gln Ser Ser Lys Lys Lys Lys Lys Lys Phe
1 5 10

<210> SEQ ID NO 363
<211> LENGTH: 11
<212> TYPE: PRT
<213> ORGANISM: Artificial Sequence
<220> FEATURE:
<223> OTHER INFORMATION: Synthetic: Scaffold Y Fragment

<400> SEQUENCE: 363

Gly Ser Gln Ser Ser Lys Lys Lys Lys Lys Lys
1 5 10

<210> SEQ ID NO 364

<211> LENGTH: 10
<212> TYPE: PRT
<213> ORGANISM: Artificial Sequence
<220> FEATURE:
<223> OTHER INFORMATION: Synthetic: Scaffold Y Fragment

<400> SEQUENCE: 364

Gly Ser Gln Ser Ser Lys Lys Lys Lys Lys
1 5 10

<210> SEQ ID NO 365
<211> LENGTH: 9
<212> TYPE: PRT
<213> ORGANISM: Artificial Sequence
<220> FEATURE:
<223> OTHER INFORMATION: Synthetic: Scaffold Y Fragment

<400> SEQUENCE: 365

Gly Ser Gln Ser Ser Lys Lys Lys Lys
1 5

<210> SEQ ID NO 366
<211> LENGTH: 8
<212> TYPE: PRT
<213> ORGANISM: Artificial Sequence
<220> FEATURE:
<223> OTHER INFORMATION: Synthetic: Scaffold Y Fragment

<400> SEQUENCE: 366

Gly Ser Gln Ser Ser Lys Lys Lys
1 5

<210> SEQ ID NO 367
<211> LENGTH: 7
<212> TYPE: PRT
<213> ORGANISM: Artificial Sequence
<220> FEATURE:
<223> OTHER INFORMATION: Synthetic: Scaffold Y Fragment

<400> SEQUENCE: 367

Gly Ser Gln Ser Ser Lys Lys
1 5

<210> SEQ ID NO 368
<211> LENGTH: 8
<212> TYPE: PRT
<213> ORGANISM: Artificial Sequence
<220> FEATURE:
<223> OTHER INFORMATION: Synthetic: Scaffold Y Fragment
<220> FEATURE:
<221> NAME/KEY: misc_feature
<222> LOCATION: (2)..(2)
<223> OTHER INFORMATION: Xaa can be any naturally occurring amino acid

<400> SEQUENCE: 368

Gly Xaa Lys Leu Ser Lys Lys Lys
1 5

<210> SEQ ID NO 369
<211> LENGTH: 119
<212> TYPE: PRT
<213> ORGANISM: Artificial Sequence
<220> FEATURE:
<223> OTHER INFORMATION: Synthetic: Brain-derived neurotrophic factor

<400> SEQUENCE: 369

His Ser Asp Pro Ala Arg Arg Gly Glu Leu Ser Val Cys Asp Ser Ile
1 5 10 15

Ser Glu Trp Val Thr Ala Ala Asp Lys Lys Thr Ala Val Asp Met Ser
20 25 30

Gly Gly Thr Val Thr Val Leu Glu Lys Val Pro Val Ser Lys Gly Gln
35 40 45

Leu Lys Gln Tyr Phe Tyr Glu Thr Lys Cys Asn Pro Met Gly Tyr Thr
50 55 60

Lys Glu Gly Cys Arg Gly Ile Asp Lys Arg His Trp Asn Ser Gln Cys
65 70 75 80

Arg Thr Thr Gln Ser Tyr Val Arg Ala Leu Thr Met Asp Ser Lys Lys
85 90 95

Arg Ile Gly Trp Arg Phe Ile Arg Ile Asp Thr Ser Cys Val Cys Thr
100 105 110

Leu Thr Ile Lys Arg Gly Arg
115

<210> SEQ ID NO 370
<211> LENGTH: 120
<212> TYPE: PRT
<213> ORGANISM: Artificial Sequence
<220> FEATURE:
<223> OTHER INFORMATION: Synthetic: nerve growth factor

<400> SEQUENCE: 370

Ser Ser Ser His Pro Ile Phe His Arg Gly Glu Phe Ser Val Cys Asp
1 5 10 15

Ser Val Ser Val Trp Val Gly Asp Lys Thr Thr Ala Thr Asp Ile Lys
20 25 30

Gly Lys Glu Val Met Val Leu Gly Glu Val Asn Ile Asn Asn Ser Val
35 40 45

Phe Lys Gln Tyr Phe Phe Glu Thr Lys Cys Arg Asp Pro Asn Pro Val
50 55 60

Asp Ser Gly Cys Arg Gly Ile Asp Ser Lys His Trp Asn Ser Tyr Cys
65 70 75 80

Thr Thr Thr His Thr Phe Val Lys Ala Leu Thr Met Asp Gly Lys Gln
85 90 95

Ala Ala Trp Arg Phe Ile Arg Ile Asp Thr Ala Cys Val Cys Val Leu
100 105 110

Ser Arg Lys Ala Val Arg Arg Ala
115 120

<210> SEQ ID NO 371
<211> LENGTH: 119
<212> TYPE: PRT
<213> ORGANISM: Artificial Sequence
<220> FEATURE:
<223> OTHER INFORMATION: Synthetic: neurotrophin-3

<400> SEQUENCE: 371

Tyr Ala Glu His Lys Ser His Arg Gly Glu Tyr Ser Val Cys Asp Ser
1 5 10 15

Glu Ser Leu Trp Val Thr Asp Lys Ser Ser Ala Ile Asp Ile Arg Gly
20 25 30

His Gln Val Thr Val Leu Gly Glu Ile Lys Thr Gly Asn Ser Pro Val
35 40 45

Lys Gln Tyr Phe Tyr Glu Thr Arg Cys Lys Glu Ala Arg Pro Val Lys
50 55 60

Asn Gly Cys Arg Gly Ile Asp Asp Lys His Trp Asn Ser Gln Cys Lys

```
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
        115


<210> SEQ ID NO 372
<211> LENGTH: 130
<212> TYPE: PRT
<213> ORGANISM: Artificial Sequence
<220> FEATURE:
<223> OTHER INFORMATION: Synthetic: neurotrophin-4

<400> SEQUENCE: 372

Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
            20                  25                  30

Leu Arg Gly Arg Glu Val Glu Val Leu Gly Glu Val Pro Ala Ala Gly
        35                  40                  45

Gly Ser Pro Leu Arg Gln Tyr Phe Phe Glu Thr Arg Cys Lys Ala Asp
    50                  55                  60

Asn Ala Glu Glu Gly Gly Pro Gly Ala Gly Gly Gly Gly Cys Arg Gly
65                  70                  75                  80

Val Asp Arg Arg His Trp Val Ser Glu Cys Lys Ala Lys Gln Ser Tyr
                85                  90                  95

Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
        115                 120                 125

Arg Ala
    130


<210> SEQ ID NO 373
<211> LENGTH: 29
<212> TYPE: PRT
<213> ORGANISM: Artificial Sequence
<220> FEATURE:
<223> OTHER INFORMATION: Synthetic: Rabies Virus Glycoprotein

<400> SEQUENCE: 373

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25


<210> SEQ ID NO 374
<211> LENGTH: 14
<212> TYPE: PRT
<213> ORGANISM: Artificial Sequence
<220> FEATURE:
<223> OTHER INFORMATION: Synthetic: Targeted Axonal Import

<400> SEQUENCE: 374

Ser Ala Cys Gln Ser Gln Ser Gln Met Arg Cys Gly Gly Gly
1               5                   10


<210> SEQ ID NO 375
```

<211> LENGTH: 7
<212> TYPE: PRT
<213> ORGANISM: Artificial Sequence
<220> FEATURE:
<223> OTHER INFORMATION: Synthetic: the TAxI transport peptide

<400> SEQUENCE: 375

Gln Ser Gln Ser Gln Met Arg
1 5

<210> SEQ ID NO 376
<211> LENGTH: 7
<212> TYPE: PRT
<213> ORGANISM: Artificial Sequence
<220> FEATURE:
<223> OTHER INFORMATION: Synthetic: TAxI transport peptide

<400> SEQUENCE: 376

Ala Ser Gly Ala Gln Ala Arg
1 5

<210> SEQ ID NO 377
<211> LENGTH: 14
<212> TYPE: PRT
<213> ORGANISM: Artificial Sequence
<220> FEATURE:
<223> OTHER INFORMATION: Synthetic: TAxI transport peptide

<400> SEQUENCE: 377

Thr Ser Thr Ala Pro His Leu Arg Leu Arg Leu Thr Ser Arg
1 5 10

<210> SEQ ID NO 378
<211> LENGTH: 7
<212> TYPE: PRT
<213> ORGANISM: Artificial Sequence
<220> FEATURE:
<223> OTHER INFORMATION: Synthetic: nuclear localizing signal

<400> SEQUENCE: 378

Pro Pro Lys Lys Arg Lys Val
1 5

<210> SEQ ID NO 379
<211> LENGTH: 6
<212> TYPE: PRT
<213> ORGANISM: Artificial Sequence
<220> FEATURE:
<223> OTHER INFORMATION: Synthetic: nuclear localizing signal

<400> SEQUENCE: 379

Pro Lys Lys Arg Lys Val
1 5

<210> SEQ ID NO 380
<211> LENGTH: 19
<212> TYPE: PRT
<213> ORGANISM: Artificial Sequence
<220> FEATURE:
<223> OTHER INFORMATION: Synthetic: Angiopep-2

<400> SEQUENCE: 380

Thr Phe Phe Tyr Gly Gly Ser Arg Gly Lys Arg Asn Asn Phe Lys Thr
1 5 10 15

Glu Glu Tyr

<210> SEQ ID NO 381
<211> LENGTH: 39
<212> TYPE: PRT
<213> ORGANISM: Artificial Sequence
<220> FEATURE:
<223> OTHER INFORMATION: Synthetic: ApoB

<400> SEQUENCE: 381

Ser Ser Val Ile Asp Ala Leu Gln Tyr Lys Leu Glu Gly Thr Thr Arg
1 5 10 15

Leu Thr Arg Lys Arg Gly Leu Lys Leu Ala Thr Ala Leu Ser Leu Ser
20 25 30

Asn Lys Phe Val Glu Gly Ser
35

<210> SEQ ID NO 382
<211> LENGTH: 9
<212> TYPE: PRT
<213> ORGANISM: Artificial Sequence
<220> FEATURE:
<223> OTHER INFORMATION: Synthetic: ApoE

<400> SEQUENCE: 382

Leu Arg Lys Leu Arg Lys Arg Leu Leu
1 5

<210> SEQ ID NO 383
<211> LENGTH: 7
<212> TYPE: PRT
<213> ORGANISM: Artificial Sequence
<220> FEATURE:
<223> OTHER INFORMATION: Synthetic: Peptide-22

<400> SEQUENCE: 383

Met Pro Arg Leu Arg Gly Cys
1 5

<210> SEQ ID NO 384
<211> LENGTH: 12
<212> TYPE: PRT
<213> ORGANISM: Artificial Sequence
<220> FEATURE:
<223> OTHER INFORMATION: Synthetic: the retro-enantio

<400> SEQUENCE: 384

Thr His Arg Pro Pro Met Trp Ser Pro Val Trp Pro
1 5 10

<210> SEQ ID NO 385
<211> LENGTH: 12
<212> TYPE: PRT
<213> ORGANISM: Artificial Sequence
<220> FEATURE:
<223> OTHER INFORMATION: Synthetic: the retro-enantio

<400> SEQUENCE: 385

Pro Trp Val Pro Ser Trp Met Pro Pro Arg His Thr
1 5 10

<210> SEQ ID NO 386
<211> LENGTH: 8
<212> TYPE: PRT
<213> ORGANISM: Artificial Sequence
<220> FEATURE:
<223> OTHER INFORMATION: Synthetic

<400> SEQUENCE: 386

Arg Thr Ile Gly Pro Ser Val Cys
1 5

<210> SEQ ID NO 387
<211> LENGTH: 30
<212> TYPE: PRT
<213> ORGANISM: Artificial Sequence
<220> FEATURE:
<223> OTHER INFORMATION: Synthetic: Leptin30

<400> SEQUENCE: 387

Tyr Gln Gln Ile Leu Thr Ser Met Pro Ser Arg Asn Val Ile Gln Ile
1 5 10 15

Ser Asn Asp Leu Glu Asn Leu Arg Asp Leu Leu His Val Leu
20 25 30

<210> SEQ ID NO 388
<211> LENGTH: 29
<212> TYPE: PRT
<213> ORGANISM: Artificial Sequence
<220> FEATURE:
<223> OTHER INFORMATION: Synthetic: RVG29

<400> SEQUENCE: 388

Tyr Thr Ile Trp Met Pro Glu Asn Pro Arg Pro Gly Thr Pro Cys Asp
1 5 10 15

Ile Phe Thr Asn Ser Arg Gly Lys Arg Ala Ser Asn Gly
20 25

<210> SEQ ID NO 389
<211> LENGTH: 16
<212> TYPE: PRT
<213> ORGANISM: Artificial Sequence
<220> FEATURE:
<223> OTHER INFORMATION: Synthetic: DCDX

<400> SEQUENCE: 389

Gly Arg Glu Ile Arg Thr Gly Arg Ala Glu Arg Trp Ser Glu Lys Phe
1 5 10 15

<210> SEQ ID NO 390
<211> LENGTH: 18
<212> TYPE: PRT
<213> ORGANISM: Artificial Sequence
<220> FEATURE:
<223> OTHER INFORMATION: Synthetic: Apamin

<400> SEQUENCE: 390

Cys Asn Cys Lys Ala Pro Glu Thr Ala Leu Cys Ala Arg Arg Cys Gln
1 5 10 15

Gln His

<210> SEQ ID NO 391
<211> LENGTH: 8
<212> TYPE: PRT
<213> ORGANISM: Artificial Sequence
<220> FEATURE:
<223> OTHER INFORMATION: Synthetic: MiniAp-4

<400> SEQUENCE: 391

Lys Ala Pro Glu Thr Ala Leu Asp
1 5

<210> SEQ ID NO 392

<211> LENGTH: 3
<212> TYPE: PRT
<213> ORGANISM: Artificial Sequence
<220> FEATURE:
<223> OTHER INFORMATION: Synthetic: GSH

<400> SEQUENCE: 392

Leu Cys Gly
1

<210> SEQ ID NO 393
<211> LENGTH: 13
<212> TYPE: PRT
<213> ORGANISM: Artificial Sequence
<220> FEATURE:
<223> OTHER INFORMATION: Synthetic: G23

<400> SEQUENCE: 393

His Leu Asn Ile Leu Ser Thr Leu Trp Lys Tyr Arg Cys
1 5 10

<210> SEQ ID NO 394
<211> LENGTH: 7
<212> TYPE: PRT
<213> ORGANISM: Artificial Sequence
<220> FEATURE:
<223> OTHER INFORMATION: Synthetic: g7

<400> SEQUENCE: 394

Gly Phe Thr Gly Phe Leu Ser
1 5

<210> SEQ ID NO 395
<211> LENGTH: 12
<212> TYPE: PRT
<213> ORGANISM: Artificial Sequence
<220> FEATURE:
<223> OTHER INFORMATION: Synthetic: TGN

<400> SEQUENCE: 395

Thr Gly Asn Tyr Lys Ala Leu His Pro His Asn Gly
1 5 10

<210> SEQ ID NO 396
<211> LENGTH: 11
<212> TYPE: PRT
<213> ORGANISM: Artificial Sequence
<220> FEATURE:
<223> OTHER INFORMATION: Synthetic: TAT

<400> SEQUENCE: 396

Tyr Gly Arg Lys Lys Arg Arg Gln Arg Arg Arg
1 5 10

<210> SEQ ID NO 397
<211> LENGTH: 18
<212> TYPE: PRT
<213> ORGANISM: Artificial Sequence -continued

```
<220> FEATURE:
<223> OTHER INFORMATION: Synthetic: SynB1

<400> SEQUENCE: 397

Arg Gly Gly Arg Leu Ser Tyr Ser Arg Arg Arg Phe Ser Thr Ser Thr
1               5                   10                  15

Gly Arg


<210> SEQ ID NO 398
<211> LENGTH: 2
<212> TYPE: PRT
<213> ORGANISM: Artificial Sequence
<220> FEATURE:
<223> OTHER INFORMATION: Synthetic: Diketopiperazines

<400> SEQUENCE: 398

Phe Phe
1


<210> SEQ ID NO 399
<211> LENGTH: 4
<212> TYPE: PRT
<213> ORGANISM: Artificial Sequence
<220> FEATURE:
<223> OTHER INFORMATION: Synthetic: PhPro

<400> SEQUENCE: 399

Pro Pro Pro Pro
1


<210> SEQ ID NO 400
<211> LENGTH: 21
<212> TYPE: PRT
<213> ORGANISM: Artificial Sequence
<220> FEATURE:
<223> OTHER INFORMATION: Synthetic: "self" peptide

<400> SEQUENCE: 400

Gly Asn Tyr Thr Cys Glu Val Thr Glu Leu Thr Arg Glu Gly Glu Thr
1               5                   10                  15

Ile Ile Glu Leu Lys
            20
```